United States Patent
Lim et al.

(10) Patent No.: US 10,329,294 B2
(45) Date of Patent: Jun. 25, 2019

(54) PYRAZOLOPYRIMIDINE INHIBITORS OF IRAK4 ACTIVITY

(71) Applicants: MERCK SHARP & DOHME CORP., Rahway, NJ (US); Jongwon Lim, Lexington, MA (US); Michael D. Altman, Needham, MA (US); Jason D. Brubaker, Cambridge, MA (US); Craig R. Gibeau, Holliston, MA (US)

(72) Inventors: Jongwon Lim, Lexington, MA (US); Michael D. Altman, Needham, MA (US); Jason D. Brubaker, Cambridge, MA (US); Craig R. Gibeau, Holliston, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/557,197

(22) PCT Filed: Mar. 7, 2016

(86) PCT No.: PCT/US2016/021119
§ 371 (c)(1),
(2) Date: Sep. 11, 2017

(87) PCT Pub. No.: WO2016/144846
PCT Pub. Date: Sep. 15, 2016

(65) Prior Publication Data
US 2018/0051028 A1    Feb. 22, 2018

Related U.S. Application Data

(60) Provisional application No. 62/132,191, filed on Mar. 12, 2015.

(51) Int. Cl.
| | |
|---|---|
| *A61K 31/519* | (2006.01) |
| *C07D 487/04* | (2006.01) |
| *A61K 31/4162* | (2006.01) |
| *C07D 519/00* | (2006.01) |
| *A61K 31/55* | (2006.01) |
| *A61K 31/551* | (2006.01) |
| *A61K 31/553* | (2006.01) |
| *A61K 45/06* | (2006.01) |
| *A61P 29/00* | (2006.01) |

(52) U.S. Cl.
CPC ........ *C07D 487/04* (2013.01); *A61K 31/4162* (2013.01); *A61K 31/519* (2013.01); *A61K 31/55* (2013.01); *A61K 31/551* (2013.01); *A61K 31/553* (2013.01); *A61K 45/06* (2013.01); *A61P 29/00* (2018.01); *C07D 519/00* (2013.01)

(58) Field of Classification Search
CPC .......................... A61K 31/519; C07D 487/04
USPC ....................................... 514/259.3; 544/281
See application file for complete search history.

(56) References Cited

U.S. PATENT DOCUMENTS

| | | |
|---|---|---|
| 2014/0194404 A1 | 7/2014 | McElroy et al. |
| 2014/0303149 A1 | 10/2014 | Arora et al. |
| 2015/0005499 A1 | 1/2015 | Haas et al. |

FOREIGN PATENT DOCUMENTS

| | | | | |
|---|---|---|---|---|
| WO | WO 2010051549 | * | 5/2010 | ........... A61K 31/519 |
| WO | WO2010051549 | | 5/2010 | |
| WO | WO2013059587 A1 | | 4/2013 | |

OTHER PUBLICATIONS

Jongwon Lim et al., Discovery of 5-Amino-N-(1H-pyrazol-4-yl)pyrazolo[1,5-a]pyrimidine-3-carboxamide Inhibitors of IRAK4, ACS Medicinal Chemistry Letters, Jun. 11, 2015, 683-688, 6-6.

Jongwon Lim, Identification of N-(1H-pyrazol-4-yl)carboxamide inhibitors of interleukin-1 receptor associated kinase 1: Bicyclic core modifications, Bioorganic & Medicinal Chemistry Letters, 2015, 5384-5388, 25.

* cited by examiner

*Primary Examiner* — Jeffrey H Murray
(74) *Attorney, Agent, or Firm* — Matthew A. Leff; Laura M. Ginkel

(57) ABSTRACT

The present invention relates to pyrazolopyrimidine inhibitors of IRAK4 of formula (I) and provides compositions comprising such inhibitors, as well as methods therewith for treating IRAK4-mediated or -associated conditions or diseases.

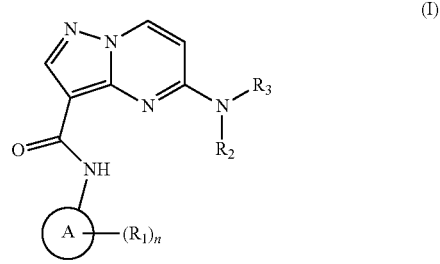

5 Claims, No Drawings

PYRAZOLOPYRIMIDINE INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4): 221-237; and O'Neill, Biochem. Soc. Trans., 2000, 28(5): 557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monomyeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to pyrazolopyrimidine inhibitors of IRAK4 of formula (I) and provides compositions comprising such inhibitors, as well as methods therewith for treating IRAK4-mediated or -associated conditions or diseases.

DETAILED DESCRIPTION OF THE INVENTION

The compounds of the instant invention are useful in the inhibition of the activity of IRAK4.

An embodiment of the instant invention is illustrated by the Formula I:

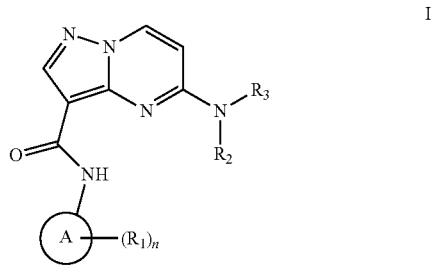

wherein:

Ring A is aryl or heterocyclyl;

n is 0, 1, 2, 3 or 4;

$R_1$ is independently selected from: $(C_1-C_4)$alkyl, $(C_3-C_6)$cycloalkyl, heterocyclyl, $CF_3$, $CHF_2$, CN, halo, said alkyl, cycloalkyl and heterocyclyl optionally substituted with halo, OH, $CH_3$, and $OCH_3$;

$R_2$ is H and $R_3$ is independently selected from: $(C_1-C_6)$alkyl, $(C_3-C_8)$cycloalkyl, and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;

$R_a$ is independently selected from $(C_1-C_4)$alkyl, $(C_3-C_6)$cycloalkyl, $CF_3$, $CHF_2$, OH, halo and $NH_2$, said alkyl optionally substituted with $(C_3-C_6)$cycloalkyl and $CF_3$; and $R_b$ is independently selected from H and $(C_1-C_4)$alkyl;

or a pharmaceutically acceptable salt thereof.

Another embodiment of the instant invention is illustrated by the Formula I:
wherein:
Ring A is pyrazolyl, pyridinyl, thiophenyl, furanyl or phenyl;
n is 0, 1 or 2;
$R_1$ is independently selected from: $(C_1-C_4)$alkyl, cyclopropyl, oxadiazolyl, pyridinyl, oxazolyl, triazolyl, pyriminidyl, $CF_3$, $CHF_2$, CN and halo, said alkyl, oxadiazolyl, pyridinyl, oxazolyl, triazolyl and pyriminidyl are optionally substituted with halo, OH, $CH_3$, and $OCH_3$;
$R_2$ is H and $R_3$ is independently selected from: $(C_1-C_4)$ alkyl, cyclohexyl, cycloheptyl, piperidinyl and azepanyl each optionally substituted with one or more F, OH, $N(R_b)_2$, or morpholinyl, or $R_2$ and $R_3$ can be taken together with the nitrogen to which they are attached to form a heterocyclyl selected from piperazinyl, diazepanyl, diazabicyclooctyl, diazabicycloheptyl, diazaspirononyl, hexahydropyrrolopyrazinyl, piperidinyl, diazabicyclononyl, oxadiazabicyclodecyl and diazatricyclodecyl, said heterocyclyl optionally substituted with one or more substituents selected from $R_a$;
$R_a$ is independently selected from $(C_1-C_4)$alkyl, cyclopropyl, $CF_3$, $CHF_2$, OH, F and $NH_2$, said alkyl optionally substituted with cyclopropyl and $CF_3$; and
$R_b$ is independently selected from H and methyl;
or a pharmaceutically acceptable salt thereof.

A compound selected from:
N-[1-methyl-3-(trifluoromethyl)-1H-pyrazol-4-yl]-5-piperazin-1-ylpyrazolo[1,5-a]pyrimidine-3-carboxamide;
5-{[(1R,2S)-2-aminocyclohexyl]amino}-N-[1-methyl-3-(trifluoromethyl)-1H-pyrazol-4-yl]pyrazolo[1,5-a]pyrimidine-3-carboxamide;
5-(cyclohexylamino)-N-(1-methyl-1H-pyrazol-4-yl)pyrazolo[1,5-a]pyrimidine-3-carboxamide;
5-{[(1R,2R)-2-amino-3,3-difluorocyclohexyl]amino}-N-[1-methyl-3-(trifluoromethyl)-1H-pyrazol-4-yl]pyrazolo[1,5-a]pyrimidine-3-carboxamide;
5-(cyclohexylamino)-N-[1-methyl-3-(trifluoromethyl)-1H-pyrazol-4-yl]pyrazolo[1,5-a]pyrimidine-3-carboxamide;
5-[4-(cyclopropylmethyl)piperazin-1-yl]-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-(piperidin-4-ylamino)pyrazolo[1,5-a]pyrimidine-3-carboxamide;
5-(1,4-diazepan-1-yl)-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-[(3R)-piperidin-3-ylamino]pyrazolo[1,5-a]pyrimidine-3-carboxamide;
5-(4-ethyl-1,4-diazepan-1-yl)-N-[1-methyl-3-(trifluoromethyl)-1H-pyrazol-4-yl]pyrazolo[1,5-a]pyrimidine-3-carboxamide;
5-(2,5-diazabicyclo[2.2.2]oct-2-yl)-N-[1-methyl-3-(trifluoromethyl)-1H-pyrazol-4-yl]pyrazolo[1,5-a]pyrimidine-3-carboxamide;
5-(azepan-3-ylamino)-N-[1-methyl-3-(trifluoromethyl)-1H-pyrazol-4-yl]pyrazolo[1,5-a]pyrimidine-3-carboxamide;
5-(2,5-diazabicyclo[2.2.1]hept-2-yl)-N-[1-methyl-3-(trifluoromethyl)-1H-pyrazol-4-yl]pyrazolo[1,5-a]pyrimidine-3-carboxamide;
5-(5,8-diazaspiro[2.6]non-5-yl)-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-[3-(trifluoromethyl)piperazin-1-yl]pyrazolo[1,5-a]pyrimidine-3-carboxamide;
5-[3-(difluoromethyl)piperazin-1-yl]-N-[1-methyl-3-(trifluoromethyl)-1H-pyrazol-4-yl]pyrazolo[1,5-a]pyrimidine-3-carboxamide;
5-(azepan-4-ylamino)-N-[1-methyl-3-(trifluoromethyl)-1H-pyrazol-4-yl]pyrazolo[1,5-a]pyrimidine-3-carboxamide;
5-(hexahydropyrrolo[1,2-a]pyrazin-2(1H)-yl)-N-[1-methyl-3-(trifluoromethyl)-1H-pyrazol-4-yl]pyrazolo[1,5-a]pyrimidine-3-carboxamide;
5-(3,6-diazabicyclo[3.1.1]hept-3-yl)-N-[1-methyl-3-(trifluoromethyl)-1H-pyrazol-4-yl]pyrazolo[1,5-a]pyrimidine-3-carboxamide;
5-{[(1S,2R)-2-hydroxycyclohexyl]amino}-N-[1-methyl-3-(trifluoromethyl)-1H-pyrazol-4-yl]pyrazolo[1,5-a]pyrimidine-3-carboxamide;
5-[(3S,5S)-3,5-dihydroxypiperidin-1-yl]-N-[1-methyl-3-(trifluoromethyl)-1H-pyrazol-4-yl]pyrazolo[1,5-a]pyrimidine-3-carboxamide;
5-[(3S)-3-hydroxypiperidin-1-yl]-N-[1-methyl-3-(trifluoromethyl)-1H-pyrazol-4-yl]pyrazolo[1,5-a]pyrimidine-3-carboxamide;
5-[(3R)-3-hydroxypiperidin-1-yl]-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-[(3R,5R)-3,5-dihydroxypiperidin-1-yl]pyrazolo[1,5-a]pyrimidine-3-carboxamide;
N-[3-(difluoromethyl)-1-methyl-1H-pyrazol-4-yl]-5-[(3R)-3-hydroxypiperidin-1-yl]pyrazolo[1,5-a]pyrimidine-3-carboxamide;
N-[3-(difluoromethyl)-1-methyl-1H-pyrazol-4-yl]-5-[(3S)-3-hydroxypiperidin-1-yl]pyrazolo[1,5-a]pyrimidine-3-carboxamide;
5-(6-fluoro-1,4-diazepan-1-yl)-N-[1-methyl-3-(trifluoromethyl)-1H-pyrazol-4-yl]pyrazolo[1,5-a]pyrimidine-3-carboxamide;
5-(3-cyclopropylpiperazin-1-yl)-N-[1-methyl-3-(trifluoromethyl)-1H-pyrazol-4-yl]pyrazolo[1,5-a]pyrimidine-3-carboxamide;
5-(2-cyclopropylpiperazin-1-yl)-N-[1-methyl-3-(trifluoromethyl)-1H-pyrazol-4-yl]pyrazolo[1,5-a]pyrimidine-3-carboxamide;
5-(3,3-dimethylpiperazin-1-yl)-N-[1-methyl-3-(trifluoromethyl)-1H-pyrazol-4-yl]pyrazolo[1,5-a]pyrimidine-3-carboxamide;
5-{[(1R,2S)-2-aminocyclohexyl]amino}-N-[3-(trifluoromethyl)pyridin-4-yl]pyrazolo[1,5-a]pyrimidine-3-carboxamide;
5-[(3R)-3-aminopiperidin-1-yl]-N-[1-methyl-3-(trifluoromethyl)-1H-pyrazol-4-yl]pyrazolo[1,5-a]pyrimidine-3-carboxamide;
5-{[(1S,2R)-2-aminocycloheptyl]amino}-N-[1-methyl-3-(trifluoromethyl)-1H-pyrazol-4-yl]pyrazolo[1,5-a]pyrimidine-3-carboxamide;
5-(4-methylpiperazin-1-yl)-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-(2,2,4-trimethylpiperazin-1-yl)pyrazolo[1,5-a]pyrimidine-3-carboxamide;
5-(6,6-difluoro-1,4-diazepan-1-yl)-N-[1-methyl-3-(trifluoromethyl)-1H-pyrazol-4-yl]pyrazolo[1,5-a]pyrimidine-3-carboxamide;

5-{[(1R,2S)-2-hydroxycyclohexyl]amino}-N-[1-methyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[2-(trifluoromethyl)phenyl]pyrazolo[1,5-a]pyrimidine-3-carboxamide;

5-{[(1R,2S)-2-aminocyclohexyl]amino}-N-(4-cyanothiophen-3-yl)pyrazolo[1,5-a]pyrimidine-3-carboxamide;

5-(1,4-diazabicyclo[3.2.2]non-4-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-[2-(2,2,2-trifluoroethyl)piperazin-1-yl]pyrazolo[1,5-a]pyrimidine-3-carboxamide;

5-{[(1R,2S)-2-aminocyclohexyl]amino}-N-(2-cyanothiophen-3-yl)pyrazolo[1,5-a]pyrimidine-3-carboxamide;

5-(1,4-diazabicyclo[3.2.1]oct-4-yl)-N-[1-methyl-3-(trifluoromethyl)-1H-pyrazol-4-yl]pyrazolo[1,5-a]pyrimidine-3-carboxamide;

5-[(3S)-3-aminopiperidin-1-yl]-N-[1-methyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[2-(trifluoromethyl)furan-3-yl]pyrazolo[1,5-a]pyrimidine-3-carboxamide;

N-[1-tert-butyl-3-(trifluoromethyl)-1H-pyrazol-4-yl]-5-piperazin-1-ylpyrazolo[1,5-a]pyrimidine-3-carboxamide;

N-[1-tert-butyl-3-(trifluoromethyl)-1H-pyrazol-4-yl]-5-(5,8-diazaspiro[2.6]non-5-yl)pyrazolo[1,5-a]pyrimidine-3-carboxamide;

N-[1-tert-butyl-3-(trifluoromethyl)-1H-pyrazol-4-yl]-5-{[(1R,2S)-2-hydroxycyclohexyl]amino}pyrazolo[1,5-a]pyrimidine-3-carboxamide;

5-{[(1R,2R)-2-amino-3,3-difluorocyclohexyl]amino}-N-[1-tert-butyl-3-(trifluoromethyl)-1H-pyrazol-4-yl]pyrazolo[1,5-a]pyrimidine-3-carboxamide;

N-[1-tert-butyl-3-(trifluoromethyl)-1H-pyrazol-4-yl]-5-(2,5-diazabicyclo[2.2.2]oct-2-yl)pyrazolo[1,5-a]pyrimidine-3-carboxamide;

5-(5,8-diazaspiro[2.6]non-5-yl)-N-[1-(1-methylethyl)-3-(trifluoromethyl)-1H-pyrazol-4-yl]pyrazolo[1,5-a]pyrimidine-3-carboxamide;

5-{[(1R,2S)-2-hydroxycyclohexyl]amino}-N-[1-(1-methylethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(1-methylethyl)-3-(trifluoromethyl)-1H-pyrazol-4-yl]pyrazolo[1,5-a]pyrimidine-3-carboxamide;

5-{[(1R,2S)-2-aminocycloheptyl]amino}-N-[1-methyl-3-(trifluoromethyl)-1H-pyrazol-4-yl]pyrazolo[1,5-a]pyrimidine-3-carboxamide;

5-{[(1R,2S)-2-aminocycloheptyl]amino}-N-[1-methyl-3-(trifluoromethyl)-1H-pyrazol-4-yl]pyrazolo[1,5-a]pyrimidine-3-carboxamide;

5-{[(1R,2R)-2-amino-3,3-difluorocyclohexyl]amino}-N-[1-(1-methylethyl)-3-(trifluoromethyl)-1H-pyrazol-4-yl]pyrazolo[1,5-a]pyrimidine-3-carboxamide;

5-{[(1R,2S)-2-hydroxycyclohexyl]amino}-N-[1-(2,2,2-trifluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(2,2,2-trifluoroethyl)-3-(trifluoromethyl)-1H-pyrazol-4-yl]pyrazolo[1,5-a]pyrimidine-3-carboxamide;

5-(5-amino-3,3-difluoropiperidin-1-yl)-N-[1-methyl-3-(trifluoromethyl)-1H-pyrazol-4-yl]pyrazolo[1,5-a]pyrimidine-3-carboxamide;

5-[(5R)-5-amino-3,3-difluoropiperidin-1-yl]-N-[1-methyl-3-(trifluoromethyl)-1H-pyrazol-4-yl]pyrazolo[1,5-a]pyrimidine-3-carboxamide;

5-[(5S)-5-amino-3,3-difluoropiperidin-1-yl]-N-[1-methyl-3-(trifluoromethyl)-1H-pyrazol-4-yl]pyrazolo[1,5-a]pyrimidine-3-carboxamide;

N-[1-(2,2-difluoroethyl)-3-(trifluoromethyl)-1H-pyrazol-4-yl]-5-piperazin-1-ylpyrazolo[1,5-a]pyrimidine-3-carboxamide;

N-[1-(2,2-difluoroethyl)-3-(trifluoromethyl)-1H-pyrazol-4-yl]-5-{[(1R,2S)-2-hydroxycyclohexyl]amino}pyrazolo[1,5-a]pyrimidine-3-carboxamide;

5-(5,8-diazaspiro[2.6]non-5-yl)-N-[1-(2,2-difluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(2,2-difluoroethyl)-3-(trifluoromethyl)-1H-pyrazol-4-yl]pyrazolo[1,5-a]pyrimidine-3-carboxamide;

5-{[(1R,2R)-2-amino-3,3-difluorocyclohexyl]amino}-N-[1-(2,2-difluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(difluoromethyl)-3-(trifluoromethyl)-1H-pyrazol-4-yl]pyrazolo[1,5-a]pyrimidine-3-carboxamide;

5-(5,8-diazaspiro[2.6]non-5-yl)-N-[1-(difluoromethyl)-3-(trifluoromethyl)-1H-pyrazol-4-yl]pyrazolo[1,5-a]pyrimidine-3-carboxamide;

5-{[(1R,2R)-2-amino-3,3-difluorocyclohexyl]amino}-N-[1-(difluoromethyl)-3-(trifluoromethyl)-1H-pyrazol-4-yl]pyrazolo[1,5-a]pyrimidine-3-carboxamide;

N-[1-(difluoromethyl)-3-(trifluoromethyl)-1H-pyrazol-4-yl]-5-{[(1R,2S)-2-hydroxycyclohexyl]amino}pyrazolo[1,5-a]pyrimidine-3-carboxamide;

5-(2,6-diazabicyclo[3.2.2]non-6-yl)-N-[1-methyl-3-(trifluoromethyl)-1H-pyrazol-4-yl]pyrazolo[1,5-a]pyrimidine-3-carboxamide;

5-(2,6-diazabicyclo[3.2.1]oct-6-yl)-N-[1-methyl-3-(trifluoromethyl)-1H-pyrazol-4-yl]pyrazolo[1,5-a]pyrimidine-3-carboxamide;

5-[(2R,5R)-2,5-dimethylpiperazin-1-yl]-N-[1-methyl-3-(trifluoromethyl)-1H-pyrazol-4-yl]pyrazolo[1,5-a]pyrimidine-3-carboxamide;

5-{[(1R,2S)-2-aminocyclohexyl]amino}-N-(4-bromothiophen-3-yl)pyrazolo[1,5-a]pyrimidine-3-carboxamide;

5[(1R,4R)-2,5-diazabicyclo[2.2.2]oct-2-yl)-N-[1-methyl-3-(trifluoromethyl)-1H-pyrazol-4-yl]pyrazolo[1,5-a]pyrimidine-3-carboxamide;

5-[(1S,4S)-2,5-diazabicyclo[2.2.2]oct-2-yl]-N-[1-methyl-3-(trifluoromethyl)-1H-pyrazol-4-yl]pyrazolo[1,5-a]pyrimidine-3-carboxamide;

5-(2,5-dimethylpiperazin-1-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-(3-oxa-7,9-diazabicyclo[3.3.2]dec-7-yl)pyrazolo[1,5-a]pyrimidine-3-carboxamide;

5-(3,8-diazabicyclo[3.2.1]oct-3-yl)-N-[1-methyl-3-(trifluoromethyl)-1H-pyrazol-4-yl]pyrazolo[1,5-a]pyrimidine-3-carboxamide;

5-(3,6-diazabicyclo[3.2.1]oct-6-yl)-N-[1-methyl-3-(trifluoromethyl)-1H-pyrazol-4-yl]pyrazolo[1,5-a]pyrimidine-3-carboxamide;

5-[(1S,5R)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide;

5-[(1R,5S)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-{[(1R,2S)-2-hydroxycyclohexyl]amino}pyrazolo[1,5-a]pyrimidine-3-carboxamide;

5-(5,8-diazaspiro[2.6]non-5-yl)-N-[3-(difluoromethyl)-1-methyl-1H-pyrazol-4-yl]pyrazolo[1,5-a]pyrimidine-3-carboxamide;

5-(1,4-diazepan-1-yl)-N-[3-(difluoromethyl)-1-methyl-1H-pyrazol-4-yl]pyrazolo[1,5-a]pyrimidine-3-carboxamide;

N-[3-(difluoromethyl)-1-methyl-1H-pyrazol-4-yl]-5-piperazin-1-ylpyrazolo[1,5-a]pyrimidine-3-carboxamide;

5-(3,9-diazabicyclo[4.2.1]non-3-yl)-N-[1-methyl-3-(trifluoromethyl)-1H-pyrazol-4-yl]pyrazolo[1,5-a]pyrimidine-3-carboxamide;

5-[(3R)-3-aminopiperidin-1-yl]-N-[3-(difluoromethyl)-1-methyl-1H-pyrazol-4-yl]pyrazolo[1,5-a]pyrimidine-3-carboxamide;

N-[3-(difluoromethyl)-1-methyl-1H-pyrazol-4-yl]-5-[(3R)-piperidin-3-ylamino]pyrazolo[1,5-a]pyrimidine-3-carboxamide;

5-[(1R,2R,5S,6S)-9,10-diazatricyclo[4.2.1.1~2,5~]dec-9-yl]-N-[1-methyl-3-(trifluoromethyl)-1H-pyrazol-4-yl]pyrazolo[1,5-a]pyrimidine-3-carboxamide;

5-[(2R,5S)-2,5-dimethylpiperazin-1-yl]-N-[1-methyl-3-(trifluoromethyl)-1H-pyrazol-4-yl]pyrazolo[1,5-a]pyrimidine-3-carboxamide;

5-(3,9-diazabicyclo[4.2.1]non-3-yl)-N-[1-methyl-3-(trifluoromethyl)-1H-pyrazol-4-yl]pyrazolo[1,5-a]pyrimidine-3-carboxamide;

5-(4,7-diazaspiro[2.6]non-4-yl)-N-[1-methyl-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[3-(difluoromethyl)-1-methyl-1H-pyrazol-4-yl]pyrazolo[1,5-a]pyrimidine-3-carboxamide;

5-{[(1R,2R)-2-amino-3,3-difluorocyclohexyl]amino}-N-[3-(difluoromethyl)-1-methyl-1H-pyrazol-4-yl]pyrazolo[1,5-a]pyrimidine-3-carboxamide;

5-(4,8-diazaspiro[2.6]non-4-yl)-N-[1-methyl-3-(trifluoromethyl)-1H-pyrazol-4-yl]pyrazolo[1,5-a]pyrimidine-3-carboxamide;

5-(azepan-3-ylamino)-N-[3-(difluoromethyl)-1-methyl-1H-pyrazol-4-yl]pyrazolo[1,5-a]pyrimidine-3-carboxamide;

5-(5,8-diazaspiro[2.6]non-5-yl)-N-(2-iodophenyl)pyrazolo[1,5-a]pyrimidine-3-carboxamide;

5-{[(1R,2S)-2-hydroxycyclohexyl]amino}-N-(2-iodophenyl)pyrazolo[1,5-a]pyrimidine-3-carboxamide;

5-(2,7-diazatricyclo[4.4.0.0~3,8~]dec-2-yl)-N-[1-methyl-3-(trifluoromethyl)-1H-pyrazol-4-yl]pyrazolo[1,5-a]pyrimidine-3-carboxamide;

5-(2,5-diazabicyclo[2.2.2]oct-2-yl)-N-(2-iodophenyl)pyrazolo[1,5-a]pyrimidine-3-carboxamide;

5-{[(1R,2S)-2-aminocyclohexyl]amino}-N-(2-chlorophenyl)pyrazolo[1,5-a]pyrimidine-3-carboxamide;

N-(2-chlorophenyl)-5-(1,4-diazepan-1-yl)pyrazolo[1,5-a]pyrimidine-3-carboxamide;

5-{[(1R,2R)-2-amino-3,3-difluorocyclohexyl]amino}-N-(2-chlorophenyl)pyrazolo[1,5-a]pyrimidine-3-carboxamide;

N-(2-chlorophenyl)-5-(2,5-diazabicyclo[2.2.2]oct-2-yl)pyrazolo[1,5-a]pyrimidine-3-carboxamide;

5-{[(1R,2R)-2-amino-3,3-difluorocyclohexyl]amino}-N-(2-bromophenyl)pyrazolo[1,5-a]pyrimidine-3-carboxamide;

N-(2-bromophenyl)-5-(1,4-diazepan-1-yl)pyrazolo[1,5-a]pyrimidine-3-carboxamide;

N-(2-cyanothiophen-3-yl)-5-(2,5-diazabicyclo[2.2.2]oct-2-yl)pyrazolo[1,5-a]pyrimidine-3-carboxamide;

N-(2-cyanothiophen-3-yl)-5-(1,4-diazepan-1-yl)pyrazolo[1,5-a]pyrimidine-3-carboxamide;

N-(2-bromophenyl)-5-(2,5-diazabicyclo[2.2.2]oct-2-yl)pyrazolo[1,5-a]pyrimidine-3-carboxamide;

5-{[(1R,2S)-2-aminocyclohexyl]amino}-N-(2-bromophenyl)pyrazolo[1,5-a]pyrimidine-3-carboxamide;

5-{[(1R,2R)-2-amino-3,3-difluorocyclohexyl]amino}-N-[2-(trifluoromethyl)phenyl]pyrazolo[1,5-a]pyrimidine-3-carboxamide;

5-(2,5-diazabicyclo[2.2.2]oct-2-yl)-N-[2-(trifluoromethyl)phenyl]pyrazolo[1,5-a]pyrimidine-3-carboxamide;

5-{[(1R,2S)-2-aminocyclohexyl]amino}-N-(2-chlorothiophen-3-yl)pyrazolo[1,5-a]pyrimidine-3-carboxamide;

N-(2-chlorothiophen-3-yl)-5-(1,4-diazepan-1-yl)pyrazolo[1,5-a]pyrimidine-3-carboxamide;

5-{[(1R,2R)-2-amino-3,3-difluorocyclohexyl]amino}-N-(2-chlorothiophen-3-yl)pyrazolo[1,5-a]pyrimidine-3-carboxamide;

5-{[(1R,2S)-2-aminocyclohexyl]amino}-N-[4-(difluoromethyl)thiophen-3-yl]pyrazolo[1,5-a]pyrimidine-3-carboxamide;

5-(1,4-diazepan-1-yl)-N-[4-(difluoromethyl)thiophen-3-yl]pyrazolo[1,5-a]pyrimidine-3-carboxamide;

5-{[(1R,2R)-2-amino-3,3-difluorocyclohexyl]amino}-N-[4-(difluoromethyl)thiophen-3-yl]pyrazolo[1,5-a]pyrimidine-3-carboxamide;

5-{[(1R,2R)-2-amino-3,3-difluorocyclohexyl]amino}-N-(4-bromothiophen-3-yl)pyrazolo[1,5-a]pyrimidine-3-carboxamide;

N-(4-bromothiophen-3-yl)-5-(1,4-diazepan-1-yl)pyrazolo[1,5-a]pyrimidine-3-carboxamide;

N-(4-bromothiophen-3-yl)-5-(2,5-diazabicyclo[2.2.2]oct-2-yl)pyrazolo[1,5-a]pyrimidine-3-carboxamide;

N-(3-cyano-1-methyl-1H-pyrazol-4-yl)-5-(1,4-diazepan-1-yl)pyrazolo[1,5-a]pyrimidine-3-carboxamide;

5-{[(1R,2R)-2-amino-3,3-difluorocyclohexyl]amino}-N-(3-cyano-1-methyl-1H-pyrazol-4-yl)pyrazolo[1,5-a]pyrimidine-3-carboxamide;

N-(2-bromothiophen-3-yl)-5-(1,4-diazepan-1-yl)pyrazolo[1,5-a]pyrimidine-3-carboxamide;

5-{[(1R,2R)-2-amino-3,3-difluorocyclohexyl]amino}-N-(2-bromothiophen-3-yl)pyrazolo[1,5-a]pyrimidine-3-carboxamide;

5-{[(1R,2S)-2-aminocyclohexyl]amino}-N-(2-bromothiophen-3-yl)pyrazolo[1,5-a]pyrimidine-3-carboxamide;

5-(1,4-diazepan-1-yl)-N-[2-(difluoromethyl)phenyl]pyrazolo[1,5-a]pyrimidine-3-carboxamide;

5-{[(1R,2S)-2-aminocyclohexyl]amino}-N-[2-(difluoromethyl)phenyl]pyrazolo[1,5-a]pyrimidine-3-carboxamide;

5-{[(1R,2R)-2-amino-3,3-difluorocyclohexyl]amino}-N-[2-(difluoromethyl)phenyl]pyrazolo[1,5-a]pyrimidine-3-carboxamide;

5-{[(1R,2R)-2-amino-3,3-difluorocyclohexyl]amino}-N-(2-cyanothiophen-3-yl)pyrazolo[1,5-a]pyrimidine-3-carboxamide;

N-(2-chlorothiophen-3-yl)-5-(2,5-diazabicyclo[2.2.2]oct-2-yl)pyrazolo[1,5-a]pyrimidine-3-carboxamide;

5-(2,5-diazabicyclo[2.2.2]oct-2-yl)-N-[4-(difluoromethyl)thiophen-3-yl]pyrazolo[1,5-a]pyrimidine-3-carboxamide;

N-(3-cyano-1-methyl-1H-pyrazol-4-yl)-5-(2,5-diazabicyclo[2.2.2]oct-2-yl)pyrazolo[1,5-a]pyrimidine-3-carboxamide;
N-(3-bromo-1-methyl-1H-pyrazol-4-yl)-5-(1,4-diazepan-1-yl)pyrazolo[1,5-a]pyrimidine-3-carboxamide;
5-{[(1R,2S)-2-aminocyclohexyl]amino}-N-(3-bromo-1-methyl-1H-pyrazol-4-yl)pyrazolo[1,5-a]pyrimidine-3-carboxamide;
5-{[(1R,2R)-2-amino-3,3-difluorocyclohexyl]amino}-N-(3-bromo-1-methyl-1H-pyrazol-4-yl)pyrazolo[1,5-a]pyrimidine-3-carboxamide;
N-(3-bromo-1-methyl-1H-pyrazol-4-yl)-5-(2,5-diazabicyclo[2.2.2]oct-2-yl)pyrazolo[1,5-a]pyrimidine-3-carboxamide;
N-(4-cyanothiophen-3-yl)-5-(1,4-diazepan-1-yl)pyrazolo[1,5-a]pyrimidine-3-carboxamide;
N-(2-bromothiophen-3-yl)-5-(2,5-diazabicyclo[2.2.2]oct-2-yl)pyrazolo[1,5-a]pyrimidine-3-carboxamide;
5-{[(1R,2R)-2-amino-3,3-difluorocyclohexyl]amino}-N-(4-cyanothiophen-3-yl)pyrazolo[1,5-a]pyrimidine-3-carboxamide;
5-{[(1R,2S)-2-aminocyclohexyl]amino}-N-[2-(trifluoromethyl)thiophen-3-yl]pyrazolo[1,5-a]pyrimidine-3-carboxamide;
N-(4-cyanothiophen-3-yl)-5-(2,5-diazabicyclo[2.2.2]oct-2-yl)pyrazolo[1,5-a]pyrimidine-3-carboxamide;
5-(2,5-diazabicyclo[2.2.2]oct-2-yl)-N-[2-(difluoromethyl)phenyl]pyrazolo[1,5-a]pyrimidine-3-carboxamide;
5-(2,5-diazabicyclo[2.2.2]oct-2-yl)-N-[2-(trifluoromethyl)thiophen-3-yl]pyrazolo[1,5-a]pyrimidine-3-carboxamide;
N-(3-chloro-1-methyl-1H-pyrazol-4-yl)-5-(1,4-diazepan-1-yl)pyrazolo[1,5-a]pyrimidine-3-carboxamide; 5-{[(1R,2S)-2-aminocyclohexyl]amino}-N-(3-chloro-1-methyl-1H-pyrazol-4-yl)pyrazolo[1,5-a]pyrimidine-3-carboxamide;
5-{[(1R,2R)-2-amino-3,3-difluorocyclohexyl]amino}-N-(3-chloro-1-methyl-1H-pyrazol-4-yl)pyrazolo[1,5-a]pyrimidine-3-carboxamide;
N-(3-chloro-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-chloro-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-(1,4-diazepan-1-yl)-N-[2-(trifluoromethyl)thiophen-3-yl]pyrazolo[1,5-a]pyrimidine-3-carboxamide;
5-[(1S,4S)-2,5-diazabicyclo[2.2.2]oct-2-yl]-N-[4-(difluoromethyl)thiophen-3-yl]pyrazolo[1,5-a]pyrimidine-3-carboxamide;
5[(1R,4R)-2,5-diazabicyclo[2.2.2]oct-2-yl]-N-[4-(difluoromethyl)thiophen-3-yl]pyrazolo[1,5-a]pyrimidine-3-carboxamide;
N-(3-cyano-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-cyano-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-[(1S,4S)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide;
5-[(3S)-azepan-3-ylamino]-N-[1-methyl-3-(trifluoromethyl)-1H-pyrazol-4-yl]pyrazolo[1,5-a]pyrimidine-3-carboxamide;
5-[(3R)-azepan-3-ylamino]-N-[1-methyl-3-(trifluoromethyl)-1H-pyrazol-4-yl]pyrazolo[1,5-a]pyrimidine-3-carboxamide;
5-[(1R,4R)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide;
5-[(3R)-azepan-3-ylamino]-N-[3-(difluoromethyl)-1-methyl-1H-pyrazol-4-yl]pyrazolo[1,5-a]pyrimidine-3-carboxamide;
5-[(3S)-azepan-3-ylamino]-N-[3-(difluoromethyl)-1-methyl-1H-pyrazol-4-yl]pyrazolo[1,5-a]pyrimidine-3-carboxamide;
N-(3-bromo-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-bromo-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-{[(1R,2S)-2-aminocyclohexyl]amino}-N-[1-methyl-5-(trifluoromethyl)-1H-pyrazol-4-yl]pyrazolo[1,5-a]pyrimidine-3-carboxamide;
N-(4-chlorothiophen-3-yl)-5-(1,4-diazepan-1-yl)pyrazolo[1,5-a]pyrimidine-3-carboxamide;
5-{[(1R,2S)-2-aminocyclohexyl]amino}-N-(4-chlorothiophen-3-yl)pyrazolo[1,5-a]pyrimidine-3-carboxamide;
N-(4-chlorothiophen-3-yl)-5-[(1S,4S)-2,5-diazabicyclo[2.2.2]oct-2-yl]pyrazolo[1,5-a]pyrimidine-3-carboxamide;
5-{[(1R,2R)-2-amino-3,3-difluorocyclohexyl]amino}-N-[2-(difluoromethyl)thiophen-3-yl]pyrazolo[1,5-a]pyrimidine-3-carboxamide;
N-(4-chlorothiophen-3-yl)-5-[(1R,4R)-2,5-diazabicyclo[2.2.2]oct-2-yl]pyrazolo[1,5-a]pyrimidine-3-carboxamide;
5-(3,8-diazabicyclo[3.2.1]oct-3-yl)-N-[3-(difluoromethyl)-1-methyl-1H-pyrazol-4-yl]pyrazolo[1,5-a]pyrimidine-3-carboxamide;
5-(5-amino-3,3-difluoropiperidin-1-yl)-N-[3-(difluoromethyl)-1-methyl-1H-pyrazol-4-yl]pyrazolo[1,5-a]pyrimidine-3-carboxamide;
5-[(3R,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3R,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4R)-3-amino-4-fluoropiperidin-1-yl]-N-[3-(difluoromethyl)-1-methyl-1H-pyrazol-4-yl]pyrazolo[1,5-a]pyrimidine-3-carboxamide;
5-[(3S,4R)-3-amino-4-fluoropiperidin-1-yl]-N-[3-(difluoromethyl)-1-methyl-1H-pyrazol-4-yl]pyrazolo[1,5-a]pyrimidine-3-carboxamide;
5-(5-amino-3,3-difluoropiperidin-1-yl)-N-[3-(difluoromethyl)-1-methyl-1H-pyrazol-4-yl]pyrazolo[1,5-a]pyrimidine-3-carboxamide;
5-{[(1R,2S)-2-aminocyclohexyl]amino}-N-thiophen-3-ylpyrazolo[1,5-a]pyrimidine-3-carboxamide;
5-[(1S,5S)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;
5-[(1S,5S)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;

5-[(1R,5R)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;
N-(2-chlorothiophen-3-yl)-5-{[(1R,2S)-2-hydroxycyclohexyl]amino}pyrazolo[1,5-a]pyrimidine-3-carboxamide;
N-(3-chloro-1-methyl-1H-pyrazol-4-yl)-5-{[(1R,2S)-2-hydroxycyclohexyl]amino}pyrazolo[1,5-a]pyrimidine-3-carboxamide;
N-(2-cyanothiophen-3-yl)-5-{[(1R,2S)-2-hydroxycyclohexyl]amino}pyrazolo[1,5-a]pyrimidine-3-carboxamide;
5-(3-amino-4,4-difluoropiperidin-1-yl)-N-[1-methyl-3-(trifluoromethyl)-1H-pyrazol-4-yl]pyrazolo[1,5-a]pyrimidine-3-carboxamide;
5-(3-amino-4,4-difluoropiperidin-1-yl)-N-[3-(difluoromethyl)-1-methyl-1H-pyrazol-4-yl]pyrazolo[1,5-a]pyrimidine-3-carboxamide;
5-{[(1R,2R)-2-amino-3,3-difluorocyclohexyl]amino}-N-(2-chlorothiophen-3-yl)pyrazolo[1,5-a]pyrimidine-3-carboxamide;
5-{[(1R,2R)-2-amino-3,3-difluorocyclohexyl]amino}-N-(2-cyanothiophen-3-yl)pyrazolo[1,5-a]pyrimidine-3-carboxamide;
5-(3-amino-4,4-difluoropiperidin-1-yl)-N-[1-methyl-3-(trifluoromethyl)-1H-pyrazol-4-yl]pyrazolo[1,5-a]pyrimidine-3-carboxamide;
5-(3-amino-4,4-difluoropiperidin-1-yl)-N-[3-(difluoromethyl)-1-methyl-1H-pyrazol-4-yl]pyrazolo[1,5-a]pyrimidine-3-carboxamide;
N-(2-chlorophenyl)-5-{[(1R,2S)-2-hydroxycyclohexyl]amino}pyrazolo[1,5-a]pyrimidine-3-carboxamide;
N-(2-bromophenyl)-5-{[(1R,2S)-2-hydroxycyclohexyl]amino}pyrazolo[1,5-a]pyrimidine-3-carboxamide;
N-(2-bromothiophen-3-yl)-5-{[(1R,2S)-2-hydroxycyclohexyl]amino}pyrazolo[1,5-a]pyrimidine-3-carboxamide;
N-[1-tert-butyl-3-(difluoromethyl)-1H-pyrazol-4-yl]-5-{[(1R,2S)-2-hydroxycyclohexyl]amino}pyrazolo[1,5-a]pyrimidine-3-carboxamide;
5-{[(1R,2R)-2-amino-3,3-difluorocyclohexyl]amino}-N-[1-tert-butyl-3-(difluoromethyl)-1H-pyrazol-4-yl]pyrazolo[1,5-a]pyrimidine-3-carboxamide;
N-[3-(difluoromethyl)-1-(1-methylethyl)-1H-pyrazol-4-yl]-5-{[(1R,2S)-2-hydroxycyclohexyl]amino}pyrazolo[1,5-a]pyrimidine-3-carboxamide;
5-{[(1R,2R)-2-amino-3,3-difluorocyclohexyl]amino}-N-[3-(difluoromethyl)-1-(1-methylethyl)-1H-pyrazol-4-yl]pyrazolo[1,5-a]pyrimidine-3-carboxamide;
5-{[(1R,2R)-2-amino-3-hydroxycyclohexyl]amino}-N-[1-methyl-3-(trifluoromethyl)-1H-pyrazol-4-yl]pyrazolo[1,5-a]pyrimidine-3-carboxamide;
5-{[(1R,2R)-2-amino-6-hydroxycyclohexyl]amino}-N-[1-methyl-3-(trifluoromethyl)-1H-pyrazol-4-yl]pyrazolo[1,5-a]pyrimidine-3-carboxamide;
5-{[(1R,2R)-2-amino-3-fluorocyclohexyl]amino}-N-[1-methyl-3-(trifluoromethyl)-1H-pyrazol-4-yl]pyrazolo[1,5-a]pyrimidine-3-carboxamide;
5-{[(1S,2R)-2-amino-5,5-difluorocyclohexyl]amino}-N-[1-methyl-3-(trifluoromethyl)-1H-pyrazol-4-yl]pyrazolo[1,5-a]pyrimidine-3-carboxamide;
5-{[(1S,2R)-2-amino-4,4-difluorocyclohexyl]amino}-N-[1-methyl-3-(trifluoromethyl)-1H-pyrazol-4-yl]pyrazolo[1,5-a]pyrimidine-3-carboxamide;
5-{[(1S,2R)-2-amino-5,5-difluorocyclohexyl]amino}-N-[1-methyl-3-(trifluoromethyl)-1H-pyrazol-4-yl]pyrazolo[1,5-a]pyrimidine-3-carboxamide;
5-{[(1S,2R)-2-amino-4,4-difluorocyclohexyl]amino}-N-[1-methyl-3-(trifluoromethyl)-1H-pyrazol-4-yl]pyrazolo[1,5-a]pyrimidine-3-carboxamide;
5-{[(1S,2R)-2-amino-5,5-difluorocyclohexyl]amino}-N-[3-(difluoromethyl)-1-methyl-1H-pyrazol-4-yl]pyrazolo[1,5-a]pyrimidine-3-carboxamide;
5-{[(1S,2R)-2-amino-4,4-difluorocyclohexyl]amino}-N-[3-(difluoromethyl)-1-methyl-1H-pyrazol-4-yl]pyrazolo[1,5-a]pyrimidine-3-carboxamide;
5-{[(1S,2R)-2-amino-5,5-difluorocyclohexyl]amino}-N-[3-(difluoromethyl)-1-methyl-1H-pyrazol-4-yl]pyrazolo[1,5-a]pyrimidine-3-carboxamide;
5-{[(1S,2R)-2-amino-4,4-difluorocyclohexyl]amino}-N-[3-(difluoromethyl)-1-methyl-1H-pyrazol-4-yl]pyrazolo[1,5-a]pyrimidine-3-carboxamide;
N-[1-methyl-3-(trifluoromethyl)-1H-pyrazol-4-yl]-5-(3-oxa-7,9-diazabicyclo[3.3.2]dec-9-yl)pyrazolo[1,5-a]pyrimidine-3-carboxamide;
5-[(1S,5R)-2,6-diazabicyclo[3.2.1]oct-2-yl]-N-[1-methyl-3-(trifluoromethyl)-1H-pyrazol-4-yl]pyrazolo[1,5-a]pyrimidine-3-carboxamide;
5-(3,6-diazabicyclo[3.1.1]hept-6-yl)-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-[2-(trifluoromethyl)piperazin-1-yl]pyrazolo[1,5-a]pyrimidine-3-carboxamide;
5-(2,2-dimethylpiperazin-1-yl)-N-[1-methyl-3-(trifluoromethyl)-1H-pyrazol-4-yl]pyrazolo[1,5-a]pyrimidine-3-carboxamide;
5-[(5,5-difluoropiperidin-3-yl)amino]-N-[1-methyl-3-(trifluoromethyl)-1H-pyrazol-4-yl]pyrazolo[1,5-a]pyrimidine-3-carboxamide;
5-{[(3S)-5,5-difluoropiperidin-3-yl]amino}-N-[1-methyl-3-(trifluoromethyl)-1H-pyrazol-4-yl]pyrazolo[1,5-a]pyrimidine-3-carboxamide;
5-{[(3R)-5,5-difluoropiperidin-3-yl]amino}-N-[1-methyl-3-(trifluoromethyl)-1H-pyrazol-4-yl]pyrazolo[1,5-a]pyrimidine-3-carboxamide;
5-(4,7-diazaspiro[2.6]non-7-yl)-N-[1-methyl-3-(trifluoromethyl)-1H-pyrazol-4-yl]pyrazolo[1,5-a]pyrimidine-3-carboxamide;
5-(3,9-diazabicyclo[4.2.1]non-9-yl)-N-[1-methyl-3-(trifluoromethyl)-1H-pyrazol-4-yl]pyrazolo[1,5-a]pyrimidine-3-carboxamide;
5-(3,9-diazabicyclo[4.2.1]non-9-yl)-N-[1-methyl-3-(trifluoromethyl)-1H-pyrazol-4-yl]pyrazolo[1,5-a]pyrimidine-3-carboxamide;
5-(3,6-diazabicyclo[3.2.1]oct-3-yl)-N-[1-methyl-3-(trifluoromethyl)-1H-pyrazol-4-yl]pyrazolo[1,5-a]pyrimidine-3-carboxamide;
5-[(1S,5S)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide;
5-[(1R,5R)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide;
5-(3,8-diazabicyclo[3.2.1]oct-8-yl)-N-[1-methyl-3-(trifluoromethyl)-1H-pyrazol-4-yl]pyrazolo[1,5-a]pyrimidine-3-carboxamide;
5-(4,8-diazaspiro[2.6]non-8-yl)-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-[(5,5-difluoropiperidin-3-yl)amino]pyrazolo[1,5-a]pyrimidine-3-carboxamide;
5-(3,8-diazabicyclo[3.2.1]oct-8-yl)-N-[3-(difluoromethyl)-1-methyl-1H-pyrazol-4-yl]pyrazolo[1,5-a]pyrimidine-3-carboxamide;

5-{[(3R,4S)-4-fluoropiperidin-3-yl]amino}-N-[1-methyl-3-(trifluoromethyl)-1H-pyrazol-4-yl]pyrazolo[1,5-a]pyrimidine-3-carboxamide;
5-{[(3S,4R)-4-fluoropiperidin-3-yl]amino}-N-[1-methyl-3-(trifluoromethyl)-1H-pyrazol-4-yl]pyrazolo[1,5-a]pyrimidine-3-carboxamide;
5-{[(3R,4R)-4-fluoropiperidin-3-yl]amino}-N-[1-methyl-3-(trifluoromethyl)-1H-pyrazol-4-yl]pyrazolo[1,5-a]pyrimidine-3-carboxamide;
5-{[(3S,4S)-4-fluoropiperidin-3-yl]amino}-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-[(4-fluoropiperidin-3-yl)amino]pyrazolo[1,5-a]pyrimidine-3-carboxamide;
N-[3-(difluoromethyl)-1-methyl-1H-pyrazol-4-yl]-5-[(5,5-difluoropiperidin-3-yl)amino]pyrazolo[1,5-a]pyrimidine-3-carboxamide;
N-[3-(difluoromethyl)-1-methyl-1H-pyrazol-4-yl]-5-[(4-fluoropiperidin-3-yl)amino]pyrazolo[1,5-a]pyrimidine-3-carboxamide;
N-[3-(difluoromethyl)-1-methyl-1H-pyrazol-4-yl]-5-[(4-fluoropiperidin-3-yl)amino]pyrazolo[1,5-a]pyrimidine-3-carboxamide;
5-[(1S,5R)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;
5-[(1S,5R)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;
5-[(1R,5S)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;
N-[3-(difluoromethyl)-1-methyl-1H-pyrazol-4-yl]-5-[(4-fluoropiperidin-3-yl)amino]pyrazolo[1,5-a]pyrimidine-3-carboxamide;
N-[3-(difluoromethyl)-1-methyl-1H-pyrazol-4-yl]-5-[(4,4-difluoropiperidin-3-yl)amino]pyrazolo[1,5-a]pyrimidine-3-carboxamide;
5-[(4,4-difluoropiperidin-3-yl)amino]-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-[(4,4-difluoropiperidin-3-yl)amino]pyrazolo[1,5-a]pyrimidine-3-carboxamide;
5-[(4,4-difluoropiperidin-3-yl)amino]-N-[1-methyl-3-(trifluoromethyl)-1H-pyrazol-4-yl]pyrazolo[1,5-a]pyrimidine-3-carboxamide;
5-[(3S,5R)-3-amino-5-fluoropiperidin-1-yl]-N-[1-methyl-3-(trifluoromethyl)-1H-pyrazol-4-yl]pyrazolo[1,5-a]pyrimidine-3-carboxamide;
5-[(3S,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide;
5-[(3S,5S)-3-amino-5-fluoropiperidin-1-yl]-N-[3-(difluoromethyl)-1-methyl-1H-pyrazol-4-yl]pyrazolo[1,5-a]pyrimidine-3-carboxamide;
5-[(3S,5R)-3-amino-5-fluoropiperidin-1-yl]-N-[3-(difluoromethyl)-1-methyl-1H-pyrazol-4-yl]pyrazolo[1,5-a]pyrimidine-3-carboxamide;
5-[(3R,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide;
5-[(3R,5S)-3-amino-5-fluoropiperidin-1-yl]-N-[3-(difluoromethyl)-1-methyl-1H-pyrazol-4-yl]pyrazolo[1,5-a]pyrimidine-3-carboxamide;
5-[(3R,5R)-3-amino-5-fluoropiperidin-1-yl]-N-[1-methyl-3-(trifluoromethyl)-1H-pyrazol-4-yl]pyrazolo[1,5-a]pyrimidine-3-carboxamide;
5-[(3R,5R)-3-amino-5-fluoropiperidin-1-yl]-N-[3-(difluoromethyl)-1-methyl-1H-pyrazol-4-yl]pyrazolo[1,5-a]pyrimidine-3-carboxamide;
5-{[(3S,5R)-5-fluoropiperidin-3-yl]amino}-N-[1-methyl-3-(trifluoromethyl)-1H-pyrazol-4-yl]pyrazolo[1,5-a]pyrimidine-3-carboxamide;
5-{[(3S,5S)-5-fluoropiperidin-3-yl]amino}-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-{[(3S,5S)-5-fluoropiperidin-3-yl]amino}pyrazolo[1,5-a]pyrimidine-3-carboxamide;
5-{[(3R,5S)-5-fluoropiperidin-3-yl]amino}-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-{[(3R,5S)-5-fluoropiperidin-3-yl]amino}pyrazolo[1,5-a]pyrimidine-3-carboxamide;
N-[3-(difluoromethyl)-1-methyl-1H-pyrazol-4-yl]-5-{[(3S,5R)-5-fluoropiperidin-3-yl]amino}pyrazolo[1,5-a]pyrimidine-3-carboxamide;
5-{[(3R,5R)-5-fluoropiperidin-3-yl]amino}-N-[1-methyl-3-(trifluoromethyl)-1H-pyrazol-4-yl]pyrazolo[1,5-a]pyrimidine-3-carboxamide;
N-[3-(difluoromethyl)-1-methyl-1H-pyrazol-4-yl]-5-{[(3R,5R)-5-fluoropiperidin-3-yl]amino}pyrazolo[1,5-a]pyrimidine-3-carboxamide;
5-{[(1R,2S)-2-(methylamino)cyclohexyl]amino}-N-[1-methyl-3-(trifluoromethyl)-1H-pyrazol-4-yl]pyrazolo[1,5-a]pyrimidine-3-carboxamide;
5-{[(1R,2S)-2-(dimethylamino)cyclohexyl]amino}-N-[1-methyl-3-(trifluoromethyl)-1H-pyrazol-4-yl]pyrazolo[1,5-a]pyrimidine-3-carboxamide;
N-[1-methyl-3-(trifluoromethyl)-1H-pyrazol-4-yl]-5-{[(1R,2S)-2-morpholin-4-ylcyclohexyl]amino}pyrazolo[1,5-a]pyrimidine-3-carboxamide;
5-{[(1R,2S)-2-aminocyclohexyl]amino}-N-(2-cyanophenyl)pyrazolo[1,5-a]pyrimidine-3-carboxamide;
N-(2-cyanophenyl)-5-{[(1R,2S)-2-hydroxycyclohexyl]amino}pyrazolo[1,5-a]pyrimidine-3-carboxamide;
N-(2-cyanophenyl)-5-(5,8-diazaspiro[2.6]non-5-yl)pyrazolo[1,5-a]pyrimidine-3-carboxamide;
5-{[(1R,2R)-2-amino-3,3-difluorocyclohexyl]amino}-N-(2-cyanophenyl)pyrazolo[1,5-a]pyrimidine-3-carboxamide;
5-[(3R)-3-aminopiperidin-1-yl]-N-(2-cyanophenyl)pyrazolo[1,5-a]pyrimidine-3-carboxamide;
N-(2-cyanophenyl)-5-[(3R)-piperidin-3-ylamino]pyrazolo[1,5-a]pyrimidine-3-carboxamide;
N-(2-cyanophenyl)-5-(2,5-diazabicyclo[2.2.2]oct-2-yl)pyrazolo[1,5-a]pyrimidine-3-carboxamide;
5-(azepan-3-ylamino)-N-(2-cyanophenyl)pyrazolo[1,5-a]pyrimidine-3-carboxamide;
N-(2-cyanophenyl)-5-(1,4-diazepan-1-yl)pyrazolo[1,5-a]pyrimidine-3-carboxamide;
N-(2-cyanophenyl)-5-piperazin-1-ylpyrazolo[1,5-a]pyrimidine-3-carboxamide;
5-{[(1R,2S)-2-aminocyclohexyl]amino}-N-[5-(hydroxymethyl)thiophen-3-yl]pyrazolo[1,5-a]pyrimidine-3-carboxamide;
5-{[(1R,2S)-2-aminocyclohexyl]amino}-N-[5-(1-hydroxyethyl)thiophen-3-yl]pyrazolo[1,5-a]pyrimidine-3-carboxamide;

5-{[(1R,2S)-2-aminocyclohexyl]amino}-N-[3-(difluoromethyl)-1-methyl-1H-pyrazol-4-yl]pyrazolo[1,5-a]pyrimidine-3-carboxamide;

5-{[(1S,2R)-2-aminocyclohexyl]amino}-N-(1-pyridin-3-yl-1H-pyrazol-4-yl)pyrazolo[1,5-a]pyrimidine-3-carboxamide;

5-{[(1R,2S)-2-aminocyclohexyl]amino}-N-(1-methyl-1H-pyrazol-4-yl)pyrazolo[1,5-a]pyrimidine-3-carboxamide;

5-{[(1R,2S)-2-aminocyclohexyl]amino}-N-[3-(methoxymethyl)-1-methyl-1H-pyrazol-4-yl]pyrazolo[1,5-a]pyrimidine-3-carboxamide;

5-{[(1R,2S)-2-aminocyclohexyl]amino}-N-[1-methyl-3-(1,3,4-oxadiazol-2-yl)-1H-pyrazol-4-yl]pyrazolo[1,5-a]pyrimidine-3-carboxamide;

5-{[(1R,2S)-2-aminocyclohexyl]amino}-N-(3-cyano-1-methyl-1H-pyrazol-4-yl)pyrazolo[1,5-a]pyrimidine-3-carboxamide;

5-{[(1R,2S)-2-aminocyclohexyl]amino}-N-[3-(2-methoxyethyl)-1-methyl-1H-pyrazol-4-yl]pyrazolo[1,5-a]pyrimidine-3-carboxamide;

5-{[(1R,2S)-2-aminocyclohexyl]amino}-N-(1-methyl-3-pyridin-4-yl-1H-pyrazol-4-yl)pyrazolo[1,5-a]pyrimidine-3-carboxamide;

5-{[(1R,2S)-2-aminocyclohexyl]amino}-N-[1-methyl-3-(5-methyl-1,3-oxazol-2-yl)-1H-pyrazol-4-yl]pyrazolo[1,5-a]pyrimidine-3-carboxamide;

5-{[(1R,2S)-2-aminocyclohexyl]amino}-N-[1-methyl-3-(4-methyl-4H-1,2,4-triazol-3-yl)-1H-pyrazol-4-yl]pyrazolo[1,5-a]pyrimidine-3-carboxamide;

5-{[(1R,2S)-2-aminocyclohexyl]amino}-N-(1-methyl-3-pyrimidin-5-yl-1H-pyrazol-4-yl)pyrazolo[1,5-a]pyrimidine-3-carboxamide;

5-{[(1R,2S)-2-aminocyclohexyl]amino}-N-[1-methyl-3-(5-methyl-1,2,4-oxadiazol-3-yl)-1H-pyrazol-4-yl]pyrazolo[1,5-a]pyrimidine-3-carboxamide;

5-{[(1R,2S)-2-aminocyclohexyl]amino}-N-[3-(2-fluoroethyl)-1-methyl-1H-pyrazol-4-yl]pyrazolo[1,5-a]pyrimidine-3-carboxamide;

N-[1-methyl-3-(trifluoromethyl)-1H-pyrazol-4-yl]-5-[(2-morpholin-4-ylethyl)amino]pyrazolo[1,5-a]pyrimidine-3-carboxamide;

5-{[(1R,2S)-2-aminocyclohexyl]amino}-N-[1-(1-methylethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(2,2-difluoroethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-cyclopropyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-tert-butyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(2,2,2-trifluoroethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(difluoromethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-methyl-3-(pentafluoroethyl)-1H-pyrazol-4-yl]pyrazolo[1,5-a]pyrimidine-3-carboxamide;

N-[1-(1-methylethyl)-3-(trifluoromethyl)-1H-pyrazol-4-yl]-5-piperazin-1-ylpyrazolo[1,5-a]pyrimidine-3-carboxamide;

5-piperazin-1-yl-N-[1-(2,2,2-trifluoroethyl)-3-(trifluoromethyl)-1H-pyrazol-4-yl]pyrazolo[1,5-a]pyrimidine-3-carboxamide;

N-[1-(difluoromethyl)-3-(trifluoromethyl)-1H-pyrazol-4-yl]-5-piperazin-1-ylpyrazolo[1,5-a]pyrimidine-3-carboxamide; and 5-{[(1R,2S)-2-aminocyclohexyl]amino}-N-[3-(trifluoromethyl)-1H-pyrazol-4-yl]pyrazolo[1,5-a]pyrimidine-3-carboxamide;

or a pharmaceutically acceptable salt thereof.

When any variable (e.g. $R_a$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. In some instances, two substituents are attached to the same carbon and come together to form a carbocyclic or heterocyclic ring (a spirocyclic ring system).

As used herein, "alkyl" is intended to include both branched and straight-chain saturated aliphatic hydrocarbon groups having the specified number of carbon atoms. For example, $C_1$-$C_6$, as in "($C_1$-$C_6$)alkyl" is defined to include groups having 1, 2, 3, 4, 5 or 6 carbons in a linear or branched arrangement. For example, "($C_1$-$C_6$)alkyl" specifically includes methyl, ethyl, n-propyl, i-propyl, n-butyl, t-butyl, i-butyl, pentyl, hexyl, and so on. For example, $C_1$-$C_4$, as in "($C_1$-$C_4$)alkyl" is defined to include groups having 1, 2, 3 or 4 carbons in a linear or branched arrangement. For example, "($C_1$-$C_4$)alkyl" specifically includes methyl, ethyl, n-propyl, i-propyl, n-butyl, t-butyl and i-butyl.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethylcyclopentyl, cyclohexyl, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes spiro, bicyclic and tricyclic groups. "Heterocyclyl" includes heteroaryls, as well as dihydro and tetrahydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The IRAK4 inhibitor compounds of the present invention, which can be in the form of a free base, may be isolated from the reaction mixture in the form of a pharmaceutically acceptable salt.

The compounds of Formula I can form salts which are also within the scope of this invention. Reference to a compound of Formula I herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The IRAK4 inhibitor compounds of the present invention may exist as amorphous forms or crystalline forms.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

Utility

According to another embodiment, the present invention provides a method of treating or reducing the severity of a disease in a patient by using a compound of Formulas I as described above, wherein said disease is selected from IRAK4 mediated pathologies, such as rheumatoid arthritis, multiple sclerosis, sepsis, osteoarthritis, inflammatory bowel disease, Parkinson's disease, cardiac contractile dysfunction, type I diabetes, type II diabetes or familial cold autoinflammatory syndrome, allergic disease, cancer, lupus, psoriasis, asthma or graft rejection.

The compounds of the invention find use in a variety of applications. As will be appreciated by those skilled in the art, the kinase activity of IRAK4 may be modulated in a variety of ways; that is, one can affect the phosphorylation/activation of IRAK4 either by modulating the initial phosphorylation of the protein or by modulating the autophosphorylation of the other active sites of the protein. Alternatively, the kinase activity of IRAK4 may be modulated by affecting the binding of a substrate of IRAK4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, U.S. Pat. No. 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272, and U.S. Pat. No. 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of the invention may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer; hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

The compounds of the invention may be useful for the treatment of activated B-cell-like diffuse large B-cell lymphoma (ABC-DLBCL), chronic lymphocytic leukemia (CLL) and Waldenström's Macroglobulinemia.

The instant compounds are useful in combination with a known anti-cancer agent. Combinations of the presently disclosed compounds with anti-cancer agents are within the scope of the invention. Examples of such anti-cancer agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-500); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of lupus.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of lupus.

The compounds of the instant invention are useful for the treatment of cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are: Ac (Acetyl); ACN or MeCN (acetonitrile); AcOH or HOAc (acetic acid); Boc or BOC (tert-butoxycarbonyl); Bu (butyl); Bz (benzoyl); calc'd (calculated); Cbz (benyzloxycarbonyl); $CDCl_3$ (chloroform-d); $CHCl_3$ (Chloroform); DAST ((diethylamino)sulfur trifluoride); DCM (dichloromethane); DIEA or Hilnig's base (N,N-diisopropylethylamine); DMAP (4-dimethylaminopyridine); DMSO (Dimethylsulfoxide); DMF (dimethylformamide); dppf (1,1'-bis(diphenylphosphino)ferrocene); Et (ethyl); EtOH (ethanol); EtOAc (ethyl acetate); g (grams); GST (glutathione S-transferase); h (hour); HATU (N,N,N',N'-tetramethyl-O-(7-azabenzotriazol-1-yl)uronium hexafluorophosphate); HCl (hydrochloric acid); HOBt (1-hydroxybenzotriazole); HPLC (high-performance liquid chromatography); IPA or iPrOH (isopropanol); iPr (isopropyl); LC (liquid chromatography); LCMS (liquid chromatography mass spectrometry); M (molar); mCPBA (m-choroperoxybenzoic acid); Me (methyl); MeOH (methanol); mg (milligrams); min (minute); μL (microliters); mL (milliliters); mmol (millimoles); MS (mass spectrometry); MTBE (methyl tert-butyl ether); NMR (nuclear magnetic resonance spectroscopy); OAc (Acetate); Pd(dppf)Cl$_2$ (1,1'-bis(diphenylphosphino)ferroceneldichloropalladium(II)); Ph (phenyl); POCl$_3$ (phosphorous oxychloride); Pr (propyl); rac (racemic mixture); RT or rt (room temperature (ambient, about 25° C.)); sat (saturated); SFC (supercritical fluid chromatography); tBu (tert-butyl); TEA (triethylamine (Et$_3$N)); TFA (trifluoroacetic acid); THF (tetrahydrofuran); TLC (thin layer chromatography); and Xantphos (4,5-bis (diphenylphosphino)-9,9-dimethylxanthene).

General Synopsis of Reaction Schemes

The following General Reaction Schemes, Schemes 1 to 2, provide useful details for preparing the instant compounds. The requisite intermediates are in some cases commercially available or can be prepared according to literature procedures. The illustrative General Reaction Schemes below are not limited by the compounds listed or by any particular substituents employed for illustrative purposes. Substituent labelings (i.e. R groups) as shown in the Reaction Schemes do not necessarily correlate to that used in the claims and often, for clarity, a single substituent is shown attached to the compound where multiple substituents are allowed under the definitions of Formula I hereinabove.

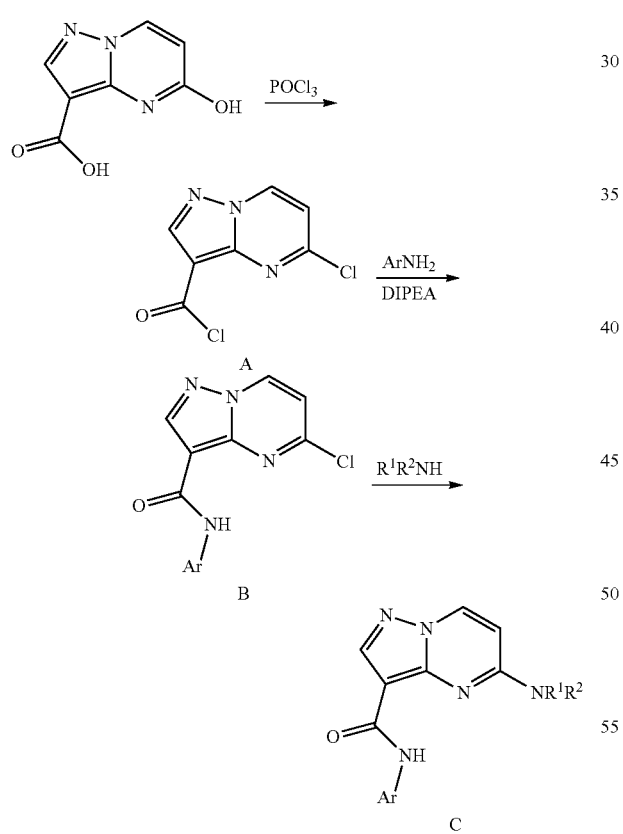

Scheme 1

Compounds of formula C are prepared via the amide formation of 5-chloropyrazolo[1,5-a]pyrimidine-3-carbonyl chloride (A) with various aryl-amines followed by the S$_N$Ar reaction between intermediates B and an array of amines (Scheme 1). Intermediate A is prepared from 5-hydroxypyrazolo[1,5-a]pyrimidine-3-carboxylic acid by chlorination with POCl$_3$.

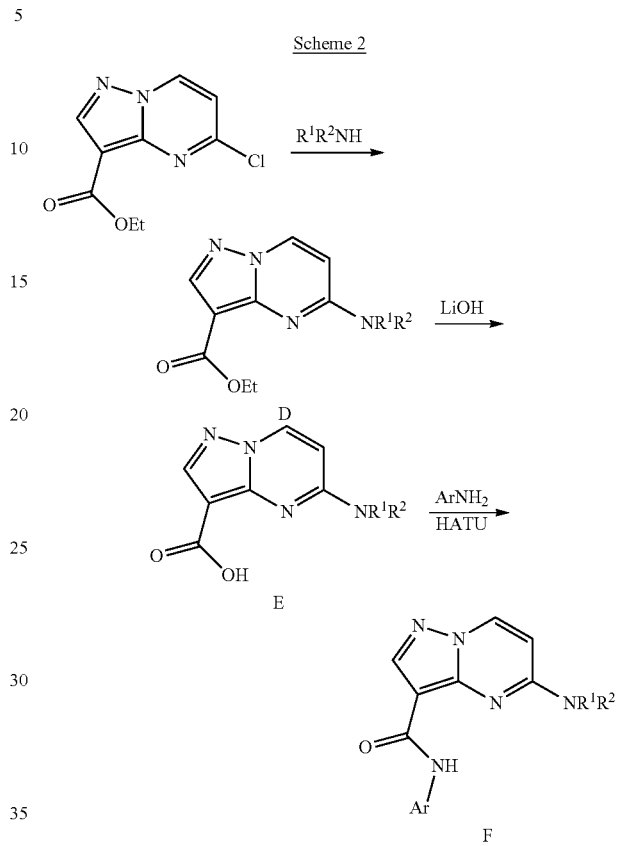

Alternatively, compounds F are prepared starting from ethyl 5-chloropyrazolo[1,5-a]pyrimidine-3-carboxylate via S$_N$Ar reaction with an array of amines followed by hydrolysis of intermediates D with LiOH (Scheme 2). Various aryl-amines are then coupled to carboxylic acids E employing coupling reagents such as HATU to afford compounds F.

Intermediate 1

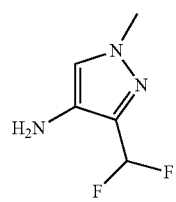

3-(Difluoromethyl)-1-methyl-1H-pyrazol-4-amine

Step 1: Into a 100 mL round bottom flask containing a solution of methyl 1-methyl-4-nitro-1H-pyrazole-3-carboxylate (1.5 g, 8 mmol) in dichloromethane (30 mL) was added diisobutylaluminum hydride (12 mL, 1 M in toluene, 12 mmol) at 0° C. and the reaction mixture was stirred at room temperature for 6 h. The reaction mixture was treated with hydrochloric acid (1.5 N, 1 mL) and extracted with ethyl acetate. The organic fraction was dried over anhydrous sodium sulfate, filtered and concentrated under reduced pressure. The residue was purified by flash chromatography eluting with methanol in dichloromethane (5-10%) to yield (1-methyl-4-nitro-1H-pyrazol-3-yl)methanol as a solid. $^1$H NMR (DMSO-$d_6$, 300 MHz): δ 8.77 (s, 1H), 5.19 (t, J=5.9 Hz, 1H), 4.63 (d, J=5.9 Hz, 2H), 3.85 (s, 3H).

Step 2: Into a 50 mL round bottom flask containing a solution of 2-iodoxybenzoic acid (2.8 g, 10 mmol) in dimethyl sulfoxide (3 mL) was added a solution of (1-methyl-4-nitro-1H-pyrazol-3-yl)methanol (800 mg, 5 mmol) in dimethyl sulfoxide (3 mL) and the reaction mixture was stirred at room temperature for 3 h. The reaction mixture was diluted with diethyl ether and washed with water and brine. The organic fraction was dried over anhydrous sodium sulfate, filtered and concentrated under reduced pressure. The residue was purified by flash chromatography eluting with methanol in dichloromethane (7-9%) to yield 1-methyl-4-nitro-1H-pyrazole-3-carbaldehyde as a solid. $^1$H NMR (CDCl$_3$, 400 MHz): δ 10.43 (s, 1H), 8.25 (s, 1H), 4.09 (s, 3H).

Step 3: Into a 25 mL round bottom flask containing a solution of 1-methyl-4-nitro-1H-pyrazole-3-carbaldehyde (300 mg, 1.9 mmol) in dichloromethane (5 mL) was added diethylaminosulfur trifluoride (0.76 mL, 5.8 mmol) at −20° C. and the reaction was stirred at room temperature for 16 h. The reaction mixture was concentrated under reduced pressure and the residue was purified by flash chromatography eluting with methanol in dichloromethane (3-5%) to yield 3-(difluoromethyl)-1-methyl-4-nitro-1H-pyrazole. $^1$H NMR (CDCl$_3$, 400 MHz): δ 8.19 (s, 1H), 7.13 (t, J=53.2 Hz, 1H), 4.03 (s, 3H).

Step 4: Into a 25 mL round bottom flask containing a solution of 3-(difluoromethyl)-1-methyl-4-nitro-1H-pyrazole (300 mg, 1.93 mmol) in methanol (3 mL) was added palladium on carbon (15 mg, 5% w/w) and the reaction was stirred at room temperature for 8 h under hydrogen bladder pressure. The reaction mixture was filtered through celite and washed with methanol and the filtrate was concentrated under reduced pressure. The residue was purified by flash chromatography eluting with methanol in dichloromethane (4-7%) to yield 3-(difluoromethyl)-1-methyl-1H-pyrazol-4-amine. $^1$H NMR (CDCl$_3$, 400 MHz): δ 7.09 (s, 1H), 6.86 (t, J=54.1 Hz, 1H), 3.70 (s, 3H). MS calc'd [M+H]$^+$ 148.1, found 148.2.

Intermediate 2

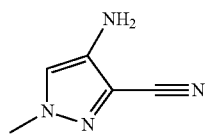

4-Amino-1-methyl-1H-pyrazole-3-carbonitrile

Step 1: Into a 250 mL round bottom flask containing a suspension of 4-nitro-1H-pyrazole-3-carboxylic acid (20.0 g, 127 mmol) in methanol (100 mL) was added concentrated sulfuric acid (4 mL) dropwise over 5 min at 0° C. and the resulting slurry was refluxed at 80° C. for 16 h. The solvent was removed under reduced pressure and the residual mass was dissolved in ethyl acetate (300 mL) and washed with saturated aqueous sodium bicarbonate solution (2×100 mL) and brine (100 mL) and dried over anhydrous sodium sulfate. The solution was filtered and concentrated under reduced pressure to give methyl 4-nitro-1H-pyrazole-3-carboxylate as a solid. The crude product was taken to the next step without further purification. MS calc'd [M−H]$^+$ 170.0, found 170.0.

Step 2: Into a 1 L round bottom flask containing a suspension of sodium hydride (60% in paraffin oil, 4.7 g, 116 mmol) in tetrahydrofuran (400 mL) at 0° C. was added methyl 4-nitro-1H-pyrazole-3-carboxylate (16.5 g, 96 mmol) in tetrahydrofuran (50 mL) dropwise and the reaction mixture was stirred for 1 h. To the reaction mixture was added methyl iodide (9 mL, 145 mmol) and the mixture was stirred at room temperature for 3 h. The reaction mixture was cooled to 0° C. and treated with saturated aqueous ammonium chloride solution and extracted with ethyl acetate (4×200 mL). The combined organic fractions were washed with brine (100 mL), dried over anhydrous sodium sulfate, filtered and concentrated under reduced pressure. The residue was purified by flash chromatography eluting with ethyl acetate in petroleum ether (15-25%) to afford methyl 1-methyl-4-nitro-1H-pyrazole-3-carboxylate as a solid. $^1$H NMR (CDCl$_3$, 400 MHz): δ 8.17 (s, 1H), 4.03 (s, 3H), 4.01 (s, 3H).

Step 3: Into a 250 mL sealed tube were added methyl 1-methyl-4-nitro-1H-pyrazole-3-carboxylate (2.5 g, 13.5 mmol) and methanol (60 mL) and the reaction mixture was cooled to −60° C. and ammonia gas was purged for 15 min and then heated at 80° C. for 4 h. The reaction mixture was cooled to −15° C. and the excess ammonia gas was carefully removed by bubbling nitrogen and concentrated under reduced pressure to afford 1-methyl-4-nitro-1H-pyrazole-3-carboxamide as a solid. $^1$H NMR (CD$_3$OD, 300 MHz): δ 8.56 (s, 1H), 3.94 (s, 3H). MS calc'd [M+H]$^+$ 171.0, found 171.2.

Step 4: Into a 250 mL sealed tube containing a solution of 1-methyl-4-nitro-1H-pyrazole-3-carboxamide (2.0 g, 12 mmol) in dichloromethane (100 mL) was added N,N-diisopropylethylamine (13 mL, 71 mmol) at 0° C. To this reaction mixture was added phosphorous oxychloride (3.3 mL, 35 mmol) dropwise and the mixture was stirred at room temperature for 1 h. The reaction was treated with saturated sodium bicarbonate solution and extracted with dichloromethane. The combined organics were washed with water and brine, dried over anhydrous sodium sulfate, filtered and concentrated under reduced pressure. The residue was purified by flash chromatography eluting with ethyl acetate in petroleum ether (25-30%) to afford 1-methyl-4-nitro-1H-pyrazole-3-carbonitrile as a solid. $^1$H NMR (CDCl$_3$, 400 MHz): δ 8.24 (s, 1H), 4.09 (s, 3H).

Step 5: Into a 250 mL round bottom flask containing a solution of 1-methyl-4-nitro-1H-pyrazole-3-carbonitrile (3.5 g, 23 mmol) in methanol (100 mL) at room temperature was added palladium on carbon (0.5 g, 15% w/w) and the reaction mixture was stirred at room temperature under hydrogen bladder atmosphere for 2 h. The reaction mixture was filtered through celite and washed with methanol and dichloromethane. The filtrate was concentrated under reduced pressure to afford 4-amino-1-methyl-1H-pyrazole-3-carbonitrile as a solid. $^1$H NMR (CD$_3$OD, 400 MHz): δ 7.22 (s, 1H), 3.84 (s, 3H). MS calc'd [M+H]$^+$ 123.1, found 123.4.

Intermediate 3

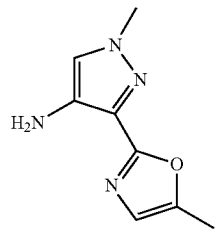

1-Methyl-3-(5-methyloxazol-2-yl)-1H-pyrazol-4-amine

Step 1: Into a 50 mL round bottom flask containing a solution of 1-methyl-4-nitro-1H-pyrazole-3-carboxylic acid (500 mg, 2.9 mmol) in dimethylformamide (20 mL) were added propargylamine (0.2 mL, 2.9 mmol) and diisopropylethylamine (1.4 mL). To the resulting solution cooled to 0° C. were added N-(3-dimethylaminopropyl)-N'-ethylcarbodiimide hydrochloride (850 mg, 4.4 mmol) and hydroxybenzotriazole (200 mg, 1.46 mmol) and the reaction mixture was stirred at room temperature overnight. The reaction mixture was treated with water (50 mL) and extracted with ethyl acetate. The organic layer was washed with water and brine, dried over anhydrous sodium sulfate, filtered and concentrated under reduced pressure. The residue was purified by flash chromatography eluting with ethyl acetate in petroleum ether (25-40%) to afford 1-methyl-4-nitro-N-(prop-2-yn-1-yl)-1H-pyrazole-3-carboxamide as a solid. MS calc'd [M+H]$^+$ 209.1, found 209.2.

Step 2: Into a 10 mL sealed tube containing a solution of 1-methyl-4-nitro-N-(prop-2-yn-1-yl)-1H-pyrazole-3-carboxamide (120 mg, 0.6 mmol) in 1,4-dioxane (2 mL) was added triflic anhydride (0.1 mL, 0.6 mmol) dropwise at room temperature and the reaction was heated at 90° C. overnight. The solvent was removed under reduced pressure and the residue was dissolved in water (20 mL) and neutralised with 10% sodium bicarbonate solution. The mixture was extracted with ethyl acetate and the organic layer was washed with water and brine successively. The solution was dried over anhydrous sodium sulfate, filtered and concentrated under reduced pressure. The residue was purified by flash chromatography eluting with methanol in dichloromethane (5-10%) to afford 5-methyl-2-(1-methyl-4-nitro-1H-pyrazol-3-yl)oxazole as a solid. $^1$H NMR (CD$_3$OD, 400 MHz): δ 8.70 (s, 1H), 7.03 (s, 1H), 4.03 (s, 3H), 2.44 (s, 3H). MS calc'd [M+H]$^+$ 209.1, found 209.2.

Step 3: Into a 25 mL round bottom flask containing a solution of 5-methyl-2-(1-methyl-4-nitro-1H-pyrazol-3-yl)oxazole (55 mg, 0.25 mmol) in methanol (5 mL) was added palladium on carbon (10 mg, 20% w/w) and the mixture was stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 1-methyl-3-(5-methyloxazol-2-yl)-1H-pyrazol-4-amine as a solid. $^1$H NMR (CD$_3$OD, 400 MHz): δ 7.23 (s, 1H), 6.89 (s. 1H), 3.85 (s, 3H), 2.40 (s, 3H). MS calc'd [M+H]$^+$ 179.1, found 179.2.

Intermediate 4

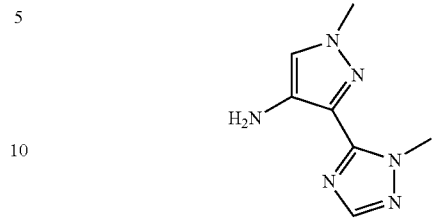

1-Methyl-3-(1-methyl-1H-1,2,4-triazol-5-yl)-1H-pyrazol-4-amine

Step 1: Into a 50 mL round bottom flask were added 1-methyl-4-nitro-1H-pyrazole-3-carboxamide (1.0 g, 5.9 mmol) in N,N-Dimethylformamide and dimethyl acetal (10 mL) and the mixture was heated at 120° C. for 15 min. The reaction mixture was cooled to room temperature and the solvent was removed under reduced pressure to afford (Z)—N-((dimethylamino)methylene)-1-methyl-4-nitro-1H-pyrazole-3-carboxamide as a liquid which is as such taken for next step without further purification. MS calc'd [M+H]$^+$ 226.1, found 226.2.

Step 2: Into a 25 mL sealed tube containing a solution of (Z)—N-((dimethylamino)methylene)-1-methyl-4-nitro-1H-pyrazole-3-carboxamide (800 mg, 3.6 mmol) in acetic acid (3 mL) was added methylhydrazine (240 mg, 5.4 mmol) and the mixture was heated at 90° C. for 3 h. The solvent was removed under reduced pressure and the residue was purified by flash chromatography eluting with methanol in dichloromethane (3-5%) to afford 1-methyl-5-(1-methyl-4-nitro-1H-pyrazol-3-yl)-1H-1,2,4-triazole as a solid MS calc'd [M+H]$^+$ 209.1, found 209.0.

Step 3: Into a 50 mL round bottom flask containing a solution of 1-methyl-5-(1-methyl-4-nitro-1H-pyrazol-3-yl)-1H-1,2,4-triazole (400 mg, 1.9 mmol) in methanol (5 mL) was added palladium on carbon (40 mg, 10% w/w) and the reaction was stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 1-methyl-3-(1-methyl-1H-1,2,4-triazol-5-yl)-1H-pyrazol-4-amine as a solid. MS calc'd [M+H]$^+$ 179.1, found 179.4.

Intermediate 5

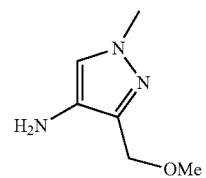

3-(Methoxymethyl)-1-methyl-1H-pyrazol-4-amine

Step 1: Into a 50 mL round bottom flask containing a solution of (1-methyl-4-nitro-1H-pyrazol-3-yl)methanol (200 mg, 1.3 mmol) in dimethylformamide (5 mL) was added sodium hydride (60% in parafine oil, 95 mg, 1.9 mmol) at 0° C. over 15 min. To this reaction mixture was added methyl iodide (0.16 mL, 2.5 mmol) and the reaction was stirred at room temperature for 4 h. The reaction mixture was treated with aqueous ammonium chloride solution and extracted with ethyl acetate. The organic fraction was washed with water and brine, dried over anhydrous sodium sulfate, filtered and concentrated under reduced pressure. The residue was purified by flash column chromatography on silica gel eluting with ethyl acetate in petroleum ether (30-40%) to furnish 3-(methoxymethyl)-1-methyl-4-nitro-1H-pyrazole as a liquid. $^1$H NMR (CDCl$_3$, 400 MHz): δ 8.15 (s, 1H), 4.81 (s, 2H), 3.97 (s, 3H), 3.54 (s, 3H).

Step 2: Into a 25 mL round bottom flask containing a solution of 3-(methoxymethyl)-1-methyl-4-nitro-1H-pyrazole (200 mg, 1.2 mmol) in methanol (5 mL) was added palladium on carbon (20 mg, 10% w/w) and the reaction was stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 3-(methoxymethyl)-1-methyl-1H-pyrazol-4-amine as a solid. $^1$H NMR (CDCl$_3$, 300 MHz): δ 6.94 (s, 1H), 4.48 (s, 2H), 3.78 (s, 3H), 3.37 (s, 3H).

Intermediate 6

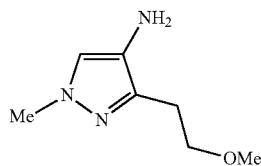

3-(2-Methoxyethyl)-1-methyl-1H-pyrazol-4-amine

Step 1: To a stirred solution of bromo(methoxy methyl)triphenylphosphine (1.2 g, 3.4 mmol) in tetrahydrofuran (2 mL) was added potassium-tert-butoxide solution (1M in THF, 3.6 mL, 3.6 mmol) and the resulting pale yellow solution was stirred at room temperature for 1 h. A solution of methyl-4-nitro-1H-pyrazole-3-carbaldehyde (400 mg, 2.3 mmol) in tetrahydrofuran (2 mL) was added and the reaction mixture was heated at 80° C. for 2 h. The reaction mixture was treated with water and extracted with ethyl acetate (3×10 mL). The combined organic fractions were washed with water and brine, dried over anhydrous sodium sulfate, filtered and concentrated under reduced pressure. The residue was purified by flash chromatography eluting with ethyl acetate in petroleum ether (5-10%) to yield (E)-3-(2-methoxyvinyl)-1-methyl-4-nitro-1H-pyrazole (300 mg, 76%). $^1$H NMR (CD$_3$OD, 300 MHz): δ 8.43 (s, 1H), 7.50 (d, J=12.9 Hz, 1H), 6.25 (d, J=12.9 Hz, 1H), 3.93 (s, 3H), 3.85 (s, 3H).

Step 2: Into a 50 mL round bottom flask containing a solution of (E)-3-(2-methoxyvinyl)-1-methyl-4-nitro-1H-pyrazole (250 mg, 1.4 mmol) in methanol (20 mL) was added palladium on carbon (50 mg, 20% w/w) and the mixture was stirred in an atmosphere of hydrogen for 2 h. The reaction mixture was filtered through celite and washed with methanol. The filtrate was concentrated under reduced pressure to yield 3-(2-methoxyethyl)-1-methyl-1H-pyrazol-4-amine as an oil. $^1$H NMR (CD$_3$OD, 300 MHz): δ 7.14 (s, 1H), 3.77 (s, 3H), 3.59 (t, J=6.5 Hz, 2H), 3.37 (s, 3H), 2.81 (t, J=6.5 Hz, 2H).

Intermediate 7

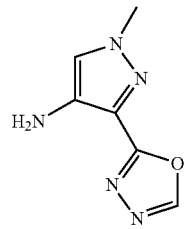

1-Methyl-3-(1,3,4-oxadiazol-2-yl)-1H-pyrazol-4-amine

Step 1: A mixture of methyl 1-methyl-4-nitro-1H-pyrazole-3-carboxylate (300 mg, 1.6 mmol), hydrazine monohydrate (160 mg, 3.2 mmol) and ethanol (5 mL) in a 25 mL sealed tube was heated at 100° C. for 12 h. The solvent was removed under reduced pressure to afford 1-methyl-4-nitro-1H-pyrazole-3-carbohydrazide (260 mg, 84% yield) as a light yellow solid which was take as such for next step without further purification. MS calc'd [M+H]$^+$ 186.1, found 186.2.

Step 2: Into a 25 mL sealed tube containing a solution of 1-methyl-4-nitro-1H-pyrazole-3-carbohydrazide (200 mg, 1.0 mmol) in acetic acid (0.5 mL) was added triethyl orthoformate (1 mL) and the mixture was heated at 100° C. for 3 h. The mixture was concentrated under reduced pressure to afford 2-(1-methyl-4-nitro-1H-pyrazol-3-yl)-1,3,4-oxadiazole as a solid which was take as such for next step without further purification. MS calc'd [M+H]$^+$ 196.0, found 196.2.

Step 3: Into a 25 mL round bottom flask containing a solution of 2-(1-methyl-4-nitro-1H-pyrazol-3-yl)-1,3,4-oxadiazole (150 mg, 0.8 mmol) in methanol (5 mL) was added palladium on carbon (15 mg, 10% w/w) and the mixture was stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 1-methyl-3-(1,3,4-oxadiazol-2-yl)-1H-pyrazol-4-amine as a solid. $^1$H NMR (CD$_3$OD, 400 MHz): δ 8.95 (s, 1H), 7.29 (s, 1H), 3.89 (s, 3H). MS calc'd [M+H]$^+$ 166.1, found 166.2.

Intermediate 8

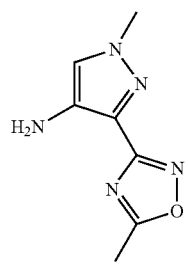

1-Methyl-3-(5-methyl-1,2,4-oxadiazol-3-yl)-1H-pyrazol-4-amine

Step 1: Into a 50 mL round bottom flask containing a solution of 1-methyl-4-nitro-1H-pyrazole-3-carbonitrile (750 mg, 5 mmol) in ethanol (10 mL) were added hydroxyl amine hydrochloride (700 mg, 10 mmol) and potassium carbonate (2.7 g, 20 mmol) and the mixture was stirred at room temperature for 12 h. The reaction mixture was concentrated under reduced pressure and the residue was dissolved in ethyl acetate and washed with water and brine. The solution was dried over anhydrous sodium sulfate, filtered, and concentrated to afford N-hydroxy-1-methyl-4-nitro-1H-pyrazole-3-carboximidamide as a solid which was taken as such to the next step without further purification. MS calc'd [M+H]$^+$ 186.1, found 186.2.

Step 2: Into a 50 mL sealed tube containing a solution of N-hydroxy-1-methyl-4-nitro-1H-pyrazole-3-carboximidiamide (200 mg, 0.9 mmol) in pyridine (2 mL) was added acetic anhydride (230 mg, 3 mmol) and the mixture was heated at 100° C. for 12 h. The reaction mixture was cooled to room temperature and concentrated under reduced pressure. The residue was dissolved in methanol (10 mL), treated with anhydrous potassium carbonate (610 mg, 4.5 mmol) and heated at 65° C. for 12 h. The reaction mixture was cooled to room temperature and filtered through celite, and the filtrate was concentrated under reduced pressure and purified by flash chromatography eluting with ethyl acetate in petroleum ether (0-10%) to afford 5-methyl-3-(1-methyl-4-nitro-1H-pyrazol-3-yl)-1,2,4-oxadiazole as a solid. $^1$H NMR (CDCl$_3$, 300 MHz): δ 8.28 (s, 1H), 4.01 (s, 3H), 2.72 (s, 3H). MS calc'd [M+H]$^+$ 210.1, found 210.2.

Step 3: Into a 25 mL round bottom flask containing a solution of 5-methyl-3-(1-methyl-4-nitro-1H-pyrazol-3-yl)-1,2,4-oxadiazole (100 mg, 0.5 mmol) in methanol (5 mL) was added palladium on carbon (10 mg, 10% w/w) and the reaction was stirred at room temperature for 6 h under hydrogen bladder pressure. The reaction mixture was filtered through celite and washed with methanol and the filtrate was concentrated under reduced pressure. The residue was purified by flash chromatography eluting with methanol in dichloromethane (5-10%) to afford 1-methyl-4-(5-methyl-1,2,4-oxadiazol-3-yl)-1H-pyrrol-3-amine as a solid. MS calc'd [M+H]$^+$ 179.1, found 179.2.

Intermediate 9

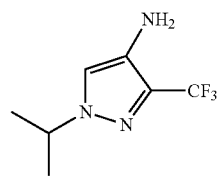

1-Isopropyl-3-(trifluoromethyl)-1H-pyrazol-4-amine

Step 1: Into a 50 mL round bottom flask containing a solution of 4-nitro-3-(trifluoromethyl)-1H pyrazole (50 mg, 0.3 mmol) in dimethylformamide (2 mL) were added isopropyl iodide (60 mg, 0.3 mmol) and potassium carbonate (75 mg, 0.6 mmol). The reaction mixture was stirred at room temperature overnight. The reaction mixture was diluted with ethyl acetate and washed with water and brine. The organic fraction was dried over anhydrous sodium sulfate, filtered and concentrated under reduced pressure. The residue was purified flash chromatography eluting with ethyl acetate in petroleum ether (40-60%) to afford 1-isopropyl-4-nitro-3-(trifluoromethyl)-1H-pyrazole as a solid.

Step 2: Into a 25 mL round bottom flask containing a solution of 1-isopropyl-4-nitro-3-(trifluoromethyl)-1H-pyrazole (55 mg, 0.24 mmol) in methanol (5 mL) was added palladium on carbon (5 mg, 10% w/w) under nitrogen. The resulting slurry was stirred at room temperature overnight under hydrogen pressure using bladder. The reaction mixture was filtered through celiete and washed with methanol. The filtrate was concentrated under reduced pressure. The residue was purified by flash chromatography eluting with methanol in dichloromethane (4-6%) to afford 1-isopropyl-3-(trifluoromethyl)-1H-pyrazol-4-amine as a solid. $^1$H NMR (CD$_3$OD, 400 MHz): δ 7.28 (s, 1H), 4.44-4.38 (m, 1H), 1.45 (d, J=6.7 Hz, 6H).

Intermediate 10

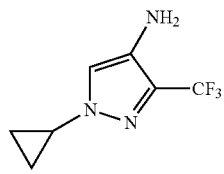 [SMILES: Nc1cn(C2CC2)nc1C(F)(F)F]

1-Cyclopropyl-3-(trifluoromethyl)-1H-pyrazol-4-amine

Step 1: Into a 50 mL round bottom flask containing a solution of 4-nitro-3-(trifluoromethyl)-1H-pyrrazole (200 mg, 1.2 mmol) in dichloroethane (20 mL) were added cyclopropyl boronic acid (190 mg, 2.3 mmol), sodium carbonate (240 mg, 2.3 mmol) and 2,2' bipyridine (175 mg, 1.2 mmol). The reaction mixture was degassed with nitrogen for 10 min, treated with copper acetate (200 mg, 1.2 mmol) and heated at 70° C. overnight. The reaction mixture was cooled to room temperature, filtered through celite and washed with ethyl acetate. The filtrate was washed with water and brine, dried over anhydrous sodium sulfate, filtered and concentrated under reduced pressure. The residue was purified by flash chromatography eluting with ethyl acetate in petroleum ether (50-70%) to afford 1-cyclopropyl-4-nitro-3-(trifluoromethyl)-1H-pyrazole as a liquid. $^1$H NMR (CD$_3$OD, 400 MHz): δ 8.31 (s, 1H), 3.91-3.88 (m, 1H), 1.25-1.22 (m, 2H), 0.92-0.88 (m, 2H).

Step 2: Into a 25 mL round bottom flask containing a solution of 1-cyclopropyl-4-nitro-3-(trifluoromethyl)-1H-pyrazole (120 mg, 0.6 mmol) in methanol (5 mL) was added palladium on carbon (20 mg, 20% w/w) under nitrogen. The resulting slurry was stirred at room temperature overnight under hydrogen pressure using bladder. The reaction mixture was filtered through celiete and washed with methanol and the filtrate was concentrated under reduced pressure. The crude was purified by flash chromatography eluting with methanol in dichloromethane (4-6%) to afford 1-cyclopropyl-3-(trifluoromethyl)-1H-pyrazol-4-amine as a solid. $^1$H NMR (CD$_3$OD, 300 MHz): δ 7.31 (s, 1H), 3.57-3.56 (m, 1H), 1.42-1.07 (m, 4H).

Intermediate 11

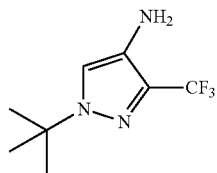

1-(tert-Butyl)-3-(trifluoromethyl)-1H-pyrazol-4-amine

Step 1: Into a 50 mL round bottom flask containing a solution of 4-nitro-3-(trifluoromethyl)-1H-pyrrazole (50 mg, 0.3 mmol) in tert-butanol (2 mL) was added sulfuric acid (5 drops) and the mixture was heated at 100° C. for 2 h. The reaction mixture was cooled to room temperature, diluted with ethyl acetate and water, and neutralized with saturated solution of sodium bicarbonate. The aqueous layer was extracted with ethyl acetate and the organic layer was dried over anhydrous sodium sulfate, filtered and concentrated under reduced pressure. The residue was purified by flash chromatography eluting with ethyl acetate in petroleum ether (50-70%) to afford 1-(tert-butyl)-4-nitro-3-(trifluoromethyl)-1H-pyrazole as a solid.

Step 2: Into a 25 mL round bottom flask containing a solution of 1-(tert-butyl)-4-nitro-3-(trifluoromethyl)-1H-pyrazole (50 mg, 0.2 mmol) in methanol (5 mL) was added palladium on carbon (10 mg, 20% w/w) under nitrogen. The resulting slurry was stirred at room temperature overnight under hydrogen pressure using bladder. The reaction mixture was filtered through celiete and washed with methanol. The filtrate was concentrated under reduced pressure and purified by flash chromatography eluting with methanol in dichloromethane (4-6%) to afford 1-(tert-butyl)-3-(trifluoromethyl)-1H-pyrazol-4-amine as a solid. $^1$H NMR (CD$_3$OD, 400 MHz): δ 8.86 (s, 1H), 1.65 (s, 9H). MS calc'd [M+H]$^+$ 208.1, found 208.2.

Intermediate 12

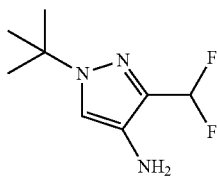

1-(tert-Butyl)-3-(difluoromethyl)-1H-pyrazol-4-amine

Step 1: Into a 50 mL round bottom flask containing a solution of 4-nitro-1H-pyrazole-3-carboxylic acid (5.0 g, 32 mmol) in tert-butanol (25 mL) was added sulfuric acid (2 mL, 32 mmol) and the mixture was heated at 100° C. for 16 h. The reaction mixture was cooled to room temperature, diluted with ethyl acetate and water, and neutralized with saturated solution of sodium bicarbonate. The aqueous layer was extracted with ethyl acetate and the combined organics were dried over anhydrous sodium sulfate, filtered and concentrated under reduced pressure. The residue was purified by flash chromatography eluting with ethyl acetate in petroleum ether (50-70%) to afford 1-(tert-butyl)-4-nitro-1H-pyrazole-3-carboxylic acid as a solid. $^1$H NMR (DMSO-d$_6$, 400 MHz): δ 13.90 (brs, 1H), 8.96 (s, 1H), 1.55 (s, 9H).

Step 2: Into a 250 mL round bottom flask containing a suspension of 1-(tert-butyl)-4-nitro-1H-pyrazole-3-carboxylic acid (2.0 g, 11 mmol) in methanol (50 mL) was added concentrated sulfuric acid (0.5 mL) dropwise at 0° C. and the reaction mixture was heated at 80° C. for 16 h. The solvent was removed under reduced pressure and the residual mixture was dissolved in ethyl acetate (50 mL), washed with saturated aqueous sodium bicarbonate (2×10 mL) and brine and dried over anhydrous sodium sulfate. The solution was filtered and concentrated under reduced pressure to give methyl 1-(tert-butyl)-4-nitro-1H-pyrazole-3-carboxylate as a solid. The crude product was taken to the next step without further purification. $^1$H NMR (DMSO-d$_6$, 400 MHz): δ 9.05 (s, 1H), 3.89 (s, 3H), 1.57 (s, 9H).

Step 3: Into a 100 mL round bottom flask containing a solution of 1-(tert-butyl)-4-nitro-1H-pyrazole-3-carboxylate (1.7 g, 10 mmol) in dichloromethane (50 mL) was added diisobutylaluminum hydride (15 mL, 1 M in toluene, 15 mmol) at 0° C. and the reaction was stirred at room temperature for 6 h. The reaction mixture was treated with saturated ammonium chloride solution. The precipitated solid was filtered through celite and the filtrate was dried over anhydrous sodium sulfate, filtered and concentrated under reduced pressure. The residue was purified by flash chromatography to yield 1-(tert-butyl)-4-nitro-1H-pyrazol-3-yl)methanol as a solid. $^1$H NMR (DMSO-d$_6$, 400 MHz): δ 8.83 (s, 1H), 5.18 (t, J=5.6 Hz, 1H), 4.66 (d, J=5.6 Hz, 2H), 1.55 (s, 9H).

Step 4: Into a 100 mL round bottom flask containing a solution of 2-iodoxybenzoic acid (1.7 g, 6 mmol) in dimethyl sulfoxide (40 mL) was added a solution of 1-(tert-butyl)-4-nitro-1H-pyrazol-3-yl)methanol (600 mg, 3 mmol) in dimethyl sulfoxide (10 mL) and the reaction mixture was stirred at room temperature for 4 h. The reaction mixture was diluted with diethyl ether, washed with water and brine, dried over anhydrous sodium sulfate, filtered and concentrated under reduced pressure. The residue was purified by flash chromatography eluting with ethyl acetate in petroleum ether (20-30%) to yield 1-(tert-butyl)-4-nitro-1H-pyrazole-3-carbaldehyde as a solid. $^1$H NMR (CDCl$_3$, 400 MHz): δ 10.43 (s, 1H), 8.32 (s, 1H), 1.68 (s, 9H).

Step 5: Into a 50 mL round bottom flask containing a solution of 1-(tert-butyl)-4-nitro-1H-pyrazole-3-carbaldehyde (300 mg, 1.5 mmol) in dichloromethane (20 mL) was added diethylaminosulfur trifluoride (0.7 mL, 6 mmol) at −20° C. and the mixture was stirred at room temperature for 16 h. The reaction mixture was concentrated under reduced pressure and the residue was purified by flash chromatography eluting with ethyl acetate in petroleum ether (10-20%) to yield 1-(tert-butyl)-3-(difluoromethyl)-4-nitro-1H-pyrazole. $^1$H NMR (CDCl$_3$, 400 MHz): δ 8.30 (s, 1H), 7.12 (t, J=53.6 Hz, 1H), 1.66 (s, 9H).

Step 6: Into a 50 mL round bottom flask containing a solution of 1-(tert-butyl)-3-(difluoromethyl)-4-nitro-1H-pyrazole (250 mg, 1.1 mmol) in methanol (15 mL) was added palladium on carbon (25 mg, 10% w/w) and the reaction was stirred at room temperature for 8 h under hydrogen bladder pressure. The reaction mixture was filtered through celite and washed with methanol and the filtrate was concentrated under reduced pressure to afford 1-(tert-butyl)-3-(difluoromethyl)-1H-pyrazol-4-amine. $^1$H NMR (DMSO-$d_6$, 400 MHz): δ 7.21 (s, 1H), 6.88 (t, J=54.4 Hz, 1H), 4.07 (brs, 2H), 1.44 (s, 9H).

Intermediate 13

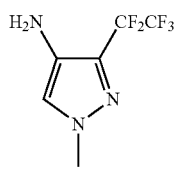

1-Methyl-3-(perfluoroethyl)-1H-pyrazol-4-amine hydrochloride

Step 1: A mixture of ethyl 4,4,5,5,5-pentafluoro-3-oxopentanoate (5.0 g, 22 mmol), triethyl orthoformate (9.0 g, 43 mmol) and acetic anhydride (6 mL, 64 mmol) in a 50 mL sealed tube was heated at 130° C. for 12 h. The reaction mixture was cooled to room temperature and concentrated under reduced pressure to afford ethyl 2-(ethoxymethylene)-4,4,5,5,5-pentafluoro-3-oxopentanoate as mixture of E/Z isomers which was taken to the next step without further purification.

Step 2: Into a 100 mL sealed tube containing a solution of ethyl 2-(ethoxymethylene)-4,4,5,5,5-pentafluoro-3-oxopentanoate in methanol (30 mL) was added hydrazine hydrate (1.6 mL, 32 mmol) and the reaction mixture was heated to reflux for 16 h. The reaction mixture was cooled to room temperature and concentrated under reduced pressure. The residue was dissolved in ethyl acetate, washed with water and brine, dried over anhydrous sodium sulfate, filtered and concentrated under reduced pressure. The residue was purified by flash chromatography eluting with ethyl acetate in petroleum ether to afford ethyl 3-(perfluoroethyl)-1H-pyrazole-4-carboxylate as a solid. $^1$H NMR (DMSO-$d_6$, 400 MHz): δ 14.22 (brs, 1H), 8.61 (s, 1H), 4.24 (q, J=7.2 Hz, 2H), 1.26 (t, J=7.2 Hz, 3H). MS calc'd [M−H]$^+$ 257.0, found 257.0.

Step 3: Into a 50 mL two neck round bottom flask containing a solution of ethyl 3-(perfluoroethyl)-1H-pyrazole-4-carboxylate (2.1 g, 8 mmol) in N,N-dimethylformamide (15 mL) at 0° C. was added sodium hydride (60% in mineral oil, 500 mg, 12 mmol) in portions and the mixture was stirred for 30 min. To this reaction mixture was added methyl iodide (1.7 g, 12 mmol) and the mixture was stirred at room temperature for 18 h. The reaction mixture was treated with saturated ammonium chloride and extracted with ethyl acetate (2×50 mL). The combined organic fractions were dried over anhydrous sodium sulfate, filtered and concentrated under reduced pressure. The residue was purified by flash chromatography eluting with ethyl acetate in petroleum ether (10-15%) to afford ethyl 1-methyl-3-(perfluoroethyl)-1H-pyrazole-4-carboxylate as a solid. $^1$H NMR (CDCl$_3$, 400 MHz): δ 7.99 (s, 1H), 4.32 (q, J=7.2 Hz, 2H), 3.99 (s, 3H), 1.35 (t, J=7.2 Hz, 3H).

Step 4: Into a 50 mL round bottom flask containing a solution of ethyl 1-methyl-3-(perfluoroethyl)-1H-pyrazole-4-carboxylate (1.2 g, 4.4 mmol) in tetrahydrofuran (15 mL) and water (5 mL) was added lithium hydroxide monohydrate (1.0 g, 44 mmol) in portions at 0° C. The reaction mixture was stirred at room temperature for 16 h. The mixture was concentrated under reduced pressure and the residue was acidified to pH 2 using diluted hydrochloric acid (1.5 N). The reaction mixture was extracted with ethyl acetate. The combined organic fractions were washed with water and brine, dried over anhydrous sodium sulfate, filtered and concentrated under reduced pressure to afford 1-methyl-3-(perfluoroethyl)-1H-pyrazole-4-carboxylic acid as a solid. $^1$H NMR (DMSO-$d_6$, 400 MHz): δ 13.01 (brs, 1H), 8.46 (s, 1H), 3.93 (s, 3H). MS calc'd [M−H]$^+$ 243.0, found 243.0.

Step 5: Into a 50 mL round bottom flask containing a stirred solution of 1-methyl-3-(perfluoroethyl)-1H-pyrazole-4-carboxylic acid (750 mg, 3 mmol) in tert-butanol (15 mL) were added triethylamine (0.65 mL, 4.6 mmol) and diphenylphosphoryl azide (1.3 g, 4.6 mmol) dropwise and the reaction mixture was stirred at room temperature for 30 min and at 65° C. for 4 h. The reaction mixture was cooled to room temperature and concentrated under reduced pressure. The crude residue was dissolved in ethyl acetate (40 mL) and washed with water and brine. The solution was dried over anhydrous sodium sulfate, filtered and concentrated under reduced pressure. The residue was purified by flash chromatography eluting with ethyl acetate in petroleum ether (5-10%) to afford tert-butyl (1-methyl-3-(perfluoroethyl)-1H-pyrazol-4-yl)carbamate as a solid. $^1$H NMR (DMSO-$d_6$, 300 MHz): δ 7.96 (s, 1H), 3.86 (s, 3H), 1.40 (s, 9H). MS calc'd [M+H]$^+$ 316.1, found 316.2.

Step 6: Into a 10 mL round bottom flask containing a solution of tert-butyl (1-methyl-3-(perfluoroethyl)-1H-pyrazol-4-yl)carbamate (419 mg, 1.3 mmol) in 1,4-dioxane (2 mL) was added hydrochloride in dioxane (5 mL) and the reaction was stirred at room temperature for 3 h. The reaction mixture was concentrated under reduced pressure and triturated with diethyl ether and petroleum ether to afford 1-methyl-3-(perfluoroethyl)-1H-pyrazol-4-amine hydrochloride as a solid. $^1$H NMR (DMSO-$d_6$, 300 MHz): δ 7.77 (s, 1H), 3.86 (s, 3H). MS calc'd [M+H]$^+$ 216.0, found 216.2.

Intermediate 14

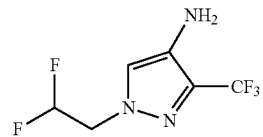 [SMILES: Nc1cn(CC(F)F)nc1C(F)(F)F]

1-(2,2-Difluoroethyl)-3-(trifluoromethyl)-1H-pyrazol-4-amine

Step 1: Into a 50 mL round bottom flask were added 3-(trifluoromethyl)-1H-pyrrazole (5.0 g, 33 mmol), sulfuric acid (25 mL) and nitration mixture (sulfuric acid and fuming nitric acid, 25 mL/25 mL) and the reaction was stirred at room temperature for 16 h. The reaction mixture was diluted with ethyl acetate (100 mL), washed with water and saturated sodium bicarbonate solution, dried over anhydrous sodium sulfate, filtered and concentrated under reduced pressure. The residue was purified by flash column chromatography eluting with ethyl acetate in petroleum ether (20-30%) to furnish 4-nitro-3-(trifluoromethyl)-1H-pyrazole as a solid. $^1$H NMR (CDCl$_3$, 400 MHz): δ 11.66 (brs, 1H), 8.47 (s, 1H). MS calc'd [M−H]$^+$ 180.0, found 180.0.

Step 2: Into a 50 mL sealed tube containing a solution of 4-nitro-3-(trifluoromethyl)-1H-pyrrazole (2.0 g, 11 mmol)

in N,N-dimethylformamide (20 mL) were added 1,1-difluoro-2-iodoethane (3.1 g, 16 mmol) and potassium carbonate (4.6 g, 33 mmol) and the reaction mixture was heated at 130° C. for 2 h. The reaction mixture was cooled to room temperature, diluted with methyl tert-butyl ether (20 mL), washed with water and brine, dried over anhydrous sodium sulfate, filtered and concentrated under reduced pressure. The residue was purified by flash column chromatography eluting with methyl tert-butyl ether in petroleum ether (3-5%) to furnish 1-(2,2-difluoroethyl)-4-nitro-3-(trifluoromethyl)-1H-pyrazole as a liquid. $^1$H NMR (CDCl$_3$, 400 MHz): δ 8.37 (s, 1H), 6.19 (tt, J=54.5, 3.9 Hz, 1H), 4.62-4.55 (m, 2H). MS [M−H]$^+$ calc'd 244.0, found 244.4.

Step 3: Into a 50 mL sealed tube containing a solution of 1-(2,2-difluoroethyl)-4-nitro-3-(trifluoromethyl)-1H-pyrazole (1.6 g, 65 mmol) in ethanol (10 mL) was added palladium on carbon (160 mg, 10% w/w) and the reaction was stirred at room temperature under hydrogen atmosphere for 2 h. The reaction mixture was filtered through celite and washed with ethanol and the filtrate was concentrated under reduced pressure to afford 1-(2,2-difluoroethyl)-3-(trifluoromethyl)-1H-pyrazol-4-amine as a liquid. $^1$H NMR (CDCl$_3$, 400 MHz): δ 7.11 (s, 1H), 6.05 (tt, J=55.2, 4.4 Hz, 1H), 4.42-4.34 (m, 2H). MS [M+H]$^+$ calc'd 216.0, found 216.0.

The following intermediates were prepared in an analogous manner of that described in Intermediate 14.

in dichloromethane (50 mL) was added trifluoroacetic acid (25 mL) and the reaction mixture was stirred at room temperature for 2 h. The reaction mixture was concentrated under reduced pressure and triturated with diethyl ether to afford 1-methyl-4-nitro-1H-pyrazol-3-amine as a solid. $^1$H NMR (DMSO-d$_6$, 300 MHz): δ 8.44 (s, 1H), 7.31 (s, 1H), 3.65 (s, 3H). MS calc'd [M+H]$^+$ 143.0, found 143.4.

Step 3: A mixture of copper(II) bromide (5.5 g, 25 mmol) and tert-butyl nitrite (2.5 g, 25 mmol) in acetonitrile (100 mL) was taken into a 250 mL round bottom flask and cooled to 0° C. A solution of 1-methyl-4-nitro-1H-pyrazol-3-amine (3.5 g, 25 mmol) in acetonitrile (20 mL) was added dropwise over a period of 5 min. The reaction mixture was slowly warmed to room temperature and stirred for 2 h. The reaction mixture was diluted with ethyl acetate, washed with water and brine, dried over anhydrous sodium sulfate, filtered and concentrated under reduced pressure. The residue was purified by flash chromatography eluting with ethyl acetate in petroleum ether (15-20%) to afford 3-bromo-1-methyl-4-nitro-1H-pyrazole as a solid. $^1$H NMR (DMSO-d$_6$, 400 MHz): δ 8.94 (s, 1H), 3.89 (s, 3H).

Step 4: Into a 25 mL round bottom flask containing a solution of 3-bromo-1-methyl-4-nitro-1H-pyrazole (1.0 g, 5 mmol) in toluene (5 mL) were added tributyl(vinyl)tin (1.7 mL, 58 mmol) and tetrakis(triphenylphosphine)palladium (0) (300 mg, 0.25 mmol) and the reaction was heated at 120° C. for 6 h. The reaction mixture was cooled to room

| Intermediate # | Structure | IUPAC Name | Exact Mass [M + H]$^+$ |
|---|---|---|---|
| 15 | ![structure] | 1-(2,2,2-trifluoroethyl)-3-(trifluoromethyl)-1H-pyrazol-4-amine | Calc'd 234.0, found 234.6 |
| 16 | ![structure] | 1-(difluoromethyl)-3-(trifluoromethyl)-1H-pyrazol-4-amine | Calc'd 202.0, found 202.4 |

Intermediate 17

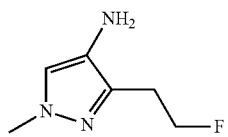

3-(2-Fluoroethyl)-1-methyl-1H-pyrazol-4-amine

Step 1 & 2: Into a 250 mL round bottom flask containing a solution of 1-methyl-4-nitro-1H-pyrazole-3-carboxylic acid (5.0 g, 29 mmol) in 1,4-dioxane (75 mL) and tert-butanol (50 mL) were added triethylamine (9.8 mL, 45 mmol) and diphenylphosphoryl azide (9.8 mL, 45 mmol) and the reaction was heated at 100° C. for 16 h. The reaction mixture was cooled to room temperature and concentrated under reduced pressure. To a stirred solution of the residue temperature, concentrated and purified by flash chromatography eluting with ethyl acetate in petroleum ether (15-20%) to afford 1-methyl-4-nitro-3-vinyl-1H-pyrazole as a solid. $^1$H NMR (CDCl$_3$, 300 MHz): δ 8.07 (s, 1H), 7.22 (dd, J=17.6, 11.2 Hz, 1H), 6.19 (dd, J=17.7, 4.6 Hz, 1H), 5.54 (dd, J=11.1, 1.6 Hz, 1H), 3.97 (s, 3H).

Step 5: Into a 25 mL round bottom flask containing a solution of 1-methyl-4-nitro-3-vinyl-1H-pyrazole (350 mg, 2.2 mmol) in tetrahydrofuran (5 mL) was added borane-dimethyl sulfide complex (2 M solution in tetrahydrofuran, 2.3 mL, 4.6 mmol) and the reaction mixture was heated at 50° C. for 2 h. The reaction mixture was cooled to room temperature, treated with sodium hydroxide (1M solution in water, 2 mL) and hydrogen peroxide solution (30 wt. % in water, 2 mL) and stirred at room temperature for 2 h. The reaction mixture was concentrated under reduced pressure and the residue was dissolved in ethyl acetate (50 mL), washed with water and brine, dried over anhydrous sodium sulfate, filtered and concentrated under reduced pressure. The residue was purified by flash chromatography eluting with ethyl acetate in petroleum ether (15-20%) to afford 2-(1-methyl-4-nitro-1H-pyrazol-3-yl)ethan-1-ol as a solid. $^1$H NMR (CDCl$_3$, 400 MHz): δ 8.15 (s, 1H), 4.03 (t, J=5.7 Hz, 2H), 3.94 (s, 3H), 3.25 (t, J=5.8 Hz, 2H). MS [M+H]$^+$ calc'd 172.1, found 172.4.

Step 6: Into a 25 mL round bottom flask containing a solution of 2-(1-methyl-4-nitro-1H-pyrazol-3-yl)ethan-1-ol (120 mg, 0.7 mmol) in dichloromethane (5 mL) was added bis(2-methoxyethyl)aminosulfur trifluoride (0.15 mL, 0.8 mmol) at 0° C. and the reaction was slowly warmed to room temperature and stirred for 16 h. The reaction mixture was diluted with dichloromethane (20 mL) and washed with saturated sodium bicarbonate solution, water and brine. The organic layer was dried over anhydrous sodium sulfate, filtered, concentrated under reduced pressure and purified by flash column chromatography eluting with ethyl acetate in petroleum ether to furnish 3-(2-fluoroethyl)-1-methyl-4-nitro-1H-pyrazole as an oil. MS [M+H]$^+$ calc'd 174.1, found 174.3.

Step 7: Into a 25 mL round bottom flask containing a solution of 3-(2-fluoroethyl)-1-methyl-4-nitro-1H-pyrazole (30 mg, 0.2 mmol) in methanol (5 mL) was added palladium on carbon (6 mg, 20% w/w) and the reaction mixture was stirred at room temperature for 2 h under hydrogen atmosphere. The mixture was filtered through celite and washed with methanol (5 mL). The filtrate was concentrated under reduced pressure to afford 3-(2-fluoroethyl)-1-methyl-1H-pyrazol-4-amine as an oil. MS calc'd [M+H]$^+$ 144.1, found 144.2.

Intermediate 18

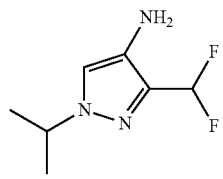

3-(Difluoromethyl)-1-isopropyl-1H-pyrazol-4-amine

Step 1: Into a 100 mL round bottom flask containing a solution of methyl 4-nitro-1H-pyrazole-3-carboxylate (5.0 g, 29 mmol) in dimethylformamide (50 mL) were added anhydrous potassium carbonate (8.0 g, 58 mmol) and 2-iodopropane (5.8 mL, 58 mmol) at 0° C. and the mixture was stirred at room temperature for 16 h. The reaction mixture was filtered through celite and washed with ethyl acetate. The filtrate was washed with water and brine, dried over anhydrous sodium sulfate, filtered and concentrated under reduced pressure. The residue was purified flash chromatography eluting with ethyl acetate in petroleum ether (10-20%) to afford a mixture of regioisomers, methyl 1-isopropyl-4-nitro-1H-pyrazole-5-carboxylate (2.2 g, 35% yield) as a colorless oil and methyl 1-isopropyl-4-nitro-1H-pyrazole-3-carboxylate as an oil. For methyl 1-isopropyl-4-nitro-1H-pyrazole-5-carboxylate; $^1$H NMR (CD$_3$OD, 400 MHz): δ 8.16 (s, 1H), 4.75-4.71 (m, 1H), 4.04 (s, 3H), 1.52 (d, J=6.6 Hz, 6H). For methyl 1-isopropyl-4-nitro-1H-pyrazole-3-carboxylate; $^1$H NMR (CD$_3$OD, 400 MHz): δ 8.68 (s, 1H), 4.66-4.59 (m, 1H), 3.95 (s, 3H), 1.55 (d, J=6.7 Hz, 6H).

Step 2: Into a 250 mL round bottom flask containing a solution of methyl 1-isopropyl-4-nitro-1H-pyrazole-3-carboxylate (4.6 g, 22 mmol) in dichloromethane (50 mL) was added diisobutylaluminum hydride (1M solution in toluene, 32 mL, 32 mmol) at 0° C. and the mixture was stirred at room temperature for 2 h. The reaction mixture was cooled to 0° C., treated with saturated aqueous ammonium chloride solution and extracted with ethyl acetate (2×200 mL). The combined organics were washed with brine, dried over anhydrous sodium sulfate, filtered, concentrated under reduced pressure and purified by flash chromatography eluting with ethyl acetate in petroleum ether (20-30%) to afford (1-isopropyl-4-nitro-1H-pyrazol-3-yl)methanol as an oil. $^1$H NMR (CD$_3$OD, 400 MHz): δ 8.60 (s, 1H), 4.88 (d, J=13.2 Hz, 2H), 4.58-4.55 (m, 1H), 1.54 (d, J=6.8 Hz, 6H). MS calc'd [M+H]$^+$ 186.1, found 186.2.

Step 3: Into a 100 mL round bottom flask containing a solution of 2-iodoxybenzoic acid (6.7 g, 24 mmol) in dimethyl sulfoxide (60 mL) was added (1-isopropyl-4-nitro-1H-pyrazol-3-yl)methanol (2.2 g, 12 mmol) and the mixture was stirred at room temperature for 2 h. The reaction mixture was treated with water (200 mL) and extracted with ethyl acetate (3×150 mL). The combined organic layers were washed with brine, dried over anhydrous sodium sulfate, filtered and concentrated under reduced pressure. The residue was purified by flash chromatography eluting with ethyl acetate in petroleum ether (30-50%) to afford 1-isopropyl-4-nitro-1H-pyrazole-3-carbaldehyde.

Step 4: Into a 50 mL round bottom flask containing a solution of 1-isopropyl-4-nitro-1H-pyrazole-3-carbaldehyde (1.5 g, 8 mmol) in dichloromethane (20 mL) was added diethylaminosulfur trifluoride (3.3 mL, 25 mmol) at −30° C. and the reaction mixture was warmed to room temperature and stirred for 16 h. The reaction mixture was diluted with dichloromethane (20 mL) and washed with saturated sodium bicarbonate solution, water and brine solution. The organic layer was dried over anhydrous sodium sulfate, filtered and concentrated under reduced pressure. The crude was purified by flash chromatography eluting with ethyl acetate in petroleum ether (20-30%) to afford 3-(difluoromethyl)-1-isopropyl-4-nitro-1H-pyrazole as an oil. $^1$H NMR (CD$_3$OD, 400 MHz): δ 8.74 (s, 1H), 7.16 (t, J=53.6 Hz, 1H), 4.68-4.61 (m, 1H), 1.56 (d, J=6.8 Hz, 6H).

Step 5: Into a 50 mL round bottom flask containing a solution of 3-(difluoromethyl)-1-isopropyl-4-nitro-1H-pyrazole (1.3 g, 6.3 mmol) in methanol (25 mL) was added palladium on carbon (330 mg, 25% w/w) and the reaction mixture was stirred under hydrogen atmosphere for 16 h. The reaction mixture was filtered through celite and washed with ethyl acetate. The filtrate was concentrated under reduced pressure to afford 3-(difluoromethyl)-1-isopropyl-1H-pyrazol-4-amine as an oil. MS calc'd [M+H]$^+$ 176.1, found 176.4.

Intermediate 19

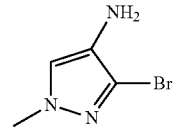

3-Bromo-1-methyl-1H-pyrazol-4-amine

Step 1: Into a 250 mL round bottom flask containing a solution of 3-amino-1-methyl-1H-pyrazole (5.0 g, 52 mmol)

in dichloromethane (100 mL) at 0° C. was added triethylamine (18 mL, 129 mmol). After 10 min, trifluoroacetic anhydride (9.5 mL, 67 mmol) was added and the reaction mixture was stirred at room temperature for 2 h. The reaction mixture was diluted with dichloromethane (50 mL), washed with water and brine, dried over anhydrous sodium sulfate, filtered and concentrated under reduced pressure to afford 2,2,2-trifluoro-N-(1-methyl-1H-pyrazol-3-yl)acetamide as a solid. $^1$H NMR (CDCl$_3$, 400 MHz): δ 9.26 (brs, 1H), 7.33 (d, J=2.2 Hz, 1H), 6.73 (d, J=2.2 Hz, 1H), 3.84 (s, 3H). MS calc'd [M+H]$^+$ 194.1, found 194.4.

Step 2: Into a 100 mL round bottom flask containing a solution of 2,2,2-trifluoro-N-(1-methyl-1H-pyrazol-3-yl)acetamide (8.5 g, 44 mmol) in concentrated sulfuric acid (14 mL) was added fuming nitric acid (14 mL) at 0° C. dropwise and the reaction was stirred at room temperature for 2 h. The reaction mixture was treated with ice cold water and extracted with ethyl acetate. The combined organic fractions were washed with saturated sodium bicarbonate solution, water and brine, dried over anhydrous sodium sulfate, filtered and concentrated under reduced pressure to afford 2,2,2-trifluoro-N-(1-methyl-4-nitro-1H-pyrazol-3-yl)acetamide which was taken to the next step without further purification. $^1$H NMR (CDCl$_3$, 300 MHz): δ 9.86 (s, 1H), 8.15 (s, 1H), 3.98 (s, 3H). MS calc'd [M−H]$^+$ 237.0, found 237.0.

Step 3: Into a 500 mL round bottom flask containing a solution of 2,2,2-trifluoro-N-(1-methyl-4-nitro-1H-pyrazol-3-yl)acetamide (8.5 g, 36 mmol) in methanol (200 mL) and water (50 mL) was added potassium carbonate (12.5 g, 89 mmol) and the reaction was stirred at room temperature for 24 h. The mixture was concentrated under reduced pressure and the residue was dissolved in ethyl acetate (150 mL), washed with water and brine, dried over anhydrous sodium sulfate, filtered and concentrated under reduced pressure. The residue was purified by column chromatography eluting with ethyl acetate to afford 1-methyl-4-nitro-1H-pyrazol-3-amine as a solid. $^1$H NMR (DMSO-d$_6$, 300 MHz): δ 8.44 (s, 1H), 6.22 (s, 2H), 3.65 (s, 3H). MS calc'd [M+H]$^+$ 143.1, found 143.2.

Step 4: Into a 250 mL round bottom flask containing a solution of copper(II) bromide (3.0 g, 14 mmol) and tert-butyl nitrite (1.7 mL, 14 mmol) in acetonitrile (150 mL) was added 1-methyl-4-nitro-1H-pyrazol-3-amine (2 g, 14 mmol) in acetonitrile (20 mL) at 0° C. and the reaction was stirred at room temperature for 2 h. The reaction mixture was concentrated under reduced pressure. The residue was dissolved in ethyl acetate (120 mL), washed with water and brine, dried over anhydrous sodium sulfate, filtered and concentrated under reduced pressure. The residue was purified by column chromatography eluting with ethyl acetate in petroleum ether (20-30%) to afford 3-bromo-1-methyl-4-nitro-1H-pyrazole as a solid. $^1$H NMR (CDCl$_3$, 300 MHz): δ 8.25 (s, 1H), 3.89 (s, 3H).

Step 5: Into a 100 mL round bottom flask containing a solution of 3-bromo-1-methyl-4-nitro-1H-pyrazole (1.0 g) in ethyl acetate (50 mL) at room temperature was added Raney Nickel (700 mg) and the reaction mixture was stirred at room temperature for 16 h under hydrogen atmosphere. The reaction mixture was filtered through celite and washed with ethyl acetate. The filtrate was concentrated under reduced pressure and purified by flash chromatography eluting with ethyl acetate in petroleum ether (40-50%) to afford 3-bromo-1-methyl-1H-pyrazol-4-amine as a liquid. $^1$H NMR (CD$_3$OD, 400 MHz): δ 7.18 (s, 1H), 3.77 (s, 3H). MS calc'd [M+H]$^+$ 176.0, found 176.2.

Intermediate 20

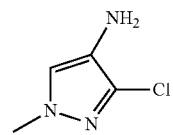

3-Chloro-1-methyl-1H-pyrazol-4-amine

Step 1: Into a 250 mL round bottom flask containing a solution of 1-methyl-4-nitro-1H-pyrazol-3-amine (4.0 g, 28 mmol) in acetonitrile (100 mL) was added concentrated hydrochloric acid (8 mL) dropwise at 0° C. To this reaction mixture was added sodium nitrite (8.0 g, 116 mmol) in portions and the reaction mixture was gradually brought to room temperature and stirred for 16 h. The reaction mixture was cooled to 0° C., treated with water (30 mL) and extracted with ethyl acetate (2×50 mL). The combined organics were washed with saturated sodium bicarbonate solution, water and brine, dried over anhydrous sodium sulfate, filtered and concentrated under reduced pressure. The residue was purified by column chromatography eluting with ethyl acetate in petroleum ether (20-30%) to furnish 3-chloro-1-methyl-4-nitro-1H-pyrazole as a solid. $^1$H NMR (CDCl$_3$, 300 MHz): δ 8.25 (s, 1H), 3.98 (s, 3H).

Step 2: Into a 100 mL round bottom flask containing a solution of 3-chloro-1-methyl-4-nitro-1H-pyrazole (2.0 g) in ethyl acetate (50 mL) was added Raney Ni (1.0 g) and the reaction mixture was stirred under hydrogen atmosphere for 24 h. The reaction mixture was filtered through celite and washed with ethyl acetate. The filtrate was concentrated under reduced pressure and purified by flash chromatography eluting with ethyl acetate in petroleum ether (40-50%) to afford 3-chloro-1-methyl-1H-pyrazol-4-amine as an oil. $^1$H NMR (CD$_3$OD, 400 MHz): δ 7.17 (s, 1H), 3.73 (s, 3H).

Intermediate 21

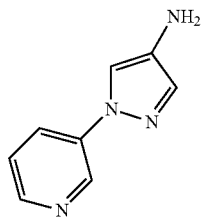 [SMILES: Nc1cnn(-c2cccnc2)c1]

1-(Pyridin-3-yl)-1H-pyrazol-4-amine

Step 1: Into a 50 mL round bottom flask containing a solution of 4-nitro-1H-pyrazole (1.0 g, 8.8 mmol) in dimethylformamide (10 mL) were added copper iodide (50 mg, 0.27 mmol), salicyladoxime (160 mg, 11.5 mmol), 3-bromopyridine (700 mg, 4.4 mmol) and cesium carbonate (2.4 g, 8.8 mmol) and the mixture was heated at 130° C. for 12 h. The reaction mixture was cooled to room temperature, diluted with ethyl acetate, washed with water and brine, dried over anhydrous sodium sulfate, filtered and concentrated under reduced pressure. The residue was purified by flash chromatography eluting with methanol in dichloromethane (0-2%) to yield 3-(4-nitro-1H-pyrazol-1-yl)pyridine. $^1$H NMR (CDCl$_3$, 400 MHz): δ 9.14 (brs, 1H), 8.73 (brs, 1H), 8.70 (s, 1H), 8.34 (s, 1H), 8.14-8.11 (m, 1H), 7.55-7.51 (m, 1H). MS calc'd [M+H]$^+$ 191.0, found 191.0.

Step 2: Into a 25 mL round bottom flask containing a solution of 3-(4-nitro-1H-pyrazol-1-yl)pyridine (150 mg, 0.8 mmol) in tetrahydrofuran (5 mL) was added palladium on carbon (15 mg, 10% w/w) and the reaction was stirred at room temperature for 8 h under hydrogen bladder pressure. The reaction mixture was filtered through celite and washed with methanol and the filtrate was concentrated under reduced pressure. The residue was purified by flash chromatography eluting with methanol in dichloromethane (4-7%) to yield 1-(pyridin-3-yl)-1H-pyrazol-4-amine. MS calc'd [M+H]$^+$ 161.1, found 161.2.

Intermediate 22

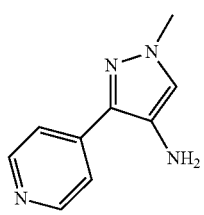

1-Methyl-3-(pyridin-4-yl)-1H-pyrazol-4-amine

Step 1: Into a 10 mL sealed tube containing a solution of 3-bromo-1-methyl-4-nitro-/H-pyrazole (800 mg, 0.4 mmol) in 1,4-dioxane (2 mL) were added potassium phosphate tribasic (140 mg, 0.7 mmol) in water (1 mL) and pyridin-4-ylboronic acid (70 mg, 0.6 mmol) and the mixture was degassed with nitrogen for 10 min. [1,1'-bis(diphenylphosphino)ferrocene]dichloropalladium(II), complex with dichloromethane (20 mg, 0.03 mmol) was added and the reaction mixture was heated at 80° C. for 14 h. The reaction mixture was filtered through celite and the filterate was concentrated under reduced pressure. The residue was purified by flash chromatography eluting with ethyl acetate in petroleum ether (10-15%) to yield 4-(1-methyl-4-nitro-1H-pyrazol-3-yl)pyridine. $^1$H NMR (DMSO-d$_6$, 300 MHz): δ 8.98 (s, 1H), 8.67 (d, J=6.1 Hz, 2H), 7.62 (d, J=6.1 Hz, 2H), 3.95 (s, 3H). MS calc'd [M+H]$^+$ 205.1, found 205.2.

Step 2: Into a 50 mL round bottom flask containing a solution of 4-(1-methyl-4-nitro-1H-pyrazol-3-yl)pyridine (50 mg, 0.24 mmol) in methanol (10 mL) was added palladium on carbon (25 mg, 50% w/w) and the reaction was stirred in an atmosphere of hydrogen for 2 h. The reaction mixture was filtered through celite and washed with methanol. The filtrate was concentrated under reduced pressure to yield 1-methyl-3-(pyridin-4-yl)-1H-pyrazol-4-amine (30 mg, 75% yield) as an oil. $^1$H NMR (DMSO-d$_6$, 300 MHz): δ 8.62 (d, J=5.9 Hz, 2H), 7.79 (dd, J=4.8, 1.5 Hz, 2H), 7.10 (s, 1H), 3.88 (s, 3H). MS calc'd [M+H]$^+$ 175.1, found 175.2.

Intermediate 23

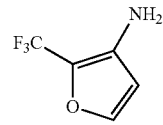

2-(Trifluoromethyl)furan-3-amine

Step 1: Into a 100 mL round bottom flask containing a solution of ethyl 4,4,4-trifluoroacetoacetate (10.0 g, 54 mmol) in pyridine (200 mL) was added chloroacetaldehyde (40% wt. in water, 58 mL) and the reaction mixture was stirred for 50 h. Ethyl 2-(trifluoromethyl)furan-3-carboxylate was isolated by vacuum distillation (25 mm Hg/80° C.) as a liquid. $^1$H NMR (CDCl$_3$, 300 MHz): δ 7.49 (d, J=0.8 Hz, 1H), 6.87 (d, J=0.8 Hz, 1H), 4.42 (q, J=7.1 Hz, 2H), 1.36 (t, J=7.1 Hz, 3H).

Step 2: Into a 100 mL round bottom flask containing a solution of ethyl 2-(trifluoromethyl)furan-3-carboxylate (7.0 g, 33 mmol) in tetrahydrofuran (70 mL) and water (35 mL) was added lithium hydroxide (2.0 g, 85 mmol) and the reaction mixture was stirred at room temperature for 12 h. The reaction mixture was concentrated under reduced pressure and purified by flash chromatography eluting with methanol in dichloromethane (5-10%) to afford 2-(trifluoromethyl)furan-3-carboxylic acid as a liquid. $^1$H NMR (DMSO-d$_6$, 400 MHz): δ 7.87 (s, 1H), 6.79 (s, 1H). MS calc'd [M−H]$^+$ 179.0, found 179.2.

Step 3: Into a 250 mL round bottom flask containing a solution of 2-(trifluoromethyl)furan-3-carboxylic acid (3.0 g, 16 mmol) in toluene (100 mL) were added diisopropylethylamine (4.5 mL, 20 mmol) and diphenylphosphoryl azide (3.2 mL, 18 mmol) and the resulting solution was stirred at room temperature for 30 min and treated with benzylalcohol (7.0 mL, 64 mmol). The reaction mixture was heated at 110° C. for 6 h. The reaction mixture was concentrated and resulting residue was dissolved in dichloromethane and washed with water and brine. The organic fraction was dried over anhydrous sodium sulfate, filtered and concentrated under reduced pressure. The reside was purified by flash chromatography using ethyl acetate in petroleum ether (0-5%) to afford benzyl (2-(trifluoromethyl)furan-3-yl)carbamate as a liquid. $^1$H NMR (CD$_3$OD, 400 MHz): δ 7.6 (s, 1H), 7.58-7.30 (m, 6H), 6.96-6.95 (m, 1H), 5.19 (s, 2H). MS calc'd [M−H]$^+$ 284.1, found 284.2.

Step 4: Into a 100 mL round bottom flask containing a solution of benzyl (2-(trifluoromethyl)furan-3-yl)carbamate (1.0 g, 3.5 mmol) in tetrahydrofuran (20 mL) was added palladium on carbon (200 mg, 20 w/w). The reaction mixture was stirred at stirred at room temperature for 6 h under hydrogen pressure using bladder. The reaction mixture was filtered through celite and washed with tetrahydrofuran. The filtrate was cooled to 0° C., treated with trifluroacetic acid (1 mL), stirred at room temperature for 20 min and concentrated under reduced pressure to afford 2-(trifluoromethyl)furan-3-amine as a solid. $^1$H NMR (CD$_3$OD, 400 MHz): δ 7.80 (s, 1H), 6.96 (s, 1H).

Intermediate 24

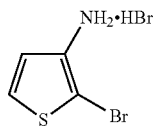

2-Bromo-3-aminothiophene hydrobromide

Step 1: Into a 100 mL round bottom flask containing a solution of thiophene-3-carboxylic acid (4.0 g, 31 mmol) in toluene (40 mL) were added diphenylphosphoryl azide (9.5 g, 34 mmol) and N,N-diisopropylethylamine (6.7 mL, 38 mmol) at 0° C. and the reaction was stirred at room temperature for 1 h. The reaction mixture was cooled to 0° C., treated with tert-butanol (12 mL, 124 mmol) and heated to 120° C. for 5 h. The reaction mixture was concentrated under reduced pressure and purified by flash chromatography eluting with ethyl acetate in petroleum ether (2-5%) to afford tert-butyl thiophen-3-ylcarbamate as a solid. $^1$H NMR (CDCl$_3$, 400 MHz): δ 7.23-7.21 (m, 2H), 6.93 (d, J=5.6 Hz, 1H), 6.71 (brs, 1H), 1.54 (s, 9H).

Step 2: Into a 100 mL round bottom flask containing a solution of tert-butyl thiophen-3-ylcarbamate (4.2 g, 21 mmol) in carbon tetrachloride (40 mL) was added N-bromosuccinimide (7.5 g, 42 mmol) and the reaction mixture was heated at 80° C. for 2 h. The reaction mixture was diluted with ethyl acetate (100 mL), washed with water and brine, dried over anhydrous sodium sulfate, filtered and concentrated under reduced pressure. The residue was purified by flash chromatography eluting with ethyl acetate in petroleum ether (2-5%) to afford tert-butyl (2-bromothiophen-3-yl)carbamate as a solid. $^1$H NMR (CDCl$_3$, 400 MHz): δ 7.59 (d, J=3.3 Hz, 1H), 7.26 (d, J=3.4 Hz, 1H), 6.58 (brs, 1H), 1.54 (s, 9H). MS calc'd [M+H]$^+$ 278.0, found 278.2.

Step 3: Into a 10 mL round bottom flask containing a solution of tert-butyl (2-bromothiophen-3-yl)carbamate (500 mg) in dichloromethane (5 mL) was added HBr in acetic acid (0.5 mL) dropwise at 0° C. and reaction mixture was stirred at room temperature for 2 h. The reaction mixture was concentrated under reduced pressure and triturated using diethyl ether to afford 2-bromothiophen-3-amine hydrobromide as a solid. $^1$H NMR (DMSO-d$_6$, 400 MHz): δ 7.66 (d, J=5.8 Hz, 1H), 6.96 (d, J=5.8 Hz, 1H).

The following intermediate was prepared in an analogous manner of that described in Intermediate 24.

| Intermediate # | Structure | IUPAC Name | Exact Mass [M + H]$^+$ |
|---|---|---|---|
| 25 | ![structure] NH$_2$·HCl, Cl on thiophene | 2-chlorothiophen-3-amine hydrochloride | Calc'd 134.0, found 134.4 |

Intermediate 26

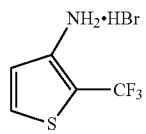

2-(Trifluoromethyl)thiophen-3-amine hydrobromide

Step 1: Into a 50 mL round bottom flask containing a solution of tert-butyl thiophen-3-ylcarbamate (1.0 g, 5 mmol) in tert-butanol (30 mL) were added 1-(trifluoromethyl)-1,2-benziodoxol-3(1H)-one (3.3 g, 10 mmol) and copper(I) chloride (100 mg, 1 mmol) and the reaction was heated at 115° C. for 8 h. The reaction mixture was diluted with ethyl acetate (20 mL) and washed with saturated sodium bicarbonate solution, water and brine. The solution was dried over anhydrous sodium sulfate, filtered, concentrated under reduced pressure and purified by flash column chromatography eluting with ethyl acetate in petroleum ether (15-20%) to furnish tert-butyl (2-(trifluoromethyl)thiophen-3-yl)carbamate as a solid. $^1$H NMR (CDCl$_3$, 300 MHz): δ 7.77 (d, J=4.4 Hz, 1H), 7.38 (d, J=5.5 Hz, 1H), 6.91 (brs, 1H), 1.53 (s, 9H).

Step 2: Into a 25 mL round bottom flask tert-butyl (2-(trifluoromethyl)thiophen-3-yl)carbamate (800 mg) in dichloromethane (10 mL) was added HBr in acetic acid (1 mL) at 0° C. and the mixture was stirred at room temperature for 2 h. The reaction mixture was concentrated under reduced pressure and triturated using diethyl ether to afford 2-(trifluoromethyl)thiophen-3-amine hydrobromide as a solid. $^1$H NMR (DMSO-d$_6$, 300 MHz): δ 7.51 (d, J=5.2 Hz, 1H), 6.59 (d, J=4.0 Hz, 1H).

Intermediate 27

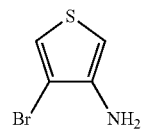

4-Bromo-3-aminothiophene

Step 1: Into a 100 mL round bottom flask containing a solution of 3,4-dibromothiophene (5.0 g, 21 mmol) in toluene (50 mL) were added benzophenone imine (4.1 g, 23 mmol), palladium acetate (140 mg, 0.6 mmol), 2,2'-bis(diphenylphosphino)-1,1'-binaphthyl (510 mg, 0.83 mmol) and cesium carbonate (13.4 g, 41 mmol) and the reaction mixture was degassed for 15 min using nitrogen gas and heated at 110° C. for 16 h. The reaction mixture was filtered through celite and washed with ethyl acetate. The filtrate was concentrated under reduced pressure and purified by flash column chromatography eluting with ethyl acetate in petroleum ether (2-5%) to afford N-(4-bromothiophen-3-yl)-1,1-diphenylmethanimine as a solid. $^1$H NMR (CDCl$_3$, 400 MHz): δ 7.85-7.82 (m, 3H), 7.64-7.60 (m, 2H), 7.53-7.49 (m, 3H), 7.45-7.42 (m, 1H), 7.39-7.36 (m, 2H), 7.23-7.18 (m, 1H). MS calc'd [M+H]$^+$ 342.0, found 342.0.

Step 2: Into a 50 mL round bottom flask containing a solution of N-(4-bromothiophen-3-yl)-1,1-diphenylmethanimine (4.0 g, 12 mmol) in dichloromethane (20 mL) was added hydrochloric acid (4 M solution in 1,4-dioxane, 10 mL) at 0° C. and the reaction was stirred at room temperature for 4 h. The reaction mixture was concentrated under reduced pressure, triturated using diethyl ether and dried under high vacuum to afford 4-bromothiophen-3-amine hydrochloride as a solid. $^1$H NMR (CDCl$_3$, 400 MHz): δ 7.15 (d, J=3.6 Hz, 1H), 6.25 (d, J=3.6 Hz, 1H). MS calc'd [M+H]$^+$ 177.9, found 178.2.

Intermediate 28

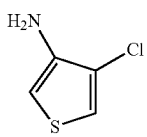

4-Chlorothiophen-3-amine

Step 1: Into a 250 mL round bottom flask containing a solution of methyl 4-aminothiophene-3-carboxylate (2.5 g, 16 mmol) in concentrated hydrochloric acid (21 mL) was added sodium nitrite (1.2 g, 18 mmol) in water (5 mL) dropwise at 0° C. and the reaction mixture was stirred at for 1 h. The mixture was treated with copper(I) chloride (2.5 g, 19 mmol) in chloroform (25 mL) and heated at 50° C. for 16 h. The reaction mixture was cooled to room temperature, treated with saturated sodium carbonate solution and extracted with dichloromethane (3×50 mL). The combined organic layers were washed with water and brine, dried over anhydrous sodium sulfate, filtered and concentrated under reduced pressure. The residue was purified by flash chromatography eluting with ethyl acetate in petroleum ether (0-4%) to furnish methyl 4-chlorothiophene-3-carboxylate as a liquid. $^1$H NMR (CDCl$_3$, 400 MHz): δ 8.13 (d, J=3.7 Hz, 1H), 7.20 (d, J=3.7 Hz, 1H), 3.90 (s, 3H).

Step 2: Into a 25 mL round bottom flask containing a solution of methyl 4-chlorothiophene-3-carboxylate (600 mg, 3.4 mmol) in tetrahydrofuran (6 mL) and water (1 mL) was added lithium hydroxide monohydrate (240 mg, 10 mmol) and the reaction was stirred at room temperature for 16 h. The mixture was concentrated under reduced pressure and acidified to pH 2 using diluted hydrochloric acid (1.5 N). The reaction mixture was extracted with ethyl acetate. The combined organic fractions were washed with water and brine, dried over anhydrous sodium sulfate, filtered and concentrated under reduced pressure to afford 4-chlorothiophene-3-carboxylic acid as a liquid. $^1$H NMR (CDCl$_3$, 300 MHz): δ 8.29 (d, J=3.7 Hz, 1H), 6.57 (d, J=3.6 Hz, 1H). MS calc'd [M–H]$^+$ 161.0, found 161.0.

Step 3: Into a 100 mL round bottom flask containing a solution of 4-chlorothiophene-3-carboxylic acid (500 mg, 3 mmol) in toluene (20 mL) were added diphenylphosphoryl azide (2.5 g, 3.4 mmol) and N,N-diisopropylethylamine (0.7 mL, 3.7 mmol) and the reaction was stirred at room temperature for 1 h. To this mixture was added tert-butanol (1.2 mL, 12 mmol) and the mixture was heated at 100° C. for 3 h. The reaction mixture was concentrated under reduced pressure, diluted with ethyl acetate (120 mL), washed with water and brine, dried over anhydrous sodium sulfate, filtered and concentrated under reduced pressure. The residue was purified by column chromatography eluting with ethyl acetate in petroleum ether (2-4%) to furnish tert-butyl (4-chlorothiophen-3-yl)carbamate as a solid. $^1$H NMR (CDCl$_3$, 400 MHz): δ 7.53 (d, J=4.8 Hz, 1H), 7.11 (d, J=3.6 Hz, 1H), 6.82 (brs, 1H), 1.43 (s, 9H). MS calc'd [M-Boc+H]$^+$ 134.0, found 134.4.

Step 4: Into a 10 mL round bottom flask containing a solution of tert-butyl (4-chlorothiophen-3-yl)carbamate (400 mg, 1.7 mmol) in dichloromethane (4 mL) was added hydrochloric acid solution (4M solution in 1,4-dioxane, 0.3 mL) and the reaction mixture was stirred at room temperature for 2 h. The reaction mixture was concentrated under reduced pressure, triturated with diethyl ether and dried under high vacuum to afford 4-chlorothiophen-3-amine hydrochloride as a solid. $^1$H NMR (CD$_3$OD, 400 MHz): δ 7.64 (s, 2H). MS calc'd [M+H]$^+$ 134.0, found 134.4.

Intermediate 29

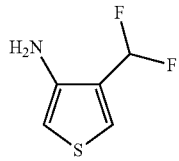

4-(Difluoromethyl)thiophen-3-amine

Step 1: Into a 100 mL round bottom flask containing a solution of 3,4-dibromothiophene (4.0 g, 17 mmol) in diethyl ether (50 mL) was added n-butyl lithium in hexane (1 M solution in hexanes, 17 mL, 17 mmol) at –78° C. over 15 min. To this mixture was added N,N-dimethylformamide and the reaction was stirred for 3 h. The reaction mixture was treated with saturated ammonium chloride solution and extracted with diethyl ether (2×50 mL). The combined organics were washed with water and brine, dried over anhydrous sodium sulfate, filtered and concentrated under reduced pressure to furnish 4-bromothiophene-3-carbaldehyde as a liquid which was directly taken to the next step without further purification. $^1$H NMR (CDCl$_3$, 400 MHz): δ 9.99 (s, 1H), 8.17 (s, 1H), 7.76 (s, 1H).

Step 2: Into a 50 mL round bottom flask containing a solution of 4-bromothiophene-3-carbaldehyde (3.5 g, 18 mmol) in dichloromethane (40 mL) was added diethylaminosulfur trifluoride (7.3 mL, 55 mmol) at 0° C. and the reaction was stirred room temperature for 16 h. The reaction mixture was diluted with dichloromethane (20 mL) and washed with saturated sodium bicarbonate solution, water and brine. The solution was dried over anhydrous sodium sulfate, filtered, concentrated under reduced pressure and purified by flash column chromatography eluting with ethyl acetate in petroleum ether (2-5%) to furnish 3-bromo-4-(difluoromethyl)thiophene as a liquid. $^1$H NMR (CDCl$_3$, 300 MHz): δ 7.68 (s, 1H), 7.35 (s, 1H), 6.67 (t, J=55.1 Hz, 1H).

Step 3: A solution of 3-bromo-4-(difluoromethyl)thiophene (800 mg, 4 mmol) in N,N-dimethylformamide (10 mL) at 0° C. was purged with ammonia gas for 1 h. To this mixture were added potassium phosphate tribasic (2.4 g, 11 mmol) and copper(II) acetylacetonate (300 mg, 1.9 mmol) and the reaction mixture was heated at 90° C. for 16 h. The reaction mixture was diluted with ethyl acetate (20 mL), washed with water and brine, dried over anhydrous sodium sulfate, filtered, concentrated under reduced pressure and purified by flash column chromatography eluting with ethyl acetate in petroleum ether (15-20%) to furnish 4-(difluoromethyl)thiophen-3-amine as a liquid. $^1$H NMR (CDCl$_3$, 300 MHz): δ 7.36 (d, J=2.9 Hz, 1H), 6.63 (t, J=55.7 Hz, 1H), 6.24 (d, J=3.3 Hz, 1H). MS calc'd [M+H]$^+$ 150.0, found 150.4.

Intermediate 30

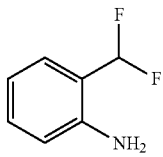

2-(Difluoromethyl)aniline hydrobromide

Step 1: Into a 250 mL round bottom flask containing a solution of methyl 2-formylbenzoate (5.0 g, 30 mmol) in dichloromethane (80 mL) were added diethylaminosulfur trifluoride (7 mL, 52 mmol) and methanol (1.5 mL) at −5° C. and the reaction was stirred at room temperature for 16 h. The reaction mixture was diluted with dichloromethane (20 mL) and washed with saturated sodium bicarbonate solution, water and brine. The solution was dried over anhydrous sodium sulfate, filtered and concentrated under reduced pressure to afford methyl 2-(difluoromethyl)benzoate as an oil which was taken to the next step without further purification.

Step 2: Into a 100 mL round bottom flask containing a solution of methyl 2-(difluoromethyl)benzoate (4.3 g, 23 mmol) in tetrahydrofuran (30 mL) and water (15 mL) was added lithium hydroxide monohydrate (2.9 g, 69 mmol) at 0° C. and the reaction mixture was stirred at room temperature for 16 h. The reaction mixture was concentrated under reduced pressure and acidified to pH 2 using diluted hydrochloric acid (1.5 N). The reaction mixture was extracted with ethyl acetate. The combined organics were washed with water and brine, dried over anhydrous sodium sulfate, filtered and concentrated under reduced pressure to afford 2-(difluoromethyl)benzoic acid (4.0 g). The crude product was taken to the next step without further purification. MS calc'd [M−H]$^+$ 171.0, found 171.0.

Step 3: Into a 100 mL round bottom flask containing a solution of 2-(difluoromethyl)benzoic acid (4.0 g, 23 mmol) in toluene (50 mL) were added diphenylphosphoryl azide (5.5 mL, 26 mmol), N,N-diisopropylethylamine (5 mL, 28 mmol) and tert-butanol (7 mL) and the mixture was stirred at room temperature for 30 min and at 110° C. for 16 h. The reaction mixture was concentrated under reduced pressure. The residue was dissolved in ethyl acetate (120 mL), washed with water and brine, dried over anhydrous sodium sulfate, filtered and concentrated under reduced pressure. The residue was purified by column chromatography eluting with ethyl acetate in petroleum ether (5-10%) to furnish tert-butyl (2-(difluoromethyl)phenyl)carbamate as a liquid. $^1$H NMR (CDCl$_3$, 300 MHz): δ 8.01 (d, J=8.2 Hz, 1H), 7.49-7.38 (m, 2H), 7.14 (t, J=7.5 Hz, 1H), 6.86 (brs, 1H), 6.68 (t, J=55.1 Hz, 1H), 1.53 (s, 9H).

Step 4: Into a 10 mL round bottom flask containing a solution of tert-butyl (2-(difluoromethyl)phenyl)carbamate (650 mg) in dichloromethane (5 mL) was added HBr in acetic acid (0.5 mL) at 0° C. and the reaction was stirred at room temperature for 2 h. The reaction mixture was concentrated under reduced pressure, triturated with diethyl ether and dried under high vacuum to afford 2-(difluoromethyl)aniline hydrobromide as a solid. $^1$H NMR (DMSO-d$_6$, 400 MHz): δ 7.37-7.35 (m, 1H), 7.32-7.28 (m, 1H), 7.07 (t, J=55.2 Hz, 1H), 6.95-6.93 (m, 1H), 6.88-6.84 (m, 1H). MS calc'd [M+H]$^+$ 144.1, found 144.4.

Intermediate 31

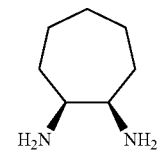

cis-Cycloheptane-1,2-diamine

Step 1: Into a 100 mL round bottom flask containing a solution of cycloheptene (1.0 g, 10.4 mmol) in t-butyl alcohol (20 mL) and water (10 mL) was added N-methyl morpholine-N-oxide (1.3 g, 10.5 mmol) followed by the addition of osmium tetroxide (4% in water, 13.2 mL, 0.2 mmol) and the reaction mixture was stirred at room temperature for 2 h. The reaction mixture was treated with water and extracted with dichloromethane and the organic layer was washed with water and brine. The solution was dried over sodium sulfate, filtered, and concentrated under reduced pressure. The residue was purified by flash chromatography using ethyl acetate in hexane (30-50%) to afford cis-cycloheptane-1,2-diol as a solid. $^1$H NMR (CD$_3$OD, 300 MHz): δ 3.80-3.77 (m, 2H), 1.84-1.31 (m, 10H).

Step 2: Into a 50 mL round bottom flask containing a solution of cis-cycloheptane-1,2-diol (500 mg, 4.0 mmol) in dichloromethane (10 mL) were added triethylamine (1.0 mL, 7.7 mmol) and methanesulfonyl chloride (0.75 mL, 9.6 mmol) at 0° C. and the reaction mixture was stirred at 0° C. for 1 h. The reaction mixture was diluted with dichloromethane and washed with saturated sodium bicarbonate solution, water and brine. The solution was dried over anhydrous sodium sulfate, filtered and concentrated under reduced pressure to afford cis-cycloheptane-1,2-diyl dimethanesulfonate (400 mg, 37%) which was carried to the next step without further purification. $^1$H NMR (CD$_3$OD, 400 MHz): δ 5.02-5.00 (m, 2H), 3.15 (s, 6H), 2.18-2.11 (m, 2H), 2.10-1.95 (m, 2H), 1.79-1.75 (m, 2H), 1.68-61 (m, 4H).

Step 3: Into a 25 mL round bottom flask containing a solution of cis-cycloheptane-1,2-diyl dimethanesulfonate (400 mg, 1.4 mmol) in dimethylformamide (5 mL) was added sodium azide (750 mg, 11.5 mmol) and the reaction was heated at 65° C. for 12 h. The reaction mixture was concentrated under reduced pressure and purified by flash chromatography eluting with methanol in dichloromethane (10-15%) to afford cis-1,2-diazidocycloheptane as a liquid. $^1$H NMR (DMSO-d$_6$, 400 MHz): δ 3.96-3.94 (m, 2H), 1.77-1.74 (m, 4H), 1.59-1.49 (m, 6H).

Step 4: Into a 25 mL round bottom flask containing a solution of cis-1,2-diazidocycloheptane (200 mg, 1.0 mmol) in ethanol (20 mL) was added palladium on carbon (20 mg, 10% w/w) under nitrogen. The resulting slurry was stirred at 65° C. for 3 h under hydrogen pressure using bladder. The reaction mixture was filtered through celiete and washed with methanol. The filtrate was concentrated under reduced pressure and purified by flash chromatography eluting with methanol in dichloromethane (4-6%) to afford cis-cycloheptane-1,2-diamine as a solid. $^1$H NMR (DMSO-$d_6$, 400 MHz): δ 3.66-3.51 (m, 2H), 1.89-1.76 (m, 4H), 1.65-1.51 (m, 6H). MS calc'd [M+H]$^+$ 129.1, found 129.2.

Intermediate 32

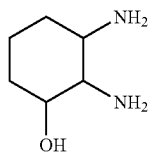

2,3-Diaminocyclohexan-1-ol

Step 1: Into a 250 mL round bottom flask containing a solution of 2-cyclohexen-1-ol (5.0 g, 51 mmol) in dichloromethane (130 mL) were added pyridine (12 mL, 153 mmol) and TBDMSCl (11.0 g, 76 mmol) at 0° C. and the reaction mixture was stirred for 6 h. The reaction mixture was concentrated under reduced pressure and purified by flash chromatography eluting with ethyl acetate in petroleum ether (2-5%) to afford tert-butyl(cyclohex-2-en-1-yloxy)dimethylsilane as a liquid. $^1$H NMR (CDCl$_3$, 400 MHz): δ 5.77-5.73 (m, 1H), 5.65-5.62 (m, 1H), 4.24-4.22 (m, 1H), 2.03-1.99 (m, 4H), 1.84-1.80 (m, 2H), 0.91 (s, 9H), 0.08 (s, 6H).

Step 2: Into a 250 mL round bottom flask containing a solution of tert-butyl(cyclohex-2-en-1-yloxy)dimethylsilane (8.7 g, 41 mmol) in acetonitrile (150 mL) was added N-methyl morpholine-N-oxide (50% in water, 19 mL, 82 mmol) at 0 followed by the addition of osmium tetroxide (4% in water, 0.3 mL) and the reaction mixture was stirred at room temperature overnight. The reaction mixture was diluted with ethyl acetate, washed with water and brine, dried over anhydrous sodium sulfate, filtered and concentrated under reduced pressure. The residue was purified by flash chromatography eluting with ethyl acetate in petroleum ether (20-25%) to afford 3-((tert-butyldimethylsilyl)oxy) cyclohexane-1,2-diol as a liquid.

Step 3: Into a 250 mL round bottom flask containing a solution of 3-((tert-butyldimethylsilyl)oxy)cyclohexane-1,2-diol (10.0 g, 41 mmol) in dichloromethane (100 mL) was added pyridine (17 mL, 206 mmol) at 0° C. followed by the addition of methanesulfonyl chloride (8.0 mL, 103 mmol) and the reaction mixture was stirred at room temperature overnight. The reaction mixture was treated with sodium bicarbonate solution (10% in water, 20 mL) and extracted with dichloromethane. The combined organic fractions were washed with water and brine, dried over anhydrous sodium sulfate, filtered and concentrated under reduced pressure. The residue was purified by flash column chromatography eluting with ethyl acetate in petroleum ether (18-22%) to afford 3-((tert-butyldimethylsilyl)oxy) cyclohexane-1,2-dimethanesulfonate as a liquid.

Step 4: Into a 250 mL round bottom flask containing a solution of 3-((tert-butyldimethylsilyl)oxy) cyclohexane-1,2-dimethanesulfonate (13.0 g, 32 mmol) in dimethylformamide (100 mL) were added HMPA (21 mL) and sodium azide (11.0 g, 164 mmol) and the reaction mixture was heated at 75° C. overnight. The reaction mixture was cooled to room temperature, diluted with diethyl ether, washed with water and brine, dried over anhydrous sodium sulfate, filtered and concentrated under reduced pressure to afford 2-azido-6-((tert-butyldimethylsilyl)oxy)cyclohexyl methanesulfonate as a solid.

Step 5: Into a 250 mL round bottom flask containing a solution of 2-azido-6-((tert-butyldimethylsilyl)oxy)cyclohexyl methanesulfonate (9.0 g, 26 mmol) in dimethylformamide (100 mL) were added HMPA (25 mL) and sodium azide (19.0 g, 294 mmol) and the reaction mixture was heated at 120° C. for 24 h. The reaction mixture was cooled to room temperature, diluted with diethyl ether, washed with water and brine, dried over anhydrous sodium sulfate, filtered and concentrated under reduced pressure. The residue was purified by flash chromatography eluting with ethyl acetate in petroleum ether (4-6%) to afford tert-butyl((2,3-diazidocyclohexyl)oxy)dimethylsilane as a liquid.

Step 6: Into a 250 mL round bottom flask containing a solution of tert-butyl((2,3-diazidocyclohexyl)oxy)dimethylsilane (4.6 g, 16 mmol) in tetrahydrofuran (150 mL) was added tetrabutyl ammonium fluoride (1 M in THF, 24 mL, 24 mmol) and the reaction mixture was stirred at room temperature for 4 h. The reaction mixture was concentrated under reduced pressure and purified by flash chromatography eluting with ethyl acetate in petroleum ether (10-15%) to afford 2,3-diazidocyclohexan-1-ol as a liquid.

Step 7: Into a 100 mL round bottom flask containing a solution of 2,3-diazidocyclohexan-1-ol (2.7 g, 15 mmol) in methanol (45 mL) was added palladium on carbon (540 mg, 20% w/w) and the reaction was stirred at room temperature overnight under hydrogen bladder pressure. The reaction mixture was filtered through celite and washed with methanol and the filtrate was concentrated under reduced pressure to afford 2,3-diaminocyclohexan-1-ol as a liquid. MS calc'd [M+H]$^+$ 131.1, found 131.2.

Intermediate 33

3-Fluorocyclohexane-1,2-diamine

Step 1: Into a 100 mL round bottom flask containing a solution of 2,3-diaminocyclohexan-1-ol (1.8 g, 14 mmol) in dichloromethane (50 mL) were added triethylamine (9.3 mL, 68 mmol) and di-tert-butyl-dicarbonate (9.8 mL, 40 mmol) and the reaction mixture was stirred at room temperature overnight. The reaction mixture was diluted with dichloromethane and washed with water and brine. The organic layer was dried over anhydrous sodium sulfate, filtered and concentrated under reduced pressure. The residue was purified by column chromatography eluting with ethyl acetate in petroleum ether (25-30%) to afford tert-butyl (2-amino-3-hydroxycyclohexyl)carbamate as a liquid. MS calc'd [M+H]$^+$ 231.2, found 231.0.

Step 2: Into a 50 mL round bottom flask containing a solution of tert-butyl (2-amino-3-hydroxycyclohexyl)carbamate (500 mg, 2 mmol) in dichloromethane (10 mL) was added diethylaminosulfur trifluoride (0.6 mL, 4.4 mmol) at −30° C. and the reaction was allowed to stir at room temperature for 3 h. The reaction mixture was diluted with dichloromethane (100 mL) and washed with saturated sodium bicarbonate solution, water and brine, dried over sodium sulfate, filtered and concentrated under reduced pressure. The residue was purified by flash column chromatography eluting with ethyl acetate in petroleum ether (15-18%) to afford of tert-butyl (2-amino-3-fluorocyclohexyl) carbamate as a solid.

Step 3: Into a 50 mL round bottom flask containing a solution of tert-butyl (2-amino-3-fluorocyclohexyl)carbamate (250 mg, 1 mmol) in dichloromethane (10 mL) was added hydrochloric acid in dioxane (4.5 N, 5 mL) and the reaction was stirred at room temperature for 2 h. The solvent was removed under reduced pressure to afford 3-fluorocyclohexane-1,2-diamine hydrochloride as a liquid. MS calc'd [M+H]$^+$ 133.1, found 133.0.

Intermediate 34

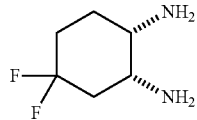

(1S,2R)- or
(1R,2S)-4,4-difluorocyclohexane-1,2-diamine

Step 1: Into a 500 mL round bottom flask containing a solution of cyclohexa-1,4-diene (5.0 g, 63 mmol) in acetonitrile (150 mL) were added N-methyl morpholine N-oxide (7.0 g, 63 mmol) and osmium tetroxide (4% wt in H$_2$O, 0.2 mL) at 0° C. and the reaction was stirred at room temperature for 5 h. The reaction mixture was diluted with ethyl acetate and washed with water and brine, dried over anhydrous sodium sulfate, filtered and concentrated under reduced pressure. The residue was purified by flash chromatography eluting with ethyl acetate in petroleum ether (65-70%) to afford cyclohex-4-ene-1,2-diol as a solid. $^1$H NMR (CDCl$_3$, 300 MHz): δ 5.63-5.52 (m, 2H), 3.97-3.88 (m, 2H), 2.41-2.21 (m, 4H), 1.99-1.92 (m, 2H).

Step 2: Into a 250 mL round bottom flask containing a solution of cyclohex-4-ene-1,2-diol (2.8 g, 25 mmol) in dichloromethane (50 mL) were added triethylamine (10.0 mL, 74 mmol) and methanesulfonic anhydride (8.5 g, 50 mmol) and the reaction mixture was stirred at room temperature for 1 h. The reaction mixture was diluted with dichloromethane and washed with water and brine, dried over anhydrous sodium sulfate, filtered and concentrated under reduced pressure. The residue was purified by flash chromatography eluting with ethyl acetate in petroleum ether (30-40%) to afford cyclohex-4-ene-1,2-diyl dimethanesulfonate as a liquid. $^1$H NMR (CDCl$_3$, 300 MHz): δ 5.63-5.58 (m, 2H), 5.06-4.99 (m, 2H), 3.11 (s, 6H), 2.65-2.41 (m, 4H).

Step 3: Into a 250 mL round bottom flask containing a solution of cyclohex-4-ene-1,2-diyl dimethanesulfonate (3.8 g, 14 mmol) in dimethyl sulfoxide (40 mL) was added sodium azide (2.7 g, 43 mmol) and the reaction mixture was stirred at 80° C. for 48 h. The reaction mixture was cooled to room temperature, diluted with ethyl acetate, washed with water and brine, dried over anhydrous sodium sulfate, filtered and concentrated under reduced pressure. The residue was purified by flash chromatography eluting with ethyl acetate in petroleum ether (20-35%) to afford 4,5-diazidocyclohex-1-ene as a solid. $^1$H NMR (CDCl$_3$, 300 MHz): δ 5.71-5.58 (m, 2H), 3.82-3.79 (m, 2H), 2.41-2.39 (m, 4H).

Step 4 & 5: Into a 250 mL round bottom flask containing a solution of 4,5-diazidocyclohex-1-ene (1.3 g, 8 mmol) in tetrahydrofuran (30 mL) was added lithium aluminum hydride (1M THF, 16 mL, 16 mmol) dropwise at 0° C. and the reaction mixture was stirred at room temperature for 1 h. The reaction mixture was treated with saturated sodium sulfate and the precipitate was filtered through celite and washed with ethyl acetate. The filtrate was concentrated under reduced pressure and crude product obtained was taken to the next step without further purification. To a stirred solution of the crude product in tetrahydrofuran (30 mL) were added triethylamine (3.8 mL, 28 mmol) and benzyl chloroformate (3.0 mL, 20 mmol) at 0° C. and the reaction was stirred at room temperature overnight. The reaction mixture was diluted with ethyl acetate, washed with water and brine, dried over anhydrous sodium sulfate, filtered and concentrated under reduced pressure. The residue was purified by flash chromatography eluting with ethyl acetate in petroleum ether (25-30%) to afford dibenzyl cyclohex-4-ene-1,2-diyldicarbamate as a solid. $^1$H NMR (CDCl$_3$, 400 MHz): δ 7.38-7.35 (m, 10H), 5.63 (s, 4H), 5.32-5.29 (m, 2H), 4.17-4.05 (m, 2H), 2.60-2.56 (m, 2H), 2.06-2.22 (m, 2H). MS calc'd [M+H]$^+$381.2, found 381.2.

Step 6: Into a 100 mL round bottom flask containing a solution of dibenzyl cyclohex-4-ene-1,2-diyldicarbamate (1.7 g, 4.4 mmol) in tetrahydrofuran (35 mL) was added borane-methyl sulfide complex (1.2 mL) at 0° C. and the reaction was stirred at room temperature for 14 h. To this reaction mixture were added sodium hydroxide (10% in water, 14 mL) and hydrogen peroxide (30%, 14 mL) and the reaction was stirred for 1 h at room temperature. The reaction mixture was diluted with ethyl acetate, washed with water and brine, dried over anhydrous sodium sulfate, filtered and concentrated under reduced pressure. The residue was purified by flash chromatography eluting with ethyl acetate in petroleum ether (80-90%) to afford dibenzyl (4-hydroxycyclohexane-1, 2-diyl) dicarbamate as a solid. MS calc'd [M+H]$^+$ 339.2, found 399.2.

Step 7: Into a 250 mL round bottom flask containing a solution of dibenzyl (4-hydroxycyclohexane-1, 2-diyl) dicarbamate (1.5 g, 3.7 mmol) in dichloromethane (60 mL) was added Dess-Martin periodinane (4.7 g, 11 mmol) at 0° C., and reaction was stirred at room temperature overnight. The reaction mixture was treated with saturated sodium bicarbonate solution, washed with water and brine, dried over anhydrous sodium sulfate, filtered and concentrated under reduced pressure. The residue was purified by flash chromatography eluting with ethyl acetate in petroleum ether (35-50%) to afford dibenzyl (4-oxocyclohexane-1, 2-diyl) dicarbamate (1.0 g, 67% yield) as solid. MS calc'd [M+H]$^+$ 397.2, found 397.0.

Step 8: Into a 50 mL round bottom flask containing a solution of dibenzyl (4-oxocyclohexane-1, 2-diyl) dicarbamate (1.0 g, 2.5 mmol) in dichloromethane (30 mL) was added diethylaminosulfur trifluoride (0.7 mL, 5 mmol) at 0° C. and the reaction was stirred at room temperature for 16 h. The reaction mixture was treated with saturated sodium bicarbonate solution, washed with water and brine, dried over anhydrous sodium sulfate, filtered and concentrated under reduced pressure. The residue was purified by flash chromatography eluting with ethyl acetate in petroleum ether (20-30%) to afford dibenzyl (4,4,-difluorocyclohexane-1,2-diyl)dicarbamate as a solid. The product was further purified by chiral SFC: [(Column: Lux C1 (250×30) mm; Mobile Phase: CO$_2$: 0.5% DEA in Methanol (75:25); Total Flow: 100 g/min; Cycle time: 10 min.; Total Run time: 15 min; Pressure: 100 bar; Wavelength: 256 nm; Inj. volume: 0.5 mL (50 mg/Injection)] to yield two enantiomers. Isomer 1: MS [M+H]$^+$ 419.4; Chiral SFC retention time: 13.77 min. Isomer 2: MS [M+H]$^+$ 419.4; Chiral SFC retention time: 16.77 min.

Step 9: A mixture of dibenzyl ((1S,2R)- or (1R,2S)-4,4-difluorocyclohexane-1,2-diyl)dicarbamate (Isomer 1) (1.4 g, 3.4 mmol) and hydrobromic acid solution (33% in acetic acid, 15 mL) was taken in a 50 mL round bottom flask and the reaction mixture was stirred at room temperature for 1 h. The solvent was removed under reduced pressure to afford (1S,2R)- or (1R,2S)-4,4-difluorocyclohexane-1,2-diamine hydrobromide. $^1$H NMR (CD$_3$OD, 400 MHz): δ 3.98-3.94 (m, 2H), 2.56-2.44 (m, 2H), 2.24-2.00 (m, 4H).

(1S,2R)- or (1R,2S)-4,4-difluorocyclohexane-1,2-diamine hydrobromide was prepared from Isomer 2 in an analogous manner of that described in Intermediate 34.

Intermediate 35

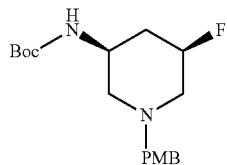

tert-Butyl ((3S,5R)-5-fluoro-1-(4-methoxybenzyl) piperidin-3-yl)carbamate

Step 1 & 2: Into a 2 L round bottom flask containing a solution of trans-4-hydroxy-L-proline (25.0 g, 191 mmol) in methanol (1.2 L) at 0° C. was added thionyl chloride (17 mL, 229 mmol) dropwise and the reaction mixture was heated at reflux for 16 h. The reaction mixture was cooled to room temperature and concentrated under reduced pressure to afford methyl (2S,4R)-4-hydroxypyrrolidine-2-carboxylate (30 g) which was taken to the next step without further purification.

To a stirred solution of the crude methyl (2S,4R)-4-hydroxypyrrolidine-2-carboxylate (30 g) in dichloromethane (1.25 L) were added triethylamine (67 mL, 476 mmol) and 4-methoxybenzyl chloride (52 mL, 381 mmol) and the reaction mixture was heated at reflux for 8 h. Sodium hydroxide solution (1M in water, 700 mL) was added to the reaction mixture and the reaction was stirred for 10 min. The organic layer was separated, washed with water and brine, dried over anhydrous sodium sulfate, filtered and concentrated under reduced pressure. The residue was purified by flash column chromatography eluting with ethyl acetate in petroleum ether (30-40%) to afford methyl (2S,4R)-4-hydroxy-1-[(4-methoxyphenyl)methyl]pyrrolidine-2-carboxylate as an oil. $^1$H NMR (CDCl$_3$, 400 MHz): δ 7.25 (d, J=8.6 Hz, 2H), 6.86 (d, J=8.6 Hz, 2H), 4.48 (brs, 1H), 3.91-3.86 (m, 1H), 3.81 (s, 3H), 3.69-3.61 (m, 5H), 3.39-3.35 (m, 1H), 2.55-2.53 (m, 1H), 2.32-2.25 (m, 1H), 2.15-2.09 (m, 1H). MS [M+H]$^+$ 266.2.

Step 3 & 4: Into a 1 L round bottom flask containing a solution of (2S,4R)-methyl 4-hydroxy-1-[(4-methoxyphenyl)methyl]pyrrolidine-2-carboxylate (20.0 g, 75 mmol) in dichloromethane (130 mL) at 0° C. were added triethylamine (45 mL, 325 mmol) and methanesulfonyl chloride (13.0 mL, 162 mmol) and the reaction mixture was stirred at room temperature for 2 h. The reaction mixture was diluted with dichloromethane (200 mL) and washed with saturated sodium bicarbonate solution (300 mL), water and brine. The solution was dried over anhydrous sodium sulfate, filtered and concentrated under reduced pressure to afford methyl (2R,4R)-1-(4-methoxybenzyl)-4-((methylsulfonyl)oxy)pyrrolidine-2-carboxylate (25.0 g) which was taken to the next step without further purification.

To a stirred solution of the crude methyl (2R,4R)-1-(4-methoxybenzyl)-4-((methylsulfonyl)oxy)pyrrolidine-2-carboxylate (25.0 g, 71 mmol) in dimethylformamide (300 mL) was added sodium azide (15.0 g, 228 mmol) and the reaction mixture was heated at 65° C. for 8 h. The reaction mixture was cooled to room temperature, poured into water (500 mL) and extracted with ethyl acetate (3×300 mL). The combined organics were washed with water and brine, dried over anhydrous sodium sulfate and concentrated under reduced pressure. The residue was purified by flash column chromatography eluting with ethyl acetate in petroleum ether (10-20%) to afford (2S,4R)-methyl 4-azido-1-(4-methoxybenzyl)pyrrolidine-2-carboxylate as a liquid. $^1$H NMR (DMSO-d$_6$, 400 MHz): δ 7.20 (d, J=8.6 Hz, 2H), 6.87 (d, J=8.6 Hz, 2H), 3.98-3.95 (m, 1H), 3.86 (brs, 1H), 3.72 (s, 3H), 3.61 (s, 3H), 3.39-3.36 (m, 1H), 2.28-2.24 (m, 1H), 2.83-2.81 (m, 1H), 2.57-2.48 (m, 2H), 1.93-1.88 (m, 1H). MS calc'd [M+H]$^+$ 291.1, found 291.2.

Step 5 & 6: Into a 1 L round bottom flask containing a suspension of lithium aluminum hydride (8.0 g, 210 mmol) in tetrahydrofuran (500 mL) at 0° C. was added a solution of methyl (2S,4R)-4-azido-1-[(4-methoxyphenyl)methyl]pyrrolidine-2-carboxylate (16 g, 55 mmol) in tetrahydrofuran (350 mL) and the reaction mixture was stirred at 0° C. for 1 h and at room temperature for 3 h. The reaction mixture was cooled to 0° C. and treated successively with water (8 mL), sodium hydroxide solution (15% in water, 8 mL) and water (24 mL) dropwise over a period of 1 h. The precipitated slurry was passed through a celite and washed with tetrahydrofuran and the filtrate was concentrated under reduced pressure to afford ((2S,4S)-4-amino-1-(4-methoxybenzyl)pyrrolidin-2-yl)methanol. The crude product was dissolved in dioxane (600 mL) and di-tert-butyl dicarbonate (25.0 g, 220 mmol) was added and the reaction mixture was stirred at room temperature for 12 h. The mixture was diluted with ethyl acetate (200 mL) and washed with water and brine, dried over anhydrous sodium sulfate, filtered and concentrated under reduced pressure. The residue was purified by flash chromatography eluting with ethyl acetate in petroleum ether (60-70%) to afford tert-butyl ((3R,5S)-5-(hydroxymethyl)-1-(4-methoxybenzyl)pyrrolidin-3-yl)carbamate as a solid. $^1$H NMR (CDCl$_3$, 400 MHz): δ 7.24 (d, J=8.4 Hz, 2H), 6.88 (d, J=8.5 Hz, 2H), 5.31 (brs, 1H), 4.13 (brs, 1H), 3.97-3.90 (m, 1H), 3.81 (s, 3H), 3.71-3.65 (m, 1H), 3.49-3.45 (m, 2H), 2.99-2.97 (m, 1H), 2.88 (brs, 1H), 2.67-2.63 (m, 1H), 2.42-2.37 (m, 1H), 1.83-1.78 (m, 1H), 1.42 (s, 9H). MS calc'd [M+H]$^+$ 337.2, found 337.2.

Step 7: Into a 500 mL round bottom flask containing a solution of tert-butyl N-[(3R,5S)-5-(hydroxymethyl)-1-[(4-methoxyphenyl)methyl]pyrrolidin-3-yl]carbamate (12.0 g, 34 mmol) in tetrahydrofuran (250 mL) was added diethylaminosulfur trifluoride (6.0 mL, 48 mmol) at 0° C. and the reaction was stirred at 0° C. for 1 h and at room temperature for 12 h. The reaction mixture was cooled to 0° C. and treated with saturated sodium bicarbonate solution (30 mL).

The reaction mixture was extracted with ethyl acetate (2×100 mL) and combined organic fractions were dried over anhydrous sodium sulfate, filtered and concentrated under reduced pressure. The residue was purified by flash chromatography eluting with ethyl acetate in petroleum ether (10-12%) to afford tert-butyl ((3S,5R)-5-fluoro-1-(4-methoxybenzyl)piperidin-3-yl)carbamate as a solid. ¹H NMR (DMSO-d₆, 400 MHz): δ 7.18 (d, J=8.0 Hz, 2H), 6.87 (d, J=8.0 Hz, 2H), 6.78 (d, J=8.3 Hz, 1H), 5.31 (brs, 1H), 4.64-4.49 (m, 1H), 3.72 (s, 3H), 3.49-3.46 (m, 2H), 2.94 (brs, 1H), 2.71-2.69 (m, 1H), 2.11 (brs, 1H), 1.91-1.87 (m, 1H), 1.73-1.68 (m, 1H), 1.33 (s, 9H). MS calc'd [M−H]⁺ ³³⁹·², found 339.2.

The following intermediates were prepared in an analogous manner of that described in Intermediate 35.

| Intermediate # | Structure | IUPAC Name | Exact Mass [M + H]⁺ |
|---|---|---|---|
| 36 | 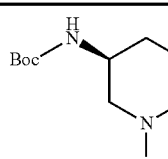 | tert-butyl ((3S,5S)-5-fluoro-1-(4-methoxybenzyl)piperidin-3-yl)carbamate | Calc'd 339.2, found 339.2 |
| 37 | 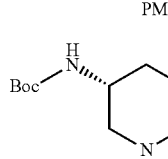 | tert-butyl ((3R,5R)-5-fluoro-1-(4-methoxybenzyl)piperidin-3-yl)carbamate | Calc'd 339.2, found 339.2 |
| 38 | 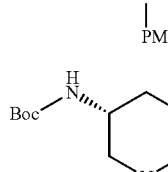 | tert-butyl ((3R,5S)-5-fluoro-1-(4-methoxybenzyl)piperidin-3-yl)carbamate | Calc'd 339.2, found 339.2 |

Intermediate 39

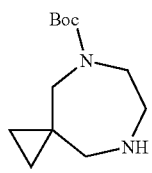

tert-Butyl 5,8-diazaspiro[2.6]nonane-5-carboxylate

Step 1: Into a 5 L 4 necked round bottomed flask was placed a solution of diethyl malonate (300 g, 1.87 mol) and 1,2-dibromoethane (634.5 g, 3.38 mol) in DMSO (1.5 L). The mixture was treated with K₂CO₃ (1020 g, 7.39 mol) and Bu₄NHSO₄ (6.4 g, 19 mmol). The resulting solution was allowed to stir for 48 h at room temperature. The reaction mixture was treated with 2 L of H₂O and extracted with 1.5 L of EtOAc (3×). The organic layers were combined, dried over Na₂SO₄ and concentrated under reduced pressure. The residue was distilled under 5-10 mmHg vacuum at 64-65° C. This resulted in diethyl cyclopropane-1,1-dicarboxylate as an oil.

Step 2: Into a 100 mL 3 necked round bottomed flask was placed THF (50 mL), then added LiAlH₄ (2 g, 53 mmol) in several batches. This was followed by the addition of a solution of diethyl cyclopropane-1,1-dicarboxylate (5 g, 27 mmol) in THF (10 mL) dropwise with stirring, while cooling to 0° C. The resulting solution was allowed to stir for 1 h at 0-5° C. in an ice bath. The reaction mixture was then treated with 2 mL of H₂O, 6 mL of 15% NaOH solution and 2 mL of H₂O. The mixture was filtered and the filtrate was concentrated under reduced pressure. The residue was extracted with 50 mL of EtOAc. The organic layer was dried over Na₂SO₄ and concentrated under reduced pressure to afford cyclopropane-1,1-diyldimethanol as a liquid.

Step 3: Into a 2 L 3 necked round bottomed flask were placed a solution of cyclopropane-1,1-diyldimethanol (42 g, 410 mmol) in DCM (200 mL) and DMAP (126 g, 1.03 mol). The mixture was treated with a solution of TsCl (173 g, 907 mmol) in DCM (500 mL) dropwise, while cooling to 0° C., over 30 min. The resulting solution was allowed to stir for 2.5 h at room temperature. The reaction mixture was washed with H₂O, HCl (1N) and brine, dried over Na₂SO₄ and concentrated under reduced pressure. This resulted in cyclopropane-1,1-diyldimethanediyl bis(4-methylbenzenesulfonate) as a solid Step 4: Into a 5 L 4 necked round bottomed flask was placed a solution of 4-methylbenzene-1-sulfonyl chloride (487 g, 2.55 mol) in ethyl ether (1 L). To the mixture was added a solution of ethane-1,2-diamine (77 g, 1.3 mol) and sodium hydroxide (102 g, 2.55 mol) in H₂O (1 L) dropwise while cooled to 0° C. The resulting solution was allowed to stir for 30 min at 0° C. in an ice bath, then overnight at room temperature. A filtration was performed and the filter cake was washed 2 times with H₂O and dried in an oven. This resulted in N,N-ethane-1,2-diylbis(4-methylbenzenesulfonamide) as a white solid.

Into a 5 L 4 necked round bottom flask were placed N,N-ethane-1,2-diylbis(4-methylbenzenesulfonamide) (150 g, 408 mmol), cyclopropane-1,1-diyldimethanediyl bis(4-methylbenzenesulfonate) (200 g, 487 mmol), 18-crown-6 (53 g, 200 mmol) and THF (2 L) followed by the addition of a solution of t-BuOK (100 g, 893 mmol) in THF (500 mL) dropwise with stirring at −30° C. The resulting solution was allowed to stir for 2 days at room temperature. The resulting mixture was concentrated under reduced pressure to remove most of THF. The residual solution was diluted with 1500 mL of H$_2$O. The precipitate was collected by filtration and dried. The residue was purified by eluting through a silica gel column with dichloromethane/petroleum ether (1:10-1:2). This resulted in 5,8-bis[(4-methylphenyl)sulfonyl]-5,8-diazaspiro[2.6]nonane as a solid.

Step 5: Into a 5 L 4 necked round bottomed flask was placed a solution of 5,8-bis[(4-methylphenyl)sulfonyl]-5,8-diazaspiro[2.6]nonane (100 g, 230 mmol) in MeOH (1500 mL). To the mixture was added magnesium (27.4 g, 1.14 mol) batchwise when the reaction mixture was warmed at 40° C. The resulting mixture was allowed to stir for 2 h at room temperature. The resulting mixture was concentrated under reduced pressure to remove MeOH. The residue was diluted with 500 mL of EtOAc and filtered. The filtrate was treated with a solution of oxalic acid (23 g, 255 mmol) in Et$_2$O (500 mL). The precipitate was collected by filtration and dried. This resulted in 5-[(4-methylphenyl)sulfonyl]-5,8-diazaspiro[2.6]nonane ethanedioate as a solid.

Step 6: Into a 2 L 3 necked round bottomed flask was placed a solution of 5-[(4-methylphenyl)sulfonyl]-5,8-diazaspiro[2.6]nonane ethanedioate (50 g, 121.48 mmol, 90%) in DCM (800 mL) and Et$_3$N (31 g, 310 mmol). To the mixture was added Boc$_2$O (26 g, 119 mmol) at 0-5° C. The resulting solution was allowed to stir overnight at room temperature. The reaction mixture was washed with 3×500 mL of H$_2$O and 1×500 mL of brine. The organic layer was dried over Na$_2$SO$_4$ and concentrated under reduced pressure. This resulted in 45 g of tert-butyl 8-[(4-methylphenyl)sulfonyl]-5,8-diazaspiro[2.6]nonane-5-carboxylate as a yellow oil.

Step 7: Into a 3 L 3 necked round bottomed flask was placed a solution of tert-butyl 8-[(4-methylphenyl)sulfonyl]-5,8-diazaspiro[2.6]nonane-5-carboxylate (110 g, 232 mmol, 80%) in MeOH (1800 mL). To the mixture was added Mg (36 g, 1.50 mol) in several batches at 40° C. The resulting solution was allowed to stir for 1 h at room temperature. The resulting mixture was concentrated under reduced pressure. The residue was diluted with 1 L of EtOAc and filtered. The filtrate was treated with a solution of oxalic acid in ether to precipitate the product. The solid was collected by filtration and washed 2 times with ether. This resulted in tert-butyl 5,8-diazaspiro[2.6]nonane-5-carboxylate ethanedioate as a solid. $^1$H-NMR (400 MHz, D$_2$O): δ 0.71-0.736 (d, J=9.6 Hz, 2H), 0.75-0.78 (d, J=9.6 Hz, 2H), 0.77 (m, 4H), 1.42 (s, 9H), 3.18 (s, 2H), 3.33-3.39 (m, 4H), 3.78 (s, 1H). MS [M+H]$^+$ 227.

Intermediate 40

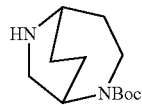

tert-Butyl 2,6-diazabicyclo[3.2.2]nonane-2-carboxylate

Step 1. Into a 10 L 4 necked round bottomed flask were placed 4-methoxybenzenamine (500 g, 4.07 mol), CH$_2$O (507.5 g, 16.92 mol), cyclohex-2-enone (780 g, 8.12 mol), L-proline (140 g, 365 mmol) and DMSO (3.5 L). The resulting solution was allowed to stir for 24 h while the temperature was maintained at 50° C. The reaction mixture was treated with 3 L of H$_2$O and extracted three times with 2 L of EtOAc. The organic layers were combined, washed 3 times with 2 L of H$_2$O, dried and concentrated under reduced pressure. The residue was purified by eluting through a silica gel column with a 15:1 EtOAc/PE solvent system. This resulted in 6-(4-methoxyphenyl)-6-aza-bicyclo[2.2.2]octan-3-one as a solid.

Step 2. Into a 3 L 4 necked round bottomed flask was placed a solution of 6-(4-methoxyphenyl)-6-aza-bicyclo[2.2.2]octan-3-one (294 g, 1.27 mol) in CH$_3$OH (2 L). To this were added K$_2$CO$_3$ (351 g, 2.54 mol) and NH$_2$OH.HCl (176 g, 2.55 mol). The resulting solution was allowed to stir for 3 h while the temperature was maintained at 30° C. The reaction mixture was concentrated under reduced pressure. The residue was washed two times with 1 L of H$_2$O and dried. This resulted in N-hydroxy-2-(4-methoxyphenyl)-2-azabicyclo[2.2.2]octan-5-imine as a solid.

Step 3. Into a 3 L 4 necked round bottomed flask was placed a solution of N-hydroxy-2-(4-methoxyphenyl)-2-azabicyclo[2.2.2]octan-5-imine (300 g, 1.22 mol) in PPA (1500 mL). The resulting solution was allowed to stir for 3 h while the temperature was maintained at 100° C. After cooled to room temperature, the reaction mixture was adjusted to pH 7 by the addition of Na$_2$CO$_3$ and extracted three times with 2 L of EtOAc. The organic layers were combined, dried over Na$_2$SO$_4$ and concentrated under reduced pressure. The residue was purified by eluting through a silica gel column with a 1:1 EtOAc:PE solvent system. This resulted in 6-(4-methoxyphenyl)-2,6-diazabicyclo[3.2.2]nonan-3-one as a solid.

Step 4. Into a 2 L 4 necked round bottomed flask were placed 6-(4-methoxyphenyl)-2,6-diaza-bicyclo[3.2.2]nonan-3-one (102 g, 415 mmol), NaBH$_4$ (46.7 g, 1.23 mol) and THF (1500 mL). To the mixture was added BF$_3$Et$_2$O (501 g, 3.53 mol) dropwise with stirring at 10° C. The resulting solution was allowed to stir for 12 h at 10° C. The reaction mixture was treated with 200 mL of diluted HCl and concentrated under reduced pressure to remove most of THF. The residual solution was extracted three times with 1 L of EtOAc. The organic layers were combined, dried over Na$_2$SO$_4$ and concentrated under reduced pressure. The residue was purified by eluting through a silica gel column with DCM. This resulted in 6-(4-methoxyphenyl)-2,6-diaza-bicyclo[3.2.2]nonane as a liquid.

Step 5. Into a 2 L 2 necked round bottomed flask were placed a solution of 6-(4-methoxyphenyl)-2,6-diaza-bicyclo[3.2.2]nonane (80 g, 346 mmol) in THF (800 mL) and NaOH (15 g, 375 mmol) followed by the addition of a solution of (Boc)$_2$O (112 g, 519 mmol) in THF (200 mL) dropwise with stirring, while cooling to a temperature of 0° C. The resulting solution was allowed to stir for 12 h at room temperature. The reaction mixture was concentrated under reduced pressure to remove most of THF. The residual solution was diluted with 500 mL of H$_2$O and extracted three times with 500 mL of PE and three times with 500 mL of EtOAc. The organic layers were combined, dried over Na$_2$SO$_4$ and concentrated under reduced pressure. This resulted in tert-butyl 6-(4-methoxyphenyl)-2,6-diazabicyclo[3.2.2]nonane-2-carboxylate as a solid.

Step 6. Into a 10 L 3 necked round bottomed flask was placed a solution of tert-butyl 6-(4-methoxyphenyl)-2,6-diazabicyclo[3.2.2]nonane-2-carboxylate (107 g, 322 mmol) in CH$_3$CN (6 L) followed by the addition of a solution of (NH$_4$)$_2$Ce(NO$_3$)$_6$ (529 g, 965 mmol) in H$_2$O (2 L) dropwise with stirring at −40° C. The resulting solution was allowed to stir for 2 h at −40° C. After warmed up to room temperature, the reaction mixture was concentrated under reduced pressure to remove most of MeCN. The pH value of the residual solution was adjusted to 12 with NaOH and the mixture was extracted three times with 2 L of ether. The organic layers were combined, dried over Na$_2$SO$_4$ and concentrated under reduced pressure. The residue was treated with a solution of oxalic acid (29 g, 322 mmol) in Et$_2$O. The solid was collected and dried to afford tert-butyl 2,6-diazabicyclo[3.2.2]nonane-2-carboxylate ethanedioate as a solid. $^1$H-NMR (400 MHz, D$_2$O): δ 4.35 (m, 1H), 3.82 (m, 2H), 3.44 (m, 1H), 3.14 (m, 3H), 1.94 (m, 6H), 1.34 (s, 9H), 1.07 (m, 1H). MS [M+H]$^+$ 227.

Intermediate 41

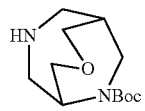

tert-Butyl 3-oxa-7,9-diazabicyclo[3.3.2]decane-9-carboxylate

Step 1. Under N$_2$, a mixture of benzylamine (51.2 g, 0.48 mol), HCl (37%, 22.40 g, 0.22 mol), glacial acetic acid (43.2 g, 0.72 mol), and paraformaldehyde (115.2 g, 3.84 mol) was mechanically stirred for 15 min at ambient temperature. In one portion, tetrahydropyran-4-one (48 g, 0.48 mol) was added to the mixture which was then brought to reflux overnight. After cooling to ambient temperature, the resulting mixture was dissolved in H$_2$O (700 mL) and made basic (pH~12) with NaOH pellets in an ice-water bath. This solution was extracted with ethyl acetate (3×700 mL), dried (Na$_2$SO$_4$), filtered, and concentrated to give 7-benzyl-3-oxa-7-azabicyclo[3.3.1]nonan-9-one as an oil which was used in the next step without further purification. $^1$H NMR (300 MHz, CDCl$_3$): δ 7.34 (m, 5H), 4.20 (d, J=11.4 Hz, 2H), 3.90 (d, J=11.1 Hz, 2H), 3.56 (s, 2H), 2.95 (d, J=11.1 Hz, 2H), 2.91 (m, 2H), 2.53 (s, 2H).

Step 2. To a stirred solution of 7-benzyl-3-oxa-7-azabicyclo[3.3.1]nonan-9-one (44.0 g, 0.14 mol) in CHCl$_3$ (720 mL) was added conc. H$_2$SO$_4$ (145 g, 1.45 mol) dropwise and the mixture was treated with sodium azide (20.2 g, 0.31 mol) in small portions at 0-5° C. The reaction mixture was heated at reflux for 16 h. After cooling to ambient temperature, the reaction mixture was poured into ice-water and the resulting mixture was neutralized with Na$_2$CO$_3$. The pH of this mixture was adjusted to 13 with 10% NaOH and extracted with CHCl$_3$ (3×500 mL). The combined organic layers were dried over Na$_2$SO$_4$, filtered, and concentrated to give a brown oil. The residue was purified by flash chromatography (PE:EA=10:1) to give 7-benzyl-3-oxa-7,9-diazabicyclo[3.3.2]decan-10-one as a solid. $^1$H NMR (300 MHz, CDCl$_3$): δ 7.32 (m, 5H), 6.29 (s, 1H), 3.94 (m, 1H), 3.89 (m, 4H), 3.66 (s, 2H), 3.37 (m, 1H), 2.80 (m, 2H), 2.72 (m, 2H). MS [M+H]$^+$ 247.

Step 3. A solution of 7-benzyl-3-oxa-7,9-diazabicyclo[3.3.2]decan-10-one (3 g, 12 mmol) in THF (60 mL) was added to a suspension of LiAlH$_4$ (1.0 g, 26 mmol) in THF (40 mL) dropwise at 0° C. After stirring for 30 min at 0° C., the reaction mixture was warmed to gentle reflux overnight. The reaction mixture was cooled to room temperature and treated with water (2 mL), 15% NaOH (2 mL) and water (6 mL). The mixture was filtered, concentrated, and purified by silica gel column chromatography (PE:EA=3:1) to give 3-benzyl-7-oxa-3,10-diaza-bicyclo[3.3.2]decane as an oil. $^1$H NMR (300 MHz, CDCl$_3$): δ 7.34 (m, 5H), 3.95 (m, 2H), 3.7 (m, 2H), 3.66 (s, 2H), 3.32 (m, 3H), 2.80 (m, 4H), 2.70 (m, 2H). MS [M+H]$^+$ 233.

Step 4. To a stirred solution of 3-benzyl-7-oxa-3,10-diaza-bicyclo[3.3.2]decane (1.34 g, 5.78 mmol) in THF (40 mL) was added K$_2$CO$_3$ (1.0 g, 7.3 mmol) followed by the addition of di-tert-butyl-dicarbonate (1.51 g, 6.93 mmol) in THF (4 mL) dropwise at 0° C. The reaction mixture was stirred for 16 h at ambient temperature. The mixture was filtered, concentrated, and purified by silica gel column chromatography (PE/EA=5:1) to give 3-benzyl-7-oxa-10-tert-butoxycarbonyl-3,10-diaza-bicyclo[3.3.2]decane as an oil. $^1$H NMR (300 MHz, CDCl$_3$): δ 7.31 (m, 5H), 3.98 (m, 1H), 3.85 (m, 1H), 3.69 (m, 6H), 2.79 (m, 4H), 2.19 (m, 1H), 1.49 (s, 9H), 0.86 (m, 1H). MS [M+H]$^+$ 333.

Step 5. To a stirred solution of 3-benzyl-7-oxa-10-tert-butoxycarbonyl-3,10-diaza-bicyclo[3.3.2]decane (1.28 g, 3.86 mmol) in ethanol (50 mL) was added 10% Pd/C (0.15 g). The mixture was stirred in an atmosphere of hydrogen (4 atm) overnight. The mixture was filtered and concentrated under reduced pressure to give 7-oxa-10-tert-butoxycarbonyl-3,10-diaza-bicyclo[3.3.2]decane as an oil. $^1$H NMR (300 MHz, CDCl$_3$): δ 4.23 (m, 2H), 3.67 (m, 4H), 3.39 (m, 2H), 3.02 (m, 2H), 2.11 (s, 2H), 1.51 (s, 9H). MS [M+H]$^+$ 243.

Intermediate 42

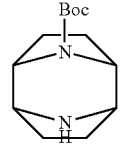

tert-Butyl 9,10-diazatricyclo[4.2.1.1$^{2,5}$]decane-9-carboxylate

Step 1. Into a 15 L three necked reactor was added cycloocta-1,5-diene (0.88 kg, 7.9 mol). The solution was kept at −10 to 15° C. while m-CPBA (1.63 kg, 8.22 mol) suspended in 12 L of methylene chloride was added under vigorous stirring. The reaction suspension was stirred at room temperature until a negative test was obtained with moist starch-iodide paper. The suspension was cooled to −5° C. for 30 min and the white solid was removed by filtration and washed with methylene chloride (500 mL×3). The filtrate was washed with 800 mL of 20% sodium bisulfate solution, three 1 L portions of 10% sodium bicarbonate solution, 1 L water, and 800 mL of brine in that order. The organic layer was dried over anhydrous magnesium sulfate, filtered, and concentrated under reduced pressure. The oil was rectified under reduced pressure (60-70° C./4 mmHg) to give 9-oxabicyclo[6.1.0]non-4-ene as a liquid. $^1$H NMR (CDCl$_3$, 300 MHz): δ 1.99-2.14 (m, 6H), 2.43 (t, 2H), 3.00-3.03 (m, 2H), 5.54-5.57 (m, 2H).

Step 2. To a stirred solution of 9-oxabicyclo[6.1.0]non-4-ene (500 g, 4.03 mol) in CH$_3$CN (250 mL) kept under nitrogen atmosphere were added benzylamine (440 g, 4.04 mol) and anhydrous LiClO$_4$ (42.8 g, 0.40 mol). The mixture was refluxed for 72 h, cooled to room temperature and treated with water (500 mL). The mixture was allowed to stir for 30 min, and a white precipitate was filtered and washed with ether. The filtrate was extracted with ether (3×). The combined organics were washed with water (2×) and brine and concentrated. The residue was cooled to −18° C. overnight, filtered, and washed with hexanes (2×) to give 8-(benzylamino)cyclooct-4-en-1-ol as a solid. $^1$H NMR (CDCl$_3$, 300 MHz): δ 1.37-1.44 (m, 2H), 2.01-2.39 (m, 6H), 2.58-2.64 (m, 1H), 3.36-3.43 (m, 1H), 3.71-3.91 (m, 2H), 5.55-5.67 (m, 2H), 7.25-7.33 (m, 5H).

Step 3. To a stirred solution of 8-(benzylamino)cyclooct-4-en-1-ol (500 g, 2.16 mol) in water (600 mL) was added concentrated sulfuric acid (569 g, 35%, 2.03 mol) at below 10° C. The resulting suspension was heated to dissolve the solid, then to distill to remove water at normal pressure until the reaction mixture reached 120° C. Toluene (200 mL) was added to the mixture to bring water out of the mixture for 6 h. The reaction mixture was distilled until the temperature reached to 120° C. The mixture was distilled under reduced pressure until the reaction mixture solidified and cooled to room temperature. THF (600 mL) was added to the mixture. The mixture was refluxed just as it could be stirred, cooled to 0° C., treated with 40% of sodium hydroxide (500 mL) at 0-15° C., refluxed for 10 h, cooled, concentrated, and treated with water (300 mL). The mixture was extracted with ethyl acetate (3×). The combined organics were washed with brine (2×) and water (4×), concentrated, and purified by flash chromatography to afford 9-benzyl-9-azabicyclo[6.1.0]non-4-ene. $^1$H NMR (CDCl$_3$, 300 MHz): δ 1.58-1.61 (m, 2H), 1.90-2.13 (m, 6H), 2.38-2.42 (m, 2H), 3.54 (s, 2H), 5.55-5.58 (m, 2H), 7.23-7.33 (m, 5H).

Step 4. A solution of 9-benzyl-9-azabicyclo[6.1.0]non-4-ene (20.1 g, 94.2 mmol), sodium azide (24.5 g, 0.38 mol), and ammonium chloride (20.15 g, 0.38 mol) in ethanol (130 mL) and water (90 mL) was refluxed for 6 h. The ethanol was evaporated under reduced pressure and the aqueous residue was extracted with CH$_2$Cl$_2$ (3×). The combined organics were washed with water and concentrated to afford 8-azido-N-benzylcyclooct-4-en-1-amine. $^1$H NMR (CDCl$_3$, 300 MHz): δ 1.62-1.86 (m, 3H), 2.13-2.23 (m, 4H), 2.41-2.51 (m, 2H), 2.83-2.84 (m, 1H), 3.62-3.67 (m, 1H), 3.71-3.88 (m, 2H), 5.60-5.63 (m, 2H), 7.25-7.35 (m, 5H).

Step 5. To a solution of 8-azido-N-benzylcyclooct-4-en-1-amine (20 g, 78 mmol) in methylene chloride (30 mL) was added a solution of 10% bromine in methylene chloride (131 g, 82 mmol) at −78 to −60° C. slowly. The reaction mixture was allowed to stir at that temperature for 2 h, treated with sodium bicarbonate (13.1 g) and warmed to room temperature. The mixture was treated with water (10 mL), left to stir for 1 h, and diluted with water (80 mL) and methylene chloride (20 mL). The organic phase was separated and the aqueous phase was extracted with methylene chloride (2×). The combined organics were washed with water (2×), concentrated, and purified by flash chromatography to afford a mixture of 2-azido-9-benzyl-5-bromo-9-azabicyclo[4.2.1]nonane and 2-azido-9-benzyl-6-bromo-9-azabicyclo[3.3.1]nonane (15 g). For 2-azido-9-benzyl-5-bromo-9-azabicyclo[4.2.1]nonane; $^1$H NMR (CDCl$_3$, 300 MHz): δ 1.25-1.27 (m, 2H), 1.70-2.03 (m, 3H), 2.10-2.19 (m, 3H), 3.24-3.36 (m, 1H), 3.52-3.58 (q, 1H), 3.73-3.82 (m, 3H), 4.12-4.28 (q, 1H), 7.25-7.41 (m, 5H).

Step 6. To a stirred solution of 2-azido-9-benzyl-5-bromo-9-azabicyclo[4.2.1]nonane and 2-azido-9-benzyl-6-bromo-9-azabicyclo[3.3.1]nonane (7.05 g, 21 mmol) in THF (25 mL) was added triphenylphosphine (6.62 g, 25 mmol) in THF (20 mL) at room temperature. The mixture was refluxed for 4 h, cooled to 0° C., treated with water (3 mL), and heated to reflux for 15 h. The mixture was concentrated and treated with ether. The resulting solid was separated, triturated with ether, and purified by flash chromatography to afford 9-benzyl-9,10-diazatricyclo[4.2.1.1$^{2,5}$]decane as a solid. $^1$H NMR (CDCl$_3$, 300 MHz): δ 1.26-1.28 (m, 2H), 2.12-2.16 (m, 4H), 2.22-2.26 (m, 2H), 2.43-2.46 (m, 2H), 3.04 (m, 2H), 3.42 (s, 2H), 7.28-7.35 (m, 5H).

Step 7. A mixture of 9-benzyl-9,10-diazatricyclo[4.2.1.1$^{2,5}$]decane (4.18 g, 13.5 mmol), water (80 mL), methylene chloride (80 mL) and sodium bicarbonate (3.4 g, 40.5 mmol) was allowed to stir for 1 h. The mixture was extracted with methylene chloride (2×), washed with water (3×), and concentrated. To the residue were added ethanol (20 mL) and (Boc)$_2$O (3.12 g, 14.3 mmol), and the mixture was allowed to stir for 1 h, concentrated, and purified by flash chromatography to afford tert-butyl 10-benzyl-9,10-diazatricyclo[4.2.1.1$^{2,5}$]decane-9-carboxylate as a solid. To a stirred solution of tert-butyl 10-benzyl-9,10-diazatricyclo[4.2.1.1$^{2,5}$]decane-9-carboxylate (1.2 g, 3.65 mmol) in ethanol (12 mL) were added 10% Pd/C (1.2 g, 60% H$_2$O) and hydrochloric acid (6 N, 2 mL). The mixture was hydrogenated at room temperature for 8 h, filtered, and washed with hot 50% aqueous ethanol. The filtrate was concentrated, dissolved in water (8 mL), treated with sodium bicarbonate (0.55 g), and left to stir for 2 h. The mixture was extracted with dichloromethane (3×). The combined organics were washed with water (2×), concentrated, and purified by flash chromatography to afford tert-butyl 9,10-diazatricyclo[4.2.1.1$^{2,5}$]decane-9-carboxylate as a solid. $^1$H NMR (CDCl$_3$, 300 MHz): δ 1.45 (s, 9H), 1.62-1.76 (m, 4H), 1.95-1.98 (m, 4H), 3.18-3.22 (m, 2H), 3.94-4.12 (m, 2H).

The following intermediate was prepared in an analogous manner of that described in Intermediate 42.

| Intermediate # | Structure | IUPAC Name | Exact Mass [M + H]$^+$ |
|---|---|---|---|
| 43 | ![Boc structure] | tert-butyl 2,7-diazatricyclo[4.4.0.0$^{3,8}$]decan-2-carboxylate | Calc'd 239, found 239. |

Example 1

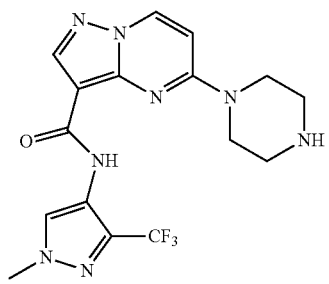 [SMILES: Cn1cc(NC(=O)c2cnn3ccc(N4CCNCC4)nc23)c(C(F)(F)F)n1]

N-(1-Methyl-3-(trifluoromethyl)-1H-pyrazol-4-yl)-5-(piperazin-1-yl)pyrazolo[1,5-a]pyrimidine-3-carboxamide (IRAK4 IC$_{50}$=10 nM)

Step 1: Into a 100 mL sealed tube were added 5-hydroxypyrazolo[1,5-a]pyrimidine-3-carboxylic acid (600 mg, 3.4 mmol), phosphorous oxychloride (10 mL) and diisopropylethylamine (1 mL) and the resulting solution was stirred at 120° C. for 8 h. The reaction mixture was cooled to room temperature and concentrated under reduced pressure. The residue thus obtained was dissolved in dichloromethane (15 mL) and concentrated to afford 5-chloropyrazolo[1,5-a]pyrimidine-3-carbonyl chloride which was taken to the next step without further purification.

Step 2: Into a 50 mL round bottomed flask were added 5-chloropyrazolo[1,5-a]pyrimidine-3-carbonyl chloride, dichloromethane (20 mL), 1-methyl-3-(trifluoromethyl)-1H-pyrazol-4-amine (665 mg, 7 mmol) and diisopropylethylamine (1.3 mL 7 mmol) and the reaction mixture was stirred at room temperature for 1 h. The reaction mixture was diluted with dichloromethane and washed with water and brine, dried over anhydrous sodium sulfate, filtered and concentrated. The residue was purified by flash chromatography eluting with methanol in dichloromethane (7-9%) to afford 5-chloro-N-(1-methyl-3-(trifluoromethyl)-1H-pyrazol-4-yl)pyrazolo[1,5-a]pyrimidine-3-carboxamide as a solid. $^1$H NMR (CD$_3$OD, 400 MHz): δ 9.12 (d, J=7.4 Hz, 1H), 8.68 (s, 1H), 8.39 (s, 1H), 7.31 (d, J=7.4 Hz, 1H), 3.98 (s, 3H). MS calc'd [M+H]$^+$ 345.0, found 345.2.

Step 3: A mixture of 5-chloro-N-(1-methyl-3-(trifluoromethyl)-1H-pyrazol-4-yl)pyrazolo[1,5-a]pyrimidine-3-carboxamide (70 mg, 0.2 mmol), tert-butyl piperazine-1-carboxylate (56 mg, 0.3 mmol), N,N-diisopropylethylamine (0.7 mL, 0.4 mmol) and ethanol (5 mL) in a 10 mL sealed tube was heated at 90° C. for 4 h. The solvent was removed under reduced pressure and the residue was purified by flash chromatography eluting with methanol in dichloromethane (3-5%) to afford tert-butyl 4-(3-((1-methyl-3-(trifluoromethyl)-1H-pyrazol-4-yl)carbamoyl)pyrazolo[1,5-a]pyrimidin-5-yl)piperazine-1-carboxylate as a solid. $^1$H NMR (CD$_3$OD, 400 MHz): δ 8.57 (d, J=8.0 Hz, 1H), 8.36 (s, 1H), 8.33 (s, 1H), 6.84 (d, J=8.0 Hz, 1H), 3.97 (s, 3H), 3.87 (t, J=4.8 Hz, 4H), 3.62 (t, J=4.8 Hz, 4H), 1.52 (s, 9H). MS calc'd [M+H]$^+$ 495.2, found 495.4.

Step 4: Into a 10 mL round bottom flask containing a solution of tert-butyl 4-(3-((1-methyl-3-(trifluoromethyl)-1H-pyrazol-4-yl)carbamoyl)pyrazolo[1,5-a]pyrimidin-5-yl)piperazine-1-carboxylate (80 mg, 0.15 mmol) in dichloromethane (1 mL) was added trifluoroacetic acid (2 mL) and the reaction was stirred for 1 h. The solvent was removed under reduced pressure and the residue was purified by trituration with dichloromethane and hexanes to afford N-(1-methyl-3-(trifluoromethyl)-1H-pyrazol-4-yl)-5-(piperazin-1-yl)pyrazolo[1,5-a]pyrimidine-3-carboxamide trifluoroacetate as a solid. $^1$H NMR (CD$_3$OD, 400 MHz): δ 8.69 (d, J=7.9 Hz, 1H), 8.40 (s, 1H), 8.38 (s, 1H), 6.93 (d, J=7.9 Hz, 1H), 4.13 (t, J=5.3 Hz, 4H), 3.98 (s, 3H), 3.43 (t, J=5.3 Hz, 4H). MS calc'd [M+H]$^+$ 395.1, found 395.2.

The following examples were prepared in an analogous manner of that described in Example 1.

| Example # | IRAK4 IC$_{50}$ (nM) | Structure | IUPAC Name | Exact Mass [M + H]$^+$ |
|---|---|---|---|---|
| 2 | 0.5 | 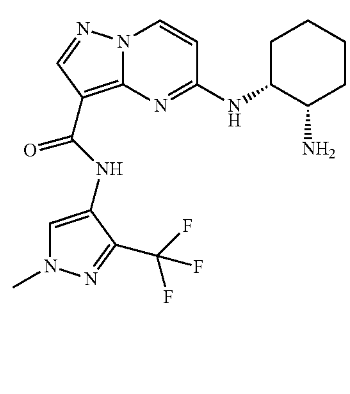 [SMILES: Cn1cc(NC(=O)c2cnn3ccc(N[C@@H]4CCCC[C@@H]4N)nc23)c(C(F)(F)F)n1] | 5-{[(1R,2S)-2-aminocyclohexyl]amino}-N-[1-methyl-3-(trifluoromethyl)-1H-pyraozl-4-yl]pyrazolo[1,5-a]pyrimidine-3-carboxamide | Calc'd 423.2, found 423.4 |
| 3 | 237 | 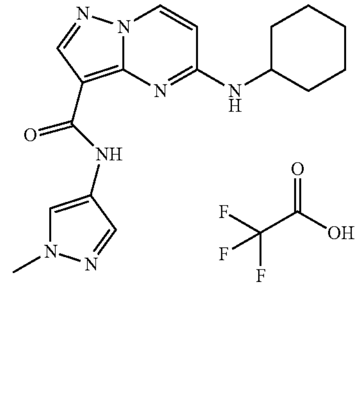 [SMILES: Cn1cc(NC(=O)c2cnn3ccc(NC4CCCCC4)nc23)cn1 ; O=C(O)C(F)(F)F] | 5-(cyclohexylamino)-N-(1-methyl-1H-pyrazol-4-yl)pyrazolo[1,5-a]pyrimidine-3-carboxamide trifluoroacetate | Calc'd 340.2, found 340.4 |

-continued

| Example # | IRAK4 IC$_{50}$ (nM) | Structure | IUPAC Name | Exact Mass [M + H]$^+$ |
|---|---|---|---|---|
| 4 | 23 | 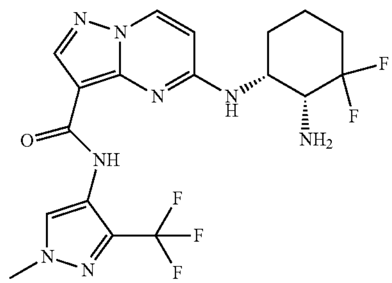 [SMILES: Cn1cc(NC(=O)c2cnn3ccc(N[C@@H]4CCCC(F)(F)[C@@H]4N)nc23)c(C(F)(F)F)n1] | 5-{[(1R,2R)-2-amino-3,3-difluorocyclohexyl]amino}-N-[1-methyl-3-(trifluoromethyl)-1H-pyrazol-4-yl]pyrazolo[1,5-a]pyrimidine-3-carboxamide | Calc'd 459.2, found 459.2 |
| 5 | 483 | 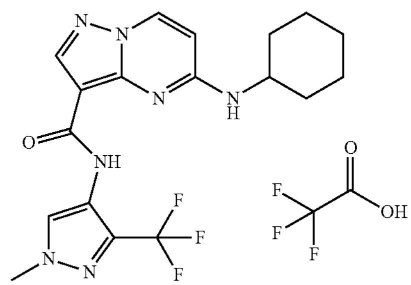 [SMILES: Cn1cc(NC(=O)c2cnn3ccc(NC4CCCCC4)nc23)c(C(F)(F)F)n1 ; O=C(O)C(F)(F)F] | 5-(cyclohexylamino)-N-[1-methyl-3-(trifluoromethyl)-1H-pyrazol-4-yl]pyrazolo[1,5-a]pyrimidine-3-carboxamide trifluoroacetate | Calc'd 408.2, found 408.2 |
| 6 | 681 | 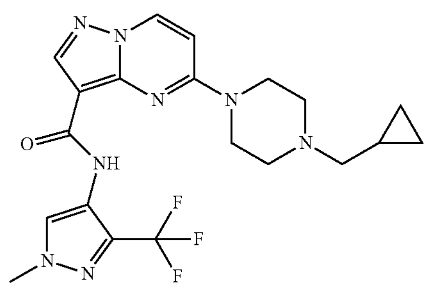 [SMILES: Cn1cc(NC(=O)c2cnn3ccc(N4CCN(CC5CC5)CC4)nc23)c(C(F)(F)F)n1] | 5-[4-(cyclopropylmethyl)piperazin-1-yl]-N-[1-methyl-3-(trifluoromethyl)-1H-pyrazol-4-yl]pyrazolo[1,5-a]pyrimidine-3-carboxamide | Calc'd 449.2, found 449.2 |
| 7 | 39 | 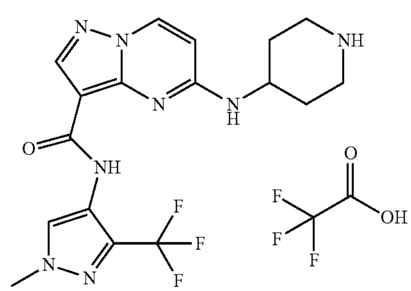 [SMILES: Cn1cc(NC(=O)c2cnn3ccc(NC4CCNCC4)nc23)c(C(F)(F)F)n1 ; O=C(O)C(F)(F)F] | N-[1-methyl-3-(trifluoromethyl)-1H-pyrazol-4-yl]-5-(piperidin-4-ylamino)pyrazolo[1,5-a]pyrimidine-3-carboxamide trifluoroacetate | Calc'd 409.2, found 409.2 |
| 8 | 66 | 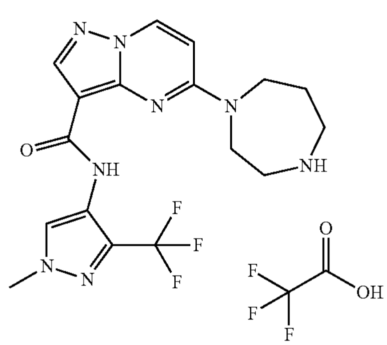 [SMILES: Cn1cc(NC(=O)c2cnn3ccc(N4CCCNCC4)nc23)c(C(F)(F)F)n1 ; O=C(O)C(F)(F)F] | 5-(1,4-diazepan-1-yl)-N-[1-methyl-3-(trifluoromethyl)-1H-pyrazol-4-yl]pyrazolo[1,5-a]pyrimidine-3-carboxamide trifluoroacetate | Calc'd 409.2, found 409.2 |

-continued

| Example # | IRAK4 IC$_{50}$ (nM) | Structure | IUPAC Name | Exact Mass [M + H]$^+$ |
|---|---|---|---|---|
| 9 | 0.5 | 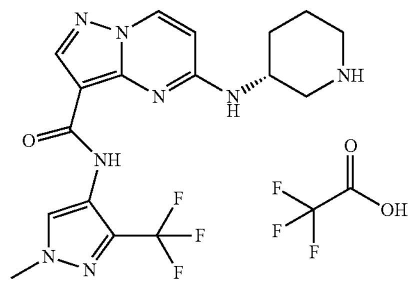 [SMILES: Cn1cc(NC(=O)c2cnn3ccc(N[C@@H]4CCCNC4)nc23)c(C(F)(F)F)n1 ; O=C(O)C(F)(F)F] | N-[1-methyl-3-(trifluoromethyl)-1H-pyrazol-4-yl]-5-[(3R)-piperidin-3-ylamino]pyrazolo[1,5-a]pyrimidine-3-carboxamide trifluoroacetate | Calc'd 409.2, found 409.2 |
| 10 | 1104 | 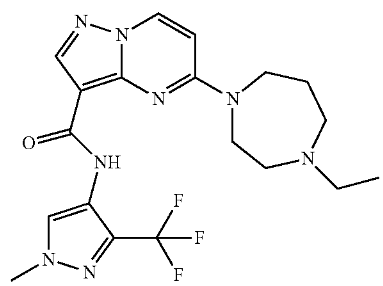 [SMILES: CCN1CCCN(c2ccn3ncc(C(=O)Nc4cn(C)nc4C(F)(F)F)c3n2)CC1] | 5-(4-ethyl-1,4-diazepan-1-yl)-N-[1-methyl-3-(trifluoromethyl)-1H-pyrazol-4-yl]pyrazolo[1,5-a]pyrimidine-3-carboxamide | Calc'd 437.2, found 437.4 |
| 11 | 28 | 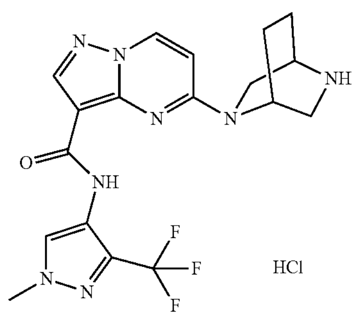 [SMILES: Cn1cc(NC(=O)c2cnn3ccc(N4CC5CCC4CN5)nc23)c(C(F)(F)F)n1 ; Cl] | 5-(2,5-diazabicyclo[2.2.2]oct-2-yl)-N-[1-methyl-3-(trifluoromethyl)-1H-pyrazol-4-yl]pyrazolo[1,5-a]pyrimidine-3-carboxamide hydrochloride | Calc'd 421.2, found 421.2 |
| 12 | 6 | 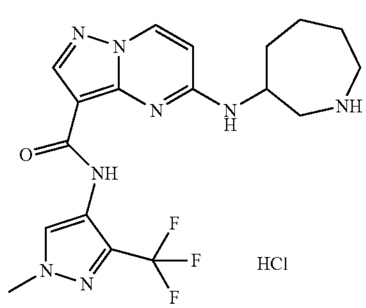 [SMILES: Cn1cc(NC(=O)c2cnn3ccc(NC4CCCCNC4)nc23)c(C(F)(F)F)n1 ; Cl] | 5-(azepan-3-ylamino)-N-[1-methyl-3-(trifluoromethyl)-1H-pyrazol-4-yl]pyrazolo[1,5-a]pyrimidine-3-carboxamide hydrochloride | Calc'd 423.2, found 423.5 |
| 13 | 179 | 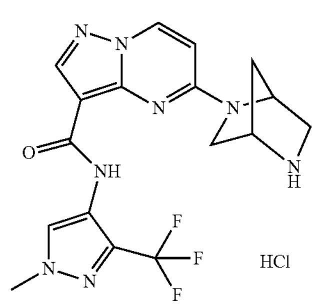 [SMILES: Cn1cc(NC(=O)c2cnn3ccc(N4CC5CC4CN5)nc23)c(C(F)(F)F)n1 ; Cl] | 5-(2,5-diazabicyclo[2.2.1]hept-2-yl)-N-[1-methyl-3-(trifluoromethyl)-1H-pyrazol-4-yl]pyrazolo[1,5-a]pyrimidine-3-carboxamide hydrochloride | Calc'd 407.2, found 407.1 |

| Example # | IRAK4 IC$_{50}$ (nM) | Structure | IUPAC Name | Exact Mass [M + H]$^+$ |
|---|---|---|---|---|
| 14 | 16 | 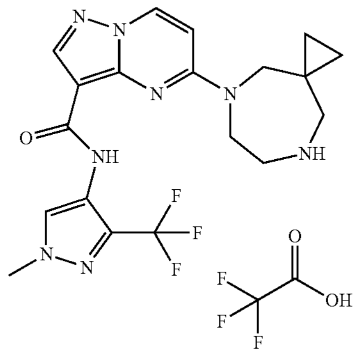 | 5-(5,8-diazaspiro[2.6]non-5-yl)-N-[1-methyl-3-(trifluoromethyl)-1H-pyrazol-4-yl]pyrazolo[1,5-15a]pyrimidine-3-carboxamide trifluoroacetate | Calc'd 435.2, found 435.2 |
| 15 | 113 | 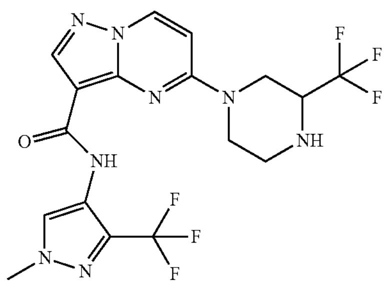 [SMILES: Cn1cc(NC(=O)c2cnn3ccc(N4CCNC(C(F)(F)F)C4)nc23)c(C(F)(F)F)n1] | N-[1-methyl-3-(trifluoromethyl)-1H-pyrazol-4-yl]-5-(3-(trifluoromethyl)piperazin-1-yl]pyrazolo[1,5-a]pyrimidine-3-carboxamide | Calc'd 463.1, found 463.2 |
| 16 | 49 | 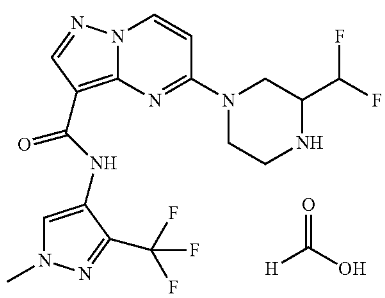 | 5-[3-(difluoromethyl)piperazin-1-yl]-N-[1-methyl-3-(trifluoromethyl)-1H-pyrazol-4-yl]pyrazolo[1,5-a]pyrimidine-3-carboxamide formate | Calc'd 445.2, found 445.4 |
| 17 | 14 | 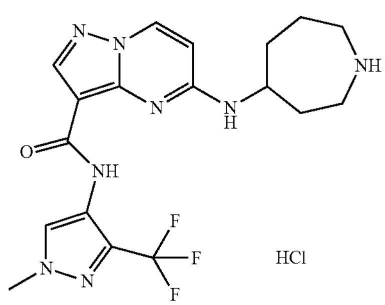 [SMILES: Cn1cc(NC(=O)c2cnn3ccc(NC4CCCNCC4)nc23)c(C(F)(F)F)n1 ; Cl] | 5-(azepan-4-ylamino)-N-[1-methyl-3-(trifluoromethyl)-1H-pyrazol-4-yl]pyrazolo[1,5-a]pyrimidine-3-carboxamide hydrochloride | Calc'd 423.2, found 423.4 |
| 18 | 97 | 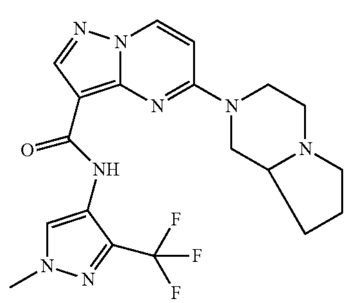 [SMILES: Cn1cc(NC(=O)c2cnn3ccc(N4CCN5CCCC5C4)nc23)c(C(F)(F)F)n1] | 5-(hexahydropyrrolo[1,2-a]pyrazin-2(1H)-yl)-N-[1-methyl-3-(trifluoromethyl)-1H-pyrazol-4-yl]pyrazolo[1,5-a]pyrimidine-3-carboxamide | Calc'd 435.2, found 435.4 |

-continued

| Example # | IRAK4 IC$_{50}$ (nM) | Structure | IUPAC Name | Exact Mass [M + H]$^+$ |
|---|---|---|---|---|
| 19 | 389 | 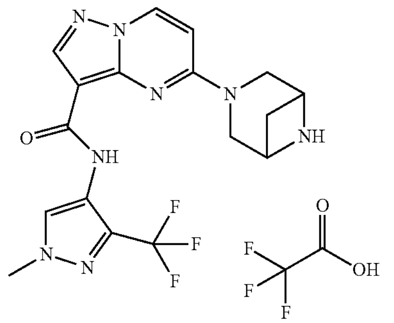 | 5-(3,6-diazabicyclo[3.1.1]hept-3-yl)-N-[1-methyl-3-(trifluoromethyl)-1H-pyrazol-4-yl]pyrazolo[1,5-a]pyrimidine-3-carboxamide trifluoroacetate | Calc'd 407.2, found 407.4 |
| 20 | 149 | 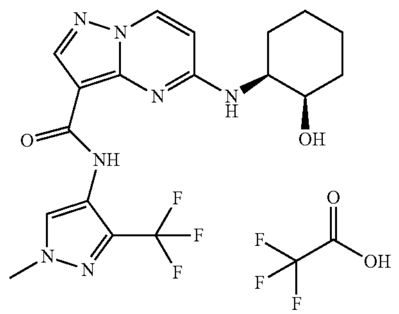 [SMILES: Cn1cc(NC(=O)c2cnn3ccc(N[C@H]4CCCC[C@H]4O)nc23)c(C(F)(F)F)n1 ; O=C(O)C(F)(F)F] | 5-{[(1S,2R)-2-hydroxycyclohexyl]amino}-N-[1-methyl-3-(trifluoromethyl)-1H-pyrazol-4-yl]pyrazolo[1,5-a]pyrimidine-3-carboxamide trifluoroacetate | Calc'd 424.2, found 424.4 |
| 21 | 20 | 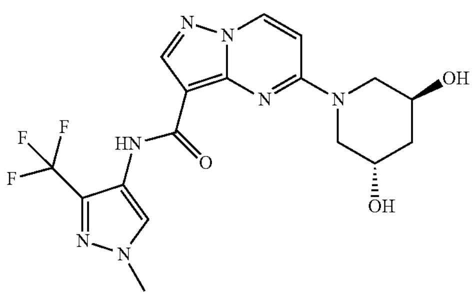 [SMILES: Cn1cc(NC(=O)c2cnn3ccc(N4C[C@@H](O)C[C@H](O)C4)nc23)c(C(F)(F)F)n1] | 5-[(3S,5S)-3,5-dihydroxypiperidin-1-yl]-N-[1-methyl-3-(trifluoromethyl)-1H-pyrazol-4-yl]pyrazolo[1,5-a]pyrimidine-3-carboxamide | Calc'd 426, found 426 |
| 22 | 2 | 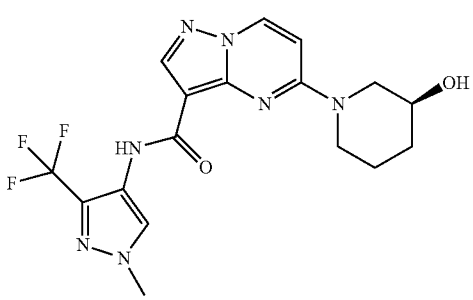 [SMILES: Cn1cc(NC(=O)c2cnn3ccc(N4CCC[C@H](O)C4)nc23)c(C(F)(F)F)n1] | 5-[(3S)-3-hydroxypiperidin-1-yl]-N-[1-methyl-3-(trifluoromethyl)-1H-pyrazol-4-yl]pyrazolo[1,5-a]pyrimidine-3-carboxamide | Calc'd 410, found 410 |
| 23 | 0.9 | 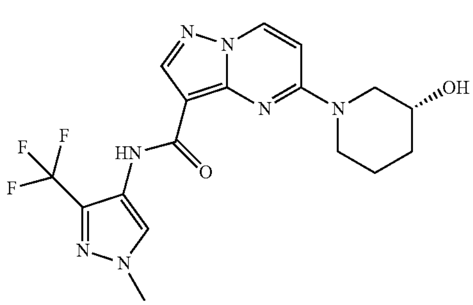 [SMILES: Cn1cc(NC(=O)c2cnn3ccc(N4CCC[C@@H](O)C4)nc23)c(C(F)(F)F)n1] | 5-[(3R)-3-hydroxypiperidin-1-yl]-N-[1-methyl-3-(trifluoromethyl)-1H-pyrazol-4-yl]pyrazolo[1,5-a]pyrimidine-3-carboxamide | Calc'd 410, found 410 |

-continued

| Example # | IRAK4 IC$_{50}$ (nM) | Structure | IUPAC Name | Exact Mass [M + H]$^+$ |
|---|---|---|---|---|
| 24 | 4 | 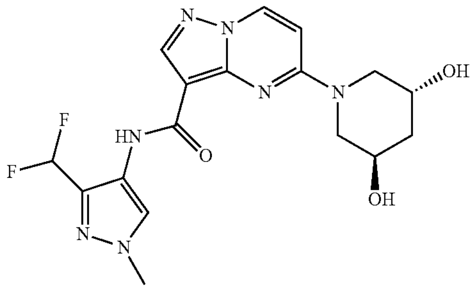 [SMILES: Cn1cc(NC(=O)c2cnn3ccc(N4C[C@H](O)C[C@@H](O)C4)nc23)c(C(F)F)n1] | N-[3-(difluoromethyl)-1-methyl-1H-pyrazol-4-yl]-5-[(3R,5R)-3,5-dihydroxypiperidin-1-yl]pyrazolo[1,5-a]pyrimidine-3-carboxamide | Calc'd 408, found 408 |
| 25 | 0.5 | 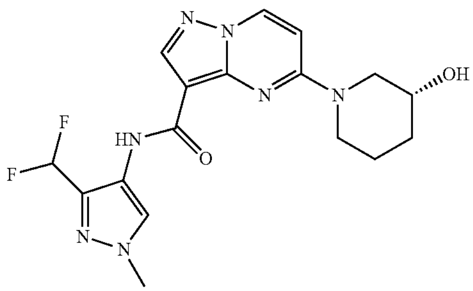 [SMILES: Cn1cc(NC(=O)c2cnn3ccc(N4CCC[C@@H](O)C4)nc23)c(C(F)F)n1] | N-[3-(difluoromethyl)-1-methyl-1H-pyrazol-4-yl]-5-[(3R)-3-hydroxypiperidin-1-yl]pyrazolo[1,5-a]pyrimidine-3-carboxamide | Calc'd 392, found 392 |
| 26 | 0.5 | 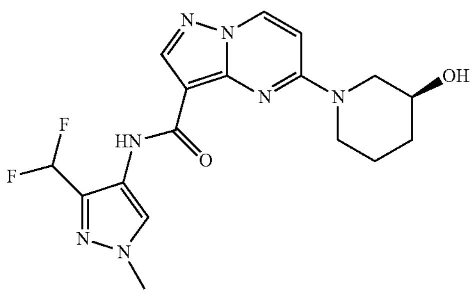 [SMILES: Cn1cc(NC(=O)c2cnn3ccc(N4CCC[C@H](O)C4)nc23)c(C(F)F)n1] | N-[3-(difluoromethyl)-1-methyl-1H-pyrazol-4-yl]-5-[(3S)-3-hydroxypiperidin-1-yl]pyrazolo[1,5-a]pyrimidine-3-carboxamide | Calc'd 392, found 392 |
| 27 | 149 | 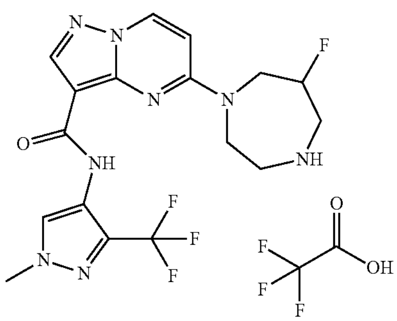 | 5-(6-fluoro-1,4-diazepan-1-yl)-N-[1-methyl-3-(trifluoromethyl)-1H-pyrazol-4-yl]pyrazolo[1,5-a]pyrimidine-3-carboxamide trifluoroacetate | Calc'd 427.2, found 427.4 |
| 28 | 72 | 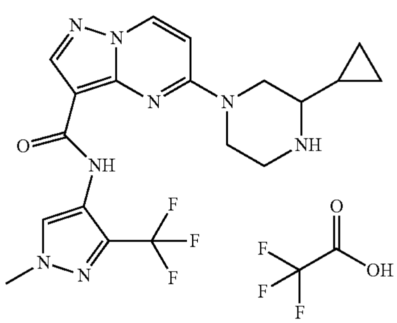 [SMILES: Cn1cc(NC(=O)c2cnn3ccc(N4CCNC(C5CC5)C4)nc23)c(C(F)(F)F)n1 ; O=C(O)C(F)(F)F] | 5-(3-cyclopropylpiperazin-1-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.4 |

-continued

| Example # | IRAK4 IC$_{50}$ (nM) | Structure | IUPAC Name | Exact Mass [M + H]$^+$ |
|---|---|---|---|---|
| 29 | 24 | 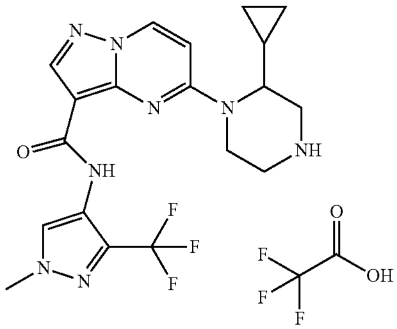 [SMILES: Cn1cc(NC(=O)c2cnn3ccc(N4CCNCC4C4CC4)nc23)c(C(F)(F)F)n1 ; O=C(O)C(F)(F)F] | 5-(2-cyclopropylpiperazin-1-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.4 |
| 30 | 71 | 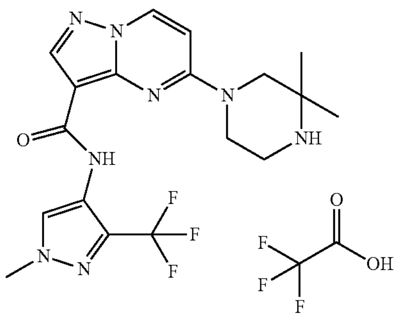 | 5-(3,3-dimethylpiperazin-1-yl)-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |
| 31 | 4 | 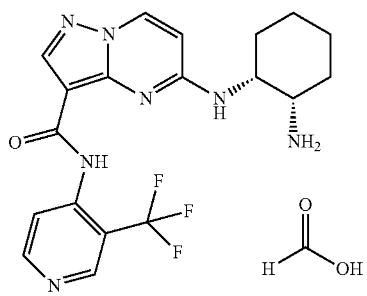 [SMILES: N[C@H]1CCCC[C@H]1Nc1ccn2ncc(C(=O)Nc3ccncc3C(F)(F)F)c2n1 ; O=CO] | 5-{[(1R,2S)-2-aminocyclohexyl]amino}-N-[3-(trifluoromethyl)pyridin-4-yl]pyrazolo[1,5-a]pyrimidine-3-carboxamide formate | Calc'd 420.2, found 420.2 |
| 32 | 3 | 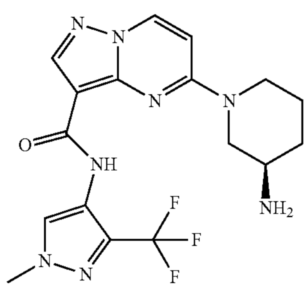 [SMILES: Cn1cc(NC(=O)c2cnn3ccc(N4CCC[C@@H](N)C4)nc23)c(C(F)(F)F)n1] | 5-[(3R)-3-aminopiperidin-1-yl]-N-[1-methyl-3-(trifluoromethyl)-1H-pyrazol-4-yl]pyrazolo[1,5-a]pyrimidine-3-carboxamide | Calc'd 409.2, found 409.2 |
| 33 | 2 | 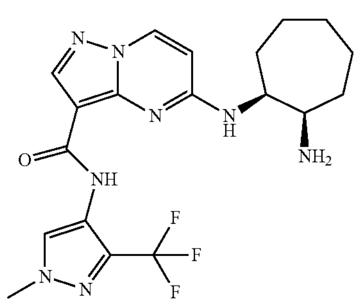 [SMILES: Cn1cc(NC(=O)c2cnn3ccc(N[C@H]4CCCCC[C@H]4N)nc23)c(C(F)(F)F)n1] | 5-{[cis-2-aminocycloheptyl]amino}-N-[1-methyl-3-(trifluoromethyl)-1H-pyrazol-4-yl]pyrazolo[1,5-a]pyrimidine-3-carboxamide | Calc'd 437.2, found 437.2 |

-continued

| Example # | IRAK4 IC$_{50}$ (nM) | Structure | IUPAC Name | Exact Mass [M + H]$^+$ |
|---|---|---|---|---|
| 34 | 269 | 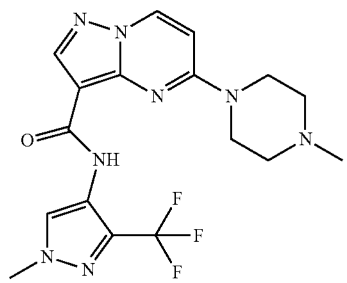 | 5-(4-methylpiperazin-1-yl)-N-[1-methyl-3-(trifluoromethyl)-1H-pyrazol-4-yl]pyrazolo[1,5-a]pyrimidine-3-carboxamide | Calc'd 409.2, found 409.2 |
| 35 | 589 | 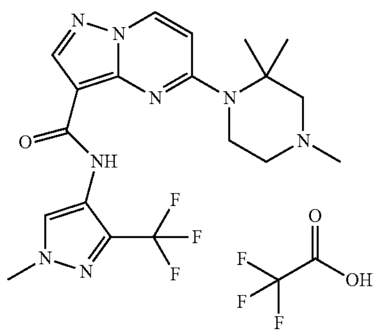 | N-[1-methyl-3-(trifluoromethyl)-1H-pyrazol-4-yl]-5-(2,2,4-trimethylpiperazin-1-yl)pyrazolo[1,5-a]pyrimidine-3-carboxamide trifluoroacetate | Calc'd 437.2, found 437.2 |
| 36 | 376 | 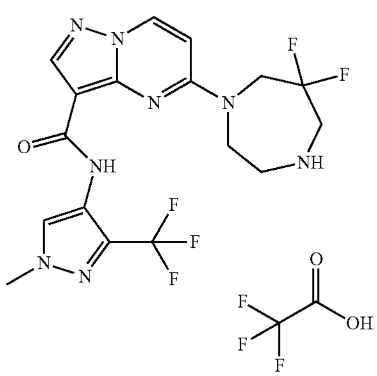 [SMILES: Cn1cc(NC(=O)c2cnn3ccc(N4CCNCC(F)(F)C4)nc23)c(C(F)(F)F)n1 ; O=C(O)C(F)(F)F] | 5-(6,6-difluoro-1,4-diazepan-1-yl)-N-[1-methyl-3-(trifluoromethyl)-1H-pyrazol-4-yl]pyrazolo[1,5-a]pyrimidine-3-carboxamide trifluoroacetate | Calc'd 445.2, found 445.2 |
| 37 | 21 | 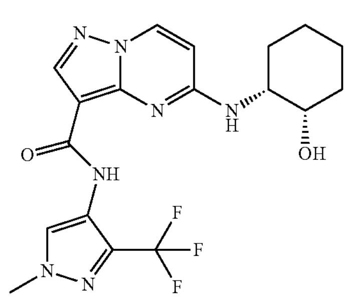 [SMILES: Cn1cc(NC(=O)c2cnn3ccc(N[C@@H]4CCCC[C@@H]4O)nc23)c(C(F)(F)F)n1] | 5-{[(1R,2S)-2-hydroxycyclohexyl]amino}-N-[1-methyl-3-(trifluoromethyl)-1H-pyraozl-4-yl]pyrazolo[1,5-a]pyrimidine-3-carboxamide | Calc'd 424.2, found 424.2 |

-continued

| Example # | IRAK4 IC$_{50}$ (nM) | Structure | IUPAC Name | Exact Mass [M + H]$^+$ |
|---|---|---|---|---|
| 38 | 16 | 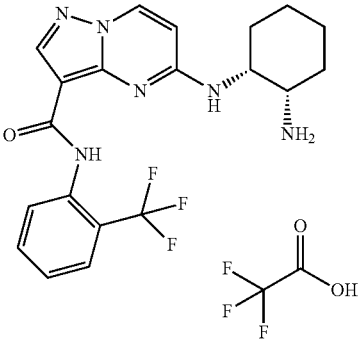 [SMILES: N[C@H]1CCCC[C@H]1Nc1ccn2ncc(C(=O)Nc3ccccc3C(F)(F)F)c2n1 ; O=C(O)C(F)(F)F] | 5-{[(1R,2S)-2-aminocyclohexyl]amino}-N-[2-(trifluoromethyl)phenyl]pyrazolo[1,5-a]pyrimidine-3-carboxamide trifluoroacetate | Calc'd 419.2, found 419.2 |
| 39 | 2 | 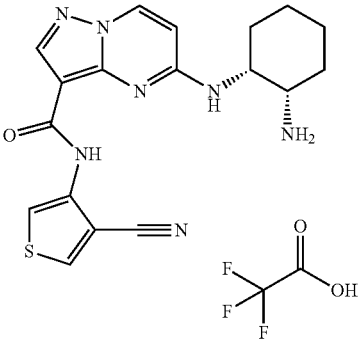 [SMILES: N#Cc1cscc1NC(=O)c1cnn2ccc(N[C@@H]3CCCC[C@@H]3N)nc12 ; O=C(O)C(F)(F)F] | 5-{[(1R,2S)-2-aminocyclohexyl]amino}-N-(4-cyanothiophen-3-yl)pyrazolo[1,5-a]pyrimidine-3-carboxamide trifluoroacetate | Calc'd 382.1, found 382.2 |
| 40 | 497 | 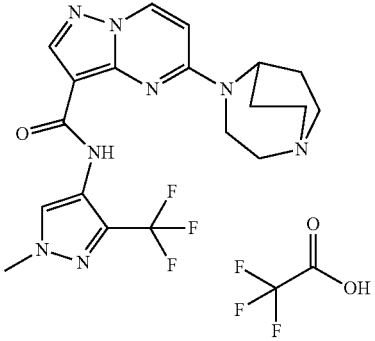 [SMILES: Cn1cc(NC(=O)c2cnn3ccc(N4CCN5CCC4CC5)nc23)c(C(F)(F)F)n1 ; O=C(O)C(F)(F)F] | 5-(1,4-diazabicyclo[3.2.2]non-4-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.2 |
| 41 | 106 | 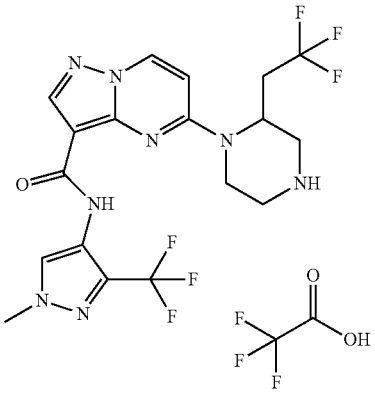 [SMILES: Cn1cc(NC(=O)c2cnn3ccc(N4CCNCC4CC(F)(F)F)nc23)c(C(F)(F)F)n1 ; O=C(O)C(F)(F)F] | N-[1-methyl-3-(trifluoromethyl)-1H-pyrazol-4-yl]-5-[2-(2,2,2-trifluoroethyl)piperazin-1-yl]pyrazolo[1,5-a]pyrimidine-3-carboxamide trifluoroacetate | Calc'd 477.2, found 477.2 |

-continued

| Example # | IRAK4 IC$_{50}$ (nM) | Structure | IUPAC Name | Exact Mass [M + H]$^+$ |
|---|---|---|---|---|
| 42 | 0.9 | 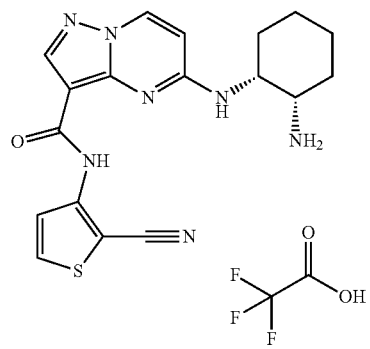 [SMILES: N#Cc1sccc1NC(=O)c1cnn2ccc(N[C@@H]3CCCC[C@@H]3N)nc12 ; O=C(O)C(F)(F)F] | 5-{[(1R,2S)-2-aminocyclohexyl]amino}-N-(2-cyanothiophen-3-yl)pyrazolo[1,5-a]pyrimidine-3-carboxamide trifluoroacetate | Calc'd 382.1, found 382.2 |
| 43 | 45 | 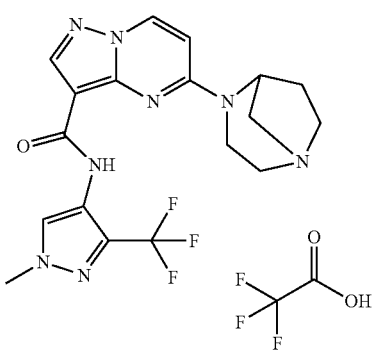 [SMILES: Cn1cc(NC(=O)c2cnn3ccc(N4CCN5CCC4C5)nc23)c(C(F)(F)F)n1 ; O=C(O)C(F)(F)F] | 5-(1,4-diazabicyclo[3.2.1]oct-4-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.2 |
| 44 | 5 | 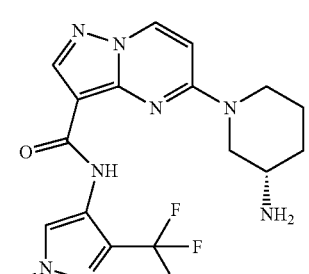 | 5-[(3S)-3-aminopiperidin-1-yl]-N-[1-methyl-3-(trifluoromethyl)-1H-pyrazol-4-yl]pyrazolo[1,5-a]pyrimidine-3-carboxamide | Calc 409.2, found 409.2 |
| 45 | 8 | 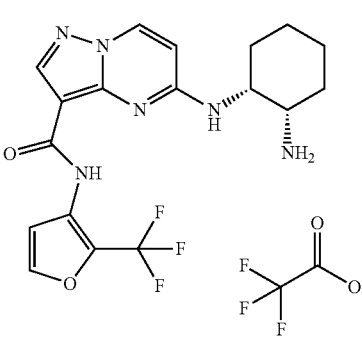 | 5-{[(1R,2S)-2-aminocyclohexyl]amino}-N-[2-(trifluoromethyl)furan-3-yl]pyrazolo[1,5-a]pyrimidine-3-carboxamide trifluoroacetate | Calc'd 409.2, found 409.2 |

-continued

| Example # | IRAK4 IC$_{50}$ (nM) | Structure | IUPAC Name | Exact Mass [M + H]$^+$ |
|---|---|---|---|---|
| 46 | 48 | 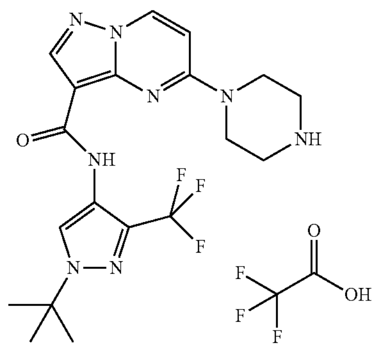 | N-[1-tert-butyl-3-(trifluoromethyl)-1H-pyrazol-4-yl]-5-piperazin-1-ylpyrazolo[1,5-a]pyrimidine-3-carboxamide trifluoroacetate | Calc'd 437.2, found 437.2 |
| 47 | 49 | 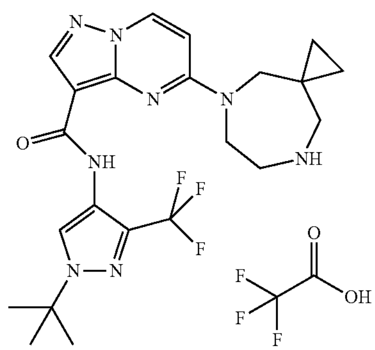 | N-[1-tert-butyl-3-(trifluoromethyl)-1H-pyrazol-4-yl]-5-(5,8-diazaspiro[2.6]non-5-yl)pyrazolo[1,5-a]pyrimidine-3-carboxamide trifluoroacetate | Calc'd 477.2, found 477.4 |
| 48 | 259 | 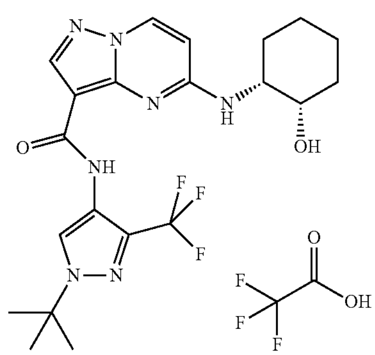 | N-[1-tert-butyl-3-(trifluoromethyl)-1H-pyrazol-4-yl]-5-{[(1R,2S)-2-hydroxycyclohexyl]amino}pyrazolo[1,5-a]pyrimidine-3-carboxamide trifluoroacetate | Calc'd 466.2, found 466.4 |
| 49 | 890 | 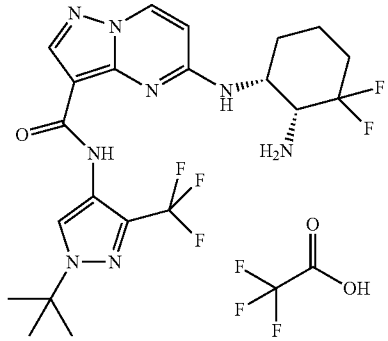 | 5-{[(1R,2R)-2-amino-3,3-difluorocyclohexyl]amino}-N-[1-tert-butyl-3-(trifluoromethyl)-1H-pyrazol-4-yl]pyrazolo[1,5-a]pyrimidine-3-carboxamide trifluoroacetate | Calc'd 501.2, found 501.2 |

-continued

| Example # | IRAK4 IC$_{50}$ (nM) | Structure | IUPAC Name | Exact Mass [M + H]$^+$ |
|---|---|---|---|---|
| 50 | 90 | 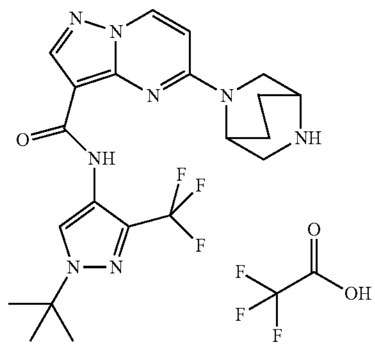 | N-[1-tert-butyl-3-(trifluoromethyl)-1H-pyrazol-4-yl]-5-(2,5-diazabicyclo[2.2.2]oct-2-yl)pyrazolo[1,5-a]pyrimidine-3-carboxamide trifluoroacetate | Calc'd 463.2, found 463.2 |
| 51 | 32 | 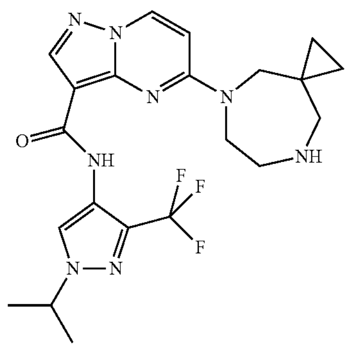 [SMILES: CC(C)n1cc(NC(=O)c2cnn3ccc(N4CCNCC5(CC5)C4)nc23)c(C(F)(F)F)n1] | 5-(5,8-diazaspiro[2.6]non-5-yl)-N-[1-(1-methylethyl)-3-(trifluoromethyl)-1H-pyrazol-4-yl]pyrazolo[1,5-a]pyrimidine-3-carboxamide | Calc'd 463.2, found 463.4 |
| 52 | 64 | 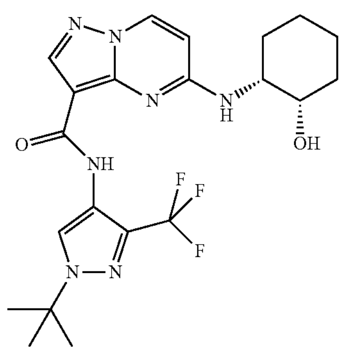 [SMILES: CC(C)(C)n1cc(NC(=O)c2cnn3ccc(N[C@@H]4CCCC[C@@H]4O)nc23)c(C(F)(F)F)n1] | 5-{[(1R,2S)-2-hydroxycyclohexyl]amino}-N-[1-(1-methylethyl)-3-(trifluoromethyl)-1H-pyrazol-4-yl]pyrazolo[1,5-a]pyrimidine-3-carboxamide | Calc'd 452.2, found 452.4 |
| 53 | 48 | 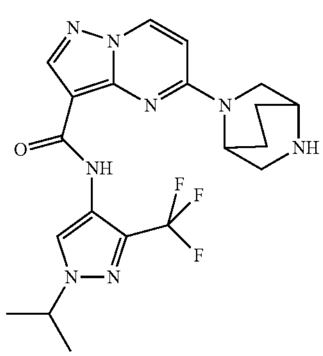 [SMILES: CC(C)n1cc(NC(=O)c2cnn3ccc(N4CC5CCC4CN5)nc23)c(C(F)(F)F)n1] | 5-(2,5-diazabicyclo[2.2.2]oct-2-yl)-N-[1-(1-methylethyl)-3-(trifluoromethyl)-1H-pyrazol-4-yl]pyrazolo[1,5-a]pyrimidine-3-carboxamide | Calc'd 449.2, found 449.4 |

-continued

| Example # | IRAK4 IC$_{50}$ (nM) | Structure | IUPAC Name | Exact Mass [M + H]$^+$ |
|---|---|---|---|---|
| 54 | 63 | 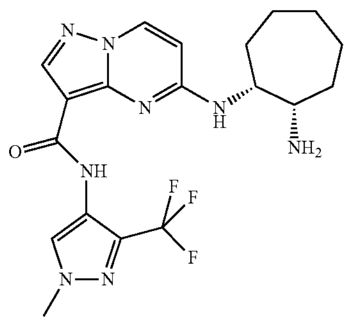 [SMILES: Cn1cc(NC(=O)c2cnn3ccc(N[C@@H]4CCCCC[C@@H]4N)nc23)c(C(F)(F)F)n1] | 5-{[(1R,2S)- or (1S,2R)-2-aminocycloheptyl]amino}-N-[1-methyl-3-(trifluoromethyl)-1H-pyrazol-4-yl]pyrazolo[1,5-a]pyrimidine-3-carboxamide | Calc'd 437.2, found 437.2 |
| 55 | 8 | 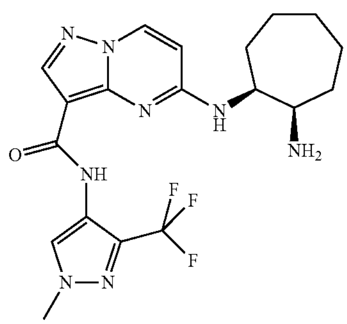 [SMILES: Cn1cc(NC(=O)c2cnn3ccc(N[C@H]4CCCCC[C@H]4N)nc23)c(C(F)(F)F)n1] | 5-{[(1R,2S)- or (1S,2R)-2-aminocycloheptyl]amino}-N-[1-methyl-3-(trifluoromethyl)-1H-pyrazol-4-yl]pyrazolo[1,5-a]pyrimidine-3-carboxamide | Calc'd 437.2, found 437.2 |
| 56 | 626 | 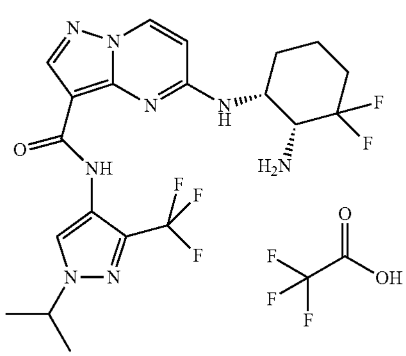 [SMILES: CC(C)n1cc(NC(=O)c2cnn3ccc(N[C@@H]4CCCC(F)(F)[C@@H]4N)nc23)c(C(F)(F)F)n1 ; O=C(O)C(F)(F)F] | 5-{[(1R,2R)-2-amino-3,3-difluorocyclohexyl]amino}-N-[1-(1-methylethyl)-3-(trifluoromethyl)-1H-pyrazol-4-yl]pyrazolo[1,5-a]pyrimidine-3-carboxamide trifluoroacetate | Calc'd 487.2, found 487.4 |
| 57 | 320 | 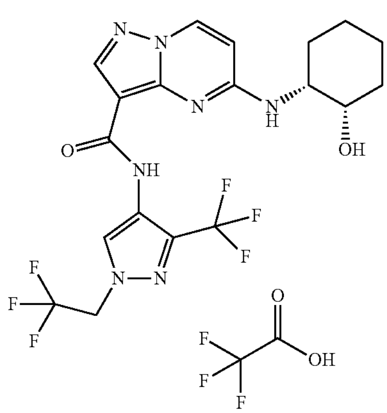 | 5-{[(1R,2S)-2-hydroxycyclohexyl]amino}-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 492.2, found 492.4 |

-continued

| Example # | IRAK4 IC$_{50}$ (nM) | Structure | IUPAC Name | Exact Mass [M + H]$^+$ |
|---|---|---|---|---|
| 58 | 267 | 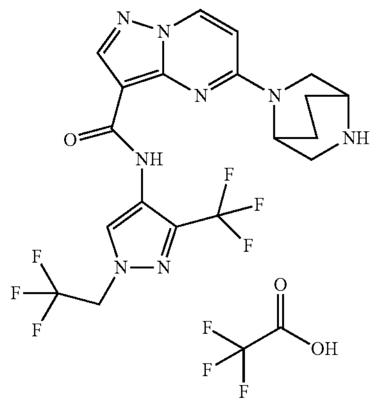 | 5-(2,5-diazabicyclo[2.2.2]oct-2-yl)-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 489.2, found 489.4 |
| 59 | 2 | 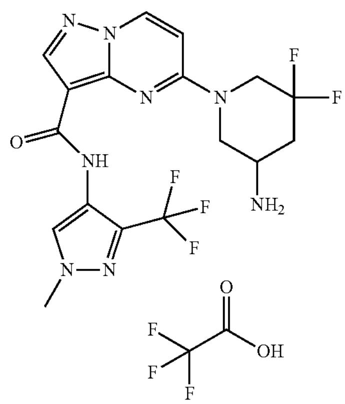 | 5-(5-amino-3,3-difluoropiperidin-1-yl)-N-[1-methyl-3-(trifluoromethyl)-1H-pyrazol-4-yl]pyrazolo[1,5-a]pyrimidine-3-carboxamide trifluoroacetate | Calc'd 445.2, found 445.4 |
| 60 | 4 | 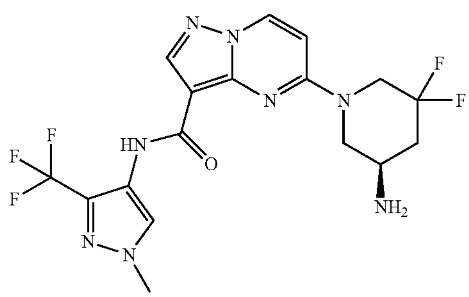 [SMILES: Cn1cc(NC(=O)c2cnn3ccc(N4C[C@H](N)CC(F)(F)C4)nc23)c(C(F)(F)F)n1] | 5-[(5R)-5-amino-3,3-difluoropiperidin-1-yl]-N-[1-methyl-3-(trifluoromethyl)-1H-pyrazol-4-yl]pyrazolo[1,5-a]pyrimidine-3-carboxamide | Calc'd 445.2, found 445.4 |
| 61 | 1 | 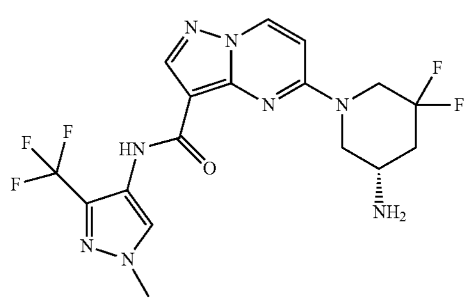 [SMILES: Cn1cc(NC(=O)c2cnn3ccc(N4C[C@@H](N)CC(F)(F)C4)nc23)c(C(F)(F)F)n1] | 5-[(5S)-5-amino-3,3-difluoropiperidin-1-yl]-N-[1-methyl-3-(trifluoromethyl)-1H-pyrazol-4-yl]pyrazolo[1,5-a]pyrimidine-3-carboxamide | Calc'd 445.2, found 445.4 |

-continued

| Example # | IRAK4 IC$_{50}$ (nM) | Structure | IUPAC Name | Exact Mass [M + H]$^+$ |
|---|---|---|---|---|
| 62 | 29 | 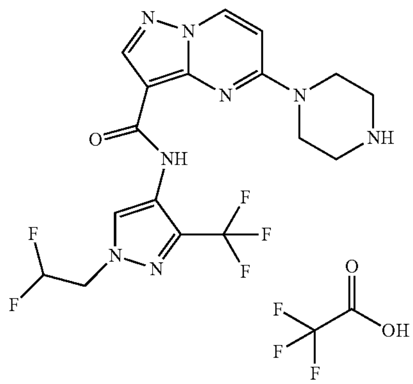 | N-[1-(2,2-difluoroethyl)-3-(trifluoromethyl)-1H-pyrazol-4-yl]-5-piperazin-1-ylpyrazolo[1,5-a]pyrimidine-3-carboxamide trifluoroacetate | Calc'd 445.2, found 445.4 |
| 63 | 38 | 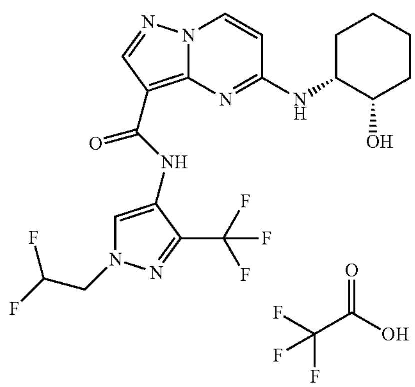 | N-[1-(2,2-difluoroethyl)-3-(trifluoromethyl)-1H-pyrazol-4-yl]-5-{[(1R,2S)-2-hydroxycyclohexyl]amino}pyrazolo[1,5-a]pyrimidine-3-carboxamide trifluoroacetate | Calc'd 474.2, found 474.4 |
| 64 | 18 | 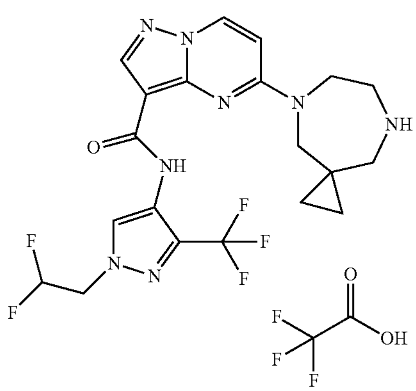 | 5-(5,8-diazaspiro[2.6]non-5-yl)-N-[1-(2,2-difluoroethyl)-3-(trifluoromethyl)-1H-pyrazol-4-yl]pyrazolo[1,5-a]pyrimidine-3-carboxamide trifluoroacetate | Calc'd 485.2, found 485.4 |
| 65 | 59 | 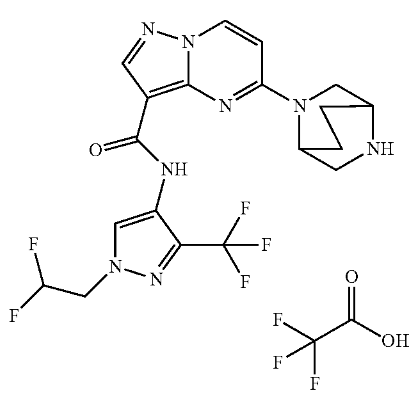 | 5-(2,5-diazabicyclo[2.2.2]oct-2-yl)-N-[1-(2,2-difluoroethyl)-3-(trifluoromethyl)-1H-pyrazol-4-yl]pyrazolo[1,5-a]pyrimidine-3-carboxamide trifluoroacetate | Calc'd 471.2, found 471.4 |

| Example # | IRAK4 IC$_{50}$ (nM) | Structure | IUPAC Name | Exact Mass [M + H]$^+$ |
|---|---|---|---|---|
| 66 | 244 | 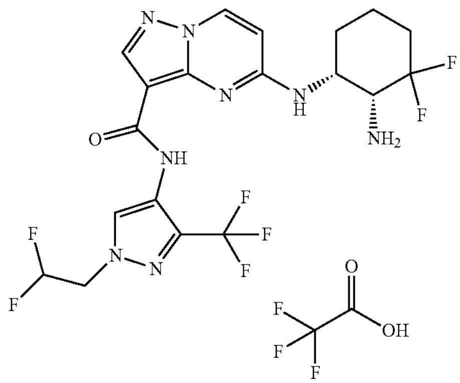 | 5-{[(1R,2R)-2-amino-3,3-difluorocyclohexyl]amino}-N-[1-(2,2-difluoroethyl)-3-(trifluoromethyl)-1H-pyrazol-4-yl]pyrazolo[1,5-a]pyrimidine-3-carboxamide trifluoroacetate | Calc'd 509.2, found 509.4 |
| 67 | 74 | 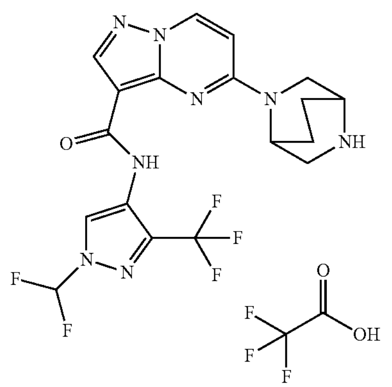 | 5-(2,5-diazabicyclo[2.2.2]oct-2-yl)-N-[1-(difluoromethyl)-3-(trifluoromethyl)-1H-pyrazol-4-yl]pyrazolo[1,5-a]pyrimidine-3-carboxamide trifluoroacetate | Calc'd 457.2, found 457.4 |
| 68 | 32 | 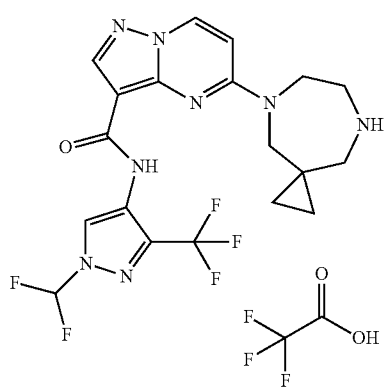 | 5-(5,8-diazaspiro[2.6]non-5-yl)-N-[1-(difluoromethyl)-3-(trifluoromethyl)-1H-pyrazol-4-yl]pyrazolo[1,5-a]pyrimidine-3-carboxamide trifluoroacetate | Calc'd 471.2, found 471.4 |
| 69 | 927 | 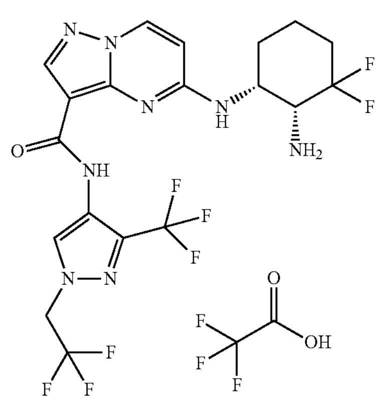 [SMILES: N[C@@H]1[C@H](Nc2ccn3ncc(C(=O)Nc4cn(CC(F)(F)F)nc4C(F)(F)F)c3n2)CCCC1(F)F ; O=C(O)C(F)(F)F] | 5-{[(1R,2R)-2-amino-3,3-difluorocyclohexyl]amino}-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 527.2, found 427.4 |

-continued

| Example # | IRAK4 IC$_{50}$ (nM) | Structure | IUPAC Name | Exact Mass [M + H]$^+$ |
|---|---|---|---|---|
| 70 | 51 | 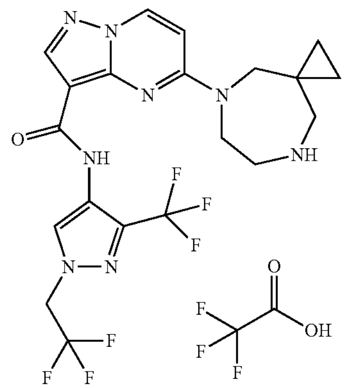 [SMILES: O=C(Nc1cn(CC(F)(F)F)nc1C(F)(F)F)c1cnn2ccc(N3CCNCC4(CC4)C3)nc12 ; O=C(O)C(F)(F)F] | 5-(5,8-diazaspiro[2.6]non-5-yl)-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 503.2, found 503.4 |
| 71 | 328 | 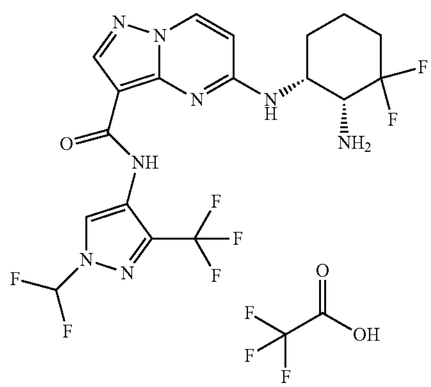 | 5-{[(1R,2R)-2-amino-3,3-difluorocyclohexyl]amino}-N-[1-(difluoromethyl)-3-(trifluoromethyl)-1H-pyrazol-4-yl]pyrazolo[1,5-a]pyrimidine-3-carboxamide trifluoroacetate | Calc'd 495.1, found 495.4 |
| 72 | 141 | 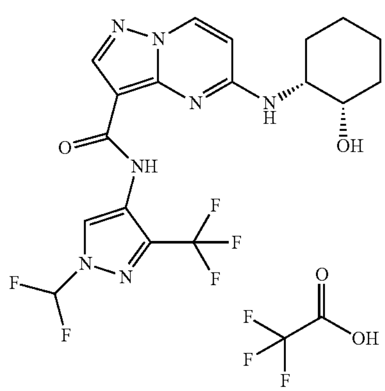 | N-[1-(difluoromethyl)-3-(trifluoromethyl)-1H-pyrazol-4-yl]-5-{[(1R,2S)-2-hydroxycyclohexyl]amino}pyrazolo[1,5-a]pyrimidine-3-carboxamide trifluoroacetate | Calc'd 460.2, found 460.4 |
| 73 | 144 | 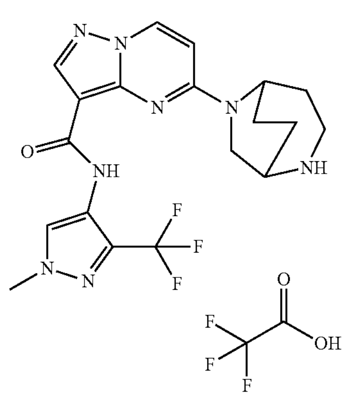 | 5-(2,6-diazabicyclo[3.2.2]non-6-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.4 |

-continued

| Example # | IRAK4 IC$_{50}$ (nM) | Structure | IUPAC Name | Exact Mass [M + H]$^+$ |
|---|---|---|---|---|
| 74 | 41 | 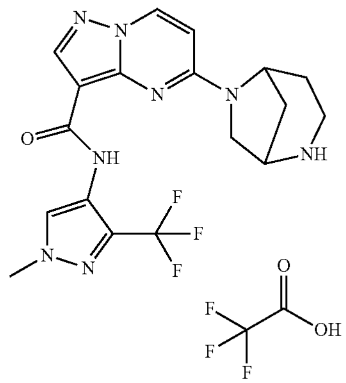 | 5-(2,6-diazabicyclo[3.2.1]oct-6-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |
| 75 | 55 | 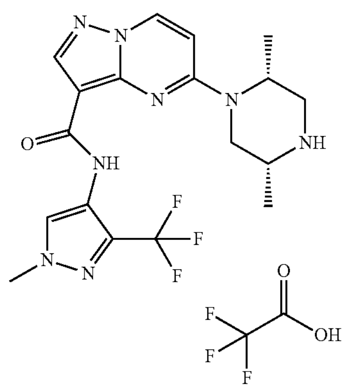 | 5-[cis-2,5-dimethylpiperazin-1-yl]-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |
| 76 | 0.9 | 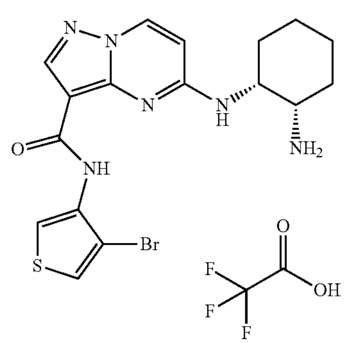 [SMILES: N[C@H]1CCCC[C@H]1Nc1ccn2ncc(C(=O)Nc3cscc3Br)c2n1 ; O=C(O)C(F)(F)F] | 5-{[(1R,2S)-2-aminocyclohexyl]amino}-N-(4-bromothiophen-3-yl)pyrazolo[1,5-a]pyrimidine-3-carboxamide trifluoroacetate | Calc'd 435.2, found 435.4 |
| 77 | 19 | 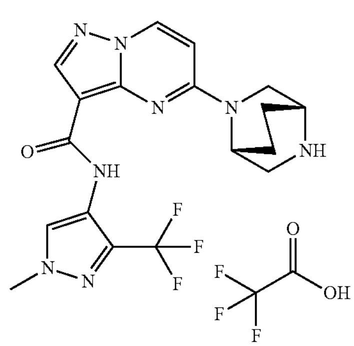 | 5-[1S,4S)- or (1R,4R)-2,5-diazabicyclo[2.2.2]oct-2-yl]-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |

| Example # | IRAK4 IC$_{50}$ (nM) | Structure | IUPAC Name | Exact Mass [M + H]$^+$ |
|---|---|---|---|---|
| 78 | 44 | 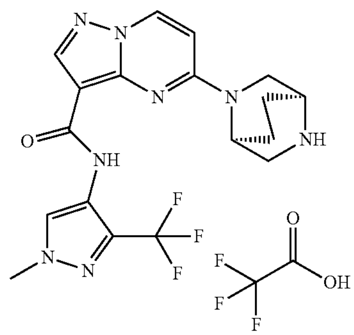 | 5-[(1S,4S)- or (1R,4R)-2,5-diazabicyclo[2.2.2]oct-2-yl]-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |
| 79 | 62 | 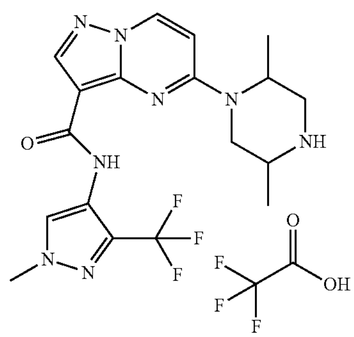 | 5-(2,5-dimethylpiperazin-1-yl)-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |
| 80 | 29 | 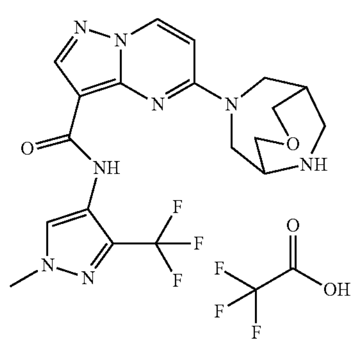 | N-[1-methyl-3-(trifluoromethyl)-1H-pyrazol-4-yl]-5-(3-oxa-7,9-diazabicyclo[3.3.2]dec-7-yl)pyrazolo[1,5-a]pyrimidine-3-carboxamide trifluoroacetate | Calc'd 451.2, found 451.4 |
| 81 | 9 | 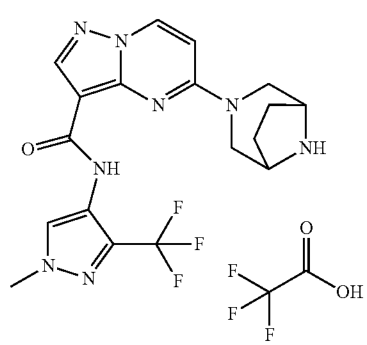 | 5-(3,8-diazabicyclo[3.2.1]oct-3-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |

| Example # | IRAK4 IC$_{50}$ (nM) | Structure | IUPAC Name | Exact Mass [M + H]$^+$ |
|---|---|---|---|---|
| 82 | 114 | 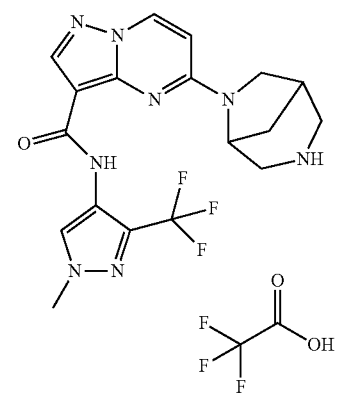 [SMILES: Cn1cc(NC(=O)c2cnn3ccc(N4CC5CNCC4C5)nc23)c(C(F)(F)F)n1 ; O=C(O)C(F)(F)F] | 5-(3,6-diazabicyclo[3.2.1]oct-6-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |
| 83 | 33 | 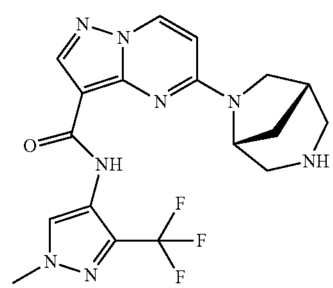 [SMILES: Cn1cc(NC(=O)c2cnn3ccc(N4C[C@@H]5CNC[C@H]4C5)nc23)c(C(F)(F)F)n1] | 5-[(1S,5R)- or (1R,5S)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide | Calc'd 421.2, found 421.4 |
| 84 | 158 | 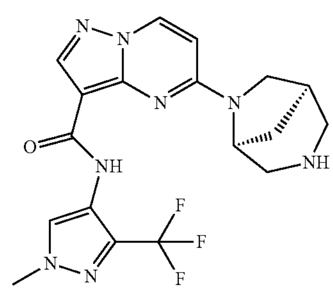 [SMILES: Cn1cc(NC(=O)c2cnn3ccc(N4C[C@H]5CNC[C@@H]4C5)nc23)c(C(F)(F)F)n1] | 5-[(1S,5R)- or (1R,5S)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide | Calc'd 421.2, found 421.4 |
| 85 | 5 | 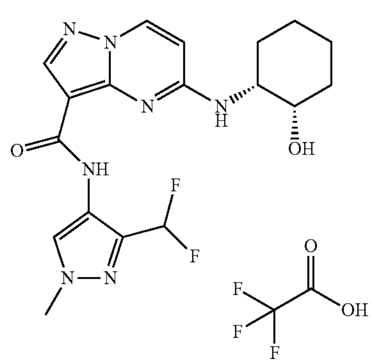 | N-[3-(difluoromethyl)-1-methyl-1H-pyrazol-4-yl]-5-{[(1R,2S)-2-hydroxycyclohexyl]amino}pyrazolo[1,5-a]pyrimidine-3-carboxamide trifluoroacetate | Calc'd 406.2, found 406.4 |

-continued

| Example # | IRAK4 IC$_{50}$ (nM) | Structure | IUPAC Name | Exact Mass [M + H]$^+$ |
|---|---|---|---|---|
| 86 | 2 | 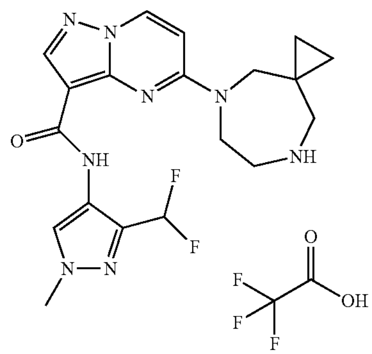 | 5-(5,8-diazaspiro[2.6]non-5-yl)-N-[3-(difluoromethyl)-1-methyl-1H-pyrazol-4-yl]pyrazolo[1,5-a]pyrimidine-3-carboxamide trifluoroacetate | Calc'd 417.2, found 417.4 |
| 87 | 4 | 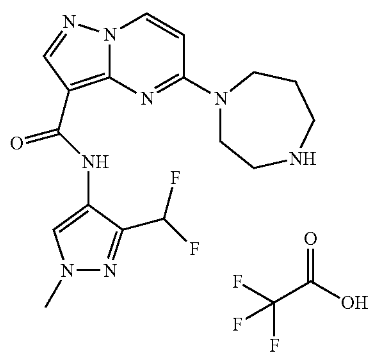 | 5-(1,4-diazepan-1-yl)-N-[3-(difluoromethyl)-1-methyl-1H-pyrazol-4-yl]pyrazolo[1,5-a]pyrimidine-3-carboxamide trifluoroacetate | Calc'd 391.2, found 391.4 |
| 88 | 1 | 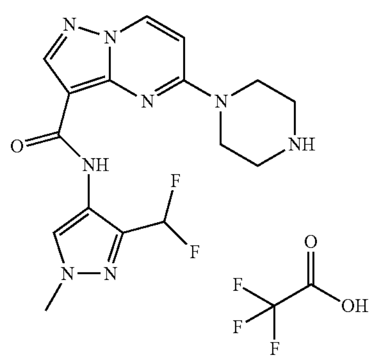 | N-[3-(difluoromethyl)-1-methyl-1H-pyrazol-4-yl]-5-piperazin-1-ylpyrazolo[1,5-a]pyrimidine-3-carboxamide trifluoroacetate | Calc'd 377.2, found 377.2 |
| 89 | 270 | 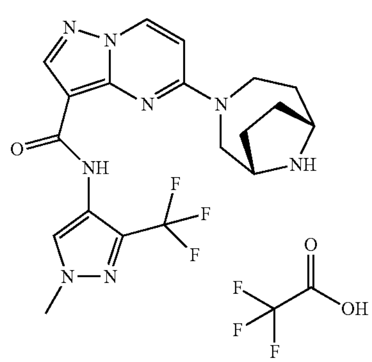 | 5-[(1R,6S)- or (1S,6R)-3,9-diazabicyclo[4.2.1]non-3-yl]-N-[1-methyl-3-(trifluoromethyl)-1H-pyrazol-4-yl]pyrazolo[1,5-a]pyrimidine-3-carboxamide trifluoroacetate | Calc'd 435.2, found 435.2 |

-continued

| Example # | IRAK4 IC$_{50}$ (nM) | Structure | IUPAC Name | Exact Mass [M + H]$^+$ |
|---|---|---|---|---|
| 90 | 0.5 | 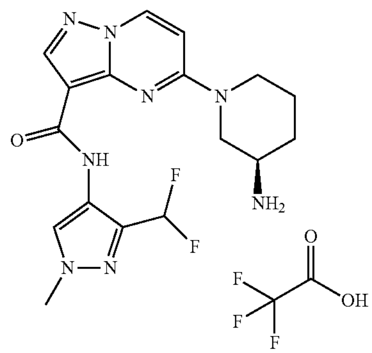 | 5-[(3R)-3-aminopiperidin-1-yl]-N-[3-(difluoromethyl)-1-methyl-1H-pyrazol-4-yl]pyrazolo[1,5-a]pyrimidine-3-carboxamide trifluoroacetate | Calc'd 391.2, found 391.6 |
| 91 | 0.5 | 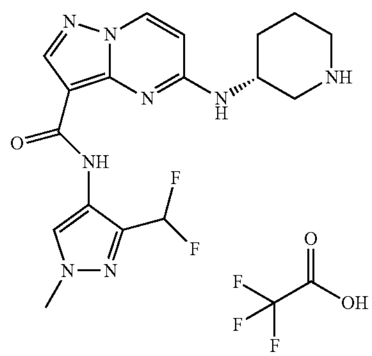 | N-[3-(difluoromethyl)-1-methyl-1H-pyrazol-4-yl]-5-[(3R)-piperidin-3-ylamino]pyrazolo[1,5-a]pyrimidine-3-carboxamide trifluoroacetate | Calc'd 391.2, found 391.4 |
| 92 | 115 | 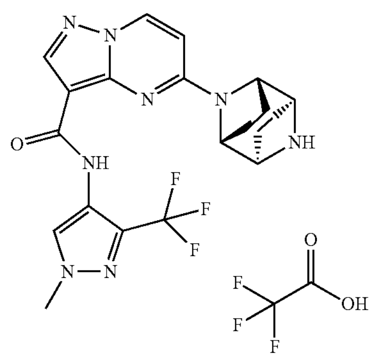 | 5-[9,10-diazatricyclo[4.2.1.1~2,5~]dec-9-yl]-N-]1-methyl-3-(trifluoromethyl)-1H-pyrazol-4-yl]pyrazolo[1,5-a]pyrimidine-3-carboxamide trifluoroacetate | Calc'd 447.2, found 447.4 |
| 93 | 30 | 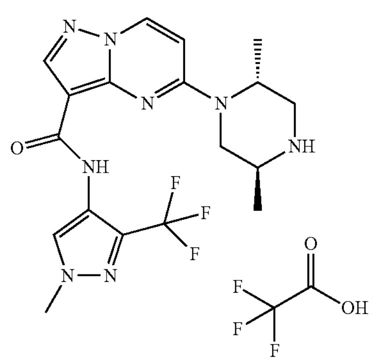 | 5-[trans-2,5-dimethylpiperazin-1-yl]-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |

-continued

| Example # | IRAK4 IC$_{50}$ (nM) | Structure | IUPAC Name | Exact Mass [M + H]$^+$ |
|---|---|---|---|---|
| 94 | 70 | 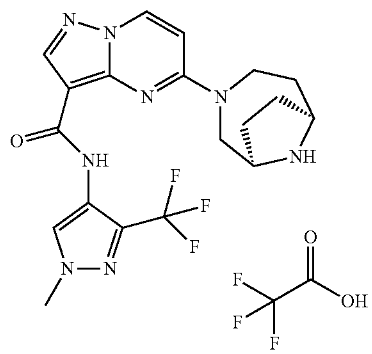 | 5-[(1R,6S)- or (1S,6R)-3,9-diazabicyclo[4.2.1]non-3-yl]-N-[1-methyl-3-(trifluoromethyl)-1H-pyrazol-4-yl]pyrazolo[1,5-a]pyrimidine-3-carboxamide trifluoroacetate | Calc'd 435.2, found 435.2 |
| 95 | 789 | 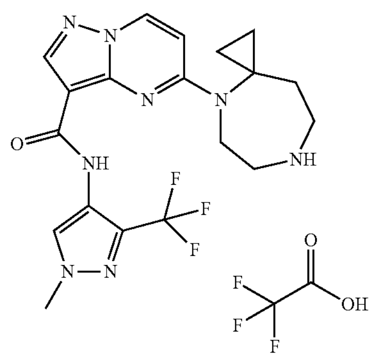 | 5-(4,7-diazaspiro[2.6]non-4-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.4 |
| 96 | 2 | 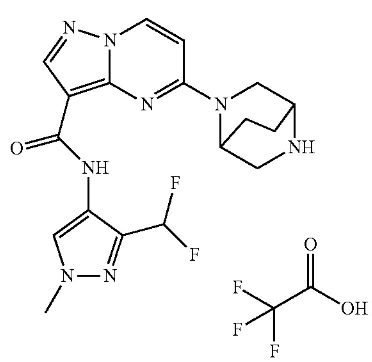 | 5-(2,5-diazabicyclo[2.2.2]oct-2-yl)-N-[3-(difluoromethyl)-1-methyl-1H-pyrazol-4-yl]pyrazolo[1,5-a]pyrimidine-3-carboxamide trifluoroacetate | Calc'd 403.2, found 403.4 |
| 97 | 13 | 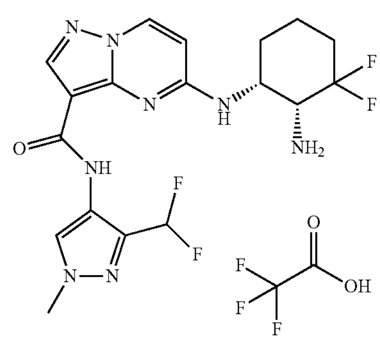 | 5-{[(1R,2R)-2-amino-3,3-difluorocylcohexyl]amino}-N-[3-(difluoromethyl)-1-methyl-1H-pyrazol-4-yl]pyrazolo[1,5-a]pyrimidine-3-carboxamide trifluoroacetate | Calc'd 441.2, found 441.4 |

-continued

| Example # | IRAK4 IC$_{50}$ (nM) | Structure | IUPAC Name | Exact Mass [M + H]$^+$ |
|---|---|---|---|---|
| 98 | 33 | 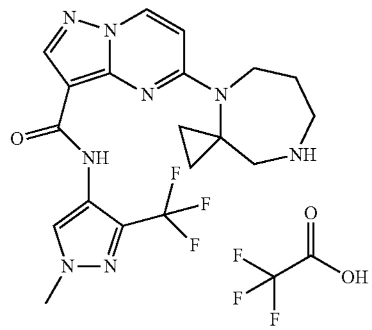 | 5-(4,8-diazaspiro[2.6]non-4-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.6 |
| 99 | 3 | 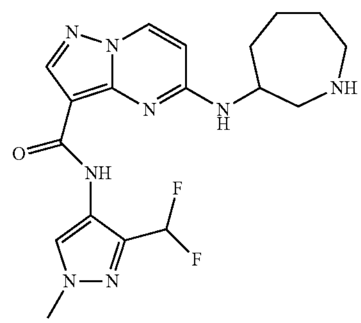 [SMILES: Cn1cc(NC(=O)c2cnn3ccc(NC4CCCCNC4)nc23)c(C(F)F)n1] | 5-(azepan-3-ylamino)-N-[3-(difluoromethyl)-1-methyl-1H-pyrazol-4-yl]pyrazolo[1,5-a]pyrimidine-3-carboxamide | Calc'd 405.2, found 405.4 |
| 100 | 8077 | 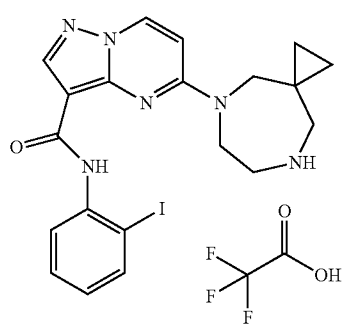 | 5-(5,8-diazaspiro[2.6]non-5-yl)-N-(2-iodophenyl)pyrazolo[1,5-a]pyrimidine-3-carboxamide trifluoroacetate | Calc'd 489.2, found 489.4 |
| 101 | 7647 | 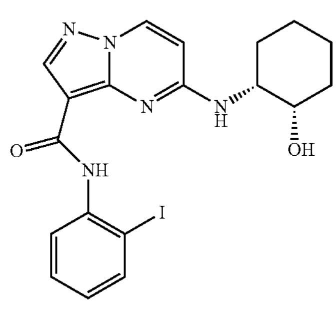 [SMILES: O=C(Nc1ccccc1I)c1cnn2ccc(N[C@@H]3CCCC[C@@H]3O)nc12] | 5-{[(1R,2S)-2-hydroxycyclohexyl]amino}-N-(2-iodophenyl)pyrazolo[1,5-a]pyrimidine-3-carboxamide | Calc'd 478.2, found 478.2 |

-continued

| Example # | IRAK4 IC$_{50}$ (nM) | Structure | IUPAC Name | Exact Mass [M + H]$^+$ |
|---|---|---|---|---|
| 102 | 163 | 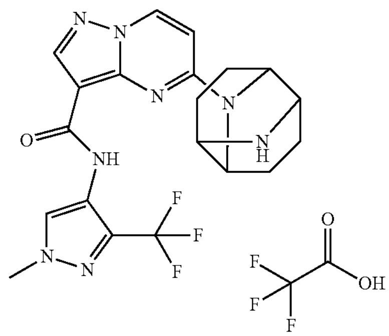 [SMILES: Cn1cc(NC(=O)c2cnn3ccc(N4C5CCC6NC5CCC64)nc23)c(C(F)(F)F)n1 ; O=C(O)C(F)(F)F] | 5-(2,7-diazatricyclo[4.4.0.0~3,8~]dec-2-yl)-N-[1-methyl-3-(trifluoromethyl)-1H-pyrazol-4-yl]pyrazolo[1,5-a]pyrimidine-3-carboxamide trifluoroacetate | Calc'd 447.2, found 447.4 |
| 103 | 6061 | 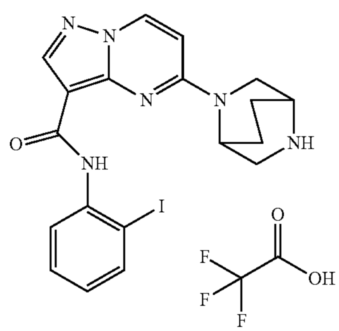 | 5-(2,5-diazabicyclo[2.2.2]oct-2-yl)-N-(2-iodophenyl)pyrazolo[1,5-a]pyrimidine-3-carboxamide trifluoroacetate | Calc'd 475.1, found 475.4 |
| 104 | 1 | 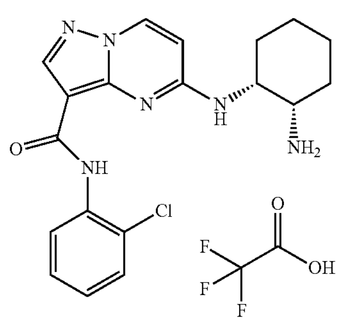 | 5-{[(1R,2)S-2-aminocyclohexyl]amino}-N-(2-chlorophenyl)pyrazolo[1,5-a]pyrimidine-3-carboxamide trifluoroacetate | Calc'd 385.2, found 385.4 |
| 105 | 1267 | 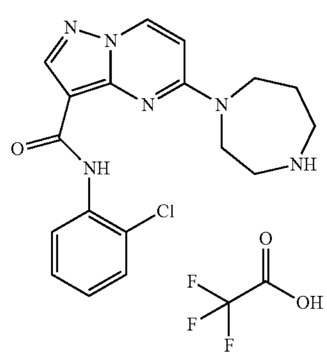 [SMILES: O=C(Nc1ccccc1Cl)c1cnn2ccc(N3CCCNCC3)nc12 ; O=C(O)C(F)(F)F] | N-(2-chlorophenyl)-5-(1,4-diazepan-1-yl)pyrazolo[1,5-a]pyrimidine-3-carboxamide trifluoroacetate | Calc'd 371.1, found 371.4 |

| Example # | IRAK4 IC$_{50}$ (nM) | Structure | IUPAC Name | Exact Mass [M + H]$^+$ |
|---|---|---|---|---|
| 106 | 788 | 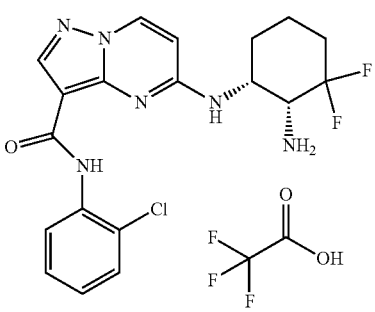 | 5-{[(1R,2R)-2-amino-3,3-difluorocyclohexyl]amino}-N-(2-chlorophenyl)pyrazolo[1,5-a]pyrimidine-3-carboxamide trifluoroacetate | Calc'd 421.2, found 421.4 |
| 107 | 521 | 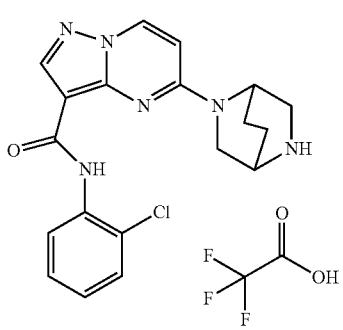 | N-(2-chlorophenyl)-5-(2,5-diazabicyclo[2.2.2]oct-2-yl)pyrazolo[1,5-a]pyrimidine-3-carboxamide trifluoroacetate | Calc'd 383.1, found 383.4 |
| 108 | 1888 | 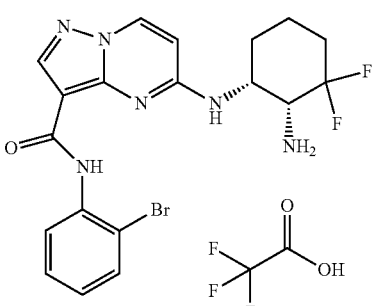 | 5-{[(1R,2R)-2-amino-3,3-difluorocyclohexyl]amino}-N-(2-bromophenyl)pyrazolo[1,5-a]pyrimidine-3-carboxamide trifluoroacetate | Calc'd 467.1, found 467.2 |
| 109 | 3363 | 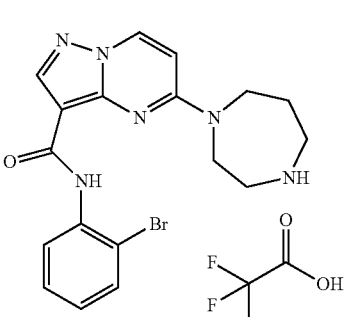 | N-(2-bromophenyl)-5-(1,4-diazepan-1-yl)pyrazolo[1,5-a]pyrimidine-3-carboxamide trifluoroacetate | Calc'd 417.2, found 417.4 |

-continued

| Example # | IRAK4 IC$_{50}$ (nM) | Structure | IUPAC Name | Exact Mass [M + H]$^+$ |
|---|---|---|---|---|
| 110 | 193 | 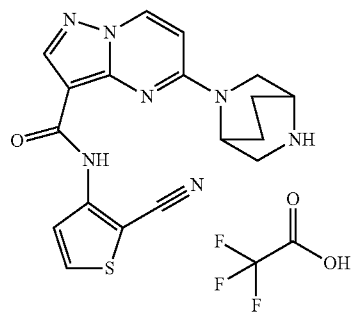 | N-(2-cyanothiophen-3-yl)-5-(2,5-diazabicyclo[2.2.2]oct-2-yl)pyrazolo[1,5-a]pyrimidine-3-carboxamide trifluoroacetate | Calc'd 380.1, found 380.2 |
| 111 | 464 | 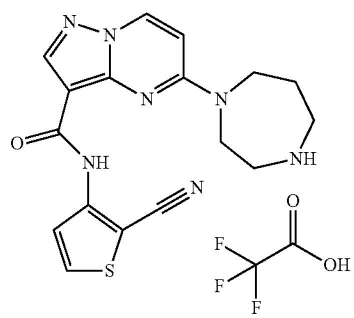 | N-(2-cyanothiophen-3-yl)-5-(1,4-diazepan-1-yl)pyrazolo[1,5-a]pyrimidine-3-carboxamide trifluoroacetate | Calc'd 368.1, found 368.4 |
| 112 | 955 | 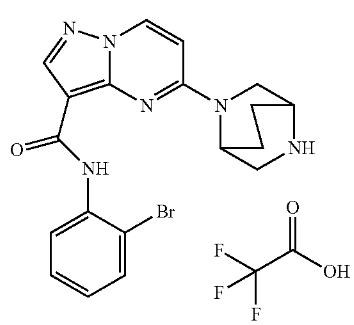 | N-(2-bromophenyl)-5-(2,5-diazabicyclo[2.2.2]oct-2-yl)pyrazolo[1,5-a]pyrimidine-3-carboxamide trifluoroacetate | Calc'd 427.1, found 427.4 |
| 113 | 2 | 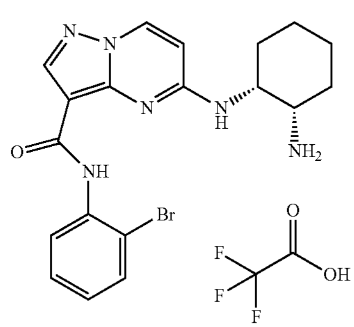 | 5-{[(1R,2S)-2-aminocyclohexyl]amino}-N-(2-bromophenyl)pyrazolo[1,5-a]pyrimidine-3-carboxamide trifluoroacetate | Calc'd 429.1, found 429.4 |

| Example # | IRAK4 IC$_{50}$ (nM) | Structure | IUPAC Name | Exact Mass [M + H]$^+$ |
|---|---|---|---|---|
| 114 | 3823 | 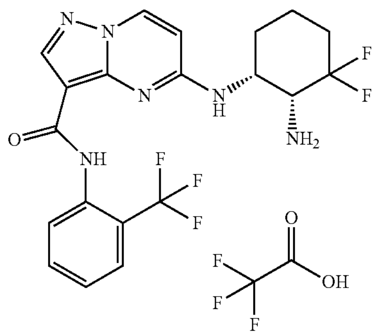 | 5-{[(1R,2R)-2-amino-3,3-difluorocyclohexyl]amino}-N-[2-(trifluoromethyl)phenyl]pyrazolo[1,5-a]pyrimidine-3-carboxamide trifluoroacetate | Calc'd 455.2, found 455.4 |
| 115 | 5602 | 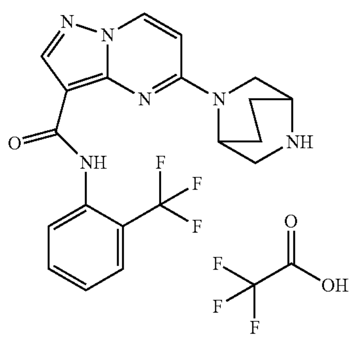 | 5-(2,5-diazabicyclo[2.2.2]oct-2-yl)-N-[2-(trifluoromethyl)phenyl]pyraozlo[1,5-a]pyrimidine-3-carboxamide trifluoroacetate | Calc'd 417.2, found 417.4 |
| 116 | 1 | 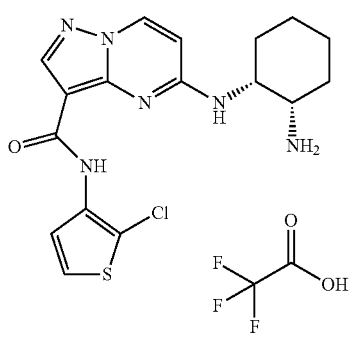 [SMILES: N[C@H]1CCCC[C@H]1Nc1ccn2ncc(C(=O)Nc3ccsc3Cl)c2n1 ; O=C(O)C(F)(F)F] | 5-{[(1R,2S)-2-aminocyclohexyl]amino}-N-(2-chlorothiophen-3-yl)pyrazolo[1,5-a]pyrimidine-3-carboxamide trifluoroacetate | Calc'd 391.2, found 391.4 |
| 117 | 403 | 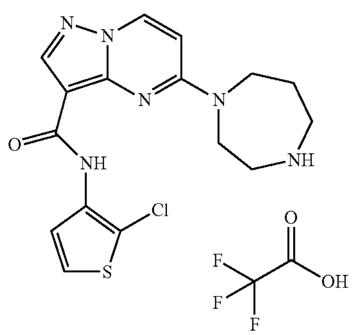 | N-(2-chlorothiophen-3-yl)-5-(1,4-diazepan-1-yl)pyrazolo[1,5-a]pyrimidine-3-carboxamide trifluoroacetate | Calc'd 377.2, found 377.4 |

-continued

| Example # | IRAK4 IC$_{50}$ (nM) | Structure | IUPAC Name | Exact Mass [M + H]$^+$ |
|---|---|---|---|---|
| 118 | 342 | 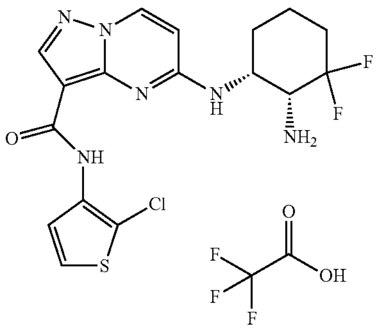 [SMILES: N[C@@H]1[C@H](Nc2ccn3ncc(C(=O)Nc4ccsc4Cl)c3n2)CCCC1(F)F ; O=C(O)C(F)(F)F] | 5-{[(1R,2R)-2-amino-3,3-difluorocyclohexyl]amino}-N-(2-chlorothiophen-3-yl)pyrazolo[1,5-a]pyrimidine-3-carboxamide trifluoroacetate | Calc'd 427.1, found 427.4 |
| 119 | 0.5 | 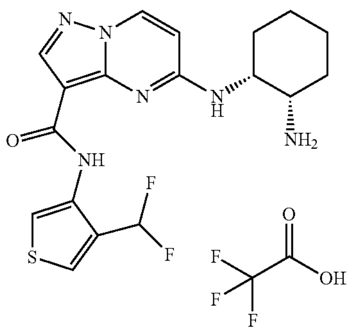 | 5-{[(1R,2S)-2-aminocyclohexyl]amino}-N-[4-(difluoromethyl)thiophen-3-yl]pyrazolo[1,5-a]pyrimidine-3-carboxamide trifluoroacetate | Calc'd 407.1, found 407.4 |
| 120 | 84 | 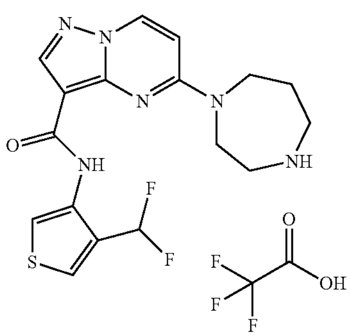 | 5-(1,4-diazepan-1-yl)-N-[4-(difluoromethyl)thiophen-3-yl]pyrazolo[1,5-a]pyrimidine-3-carboxamide trifluoroacetate | Calc'd 393.1, found 393.4 |
| 121 | 124 | 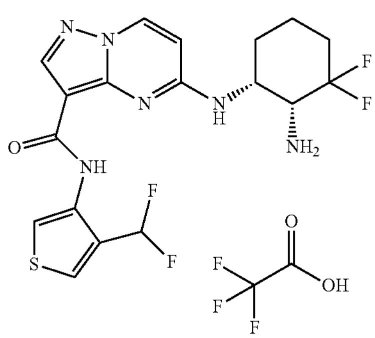 | 5-{[(1R,2R)-2-amino-3,3-difluorocyclohexyl]amino}-N-[4-(difluoromethyl)thiophen-3-yl]pyrazolo[1,5-a]pyrimidine-3-carboxamide trifluoroacetate | Calc'd 443.1, found 443.1 |

| Example # | IRAK4 IC$_{50}$ (nM) | Structure | IUPAC Name | Exact Mass [M + H]$^+$ |
|---|---|---|---|---|
| 122 | 1145 | 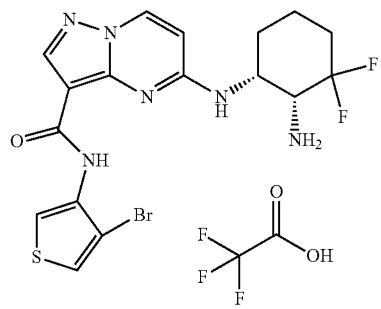 | 5-{[(1R,2R)-2-amino-3,3-difluorocyclohexyl]amino}-N-(4-bromothiophen-3-yl)pyrazolo[1,5-a]pyrimidine-3-carboxamide trifluoroacetate | Calc'd 471.2, found 471.2 |
| 123 | 389 | 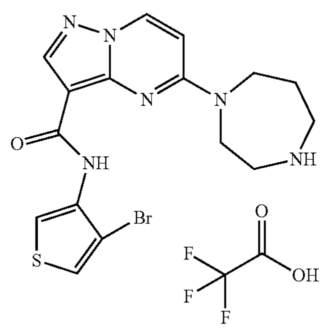 | N-(4-bromothiophen-3-yl)-5-(1,4-diazepan-1-yl)pyrazolo[1,5-a]pyrimidine-3-carboxamide trifluoroacetate | Calc'd 421.2, found 421.2 |
| 124 | 245 | 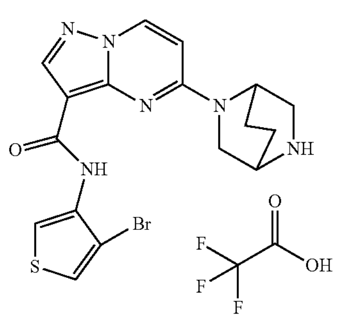 | N-(4-bromothiophen-3-yl)-5-(2,5-diazabicyclo[2.2.2]oct-2-yl)pyrazolo[1,5-a]pyrimidine-3-carboxamide trifluoroacetate | Calc'd 435.2, found 435.4 |
| 125 | 119 | 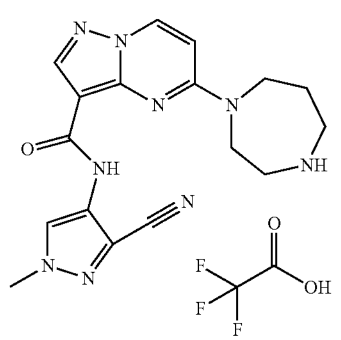 | N-(3-cyano-1-methyl-1H-pyrazol-4-yl)-5-(1,4-diazepan-1-yl)pyrazolo[1,5-a]pyrimidine-3-carboxamide trifluoroacetate | Calc'd 366.2, found 366.4 |

-continued

| Example # | IRAK4 IC$_{50}$ (nM) | Structure | IUPAC Name | Exact Mass [M + H]$^+$ |
|---|---|---|---|---|
| 126 | 70 | 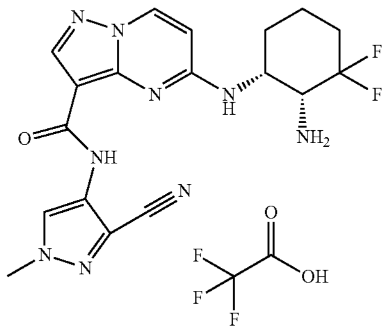 [SMILES: Cn1cc(NC(=O)c2cnn3ccc(N[C@@H]4CCCC(F)(F)[C@@H]4N)nc23)c(C#N)n1 ; O=C(O)C(F)(F)F] | 5-{[(1R,2R)-2-amino-3,3-difluorocyclohexyl]amino}-N-(3-cyano-1-methyl-1H-pyrazol-4-yl)pyrazolo[1,5-a]pyrimidine-3-carboxamide trifluoroacetate | Calc'd 416.2, found 416.2 |
| 127 | 419 | 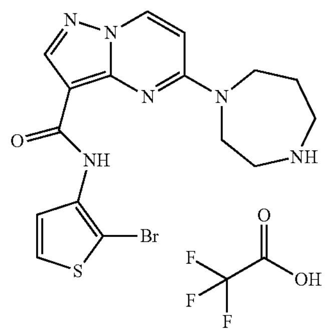 | N-(2-bromothiophen-3-yl)-5-(1,4-diazepan-1-yl)pyrazolo[1,5-a]pyrimidine-3-carboxamide trifluoroacetate | Calc'd 423.2, found 423.2 |
| 128 | 1245 | 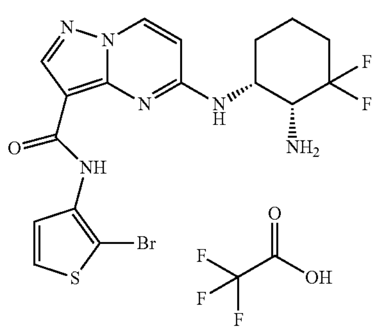 | 5-{[(1R,2R)-2-amino-3,3-difluorocyclohexyl]amino}-N-(2-bromothiophen-3-yl)pyrazolo[1,5-a]pyrimidine-3-carboxamide trifluoroacetate | Calc'd 471.2, found 473.4 |
| 129 | 2 | 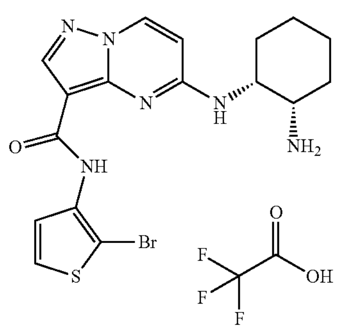 | 5-{[(1R,2S)-2-aminocyclohexyl]amino}-N-(2-bromothiophen-3-yl)pyrazolo[1,5-a]pyrimidine-3-carboxamide trifluoroacetate | Calc'd 435.2, found 435.4 |

-continued

| Example # | IRAK4 IC$_{50}$ (nM) | Structure | IUPAC Name | Exact Mass [M + H]$^+$ |
|---|---|---|---|---|
| 130 | 8811 | 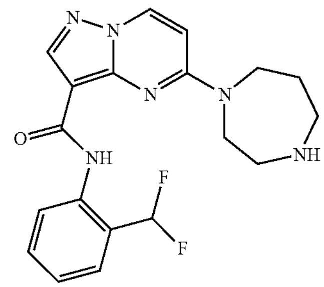 [SMILES: O=C(Nc1ccccc1C(F)F)c1cnn2ccc(N3CCCNCC3)nc12] | 5-(1,4-diazepan-1-yl)-N-[2-(difluoromethyl)phenyl]pyrazolo[1,5-a]pyrimidine-3-carboxamide | Calc'd 387.2, found 387.2 |
| 131 | 8 | 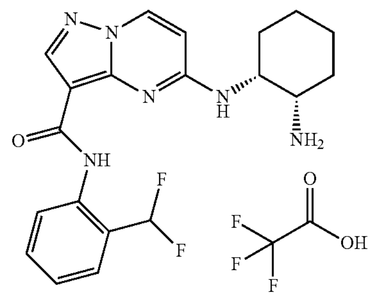 | 5-{[(1R,2S)-2-aminocyclohexyl]amino}-N-[2-(difluoromethyl)phenyl]pyrazolo[1,5-a]pyrimidine-3-carboxamide trifluoroacetate | Calc'd 401.2, found 401.4 |
| 132 | 2099 | 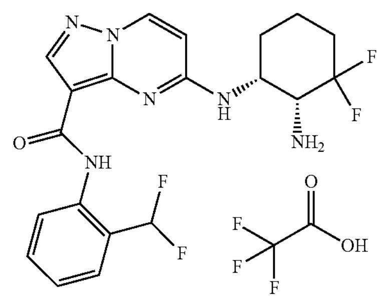 | 5-{[(1R,2R)-2-amino-3,3-difluorocyclohexyl]amino}-N-[2-(difluoromethyl)phenyl]pyrazolo[1,5-a]pyrimidine-3-carboxamide trifluoroacetate | Calc'd 437.2, found 437.2 |
| 133 | 95 | 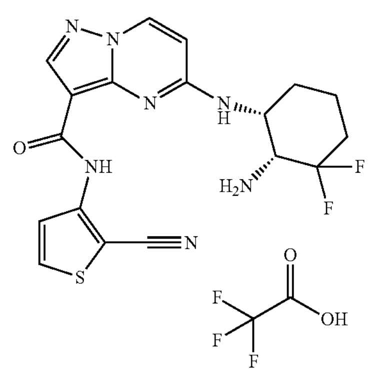 | 5-{[(1R,2R)-2-amino-3,3-difluorocyclohexyl]amino}-N-(2-cyanothiophen-3-yl)pyrazolo[1,5-a]pyrimidine-3-carboxamide trifluoroacetate | Calc'd 418.1, found 418.4 |
| 134 | 306 | 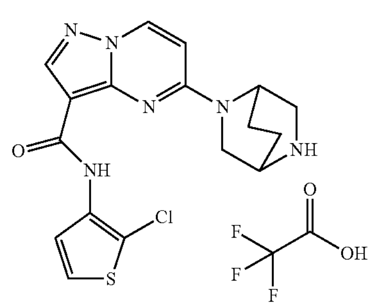 | N-(2-chlorothiophen-3-yl)-5-(2,5-diazabicyclo[2.2.2]oct-2-yl)pyrazolo[1,5-a]pyrimidine-3-carboxamide trifluoroacetate | Calc'd 389.1, found 389.4 |

-continued

| Example # | IRAK4 IC$_{50}$ (nM) | Structure | IUPAC Name | Exact Mass [M + H]$^+$ |
|---|---|---|---|---|
| 135 | 48 | 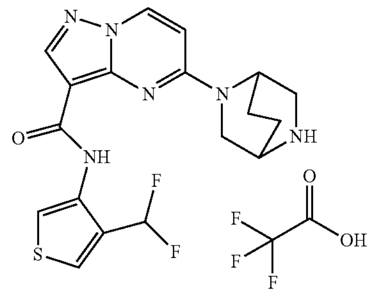 | 5-(2,5-diazabicyclo[2.2.2]oct-2-yl)-N-[4-(difluoromethyl)thiopen-3-yl]pyrazolo[1,5-a]pyrimidine-3-carboxamide trifluoroacetate | Calc'd 405.2, found 405.4 |
| 136 | 49 | 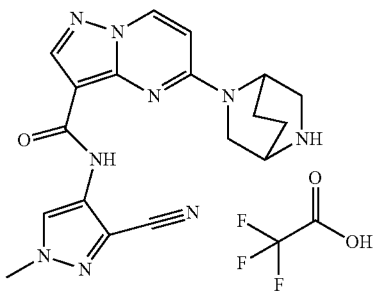 | N-(3-cyano-1-methyl-1H-pyrazol-4-yl)-5-(2,5-diazabicyclo[2.2.2]oct-2-yl)pyrazolo[1,5-a]pyrimidine-3-carboxamide trifluoroacetate | Calc'd 378.2, found 378.4 |
| 137 | 72 | 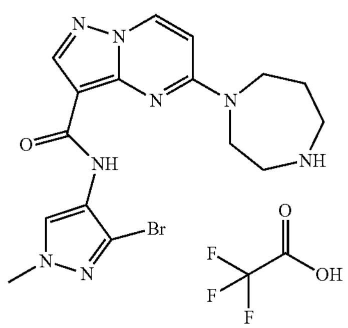 | N-(3-bromo-1-methyl-1H-pyrazol-4-yl)-5-(1,4-diazepan-1-yl)pyrazolo[1,5-a]pyrimidine-3-carboxamide trifluoroacetate | Calc'd 419.2, found 421.4 |
| 138 | 0.3 | 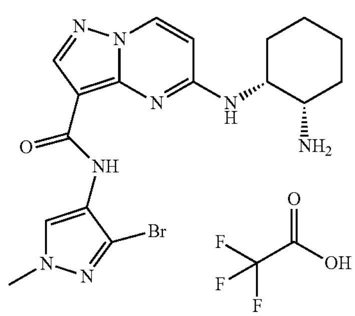 | 5-{[(1R,2S)-2-aminocyclohexyl]amino}-N-(3-bromo-1-methyl-1H-pyrazol-4-yl)pyrazolo[1,5-a]pyrimidine-3-carboxamide trifluoroacetate | Calc'd 433.1, found 433.4 |
| 139 | 126 | 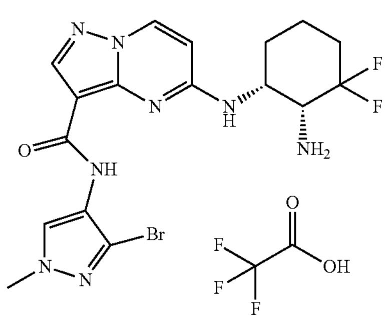 | 5-{[(1R,2R)-2-amino-3,3-difluorocyclohexyl]amino}-N-(3-bromo-1-methyl-1H-pyrazol-4-yl)pyrazolo[1,5-a]pyrimidine-3-carboxamide trifluoroacetate | Calc'd 469.1, found 469.2 |

| Example # | IRAK4 IC$_{50}$ (nM) | Structure | IUPAC Name | Exact Mass [M + H]$^+$ |
|---|---|---|---|---|
| 140 | 42 | 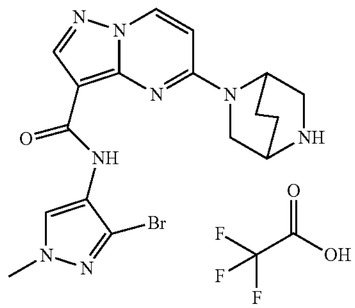 | N-(3-bromo-1-methyl-1H-pyrazol-4-yl)-5-(2,5-diazabicyclo[2.2.2]oct-2-yl)pyrazolo[1,5-a]pyrimidine-3-carboxamide trifluoroacetate | Calc'd 431.1, found 433.4 |
| 141 | 359 | 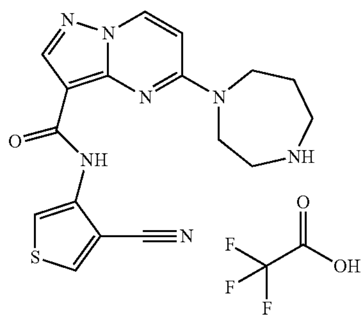 | N-(4-cyanothiophen-3-yl)-5-(1,4-diazepan-1-yl)pyrazolo[1,5-a]pyrimidine-3-carboxamide trifluoroacetate | Calc'd 368.1, found 368.4 |
| 142 | 524 | 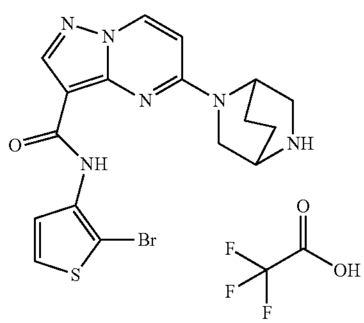 [SMILES: O=C(Nc1ccsc1Br)c1cnn2ccc(N3CC4CCC3CN4)nc12 ; O=C(O)C(F)(F)F] | N-(2-bromothiophen-3-yl)-5-(2,5-diazabicyclo[2.2.2]oct-2-yl)pyrazolo[1,5-a]pyrimidine-3-carboxamide trifluoroacetate | Calc'd 433.1, found 433.2 |
| 143 | 192 | 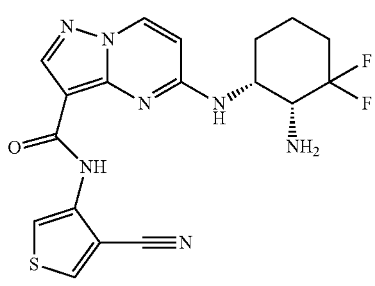 [SMILES: N#Cc1cscc1NC(=O)c1cnn2ccc(N[C@@H]3CCCC(F)(F)[C@@H]3N)nc12] | 5-{[(1R,2R)-2-amino-3,3-difluorocyclohexyl]amino}-N-(4-cyanothiophen-3-yl)pyrazolo[1,5-a]pyrimidine-3-carboxamide | Calc'd 418.1, found 418.2 |
| 144 | 7 | 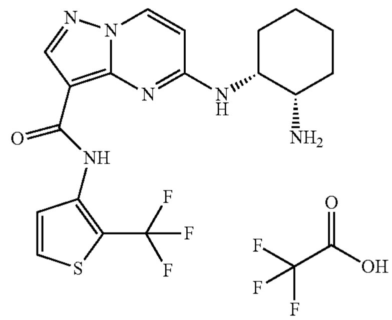 [SMILES: N[C@H]1CCCC[C@H]1Nc1ccn2ncc(C(=O)Nc3ccsc3C(F)(F)F)c2n1 ; O=C(O)C(F)(F)F] | 5-{[(1R,2S)-2-aminocyclohexyl]amino}-N-[2-(trifluoromethyl)thiophen-3-yl]pyrazolo[1,5-a]pyrimidine-3-carboxamide trifluoroacetate | Calc'd 425.1, found 425.4 |

-continued

| Example # | IRAK4 IC$_{50}$ (nM) | Structure | IUPAC Name | Exact Mass [M + H]$^+$ |
|---|---|---|---|---|
| 145 | 165 | 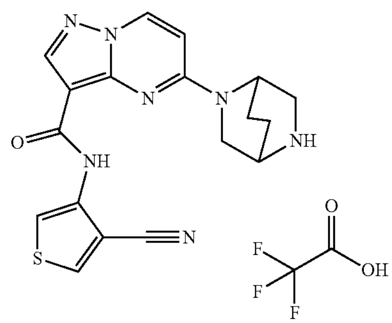 [SMILES: N#Cc1cscc1NC(=O)c1cnn2ccc(N3CC4CCC3CN4)nc12 ; O=C(O)C(F)(F)F] | N-(4-cyanothiophen-3-yl)-5-(2,5-diazabicyclo[2.2.2]oct-2-yl)pyrazolo[1,5-a]pyrimidine-3-carboxamide trifluoroacetate | Calc'd 380.1, found 380.4 |
| 146 | 1456 | 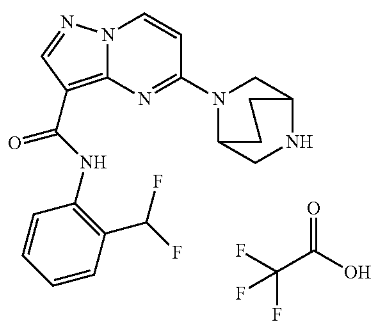 [SMILES: O=C(Nc1ccccc1C(F)F)c1cnn2ccc(N3CC4CCC3CN4)nc12 ; O=C(O)C(F)(F)F] | 5-(2,5-diazabicyclo[2.2.2]oct-2-yl)-N-[2-(difluoromethyl)phenyl]pyrazolo[1,5-a]pyrimidine-3-carboxamide trifluoroacetate | Calc'd 399.2, found 399.4 |
| 147 | 979 | 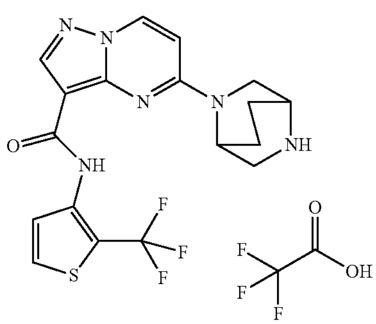 | 5-(2,5-diazabicyclo[2.2.2]oct-2-yl)-N-[2-(trifluoromethyl)thiophen-3-yl]pyrazolo[1,5-a]pyrimidine-3-carboxamide trifluoroacetate | Calc'd 423.2, found 423.4 |
| 148 | 113 | 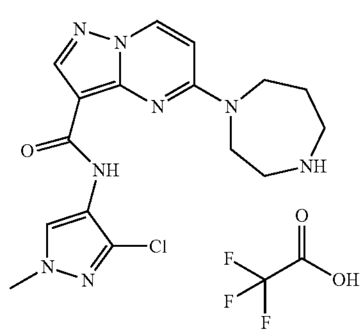 | N-(3-chloro-1-methyl-1H-pyrazol-4-yl)-5-(1,4-diazepan-1-yl)pyrazolo[1,5-a]pyrimidine-3-carboxamide trifluoroacetate | Calc'd 375.1, found 375.4 |

| Example # | IRAK4 IC$_{50}$ (nM) | Structure | IUPAC Name | Exact Mass [M + H]$^+$ |
|---|---|---|---|---|
| 149 | 0.5 | 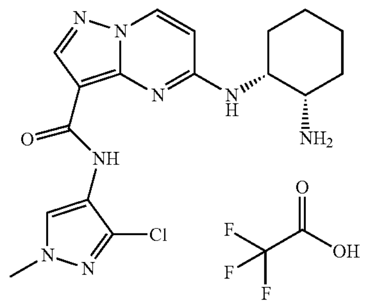 | 5-{[(1R,2S)-2-aminocyclohexyl]amino}-N-(3-chloro-1-methyl-1H-pyrazol-4-yl)pyrazolo[1,5-a]pyrimidine-3-carboxamide trifluoroacetate | Calc'd 389.1, found 389.4 |
| 150 | 109 | 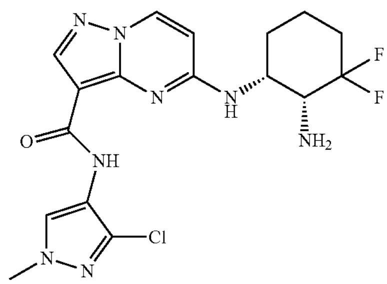 [SMILES: Cn1cc(NC(=O)c2cnn3ccc(N[C@@H]4CCCC(F)(F)[C@@H]4N)nc23)c(Cl)n1] | 5-{[(1R,2R)-2-amino-3,3-difluorocyclohexyl]amino}-N-(3-chloro-1-methyl-1H-pyrazol-4-yl)pyrazolo[1,5-a]pyrimidine-3-carboxamide | Calc'd 425.1, found 425.4 |
| 151 | 128 | 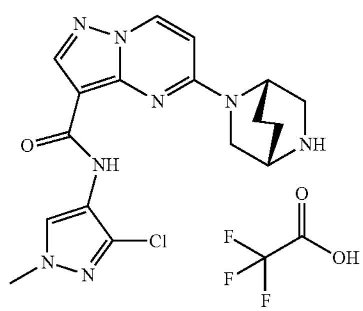 | N-(3-chloro-1-methyl-1H-pyrazol-4-yl)-5-[(1S,4S)- or (1R,4R)-(2,5-diazabicyclo[2.2.2]oct-2-yl]pyrazolo[1,5-a]pyrimidine-3-carboxamide trifluoroacetate | Calc'd 387.2, found 387.4 |
| 152 | 28 | 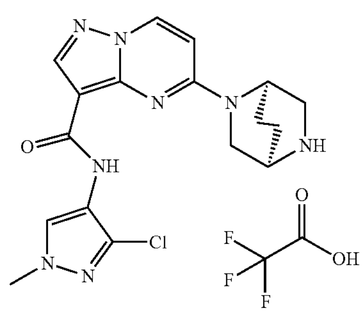 | N-(3-chloro-1-methyl-1H-pyrazol-4-yl)-5-[(1S,4S)- or (1R,4R)-(2,5-diazabicyclo[2.2.2]oct-2-yl]pyrazolo[1,5-a]pyrimidine-3-carboxamide trifluoroacetate | Calc'd 387.2, found 387.4 |
| 153 | 1013 | 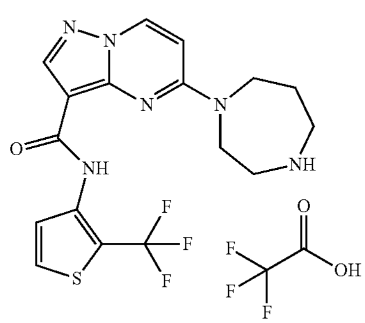 | 5-(1,4-diazepan-1-yl)-N-[2-(trifluoromethyl)thiophen-3-yl]pyrazolo[1,5-a]pyrimidine-3-carboxamide trifluoroacetate | Calc'd 411.1, found 411.4 |

-continued

| Example # | IRAK4 IC$_{50}$ (nM) | Structure | IUPAC Name | Exact Mass [M + H]$^+$ |
|---|---|---|---|---|
| 154 | 86 | 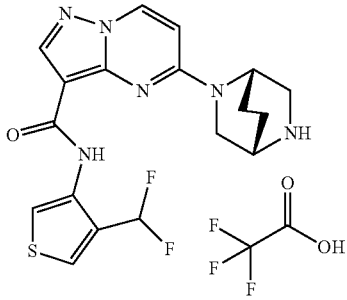 | 5-[(1S,4S)- or (1R,4R)-2,5-diazabicyclo[2.2.2]oct-2-yl]-N-[4-(difluoromethyl)thiophen-3-yl]pyrazolo[1,5-a]pyrimidine-3-carboxamide trifluoroacetate | Calc'd 405.2, found 405.4 |
| 155 | 32 | 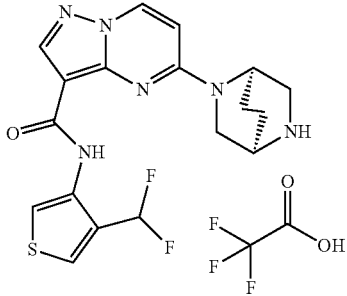 | 5-[(1S,4S)- or (1R,4R)-2,5-diazabicyclo[2.2.2]oct-2-yl]-N-[4-(difluoromethyl)thiophen-3-yl]pyrazolo[1,5-a]pyrimidine-3-carboxamide trifluoroacetate | Calc'd 405.2, found 405.4 |
| 156 | 41 | 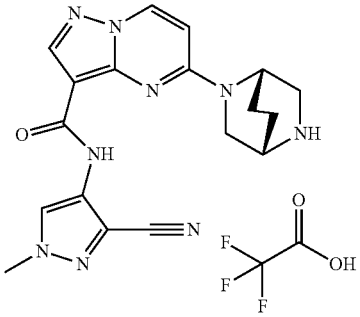 | N-(3-cyano-1-methyl-1H-pyrazol-4-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 378.2, found 378.4 |
| 157 | 60 | 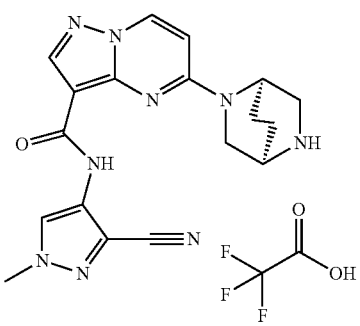 | N-(3-cyano-1-methyl-1H-pyrazol-4-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 378.2, found 378.4 |

-continued

| Example # | IRAK4 IC$_{50}$ (nM) | Structure | IUPAC Name | Exact Mass [M + H]$^+$ |
|---|---|---|---|---|
| 158 | 3 | 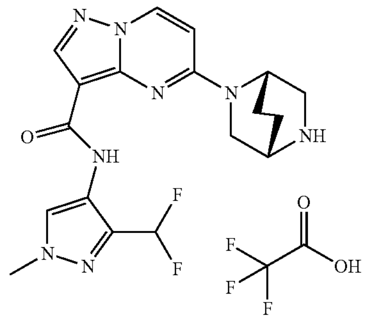 | 5-[(1S,4S)- or (1R,4R)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide trifluoroacetate | Calc'd 403.2, found 403.4 |
| 159 | 18 | 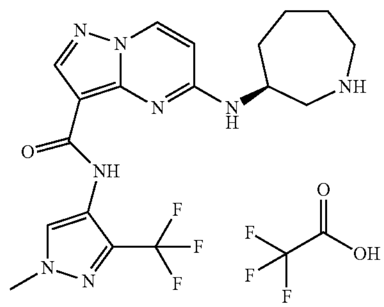 | 5-[(3S)- or (3R)-azepan-3-ylamino]-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |
| 160 | 0.5 | 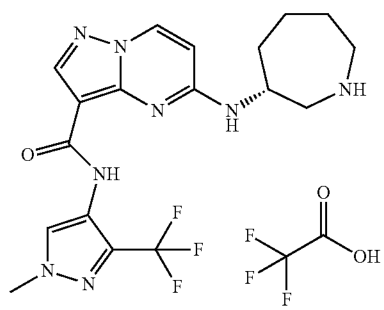 | 5-[(3S)- or (3R)-azepan-3-ylamino]-N-[1-methyl-3-(trifluoromethyl)-1H-pyrazol-4-yl]pyrazolo[1,5-a]pyrimidine-3-carboxamide trifluoroacetate | Calc'd 423.2, found 423.4 |
| 161 | 2 | 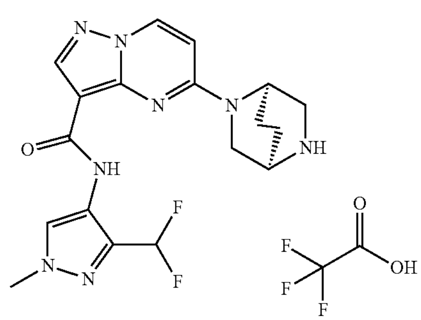 [SMILES: Cn1cc(NC(=O)c2cnn3ccc(N4C[C@H]5CC[C@@H]4CN5)nc23)c(C(F)F)n1 ; O=C(O)C(F)(F)F] | 5-[(1S,4S)- or (1R,4R)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide trifluoroacetate | Calc'd 403.2, found 403.4 |
| 162 | 0.2 | 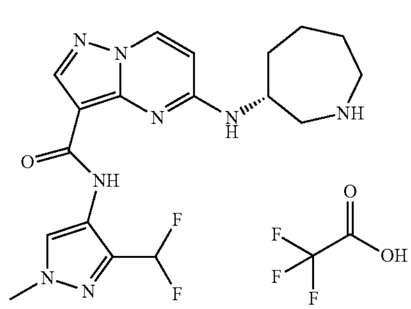 [SMILES: Cn1cc(NC(=O)c2cnn3ccc(N[C@@H]4CCCCNC4)nc23)c(C(F)F)n1 ; O=C(O)C(F)(F)F] | 5-[(3S)- or (3R)-azepan-3-ylamino]-N-[3-(difluoromethyl)-1-methyl-1H-pyrazol-4-yl]pyrazolo[1,5-a]pyrimidine-3-carboxamide trifluoroacetate | Calc'd 405.2, found 405.6 |

-continued

| Example # | IRAK4 IC$_{50}$ (nM) | Structure | IUPAC Name | Exact Mass [M + H]$^+$ |
|---|---|---|---|---|
| 163 | 7 | 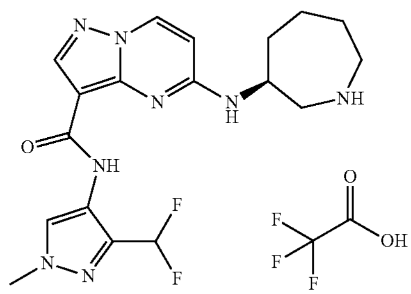 [SMILES: Cn1cc(NC(=O)c2cnn3ccc(N[C@H]4CCCCNC4)nc23)c(C(F)F)n1 ; O=C(O)C(F)(F)F] | 5-[(3S)- or (3R)-azepan-3-ylamino]-N-[3-(difluoromethyl)-1-methyl-1H-pyrazol-4-yl]pyrazolo[1,5-a]pyrimidine-3-carboxamide trifluoroacetate | Calc'd 405.2, found 405.4 |
| 164 | 50 | 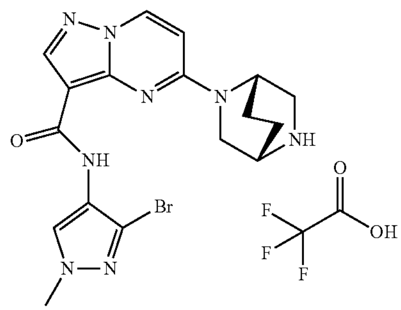 | N-(3-bromo-1-methyl-1H-pyrazol-4-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 431.1, found 431.4 |
| 165 | 19 | 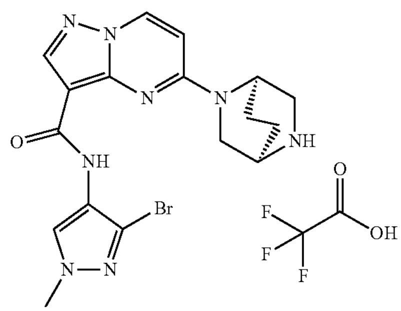 | N-(3-bromo-1-methyl-1H-pyrazol-4-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 431.1, found 431.4 |
| 166 | 15 | 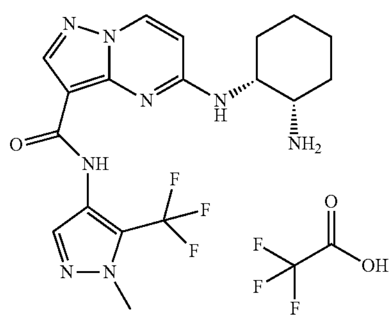 [SMILES: Cn1ncc(NC(=O)c2cnn3ccc(N[C@@H]4CCCC[C@@H]4N)nc23)c1C(F)(F)F ; O=C(O)C(F)(F)F] | 5-{[(1R,2S)-2-aminocyclohexyl]amino}-N-[1-methyl-5-(trifluoromethyl)-1H-pyrazol-4-yl]pyrazolo[1,5-a]pyrimidine-3-carboxamide trifluoroacetate | Calc'd 423.2, found 423.4 |
| 167 | 480 | 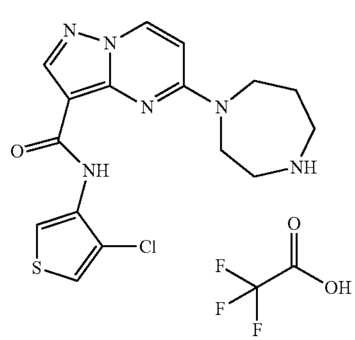 | N-(4-chlorothiophen-3-yl)-5-(1,4-diazepan-1-yl)pyrazolo[1,5-a]pyrimidine-3-carboxamide trifluoroacetate | Calc'd 377.2, found 377.2 |

-continued

| Example # | IRAK4 IC$_{50}$ (nM) | Structure | IUPAC Name | Exact Mass [M + H]$^+$ |
|---|---|---|---|---|
| 168 | 1 | 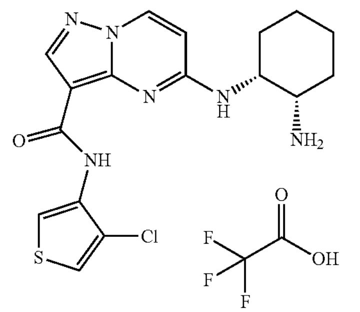 | 5-{[(1R,2S)-2-aminocyclohexyl]amino}-N-(4-chlorothiophen-3-yl)pyrazolo[1,5-a]pyrimidine-3-carboxamide trifluoroacetate | Calc'd 391.2, found 391.2 |
| 169 | 150 | 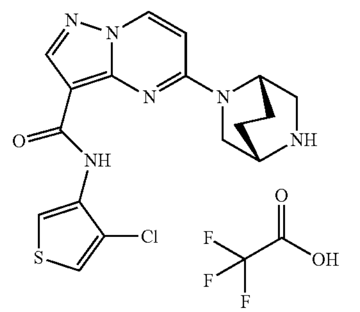 | N-(4-chlorothiophen-3-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 389.1, found 389.4 |
| 170 | 560 | 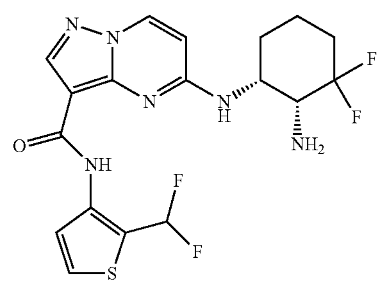 [SMILES: N[C@@H]1[C@H](Nc2ccn3ncc(C(=O)Nc4ccsc4C(F)F)c3n2)CCCC1(F)F] | 5-{[(1R,2R)-2-amino-3,3-difluorocyclohexyl]amino}-N-[2-(difluoromethyl)thiophen-3-yl]pyrazolo[1,5-a]pyrimidine-3-carboxamide | Calc'd 443.1, found 443.1 |
| 171 | 383 | 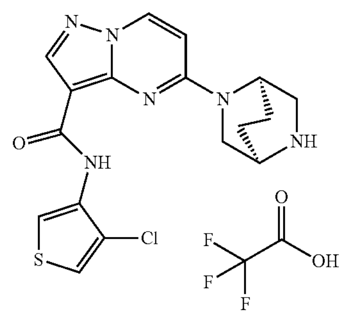 | N-(4-chlorothiophen-3-yl)-5-[(1S,4S)- or (1R,4R)-2,5-diazabicyclo[2.2.2]oct-2-yl]pyrazolo[1,5-a]pyrimidine-3-carboxamide trifluoroacetate | Calc'd 389.1, found 389.4 |
| 172 | 1 | 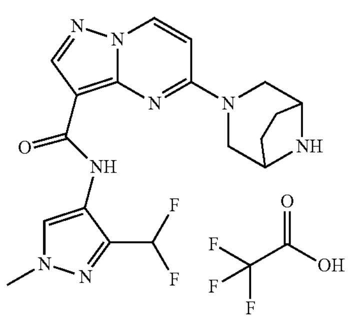 | 5-(3,8-diazabicyclo[3.2.1]oct-3-yl)-N-[3-(difluoromethyl)-1-methyl-1H-pyrazol-4-yl]pyrazolo[1,5-a]pyrimidine-3-carboxamide trifluoroacetate | Calc'd 403.2, found 403.4 |

| Example # | IRAK4 IC$_{50}$ (nM) | Structure | IUPAC Name | Exact Mass [M + H]$^+$ |
|---|---|---|---|---|
| 173 | 0.8 | 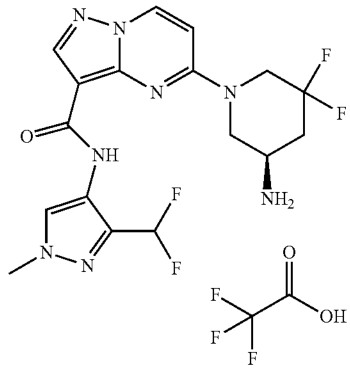 | 5-[(4R)- or (4S)-5-amino-3,3-difluoropiperidin-1-yl)-N-[3-(difluoromethyl)-1-methyl-1H-pyrazol-4-yl]pyrazolo[1,5-a]pyrimidine-3-carboxamide trifluoroacetate | Calc'd 427.1, found 427.4 |
| 174 | 1 | 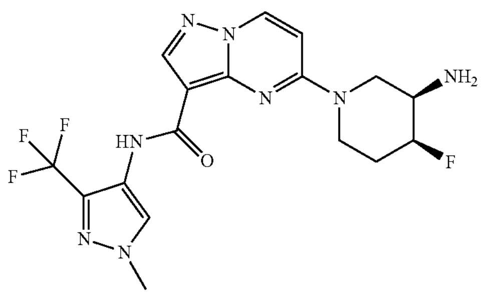 [SMILES: Cn1cc(NC(=O)c2cnn3ccc(N4CC[C@H](F)[C@H](N)C4)nc23)c(C(F)(F)F)n1] | 5-[(3R,4S)- or (3S,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide | Calc'd 427, found 427 |
| 175 | 21 | 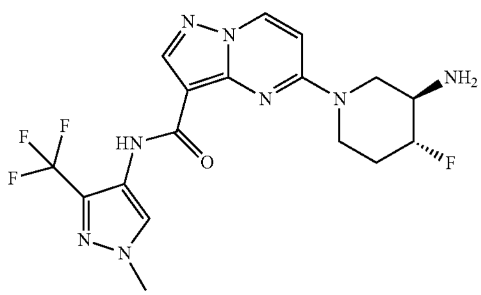 [SMILES: Cn1cc(NC(=O)c2cnn3ccc(N4CC[C@@H](F)[C@H](N)C4)nc23)c(C(F)(F)F)n1] | 5-[(3R,4R)- or (3S,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide | Calc'd 427, found 427 |
| 176 | 12 | 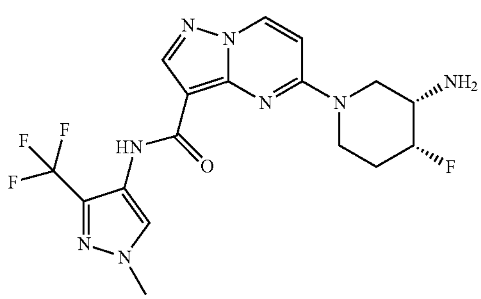 [SMILES: Cn1cc(NC(=O)c2cnn3ccc(N4CC[C@@H](F)[C@@H](N)C4)nc23)c(C(F)(F)F)n1] | 5-[(3R,4S)- or (3S,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide | Calc'd 427, found 427 |
| 177 | 1 | 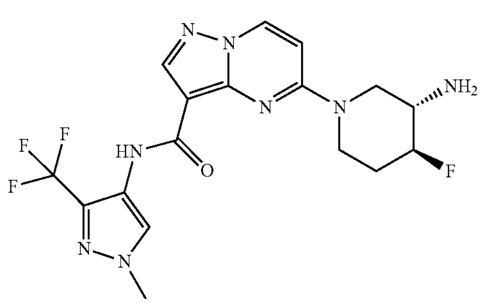 [SMILES: Cn1cc(NC(=O)c2cnn3ccc(N4CC[C@H](F)[C@@H](N)C4)nc23)c(C(F)(F)F)n1] | 5-[(3R,4R)- or (3S,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide | Calc'd 427, found 427 |

| Example # | IRAK4 IC$_{50}$ (nM) | Structure | IUPAC Name | Exact Mass [M + H]$^+$ |
|---|---|---|---|---|
| 178 | 4 | 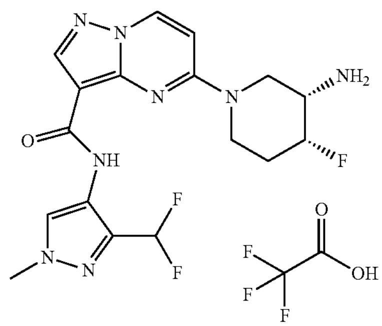 | 5-[(3S,4R)- or (3R,4S)-3-amino-4-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.4 |
| 179 | 0.5 | 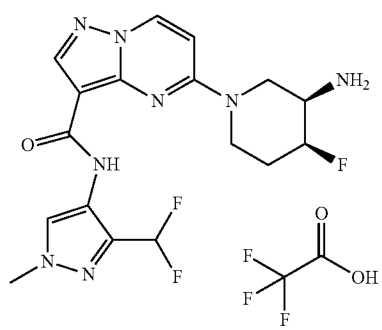 | 5-[(3S,4R)- or (3R,4S)-3-amino-4-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.4 |
| 180 | 0.5 | 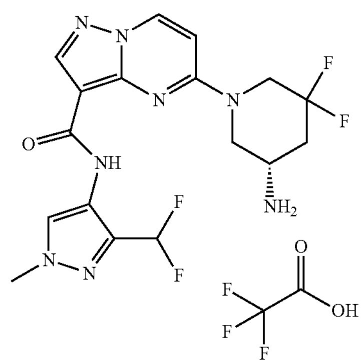 | 5-[(4R)- or (4S)-(5-amino-3,3-difluoropiperidin-1-yl)-N-[3-(difluoromethyl)-1-methyl-1H-pyrazol-4-yl]pyrazolo[1,5-a]pyrimidine-3-carboxamide trifluoroacetate | Calc'd 427.1, found 427.4 |
| 181 | 54 | 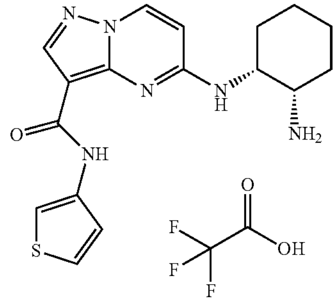 [SMILES: N[C@H]1CCCC[C@H]1Nc1ccn2ncc(C(=O)Nc3ccsc3)c2n1 ; O=C(O)C(F)(F)F] | 5-{[(1R,2S)-2-aminocyclohexyl]amino}-N-thiophen-3-ylpyrazolo[1,5-a]pyrimidine-3-carboxamide trifluoroacetate | Calc'd 357.1, found 357.4 |

| Example # | IRAK4 IC$_{50}$ (nM) | Structure | IUPAC Name | Exact Mass [M + H]$^+$ |
|---|---|---|---|---|
| 182 | 14 | 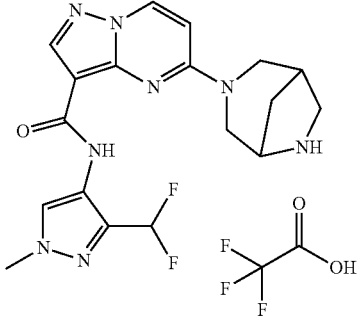 | 5-[(3,6-diazabicyclo[3.2.1]oct-3-yl]-N-[3-(difluoromethyl)-1-methyl-1H-pyrazol-4-yl]pyrazolo[1,5-a]pyrimidine-3-carboxamide trifluoroacetate | Calc'd 403.2, found 403.6 |
| 183 | 6 | 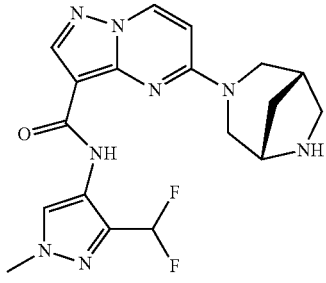 [SMILES: Cn1cc(NC(=O)c2cnn3ccc(N4C[C@@H]5CN[C@@H](C5)C4)nc23)c(C(F)F)n1] | 5-[(1S,5S)- or (1R,5R)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide trifluoroacetate | Calc'd 403.2, found 403.6 |
| 184 | 47 | 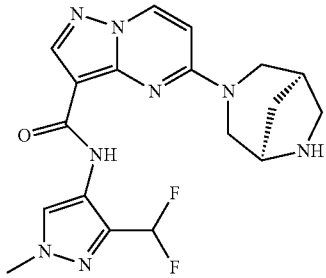 [SMILES: Cn1cc(NC(=O)c2cnn3ccc(N4C[C@H]5CN[C@H](C5)C4)nc23)c(C(F)F)n1] | 5-[(1S,5S)- or (1R,5R)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide trifluoroacetate | Calc'd 403.2, found 403.6 |
| 185 | 1577 | 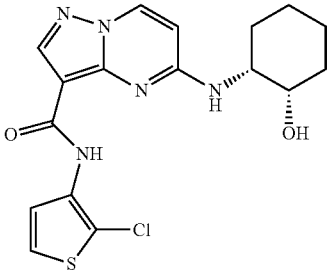 [SMILES: O=C(Nc1ccsc1Cl)c1cnn2ccc(N[C@@H]3CCCC[C@@H]3O)nc12] | N-(2-chlorothiophen-3-yl)-5-{[(1R,2S)-2-hydroxycyclohexyl]amino}pyrazolo[1,5-a]pyrimidine-3-carboxamide | Calc'd 392.1, found 392.2 |
| 186 | 24 | 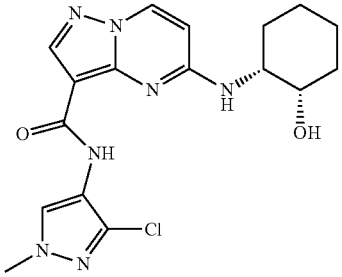 [SMILES: Cn1cc(NC(=O)c2cnn3ccc(N[C@@H]4CCCC[C@@H]4O)nc23)c(Cl)n1] | N-(3-chloro-1-methyl-1H-pyrazol-4-yl)-5-{[(1R,2S)-2-hydroxycyclohexyl]amino}pyrazolo[1,5-a]pyrimidine-3-carboxamide | Calc'd 390.1, found 390.2 |

| Example # | IRAK4 IC$_{50}$ (nM) | Structure | IUPAC Name | Exact Mass [M + H]$^+$ |
|---|---|---|---|---|
| 187 | 250 | 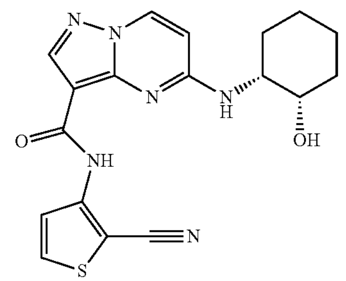 [SMILES: N#Cc1sccc1NC(=O)c1cnn2ccc(N[C@@H]3CCCC[C@@H]3O)nc12] | N-(2-cyanothiophen-3-yl)-5-{[(1R,2S)-2-hydroxycyclohexyl]amino}pyrazolo[1,5-a]pyrimidine-3-carboxamide | Calc'd 383.1, found 383.4 |
| 188 | 60 | 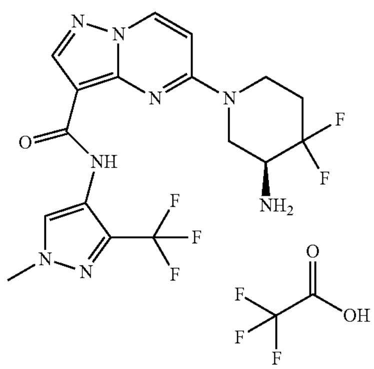 [SMILES: Cn1cc(NC(=O)c2cnn3ccc(N4CCC(F)(F)[C@@H](N)C4)nc23)c(C(F)(F)F)n1 ; O=C(O)C(F)(F)F] | 5-[(4R)- or (4S)- (3-amino-4,4-difluoropiperidin-1-yl)-N-[1-methyl-3-(trifluoromethyl)-1H-pyrazol-4-yl]pyrazolo[1,5-a]pyrimidine-3-carboxamide trifluoroacetate | Calc'd 445.2, found 445.4 |
| 189 | 2 | 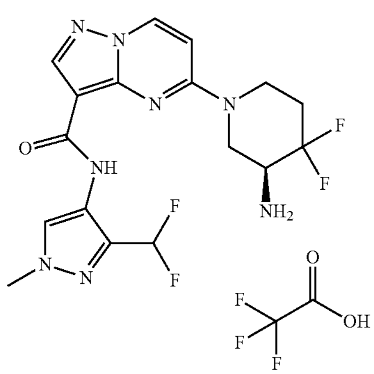 [SMILES: Cn1cc(NC(=O)c2cnn3ccc(N4CCC(F)(F)[C@@H](N)C4)nc23)c(C(F)F)n1 ; O=C(O)C(F)(F)F] | 5-[(4R)- or (4S)- (3-amino-4,4-difluoropiperidin-1-yl)-N-[3-(difluoromethyl)-1-methyl-1H-pyrazol-4-yl]pyrazolo[1,5-a]pyrimidine-3-carboxamide trifluoroacetate | Calc'd 427.1, found 427.4 |
| 190 | 891 | 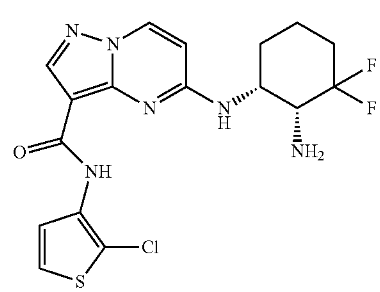 [SMILES: N[C@@H]1[C@H](Nc2ccn3ncc(C(=O)Nc4ccsc4Cl)c3n2)CCCC1(F)F] | 5-{[(1R,2R)-2-amino-3,3-difluorocyclohexyl]amino}-N-(2-chlorothiophen-3-yl)pyrazolo[1,5-a]pyrimidine-3-carboxamide | Calc'd 427.1, found 427.2 |

-continued

| Example # | IRAK4 IC$_{50}$ (nM) | Structure | IUPAC Name | Exact Mass [M + H]$^+$ |
|---|---|---|---|---|
| 191 | 156 | 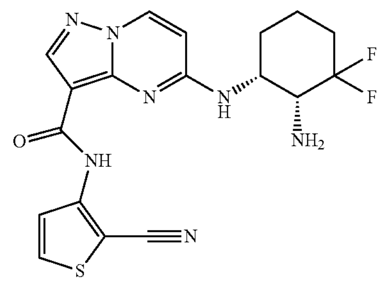 [SMILES: N#Cc1sccc1NC(=O)c1cnn2ccc(N[C@@H]3CCCC(F)(F)[C@@H]3N)nc12] | 5-{[(1R,2R)-2-amino-3,3-difluorocyclohexyl]amino}-N-(2-cyanothiophen-3-yl)pyrazolo[1,5-a]pyrimidine-3-carboxamide | Calc'd 418.1, found 418.4 |
| 192 | 23 | 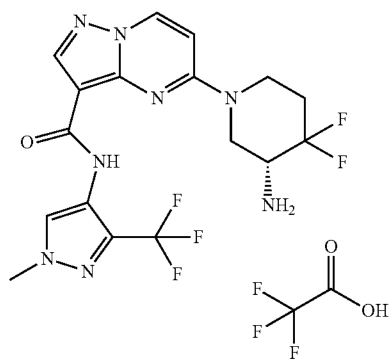 [SMILES: Cn1cc(NC(=O)c2cnn3ccc(N4CCC(F)(F)[C@H](N)C4)nc23)c(C(F)(F)F)n1 ; O=C(O)C(F)(F)F] | 5-[(4R)- or (4S)- (3-amino-4,4-difluoropiperidin-1-yl)-N-[1-methyl-3-(trifluoroemthyl)-1H-pyrazol-4-yl]pyrazolo[1,5-a]pyrimidine-3-carboxamide trifluoroacetate | Calc'd 445.2, found 445.4 |
| 193 | 2 | 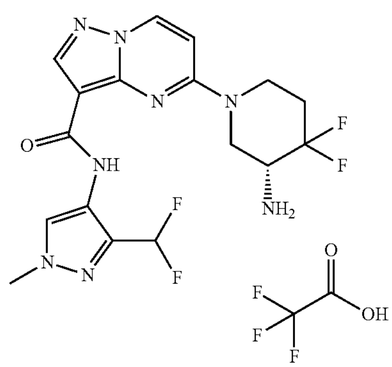 [SMILES: Cn1cc(NC(=O)c2cnn3ccc(N4CCC(F)(F)[C@H](N)C4)nc23)c(C(F)F)n1 ; O=C(O)C(F)(F)F] | 5-[(4R)- or (4S)- (3-amino-4,4-difluoropiperidin-1-yl)-N-[3-(difluoromethyl)-1-methyl-1H-pyrazol-4-yl]pyrazolo[1,5-a]pyrimidine-3-carboxamide trifluoroacetate | Calc'd 427.1, found 427.4 |
| 194 | 1748 | 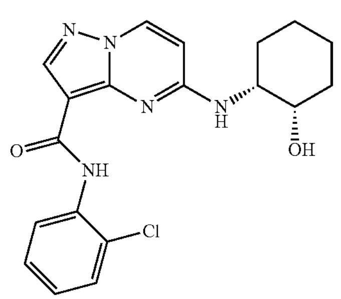 [SMILES: O=C(Nc1ccccc1Cl)c1cnn2ccc(N[C@@H]3CCCC[C@@H]3O)nc12] | N-(2-chlorophenyl)-5-{[(1R,2S)-2-hydroxycyclohexyl]amino}pyrazolo[1,5-a]pyrimidine-3-carboxamide | Calc'd 386.1, found 386.4 |

-continued

| Example # | IRAK4 IC$_{50}$ (nM) | Structure | IUPAC Name | Exact Mass [M + H]$^+$ |
|---|---|---|---|---|
| 195 | 2932 | 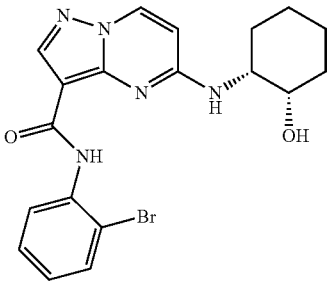 [SMILES: O=C(Nc1ccccc1Br)c1cnn2ccc(N[C@@H]3CCCC[C@@H]3O)nc12] | N-(2-bromophenyl)-5-{[(1R,2S)-2-hydroxycyclohexyl]amino}pyrazolo[1,5-a]pyrimidine-3-carboxamide | Calc'd 430.1, found 430.2 |
| 196 | 2651 | 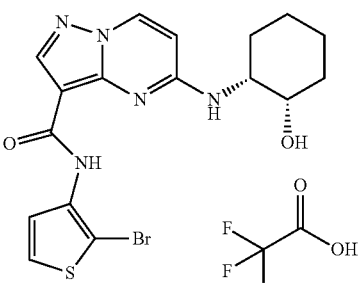 | N-(2-bromothiophen-3-yl)-5-{[(1R,2S)-2-hydroxycyclohexyl]amino}pyrazolo[1,5-a]pyrimidine-3-carboxamide trifluoroacetate | Calc'd 436.2, found 436.2 |
| 197 | 65 | 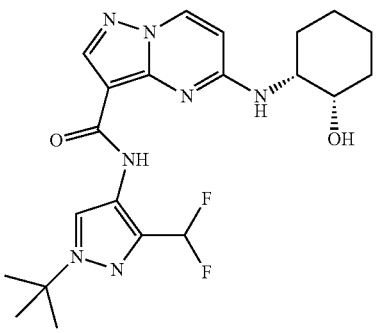 | N-[1-tert-butyl-3-(difluoromethyl)-1H-pyrazol-4-yl]-5-{[(1R,2S)-2-hydroxycyclohexyl]amino}pyrazolo[1,5-a]pyrimidine-3-carboxamide | Calc'd 448.2, found 448.2 |
| 198 | 223 | 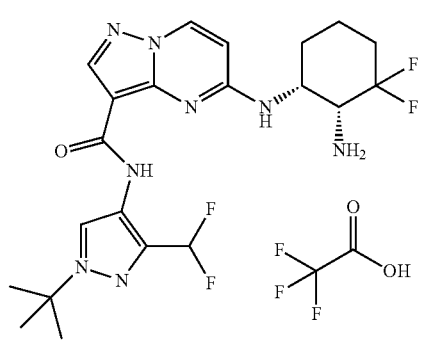 | 5-{[(1R,2R)-2-amino-3,3-difluorocyclohexyl]amino}-N-[1-tert-butyl-3-(difluoromethyl)-1H-pyrazol-4-yl]pyrazolo[1,5-a]pyrimidine-3-carboxamide trifluoroacetate | Calc'd 483.2, found 483.4 |

-continued

| Example # | IRAK4 IC$_{50}$ (nM) | Structure | IUPAC Name | Exact Mass [M + H]$^+$ |
|---|---|---|---|---|
| 199 | 9 | 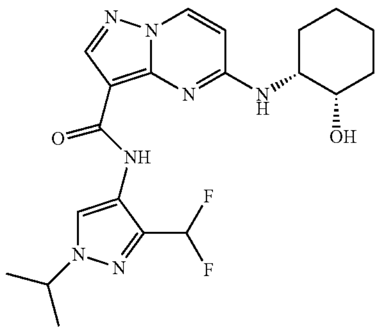 [SMILES: CC(C)n1cc(NC(=O)c2cnn3ccc(N[C@@H]4CCCC[C@@H]4O)nc23)c(C(F)F)n1] | N-[3-(difluoromethyl)-1-(1-methylethyl)-1H-pyrazol-4-yl]-5-{[(1R,2S)-2-hydroxycyclohexyl]amino}pyrazolo[1,5-a]pyrimidine-3-carboxamide | Calc'd 434.2, found 434.4 |
| 200 | 36 | 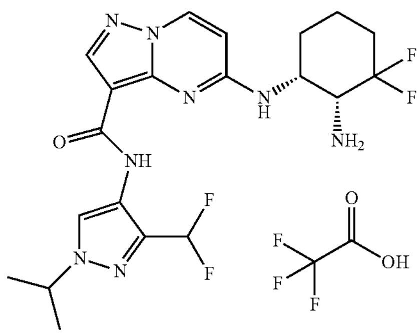 | 5-{[(1R,2R)-2-amino-3,3-difluorocyclohexyl]amino}-N-[3-(difluoromethyl)-1-(1-methylethyl)-1H-pyrazol-4-yl]pyrazolo[1,5-a]pyrimidine-3-carboxamide trifluoroacetate | Calc'd 469.1, found 469.4 |
| 201 | 4 | 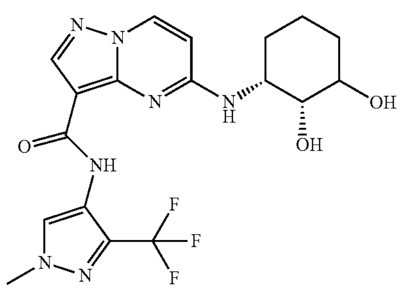 [SMILES: Cn1cc(NC(=O)c2cnn3ccc(N[C@@H]4CCCC(O)[C@@H]4O)nc23)c(C(F)(F)F)n1] | 5-{[(1R,2R)- or (1S,2S)-2-amino-3-hydroxycyclohexyl]amino}-N-[1-methyl-3-(trifluoromethyl)-1H-pyrazol-4-yl]pyrazolo[1,5-a]pyrimidine-3-carboxamide | Calc'd 439.2, found 439.2 |
| 202 | 4 | 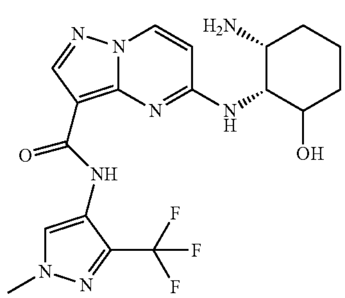 [SMILES: Cn1cc(NC(=O)c2cnn3ccc(N[C@H]4C(O)CCC[C@H]4N)nc23)c(C(F)(F)F)n1] | 5-{[(1R,2R)- or (1S,2S)-2-amino-6-hydroxycyclohexyl]amino}-N-[1-methyl-3-(trifluoromethyl)-1H-pyrazol-4-yl]pyrazolo[1,5-a]pyrimidine-3-carboxamide | Calc'd 439.2, found 439.2 |
| 203 | 7 | 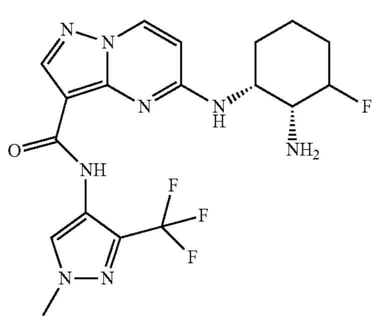 [SMILES: Cn1cc(NC(=O)c2cnn3ccc(N[C@@H]4CCCC(F)[C@@H]4N)nc23)c(C(F)(F)F)n1] | 5-{[(1R,2R)- or (1S,2S)-2-amino-3-fluorocyclohexyl]amino}-N-[1-methyl-3-(trifluoromethyl)-1H-pyrazol-4-yl]pyrazolo[1,5-a]pyrimidine-3-carboxamide | Calc'd 441.2, found 441.4 |

| Example # | IRAK4 IC$_{50}$ (nM) | Structure | IUPAC Name | Exact Mass [M + H]$^+$ |
|---|---|---|---|---|
| 204 | 78 | 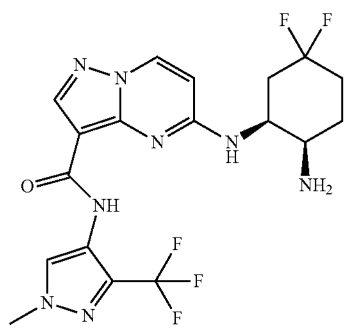 [SMILES: Cn1cc(NC(=O)c2cnn3ccc(N[C@H]4CC(F)(F)CC[C@H]4N)nc23)c(C(F)(F)F)n1] | 5-{[(1S,2R)- or (1R,2S)-2-amino-5,5-difluorocyclohexyl]amino}-N-[1-methyl-3-(trifluoromethyl)-1H-pyrazol-4-yl]pyrazolo[1,5-a]pyrimidine-3-carboxamide | Calc'd 459.2, found 459.2 |
| 205 | 0.9 | 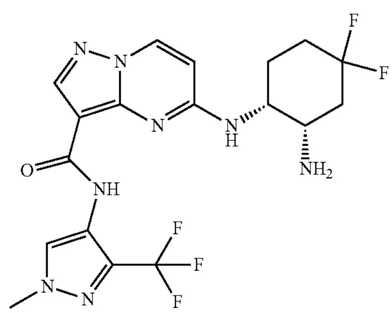 [SMILES: Cn1cc(NC(=O)c2cnn3ccc(N[C@@H]4CCC(F)(F)C[C@@H]4N)nc23)c(C(F)(F)F)n1] | 5-{[(1S,2R)- or (1R,2S)-2-amino-4,4-difluorocyclohexyl]amino}-N-[1-methyl-3-(trifluoromethyl)-1H-pyrazol-4-yl]pyrazolo[1,5-a]pyrimidine-3-carboxamide | Calc'd 459.2, found 459.2 |
| 206 | 0.5 | 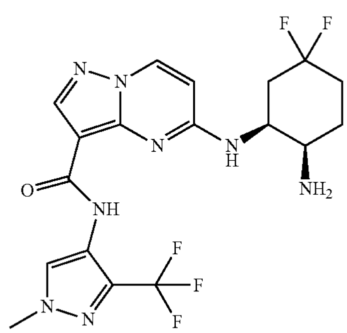 [SMILES: Cn1cc(NC(=O)c2cnn3ccc(N[C@H]4CC(F)(F)CC[C@H]4N)nc23)c(C(F)(F)F)n1] | 5-{[(1S,2R)- or (1R,2S)-2-amino-5,5-difluorocylcohexyl]amino}-N-[1-methyl-3-(trifluoromethyl)-1H-pyrazol-4-yl]pyrazolo[1,5-a]pyrimidine-3-carboxamide | Calc'd 459.2, found 459.4 |
| 207 | 23 | 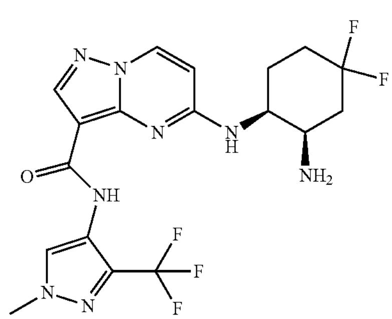 [SMILES: Cn1cc(NC(=O)c2cnn3ccc(N[C@H]4CCC(F)(F)C[C@H]4N)nc23)c(C(F)(F)F)n1] | 5-{[(1S,2R)- or (1R,2S)-2-amino-4,4-difluorocyclohexyl]amino}-N-[1-methyl-3-(trifluoromethyl)-1H-pyrazol-4-yl]pyrazolo[1,5-a]pyrimidine-3-carboxamide | Calc'd 459.2, found 459.2 |

| Example # | IRAK4 IC$_{50}$ (nM) | Structure | IUPAC Name | Exact Mass [M + H]$^+$ |
|---|---|---|---|---|
| 208 | 38 | 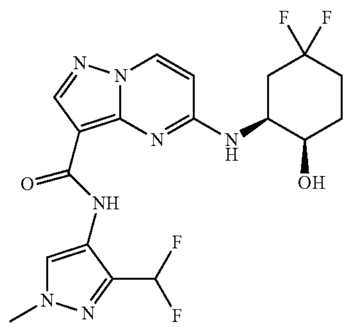 [SMILES: Cn1cc(NC(=O)c2cnn3ccc(N[C@H]4CC(F)(F)CC[C@H]4O)nc23)c(C(F)F)n1] | 5-{[(1S,2R)- or (1R,2S)-2-amino-5,5-difluorocyclohexyl]amino}-N-[3-(difluoromethyl)-1-methyl-1H-pyrazol-4-yl]pyrazolo[1,5-a]pyrimidine-3-carboxamide | Calc'd 441.2, found 441.4 |
| 209 | 1 | 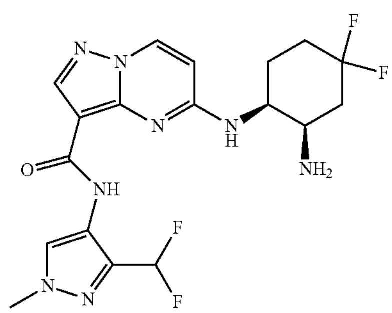 [SMILES: Cn1cc(NC(=O)c2cnn3ccc(N[C@H]4CCC(F)(F)C[C@H]4N)nc23)c(C(F)F)n1] | 5-{[(1S,2R)- or (1R,2S)-2-amino-4,4-difluorocyclohexyl]amino}-N-[3-(difluoromethyl)-1-methyl-1H-pyrazol-4-yl]pyrazolo[1,5-a]pyrimidine-3-carboxamide | Calc'd 441.2, found 441.4 |
| 210 | 1 | 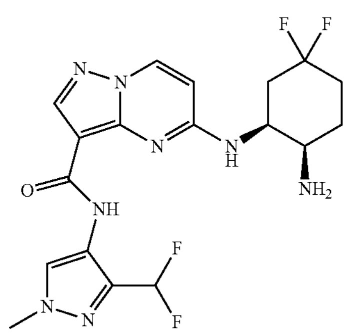 [SMILES: Cn1cc(NC(=O)c2cnn3ccc(N[C@H]4CC(F)(F)CC[C@H]4N)nc23)c(C(F)F)n1] | 5-{[(1S,2R)- or (1R,2S)-2-amino-5,5-difluorocyclohexyl]amino}-N-[3-(difluoromethyl)-1-methyl-1H-pyrazol-4-yl]pyrazolo[1,5-a]pyrimidine-3-carboxamide | Calc'd 441.2, found 441.4 |
| 211 | 27 | 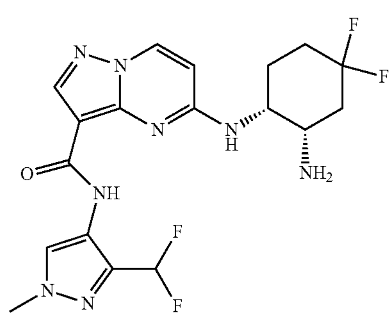 [SMILES: Cn1cc(NC(=O)c2cnn3ccc(N[C@@H]4CCC(F)(F)C[C@@H]4N)nc23)c(C(F)F)n1] | 5-{[(1S,2R)- or (1R,2S)-2-amino-4,4-difluorocyclohexyl]amino}-N-[3-(difluoromethyl)-1-methyl-1H-pyrazol-4-yl]pyrazolo[1,5-a]pyrimidine-3-carboxamide | Calc'd 441.2, found 441.4 |

Example 212

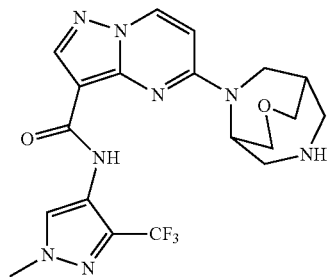 [SMILES: Cn1cc(NC(=O)c2cnn3ccc(N4CC5CNCC4COC5)nc23)c(C(F)(F)F)n1]

5-(3-Oxa-7,9-diazabicyclo[3.3.2]decan-9-yl)-N-(1-methyl-3-(trifluoromethyl)-1H-pyrazol-4-yl)pyrazolo[1,5-a]pyrimidine-3-carboxamide (IRAK4 IC$_{50}$=9 nM)

Step 1: Into a 25 mL round bottom flask containing a solution of tert-butyl 3-oxa-7,9-diazabicyclo[3.3.2]decane-9-carboxylate (100 mg, 0.4 mmol) in dichloromethane (5 mL) were added benzyl chloroformate (0.1 mL, 0.7 mmol) and triethylamine (0.16 mL, 1.2 mmol) at 0° C. and the mixture was stirred at room temperature for 16 h. The reaction mixture was diluted with dichloromethane (20 mL), washed with water and brine, dried over anhydrous sodium sulfate, filtered and concentrated under reduced pressure. The residue was purified by flash column chromatography eluting with ethyl acetate in petroleum ether (0-3%) to furnish 7-benzyl 9-(tert-butyl) 3-oxa-7,9-diazabicyclo[3.3.2]decane-7,9-dicarboxylate as a liquid. MS calc'd [M+H]$^+$ 377.2, found 377.2.

Step 2: Into a 25 mL round bottom flask containing a solution of 7-benzyl 9-(tert-butyl) 3-oxa-7,9-diazabicyclo[3.3.2]decane-7,9-dicarboxylate (130 mg, 0.3 mmol) in le;2qdichloromethane (40 mL) was added trifluoroacetic acid (1 mL) at 0° C. and the reaction was stirred at room temperature for 1 h. The reaction mixture was concentrated under reduced pressure to afford benzyl 3-oxa-7,9-diazabicyclo[3.3.2]decane-7-carboxylate trifluoroacetate as a liquid. The crude product was taken directly to the next step without further purification. MS calc'd [M+H]$^+$ 277.1, found 277.4.

Step 3: Into a 10 mL round bottomed flask were added 5-chloro-N-(1-methyl-3-(trifluoromethyl)-1H-pyrazol-4-yl)pyrazolo[1,5-a]pyrimidine-3-carboxamide (70 mg, 0.2 mmol) in absolute ethanol (2 mL), N,N-diisopropylethylamine (0.1 mL, 0.6 mmol) and benzyl 3-oxa-7,9-diazabicyclo[3.3.2]decane-7-carboxylate trifluoroacetate (80 mg, 0.2 mmol), and the mixture was heated at 80° C. for 2 h. The reaction mixture was concentrated under reduced pressure and purified by column chromatography eluting with ethyl acetate in petroleum ether (20-30%) to afford benzyl 9-(3-((1-methyl-3-(trifluoromethyl)-1H-pyrazol-4-yl)carbamoyl)pyrazolo[1,5-a]pyrimidin-5-yl)-3-oxa-7,9-diazabicyclo[3.3.2]decane-7-carboxylate as a solid. MS calc'd [M+H]$^+$ 585.2, found 585.4.

Step 4: Into a 10 mL round bottom flask containing a solution of benzyl 9-(3-((1-methyl-3-(trifluoromethyl)-1H-pyrazol-4-yl)carbamoyl)pyrazolo[1,5-a]pyrimidin-5-yl)-3-oxa-7,9-diazabicyclo[3.3.2]decane-7-carboxylate (50 mg, 0.09 mmol) in ethyl acetate (1 mL) and ethanol (1 mL) was added palladium on carbon (10 mg, 20% w/w) and the reaction mixture was stirred under hydrogen atmosphere for 6 h. The reaction mixture was filtered through celite, and the filtrate was concentrated under reduced pressure and purified by preparative HPLC to afford 5-(3-oxa-7,9-diazabicyclo[3.3.2]decan-9-yl)-N-(1-methyl-3-(trifluoromethyl)-1H-pyrazol-4-yl)pyrazolo[1,5-a]pyrimidine-3-carboxamide trifluoroacetate as a solid. $^1$H NMR (CD$_3$OD, 400 MHz): δ 9.20 (brs, 1H), 8.69 (d, J=7.9 Hz, 1H), 8.40 (s, 1H), 8.36 (s, 1H), 6.83 (d, J=7.2 Hz, 1H), 4.51-4.47 (m, 2H), 4.04 (brs, 2H), 3.98 (s, 3H), 3.96-3.89 (m, 5H), 3.46-3.42 (m, 2H), 2.71 (brs, 1H). MS calc'd [M+H]$^+$ 451.2, found 451.4.

The following examples were prepared in an analogous manner of that described in Example 212.

| Example # | IRAK4 IC$_{50}$ (nM) | Structure | IUPAC Name | Exact Mass [M + H]+ |
|---|---|---|---|---|
| 213 | 3 | 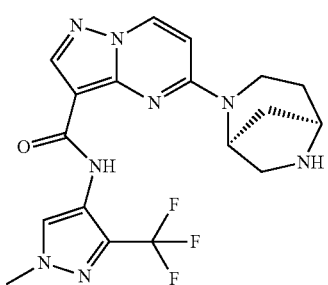 [SMILES: Cn1cc(NC(=O)c2cnn3ccc(N4CC[C@@H]5C[C@H]4CN5)nc23)c(C(F)(F)F)n1] | 5-[(1S,5R)-2,6-diazabicyclo[3.2.1]oct-2-yl]-N-[1-methyl-3-(trifluoromethyl)-1H-pyrazol-4-yl]pyrazolo[1,5-a]pyrimidine-3-carboxamide | Calc'd 421.2, found 421.4 |

| Example # | IRAK4 IC$_{50}$ (nM) | Structure | IUPAC Name | Exact Mass [M + H]+ |
|---|---|---|---|---|
| 214 | 38 | 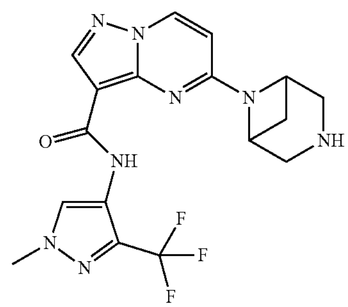 [SMILES: Cn1cc(NC(=O)c2cnn3ccc(N4C5CNCC4C5)nc23)c(C(F)(F)F)n1] | 5-(3,6-diazabicyclo[3.1.1]hept-6-yl)-N-[1-methyl-3-(trifluoromethyl)-1H-pyrazol-4-yl]pyrazolo[1,5-a]pyrimidine-3-carboxamide | Calc'd 407.1, found 407.4 |
| 215 | 121 | 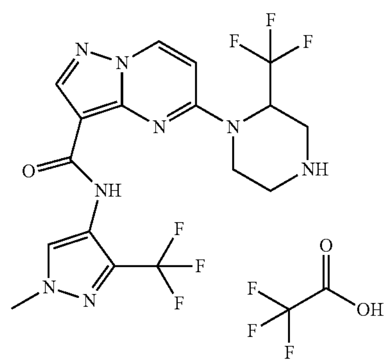 | N-[1-methyl-3-(trifluoromethyl)-1H-pyrazol-4-yl]-5-[2-(trifluoromethyl)piperazin-1-yl]pyrazolo[1,5-a]pyrimidine-3-carboxamide trifluoroacetate | Calc'd 463.1, found 463.4 |
| 216 | 127 | 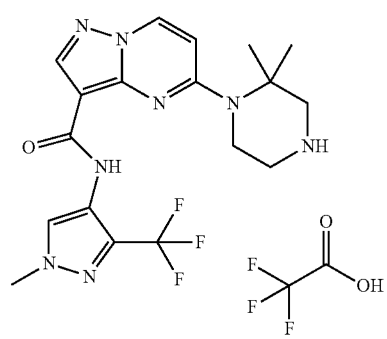 | 5-(2,2-dimethylpiperazin-1-yl)-N-[1-methyl-3-(trifluoromethyl)-1H-pyrazol-4-yl]pyrazolo[1,5-a]pyrimidine-3-carboxamide trifluoroacetate | Calc'd 423.2, found 423.2 |
| 217 | 47 | 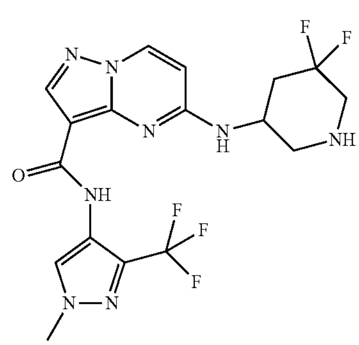 [SMILES: Cn1cc(NC(=O)c2cnn3ccc(NC4CNCC(F)(F)C4)nc23)c(C(F)(F)F)n1] | 5-[(5,5-difluoropiperidin-3-yl)amino]-N-[1-methyl-3-(trifluoromethyl)-1H-pyrazol-4-yl]pyrazolo[1,5-a]pyrimidine-3-carboxamide | Calc'd 445.2, found 445.4 |

-continued

| Example # | IRAK4 IC$_{50}$ (nM) | Structure | IUPAC Name | Exact Mass [M + H]+ |
|---|---|---|---|---|
| 218 | 685 | 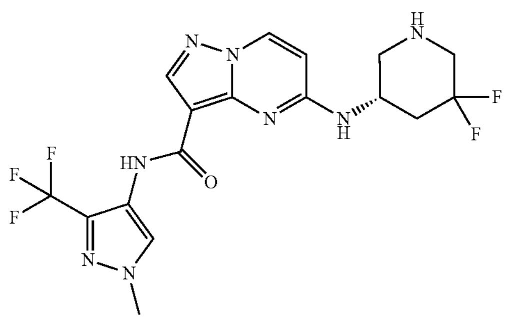 [SMILES: Cn1cc(NC(=O)c2cnn3ccc(N[C@@H]4CNCC(F)(F)C4)nc23)c(C(F)(F)F)n1] | 5-{[(3S)- or (3R)-5,5-difluoropiperidin-3-yl]amino}-N-[1-methyl-3-(trifluoromethyl)-1H-pyrazol-4-yl]pyrazolo[1,5-a]pyrimidine-3-carboxamide | Calc'd 445.2, found 445.4 |
| 219 | 7 | 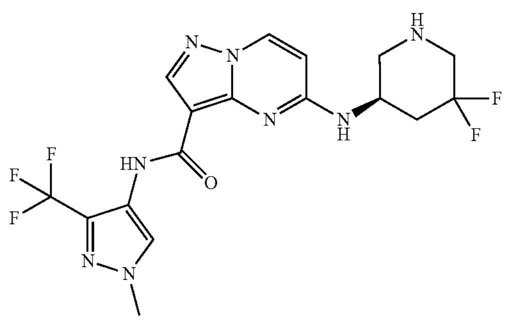 [SMILES: Cn1cc(NC(=O)c2cnn3ccc(N[C@H]4CNCC(F)(F)C4)nc23)c(C(F)(F)F)n1] | 5-{[(3S)- or (3R)-5,5-difluoropiperidin-3-yl]amino}-N-[1-methyl-3-(trifluoromethyl)-1H-pyrazol-4-yl]pyrazolo[1,5-a]pyrimidine-3-carboxamide | Calc'd 445.2, found 445.4 |
| 220 | 153 | 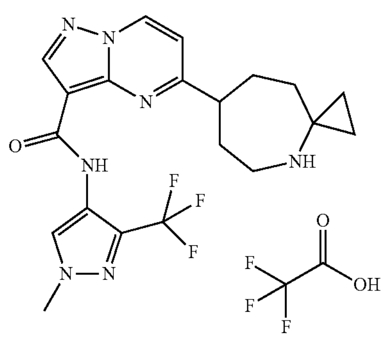 | 5-(4,7-diazaspiro[2.6]non-7-yl)-N-[1-methyl-3-(trifluoromethyl)-1H-pyrazol-4-yl]pyrazolo[1,5-a]pyrimidine-3-carboxamide trifluoroacetate | Calc'd 435.2, found 435.4 |
| 221 | 330 | 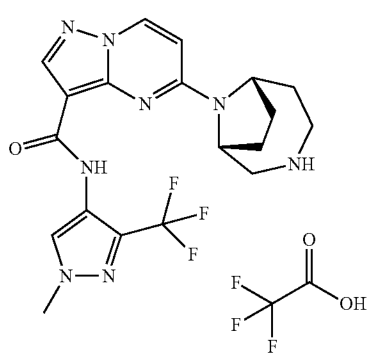 | 5-[(1R,6S)- or (1S,6R)-3,9-diazabicyclo[4.2.1]non-9-yl]-N-[1-methyl-3-(trifluoromethyl)-1H-pyrazol-4-yl]pyrazolo[1,5-a]pyrimidine-3-carboxamide trifluoroacetate | Calc'd 435.2, found 435.0 |

-continued

| Example # | IRAK4 IC$_{50}$ (nM) | Structure | IUPAC Name | Exact Mass [M + H]+ |
|---|---|---|---|---|
| 222 | 168 | 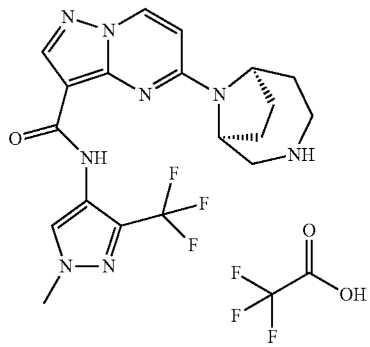 | 5-[(1R,6S)- or (1S,6R)-3,9-diazabicyclo[4.2.1]non-9-yl]-N-[1-methyl-3-(trifluoromethyl)-1H-pyrazol-4-yl]pyrazolo[1,5-a]pyrimidine-3-carboxamide trifluoroacetate | Calc'd 435.2, found 435.0 |
| 223 | 57 | 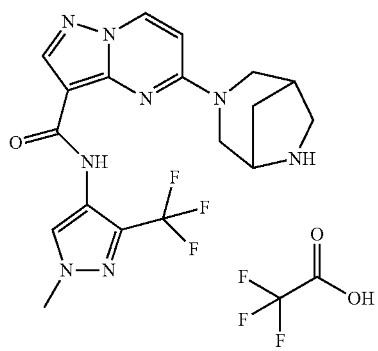 | 5-(3,6-diazabicyclo[3.2.1]oct-3-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |
| 224 | 70 | 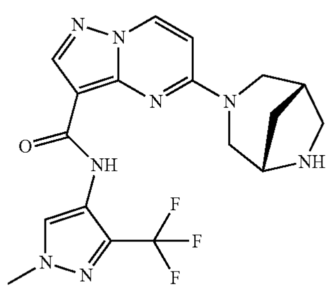 [SMILES: Cn1cc(NC(=O)c2cnn3ccc(N4C[C@@H]5CN[C@@H](C5)C4)nc23)c(C(F)(F)F)n1] | 5-[(1S,5S)- or (1R,5R)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide | Calc'd 421.2, found 421.4 |
| 225 | 310 | 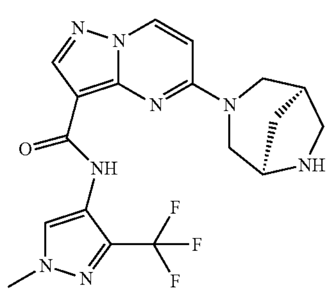 [SMILES: Cn1cc(NC(=O)c2cnn3ccc(N4C[C@H]5CN[C@H](C5)C4)nc23)c(C(F)(F)F)n1] | 5-[(1S,5S)- or (1R,5R)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide | Calc'd 421.2, found 421.4 |

| Example # | IRAK4 IC$_{50}$ (nM) | Structure | IUPAC Name | Exact Mass [M + H]+ |
|---|---|---|---|---|
| 226 | 2 | 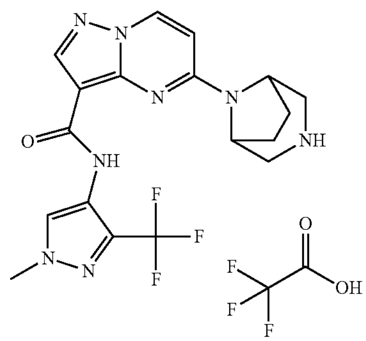 | 5-(3,8-diazabicyclo[3.2.1]oct-8-yl)-N-[1-methyl-3-(trifluoromethyl)-1H-pyrazol-4-yl]pyrazolo[1,5-a]pyrimidine-3-carboxamide trifluoroacetate | Calc'd 421.2, found 421.4 |
| 227 | 451 | 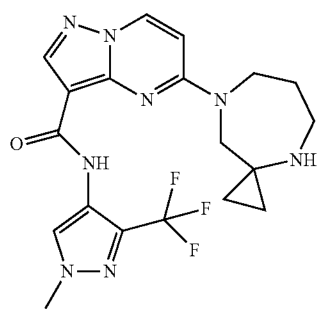 [SMILES: Cn1cc(NC(=O)c2cnn3ccc(N4CCCNC5(CC5)C4)nc23)c(C(F)(F)F)n1] | 5-(4,8-diazaspiro[2.6]non-8-yl)-N-[1-methyl-3-(trifluoromethyl)-1H-pyrazol-4-yl]pyrazolo[1,5-a]pyrimidine-3-carboxamide | Calc'd 435.2, found 435.4 |
| 228 | 59 | 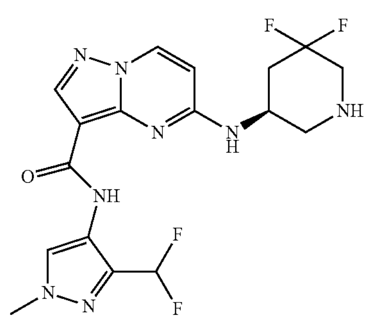 [SMILES: Cn1cc(NC(=O)c2cnn3ccc(N[C@@H]4CNCC(F)(F)C4)nc23)c(C(F)F)n1] | N-[3-(difluoromethyl)-1-methyl-1H-pyrazol-4-yl]-5-{[(3S)- or (3R)-5,5-difluoropiperidin-3-yl]amino}pyrazolo[1,5-a]pyrimidine-3-carboxamide | Calc'd 427.1, found 427.2 |
| 229 | 0.5 | 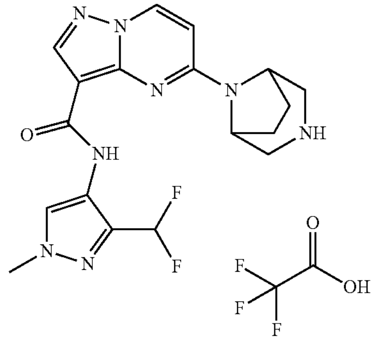 [SMILES: Cn1cc(NC(=O)c2cnn3ccc(N4C5CCC4CNC5)nc23)c(C(F)F)n1 ; O=C(O)C(F)(F)F] | 5-(3,8-diazabicyclo[3.2.1]oct-8-yl)-N-[3-(difluoromethyl)-1-methyl-1H-pyrazol-4-yl]pyrazolo[1,5-a]pyrimidine-3-carboxamide trifluoroacetate | Calc'd 403.2, found 403.4 |

-continued

| Example # | IRAK4 IC$_{50}$ (nM) | Structure | IUPAC Name | Exact Mass [M + H]+ |
|---|---|---|---|---|
| 230 | 0.5 | 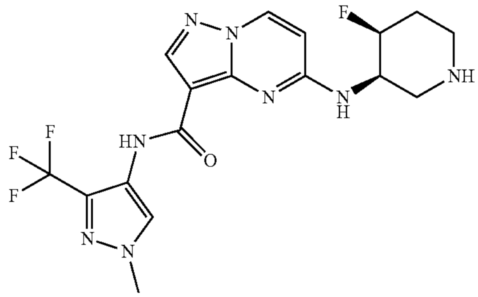 [SMILES: Cn1cc(NC(=O)c2cnn3ccc(N[C@@H]4CNCC[C@@H]4F)nc23)c(C(F)(F)F)n1] | 5-{[(3R,4S)- or (3S,4R)-4-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427, found 427 |
| 231 | 47 | 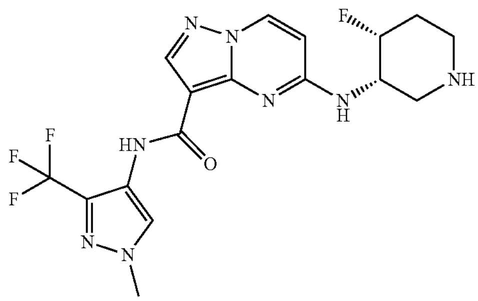 [SMILES: Cn1cc(NC(=O)c2cnn3ccc(N[C@H]4CNCC[C@H]4F)nc23)c(C(F)(F)F)n1] | 5-{[(3R,4S)- or (3S,4R)-4-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427, found 427 |
| 232 | 13 | 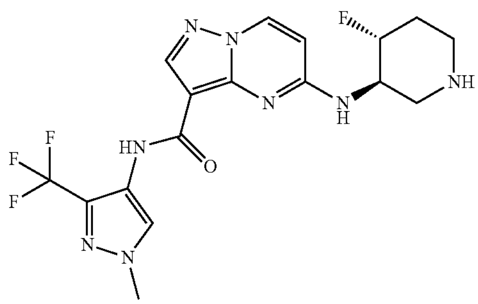 [SMILES: Cn1cc(NC(=O)c2cnn3ccc(N[C@@H]4CNCC[C@H]4F)nc23)c(C(F)(F)F)n1] | 5-{[(3R,4R)- or (3S,4S)-4-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427, found 427 |
| 233 | 0.5 | 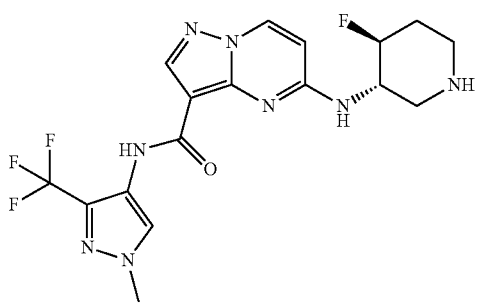 [SMILES: Cn1cc(NC(=O)c2cnn3ccc(N[C@H]4CNCC[C@@H]4F)nc23)c(C(F)(F)F)n1] | 5-{[(3R,4R)- or (3S,4S)-4-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427, found 427 |
| 234 | 5 | 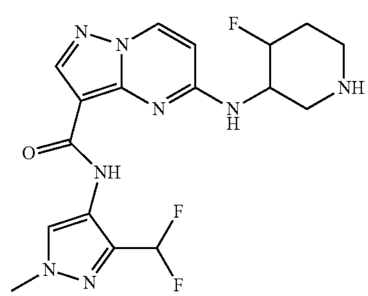 [SMILES: Cn1cc(NC(=O)c2cnn3ccc(NC4CNCCC4F)nc23)c(C(F)F)n1] | N-[3-(difluoromethyl)-1-methyl-1H-pyrazol-4-yl]-5-[(3R or S, 4R or S-4-fluoropiperidin-3-yl)amino]pyrazolo[1,5-a]pyrimidine-3-carboxamide | Calc'd 409.2, found 409.4 |

-continued

| Example # | IRAK4 IC$_{50}$ (nM) | Structure | IUPAC Name | Exact Mass [M + H]+ |
|---|---|---|---|---|
| 235 | 0.7 | 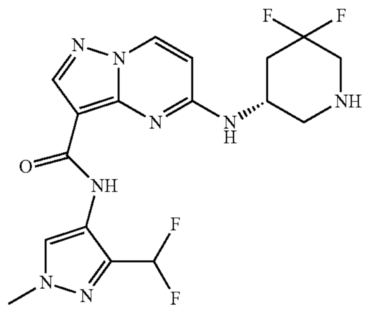 [SMILES: Cn1cc(NC(=O)c2cnn3ccc(N[C@H]4CNCC(F)(F)C4)nc23)c(C(F)F)n1] | N-[3-(difluoromethyl)-1-methyl-1H-pyrazol-4-yl]-5-{[(3S)- or (3R)-5,5-difluoropiperidin-3-yl]amino}pyrazolo[1,5-a]pyrimidine-3-carboxamide | Calc'd 427.1, found 427.2 |
| 236 | 0.6 | 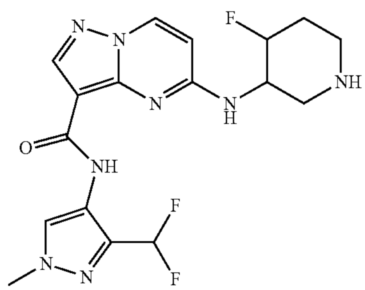 [SMILES: Cn1cc(NC(=O)c2cnn3ccc(NC4CNCCC4F)nc23)c(C(F)F)n1] | N-[3-(difluoromethyl)-1-methyl-1H-pyrazol-4-yl]-5-[(3R or S, 4R or S-4-fluoropiperidin-3-yl)amino]pyrazolo[1,5-a]pyrimidine-3-carboxamide | Calc'd 409.2, found 409.4 |
| 237 | 0.6 | 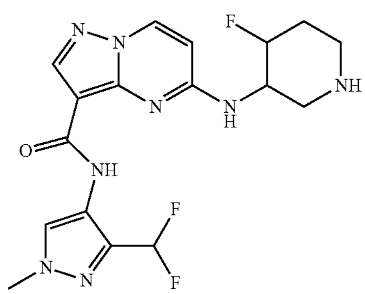 [SMILES: Cn1cc(NC(=O)c2cnn3ccc(NC4CNCCC4F)nc23)c(C(F)F)n1] | N-[3-(difluoromethyl)-1-methyl-1H-pyrazol-4-yl]-5-[(3R or S, 4R or S-4-fluoropiperidin-3-yl)amino]pyrazolo[1,5-a]pyrimidine-3-carboxamide | Calc'd 409.2, found 409.4 |
| 238 | 4 | 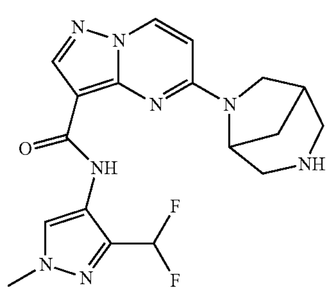 [SMILES: Cn1cc(NC(=O)c2cnn3ccc(N4CC5CNCC4C5)nc23)c(C(F)F)n1] | 5-[3,6-diazabicyclo[3.2.1]oct-6-yl]-N-[3-(difluoromethyl)-1-methyl-1H-pyrazol-4-yl]pyrazolo[1,5-a]pyrimidine-3-carboxamide | Calc'd 403.2, found 403.4 |
| 239 | 3 | 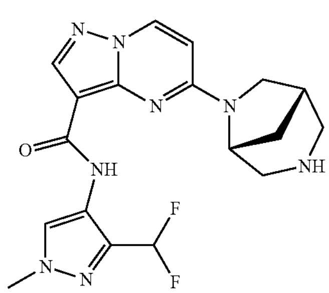 [SMILES: Cn1cc(NC(=O)c2cnn3ccc(N4C[C@@H]5CNC[C@H]4C5)nc23)c(C(F)F)n1] | 5-[(1S,5R)- or (1R,5S)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide | Calc'd 403, found 403 |

| Example # | IRAK4 IC$_{50}$ (nM) | Structure | IUPAC Name | Exact Mass [M + H]+ |
|---|---|---|---|---|
| 240 | 43 | 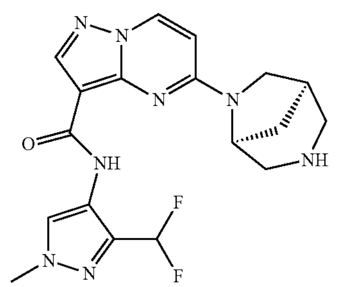 [SMILES: Cn1cc(NC(=O)c2cnn3ccc(N4C[C@H]5CNC[C@@H]4C5)nc23)c(C(F)F)n1] | 5-[(1S,5R)- or (1R,5S)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide | Calc'd 403, found 403 |
| 241 | 3 | 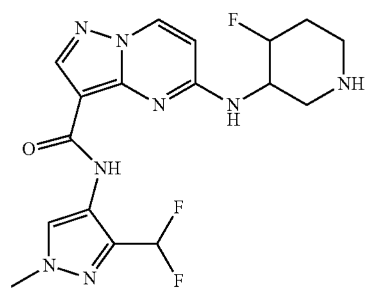 [SMILES: Cn1cc(NC(=O)c2cnn3ccc(NC4CNCCC4F)nc23)c(C(F)F)n1] | N-[3-(difluoromethyl)-1-methyl-1H-pyrazol-4-yl]-5-[(3R or S, 4R or S-4-fluoropiperidin-3-yl)amino]pyrazolo[1,5-a]pyrimidine-3-carboxamide | Calc'd 409.2, found 409.4 |
| 242 | 2 | 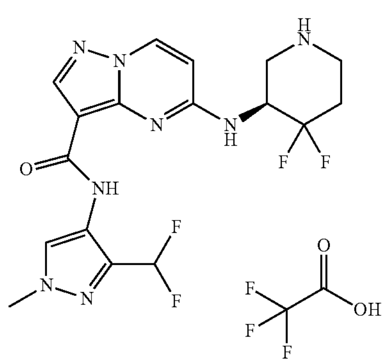 [SMILES: Cn1cc(NC(=O)c2cnn3ccc(N[C@H]4CNCCC4(F)F)nc23)c(C(F)F)n1 ; O=C(O)C(F)(F)F] | N-[(R or S)-3-(difluoromethyl)-1-methyl-1H-pyrazol-4-yl]-5-[(4,4-difluoropiperidin-3-yl)amino]pyrazolo[1,5-a]pyrimidine-3-carboxamide trifluoroacetate | Calc'd 427.1, found 427.4 |
| 243 | 0.5 | 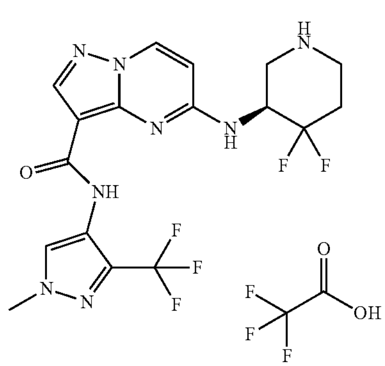 | 5-[(R or S)-(4,4-difluoropiperidin-3-yl)amino]-N-[1-methyl-3-(trifluoromethyl)-1H-pyrazol-4-yl]pyrazolo[1,5-a]pyrimidine-3-carboxamide trifluoroacetate | Calc'd 445.2, found 445.4 |

-continued

| Example # | IRAK4 IC$_{50}$ (nM) | Structure | IUPAC Name | Exact Mass [M + H]+ |
|---|---|---|---|---|
| 244 | 0.5 | 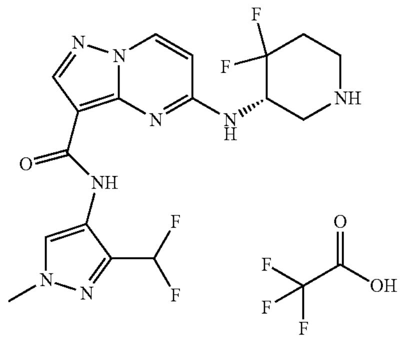 [SMILES: Cn1cc(NC(=O)c2cnn3ccc(N[C@H]4CNCCC4(F)F)nc23)c(C(F)F)n1 ; O=C(O)C(F)(F)F] | N-[(R or S)-3-(difluoromethyl)-1-methyl-1H-pyrazol-4-yl]-5-[(4,4-difluoropiperidin-3-yl)amino]pyrazolo[1,5-a]pyrimidine-3-carboxamide trifluoroacetate | Calc'd 427.1, found 427.4 |
| 245 | 8 | 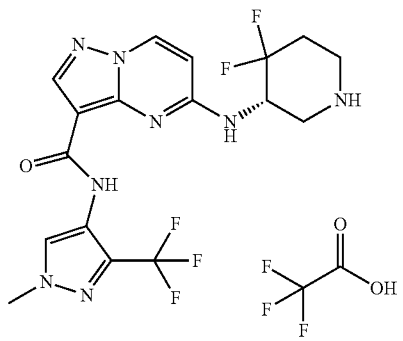 [SMILES: Cn1cc(NC(=O)c2cnn3ccc(N[C@H]4CNCCC4(F)F)nc23)c(C(F)(F)F)n1 ; O=C(O)C(F)(F)F] | 5-[(R or S)-(4,4-difluoropiperidin-3-yl)amino]-N-[1-methyl-3-(trifluoromethyl)-1H-pyrazol-4-yl]pyrazolo[1,5-a]pyrimidine-3-carboxamide trifluoroacetate | Calc'd 445.2, found 445.4 |

Example 246

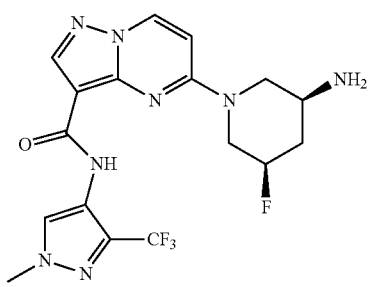 [SMILES: Cn1cc(NC(=O)c2cnn3ccc(N4C[C@@H](N)C[C@@H](F)C4)nc23)c(C(F)(F)F)n1]

5-((3S,5R)-3-Amino-5-fluoropiperidin-1-yl)-N-(1-methyl-3-(trifluoromethyl)-1H-pyrazol-4-yl)pyrazolo[1,5-a]pyrimidine-3-carboxamide (IRAK4 IC$_{50}$=9 nM)

Step 1: A mixture of tert-butyl N-[(3S,5R)-5-fluoro-1-[(4-methoxyphenyl)methyl]-3-piperidyl]carbamate (1.0 g, 3 mmol), palladium on carbon (500 mg), formic acid (1 mL, 26 mmol), piperidine (1 mL, 10 mmol), methanol (12 mL) and water (8 mL) in a microwave vial was irradiated with microwave for 1 h at 55° C. The reaction mixture was filtered through celite, and the filtrate was diluted with ethyl acetate, washed with saturated sodium hydrogen carbonate solution, water and brine, dried over anhydrous sodium sulfate, filtered and concentrated under reduced pressure to afford tert-butyl ((3S,5R)-5-fluoropiperidin-3-yl)carbamate as a solid which was taken to the next step without further purification. $^1$H NMR (DMSO-d$_6$, 400 MHz): δ 6.80 (d, J=8.0 Hz, 1H), 4.52-4.32 (m, 1H), 3.03-3.00 (m, 1H), 2.81-2.78 (m, 1H), 2.30-2.27 (m, 2H), 2.26-2.25 (m, 2H), 1.42 (s, 9H). MS calc'd [M+H]$^+$ 219.1, found 219.3.

Step 2: A mixture of 5-chloro-N-(1-methyl-3-(trifluoromethyl)-1H-pyrazol-4-yl)pyrazolo[1,5-a]pyrimidine-3-carboxamide (40 mg, 0.1 mmol), tert-butyl ((3S,5R)-5-fluoropiperidin-3-yl)carbamate (28 mg, 0.1 mmol), N,N-diisopropylethylamine (0.04 mL, 0.2 mmol) and ethanol (1 mL) in a 10 mL sealed tube and was heated at 90° C. overnight. The solvent was removed under reduced pressure and the residue was purified by flash chromatography eluting with methanol in dichloromethane (3-5%) to afford tert-butyl ((3S,5R)-5-fluoro-1-(3-((1-methyl-3-(trifluoromethyl)-1H-pyrazol-4-yl)carbamoyl)pyrazolo[1,5-a]pyrimidin-5-yl)piperidin-3-yl)carbamate as a solid. MS calc'd [M+H]$^+$ 527.2, found 527.2.

Step 3: Into a 10 mL round bottom flask containing a solution of tert-butyl ((3S,5R)-5-fluoro-1-(3-((1-methyl-3-(trifluoromethyl)-1H-pyrazol-4-yl)carbamoyl)pyrazolo[1,5-a]pyrimidin-5-yl)piperidin-3-yl)carbamate (55 mg, 0.1 mmol) in dichloromethane (2 mL) was added trifluoroacetic acid (1 mL) and the reaction was stirred for 1 h. The solvent was removed under reduced pressure and the residue was purified by trituration with dichloromethane and hexanes to afford 5-((3S,5R)-3-amino-5-fluoropiperidin-1-yl)-N-(1-methyl-3-(trifluoromethyl)-1H-pyrazol-4-yl)pyrazolo[1,5-a]pyrimidine-3-carboxamide trifluoroacetate as a solid. $^1$H NMR (CD$_3$OD, 400 MHz): δ 8.68 (d, J=8.0 Hz, 1H), 8.39 (s, 1H), 8.36 (s, 1H), 6.93 (d, J=8.0 Hz, 1H), 5.18-5.07 (m, 1H), 4.78-4.65 (m, 1H), 3.98 (s, 3H), 3.77-3.76 (m, 1H), 3.72-3.69 (m, 2H), 3.60-3.56 (m, 1H), 2.50-2.27 (m, 2H).
MS calc'd [M+H]+ 427.2, found 427.1.

The following examples were prepared in an analogous manner of that described in Example 246.

| Example # | IRAK4 IC$_{50}$ (nM) | Structure | IUPAC Name | Exact Mass [M + H]+ |
|---|---|---|---|---|
| 247 | 4 | 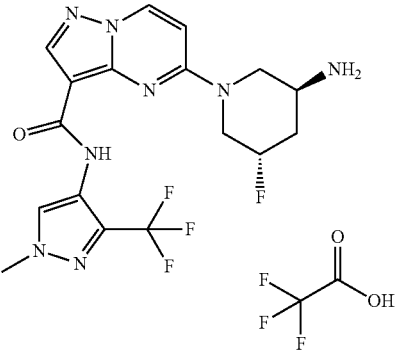 [SMILES: Cn1cc(NC(=O)c2cnn3ccc(N4C[C@@H](N)C[C@H](F)C4)nc23)c(C(F)(F)F)n1 ; O=C(O)C(F)(F)F] | 5-[(3S,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide trifluoroacetate | Calc'd 427.2, found 427.2 |
| 248 | 0.9 | 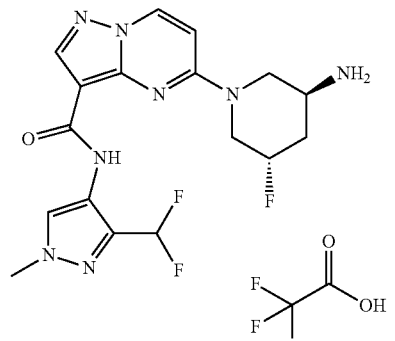 | 5-[(3S,5S)-3-amino-5-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.2 |
| 249 | 1 | 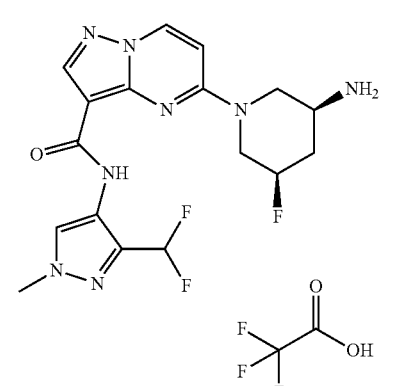 | 5-[(3S,5R)-3-amino-5-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.2 |
| 250 | 2 | 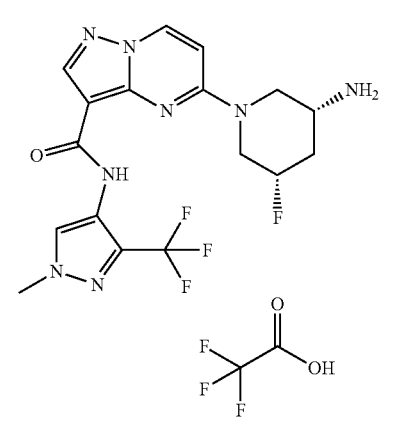 [SMILES: Cn1cc(NC(=O)c2cnn3ccc(N4C[C@H](N)C[C@H](F)C4)nc23)c(C(F)(F)F)n1 ; O=C(O)C(F)(F)F] | 5-[(3R,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide trifluoroacetate | Calc'd 427.2, found 427.4 |

-continued

| Example # | IRAK4 IC$_{50}$ (nM) | Structure | IUPAC Name | Exact Mass [M + H]+ |
|---|---|---|---|---|
| 251 | 0.7 | 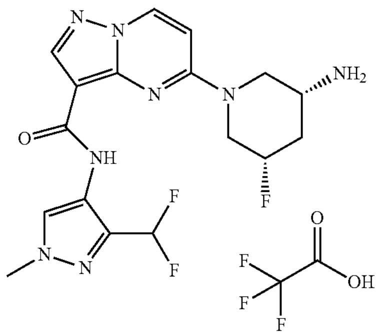 | 5-[(3R,5S)-3-amino-5-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.4 |
| 252 | 0.8 | 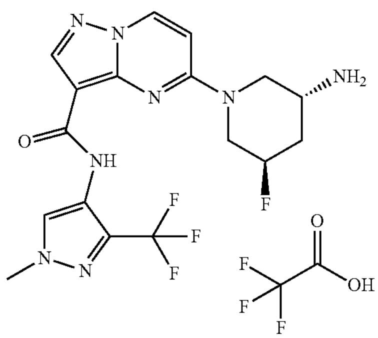 | 5-[(3R,5R)-3-amino-5-fluoropiperidin-1-yl]-N-[1-methyl-3-(trifluoromethyl)-1H-pyrazol-4-yl]pyrazolo[1,5-a]pyrimidine-3-carboxamide trifluoroacetate | Calc'd 427.2, found 427.4 |
| 253 | 0.5 | 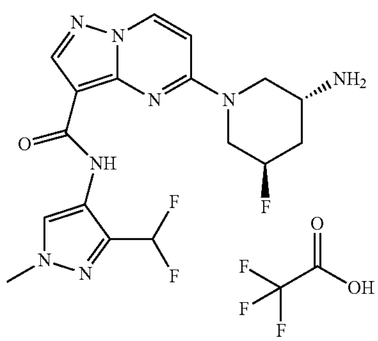 | 5-[(3R,5R)-3-amino-5-fluoropiperidin-1-yl]-N-[3-(difluoromethyl)-1-methyl-1H-pyrazol-4-yl]pyrazolo[1,5-a]pyrimidine-3-carboxamide trifluoroacetate | Calc'd 409.2, found 409.4 |

Example 254

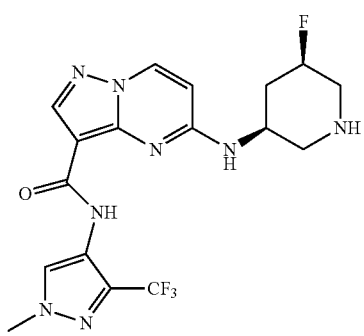 [SMILES: Cn1cc(NC(=O)c2cnn3ccc(N[C@@H]4CNC[C@H](F)C4)nc23)c(C(F)(F)F)n1]

5-(((3S,5R)-5-Fluoropiperidin-3-yl)amino)-N-(1-methyl-3-(trifluoromethyl)-1H-pyrazol-4-yl)pyrazolo[1,5-a]pyrimidine-3-carboxamide (IRAK4 IC$_{50}$=876 nM)

Step 1: Into a 25 mL round bottom flask containing a solution of tert-butyl ((3S,5R)-5-fluoro-1-(4-methoxybenzyl)piperidin-3-yl)carbamate (1.0 g, 3 mmol) in dichloromethane (10 mL) was added trifluoroacetic acid (6 mL) and the reaction was stirred for 3 h. The reaction mixture was diluted with dichloromethane (20 mL) and washed with saturated sodium bicarbonate solution, water and brine, dried over anhydrous sodium sulfate, filtered and concentrated under reduced pressure to afford (3S,5R)-5-fluoro-1-(4-methoxybenzyl)piperidin-3-amine. MS calc'd [M+H]$^{-1}$ 239.1, found 239.4.

Step 2: A mixture of 5-chloro-N-(1-methyl-3-(trifluoromethyl)-1H-pyrazol-4-yl)pyrazolo[1,5-a]pyrimidine-3-carboxamide (40 mg, 0.1 mmol), (3S,5R)-5-fluoro-1-(4-methoxybenzyl)piperidin-3-amine (30 mg, 0.1 mmol), N,N- diisopropylethylamine (0.04 mL, 0.2 mmol) and ethanol (1 mL) in a 10 mL sealed tube and heated at 90° C. overnight. The solvent was removed under reduced pressure and the residue was purified by flash chromatography eluting with ethyl acetate in petroleum ether (30-60%) to afford 5-(((3S,5R)-5-fluoro-1-(4-methoxybenzyl)piperidin-3-yl)amino)-N-(1-methyl-3-(trifluoromethyl)-1H-pyrazol-4-yl)pyrazolo[1,5-a]pyrimidine-3-carboxamide as a solid. MS calc'd [M+H]+ 547.2, found 547.2.

Step 3: A mixture of 5-(((3S,5R)-5-fluoro-1-(4-methoxybenzyl)piperidin-3-yl)amino)-N-(1-methyl-3-(trifluoromethyl)-1H-pyrazol-4-yl)pyrazolo[1,5-a]pyrimidine-3-carboxamide (38 mg, 0.07 mmol) and 1-chloroethyl chloroformate (0.08 mL, 0.7 mmol) in dichloroethane (5 mL) were taken into a 25 mL round bottom flask and heated at 100° C. for 2 h. The reaction mixture was cooled to room temperature and concentrated under reduced pressure. The residue was taken in methanol (5 mL) and heated at 80° C. overnight. The reaction mixture was cooled to room temperature and concentrated under reduced pressure. The residue was purified by preparative HPLC conditions to afford 5-(((3S,5R)-5-fluoropiperidin-3-yl)amino)-N-(1-methyl-3-(trifluoromethyl)-1H-pyrazol-4-yl)pyrazolo[1,5-a]pyrimidine-3-carboxamide trifluoroacetate. $^1$H NMR (CD$_3$OD, 400 MHz): δ 8.43 (d, J=7.6 Hz, 1H), 8.31 (s, 1H), 8.28 (s, 1H), 6.47 (d, J=7.6 Hz, 1H), 4.73-4.72 (m, 1H), 4.43 (brs, 1H), 3.98 (s, 3H), 3.18-3.02 (m, 3H), 2.96-2.92 (m, 1H), 2.36-2.24 (m, 1H), 2.13-2.08 (m, 1H). MS calc'd [M+H]+ 427.2, found 427.2.

The following examples were prepared in an analogous manner of that described in Example 254.

| Example # | IRAK4 IC$_{50}$ (nM) | Structure | IUPAC Name | Exact Mass [M + H]+ |
|---|---|---|---|---|
| 255 | 36 | 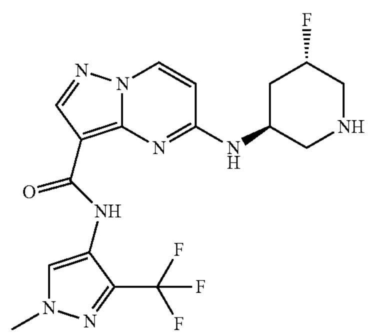 [SMILES: Cn1cc(NC(=O)c2cnn3ccc(N[C@@H]4CNC[C@@H](F)C4)nc23)c(C(F)(F)F)n1] | 5-{[(3S,5S)-5-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427.2, found 427.4 |
| 256 | 8 | 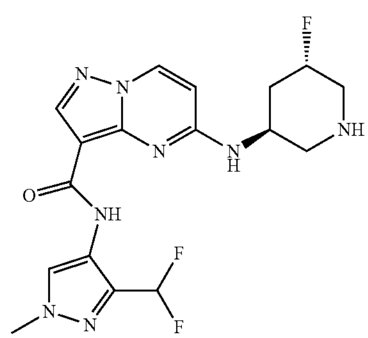 [SMILES: Cn1cc(NC(=O)c2cnn3ccc(N[C@@H]4CNC[C@@H](F)C4)nc23)c(C(F)F)n1] | N-[3-(difluoromethyl)-1-methyl-1H-pyrazol-4-yl]-5-{[(3S,5S)-5-fluoropiperidin-3-yl]amino}pyrazolo[1,5-a]pyrimidine-3-carboxamide | Calc'd 409.2, found 409.2 |
| 257 | 0.6 | 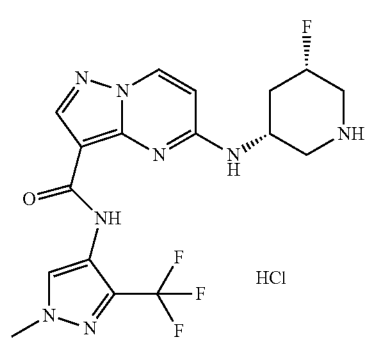 [SMILES: Cn1cc(NC(=O)c2cnn3ccc(N[C@H]4CNC[C@@H](F)C4)nc23)c(C(F)(F)F)n1 ; Cl] | 5-{[(3R,5S)-5-fluoropiperidin-3-yl]amino}-N-[1-methyl-3-(trifluoromethyl)-1H-pyrazol-4-yl]pyrazolo[1,5-a]pyrimidine-3-carboxamide hydrochloride | Calc'd 427.2, found 427.4 |

| Example # | IRAK4 IC$_{50}$ (nM) | Structure | IUPAC Name | Exact Mass [M + H]+ |
|---|---|---|---|---|
| 258 | 0.5 | 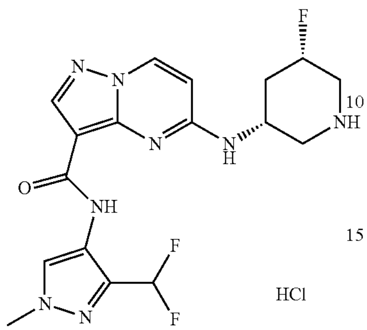 | N-[3-(difluoromethyl)-1-methyl-1H-pyrazol-4-yl]-5-{[(3R,5S)-5-fluoropiperidin-3-yl]amino}pyrazolo[1,5-a]pyrimidine-3-carboxamide hydrochloride | Calc'd 409.2, found 409.4 |
| 259 | 156 | 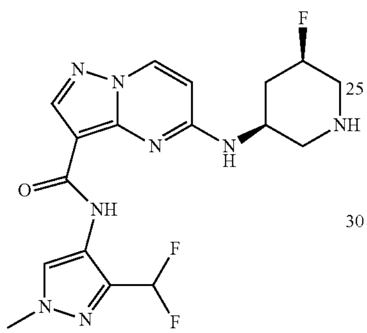 | N-[3-(difluoromethyl)-1-methyl-1H-pyrazol-4-yl]-5-{[(3S,5R)-5-fluoropiperidin-3-yl]amino}pyrazolo[1,5-a]pyrimidine-3-carboxamide | Calc'd 409.2, found 409.2 |
| 260 | 4 | 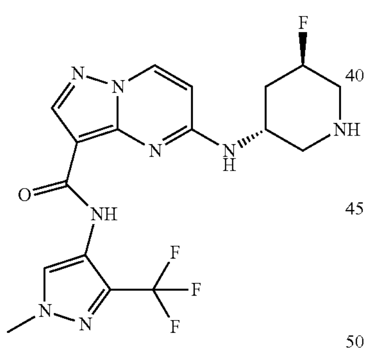 | 5-{[(3R,5R)-5-fluoropiperidin-3-yl]amino}-N-[1-methyl-3-(trifluoromethyl)-1H-pyrazol-4-yl]pyrazolo[1,5-a]pyrimidine-3-carboxamide | Calc'd 427.2, found 427.2 |
| 261 | 0.5 | 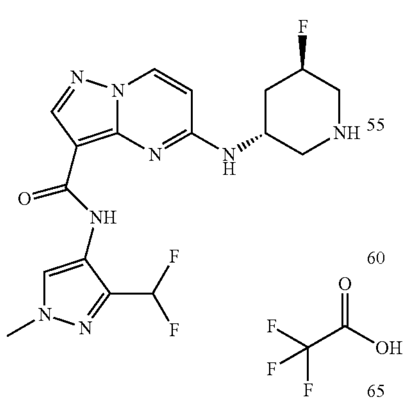 [SMILES: Cn1cc(NC(=O)c2cnn3ccc(N[C@H]4CNC[C@H](F)C4)nc23)c(C(F)F)n1 ; O=C(O)C(F)(F)F] | N-[3-(difluoromethyl)-1-methyl-1H-pyrazol-4-yl]-5-{[(3R,5R)-5-fluoropiperidin-3-yl]amino}pyrazolo[1,5-a]pyrimidine-3-carboxamide trifluoroacetate | Calc'd 409.2, found 409.4 |

Example 262

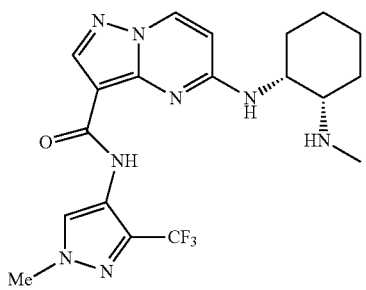 [SMILES: CN[C@H]1CCCC[C@H]1Nc1ccn2ncc(C(=O)Nc3cn(C)nc3C(F)(F)F)c2n1]

N-(1-Methyl-3-(trifluoromethyl)-1H-pyrazol-4-yl)-
5-(((1R,2S)-2-(methylamino)cyclohexyl)amino)
pyrazolo[1,5-a]pyrimidine-3-carboxamide (IRAK4
IC$_{50}$=24 nM)

Step 1: A mixture of 5-chloro-N-(1-methyl-3-(trifluoromethyl)-1H-pyrazol-4-yl)pyrazolo[1,5-a]pyrimidine-3-carboxamide (100 mg, 0.3 mmol), tert-butyl ((1S,2R)-2-aminocyclohexyl)carbamate (100 mg, 0.4 mmol) and N,N-diisopropylethylamine (0.1 mL 7 mmol) in ethanol (5 mL) was taken in a 10 mL sealed tube and heated at 90° C. for 4 h. The solvent was removed under reduced pressure and the residue was purified by flash chromatography eluting with methanol in dichloromethane (3-5%) to afford tert-butyl ((1S,2R)-2-((3-((1-methyl-3-(trifluoromethyl)-1H-pyrazol-4-yl)carbamoyl)pyrazolo[1,5-a]pyrimidin-5-yl) amino)cyclohexyl)carbamate as a solid. MS calc'd [M+H]$^+$ 523.2, found 523.2.

Step 2: In to a 25 mL round bottom flask containing a solution of tert-butyl ((1S,2R)-2-((3-((1-methyl-3-(trifluoromethyl)-1H-pyrazol-4-yl)carbamoyl)pyrazolo[1,5-a]pyrimidin-5-yl)amino)cyclohexyl)carbamate (70 mg, 0.13 mmol) in tetrahydrofuran (5 mL) was added lithium aluminum hydride solution (2M in THF, 0.15 mL) dropwise at 0° C. and the reaction mixture was stirred for 6 h at room temperature. The reaction mixture was cooled to 0° C. and treated with saturated sodium sulfate solution and the resulting slurry was filtered through celite and washed with hot ethyl acetate. The filtrate was concentrated under reduced pressure and purified by prep-HPLC to afford N-(1-methyl-3-(trifluoromethyl)-1H-pyrazol-4-yl)-5-(((1R,2S)-2-(methylamino)cyclohexyl)amino)pyrazolo[1,5-a]pyrimidine-3-carboxamide trifluoroacetate as a solid. $^1$H NMR (CD$_3$OD, 400 MHz): δ 8.53 (d, J=7.6 Hz, 1H), 8.34 (s, 1H), 8.32 (s, 1H), 6.70 (d, J=7.6 Hz, 1H), 5.12 (brs, 1H), 3.97 (s, 3H), 3.44-3.40 (m, 1H), 2.69 (s, 3H), 2.06-1.96 (m, 3H), 1.76-1.61 (m, 5H). MS calc'd. [M+H]$^+$ 437.2, found 437.2.

Example 263

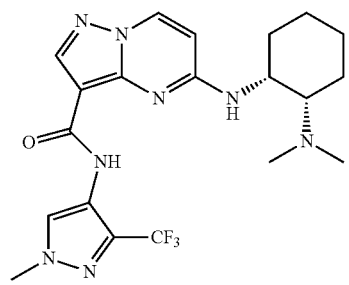

5-(((1R,2S)-2-(Dimethylamino)cyclohexyl)amino)-
N-(1-methyl-3-(trifluoromethyl)-1H-pyrazol-4-yl)
pyrazolo[1,5-a]pyrimidine-3-carboxamide (IRAK4
IC$_{50}$=72 nM)

Into a 25 mL round bottom flask containing 5-(((1R,2S)-2-aminocyclohexyl)amino)-N-(1-methyl-3-(trifluoromethyl)-1H-pyrazol-4-yl)pyrazolo[1,5-a]pyrimidine-3-carboxamide (100 mg, 0.15 mmol) in methanol (5 mL) were added formaldehyde solution (37% in water, 0.02 mL, 0.2 mmol) and sodium borohydride (8.5 mg, 0.2 mmol) and the reaction was stirred overnight at room temperature. The reaction mixture was treated with hydrochloric acid (1.5 N, 1 mL) and concentrated under reduced pressure. The residue was purified by prep-HPLC to afford 5-(((1R,2S)-2-(dimethylamino)cyclohexyl)amino)-N-(1-methyl-3-(trifluoromethyl)-1H-pyrazol-4-yl)pyrazolo[1,5-a]pyrimidine-3-carboxamide trifluoroacetate as a solid. $^1$H NMR (CD$_3$OD, 400 MHz): δ 8.56 (d, J=7.6 Hz, 1H), 8.35 (s, 1H), 8.34 (s, 1H), 6.69 (d, J=7.6 Hz, 1H), 5.23 (brs, 1H), 3.97 (s, 3H), 3.49-3.44 (m, 1H), 2.95 (s, 3H), 2.89 (s, 3H), 2.29-2.26 (m, 1H), 2.07-2.04 (m, 2H), 1.86-1.66 (m, 5H). MS calc'd [M+H]$^+$ 451.2, found 451.2.

Example 264

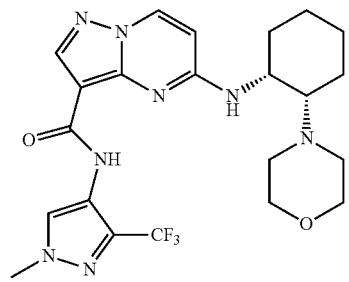 [SMILES: Cn1cc(NC(=O)c2cnn3ccc(N[C@@H]4CCCC[C@@H]4N4CCOCC4)nc23)c(C(F)(F)F)n1]

N-(1-Methyl-3-(trifluoromethyl)-1H-pyrazol-4-yl)-
5-(((1R,2S)-2-morpholinocyclohexyl)amino)pyra-
zolo[1,5-a]pyrimidine-3-carboxamide (IRAK4
IC$_{50}$=19 nM)

A mixture of 5-(((1R,2S)-2-aminocyclohexyl)amino)-N-(1-methyl-3-(trifluoromethyl)-1H-pyrazol-4-yl)pyrazolo[1, 5-a]pyrimidine-3-carboxamide (80 mg, 0.1 mmol), 2-chloroethyl ether (20 mg, 0.1 mmol) and potassium carbonate (50 mg, 0.3 mmol) in dimethylformamide (3 mL) was taken in a 25 mL sealed tube and the mixture was heated to 80° C. overnight. The reaction mixture was cooled to room temperature and filtered through celite. The filtrate was concentrated under reduced pressure and purified by prep-HPLC to afford N-(1-methyl-3-(trifluoromethyl)-1H-pyrazol-4-yl)-5-(((1R,2S)-2-morpholinocyclohexyl)amino)pyrazolo[1,5-a]pyrimidine-3-carboxamide trifluoroacetate as a solid. $^1$H NMR (CD$_3$OD, 400 MHz): δ 8.57 (d, J=7.6 Hz, 1H), 8.35 (s, 2H), 6.69 (d, J=7.6 Hz, 1H), 5.22 (brs, 1H), 4.11-4.01 (m, 2H), 3.98 (s, 3H), 3.81-3.78 (m, 2H), 3.62-3.49 (m, 4H), 3.32-3.29 (m, 1H), 2.34-2.3 (m, 1H), 2.11-2.05 (m, 2H), 1.89-1.8 (m, 1H), 1.72-1.54 (m, 4H). MS calc'd [M+H]$^+$ 493.2, found 493.2.

Example 265

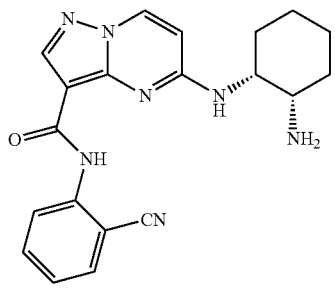 [SMILES: N#Cc1ccccc1NC(=O)c1cnn2ccc(N[C@@H]3CCCC[C@@H]3N)nc12]

5-(((1R,2S)-2-Aminocyclohexyl)amino)-N-(2-cyanophenyl)pyrazolo[1,5-a]pyrimidine-3-carboxamide
(IRAK4 IC$_{50}$=1 nM)

Step 1: Into a 50 mL round bottom flask were added 5-chloropyrazolo[1,5-a]pyrimidine-3-carbonyl chloride (250 mg, 1 mmol), 2-amino-iodobenzene (300 mg, 1.4 mmol), dichloromethane (5 mL) and diisopropylethylamine (0.6 mL, 3.2 mmol) at 0° C. and the reaction mixture was stirred at room temperature for 1 h. The reaction mixture was diluted with dichloromethane and washed with water and brine, dried over anhydrous sodium sulfate, filtered and concentrated. The residue was purified by flash chromatography eluting with ethyl acetate in petroleum ether (20-70%) to afford 5-chloro-N-(2-iodophenyl)pyrazolo[1,5-a]pyrimidine-3-carboxamide as a solid. $^1$H NMR (CDCl$_3$, 400 MHz): δ 9.64 (brs, 1H), 8.76 (s, 1H), 8.72 (d, J=7.2 Hz, 1H), 8.45 (dd, J=8.0, 1.6 Hz, 1H), 7.87 (dd, J=8.0, 1.6 Hz, 1H), 7.42-7.38 (m, 1H), 7.04 (d, J=7.2 Hz, 1H), 6.90-6.85 (m, 1H). MS calc'd. [M+H]$^+$ 398.9, found 398.8.

Step 2: A mixture of 5-chloro-N-(2-iodophenyl)pyrazolo[1,5-a]pyrimidine-3-carboxamide (50 mg, 0.1 mmol) and tert-butyl ((1S,2R)-2-aminocyclohexyl)carbamate (26 mg, 0.12 mmol) in ethanol (5 mL) was taken in a 10 mL sealed tube and the mixture was heated at 90° C. overnight. The solvent was removed under reduced pressure and the residue was purified by flash chromatography eluting with methanol in dichloromethane (2-5%) to afford tert-butyl ((1S,2R)-2-((3-((2-iodophenyl)carbamoyl)-7H-pyrrolo[3,2-b]pyridin-5-yl)amino)cyclohexyl)carbamate as a solid. MS calc'd. [M+H]$^+$ 577.1, found 577.2.

Step 3: Into a 10 mL microwave reaction vessel containing a solution tert-butyl ((1S,2R)-2-((3-((2-iodophenyl)carbamoyl)-7aH-pyrrolo[3,2-b]pyridin-5-yl)amino)cyclohexyl)carbamate (50 mg, 0.1 mmol) in dimethylformamide (1 mL) were added tetramethylethylene diamine (0.003 mL, 0.01 mmol) and Xantphos (3.0 mg, 0.005 mmol), and the mixture was degassed with nitrogen for 5 min. To this were added zinc cyanide (8.0 mg, 0.07 mmol) and tris(dibenzylideneacetone)dipalladium(0) (5 mg, 0.006 mmol) and the reaction mixture was heated at 120° C. for 10 min. The reaction mixture was cooled to room temperature, filtered through celite, and washed with ethyl acetate and the filtrate was concentrated under reduced pressure. The residue was purified by flash chromatography eluting with methanol in dichloromethane (0-10%) to afford tert-butyl ((1S,2R)-2-((3-((2-cyanophenyl)carbamoyl)-7aH-pyrrolo[3,2-b]pyridin-5-yl)amino)cyclohexyl)carbamate as a solid. MS calc'd. [M+H]$^+$ 476.2, found 476.2.

Step 4: Into a 10 mL round bottom flask containing a solution of tert-butyl ((1S,2R)-2-((3-((2-cyanophenyl)carbamoyl)-7aH-pyrrolo[3,2-b]pyridin-5-yl)amino)cyclohexyl)carbamate (20 mg, 0.04 mmol) in dichloromethane (3 mL) was added trifluoroacetic acid (2 mL) and the reaction was stirred for 1 h. The solvent was removed under reduced pressure and the residue was purified by trituration with dichloromethane and hexanes to afford 5-(((1R,2S)-2-aminocyclohexyl)amino)-N-(2-cyanophenyl)pyrazolo[1,5-a]pyrimidine-3-carboxamide trifluoroacetate as a solid. $^1$H NMR (CD$_3$OD, 400 MHz): δ 8.52 (d, J=6.1 Hz, 1H), 8.39-8.36 (m, 2H), 7.79 (d, J=7.2 Hz, 1H), 7.73-7.69 (m, 1H), 7.30 (t, J=7.3 Hz, 1H), 6.65 (d, J=7.5 Hz, 1H), 5.23-5.21 (m, 1H), 3.63-3.60 (m, 1H), 1.95-1.54 (m, 8H). MS calc'd. [M+H]$^+$ 376.2, found 376.2.

The following examples were prepared in an analogous manner of that described in Example 265.

| Example # | IRAK4 IC$_{50}$ (nM) | Structure | IUPAC Name | Exact Mass [M + H]+ |
|---|---|---|---|---|
| 266 | 562 | 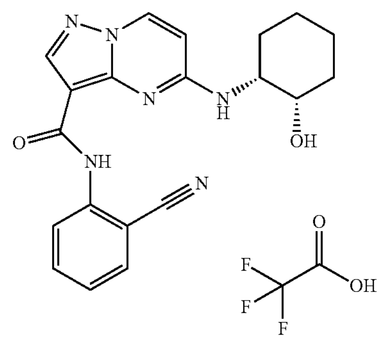 [SMILES: N#Cc1ccccc1NC(=O)c1cnn2ccc(N[C@@H]3CCCC[C@@H]3O)nc12 ; O=C(O)C(F)(F)F] | N-(2-cyanophenyl)-5-{[(1R,2S)-2-hydroxycyclohexyl]amino}pyrazolo[1,5-a]pyrimidine-3-carboxamide trifluoroacetate | Calc'd 377.2, found 377.4 |
| 267 | 351 | 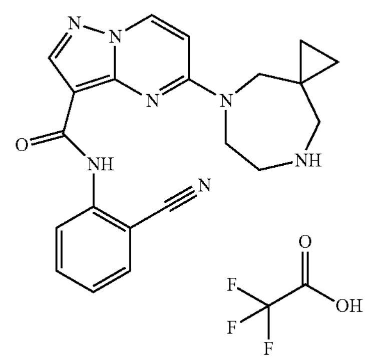 [SMILES: N#Cc1ccccc1NC(=O)c1cnn2ccc(N3CCNCC4(CC4)C3)nc12 ; O=C(O)C(F)(F)F] | N-(2-cyanophenyl)-5-(5,8-diazaspiro[2.6]non-5-yl)pyrazolo[1,5-a]pyrimidine-3-carboxamide trifluoroacetate | Calc'd 388.2, found 388.4 |
| 268 | 268 | 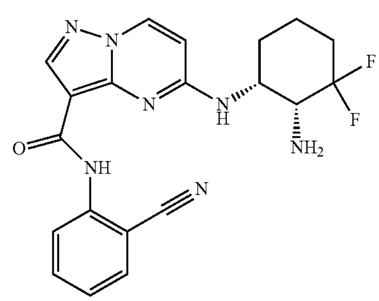 [SMILES: N#Cc1ccccc1NC(=O)c1cnn2ccc(N[C@@H]3CCCC(F)(F)[C@@H]3N)nc12] | 5-{[(1R,2R)-2-amino-3,3-difluorocyclohexyl]amino}-N-(2-cyanophenyl)pyrazolo[1,5-a]pyrimidine-3-carboxamide | Calc'd 412.2, found 412.4 |
| 269 | 143 | 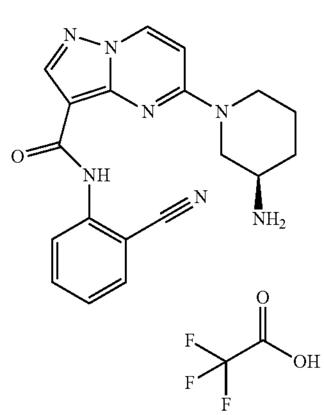 [SMILES: N#Cc1ccccc1NC(=O)c1cnn2ccc(N3CCC[C@@H](N)C3)nc12 ; O=C(O)C(F)(F)F] | 5-[(3R)-3-aminopiperidin-1-yl]-N-(2-cyanophenyl)pyrazolo[1,5-a]pyrimidine-3-carboxamide trifluoroacetate | Calc'd 362.2, found 362.4 |

| Example # | IRAK4 IC$_{50}$ (nM) | Structure | IUPAC Name | Exact Mass [M + H]+ |
|---|---|---|---|---|
| 270 | 10 | 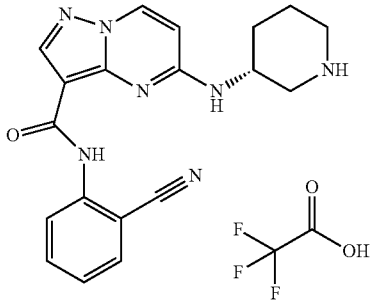 [SMILES: N#Cc1ccccc1NC(=O)c1cnn2ccc(N[C@@H]3CCCNC3)nc12 ; O=C(O)C(F)(F)F] | N-(2-cyanophenyl)-5-[(3R)-piperidin-3-ylamino]pyrazolo[1,5-a]pyrimidine-3-carboxamide trifluoroacetate | Calc'd 362.2, found 362.2 |
| 271 | 403 | 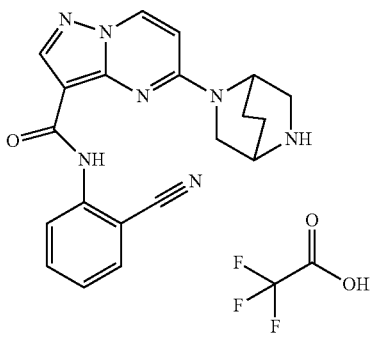 [SMILES: N#Cc1ccccc1NC(=O)c1cnn2ccc(N3CC4CCC3CN4)nc12 ; O=C(O)C(F)(F)F] | N-(2-cyanophenyl)-5-(2,5-diazabicyclo[2.2.2]oct-2-yl)pyrazolo[1,5-a]pyrimidine-3-carboxamide trifluoroacetate | Calc'd 374.2, found 374.4 |
| 272 | 57 | 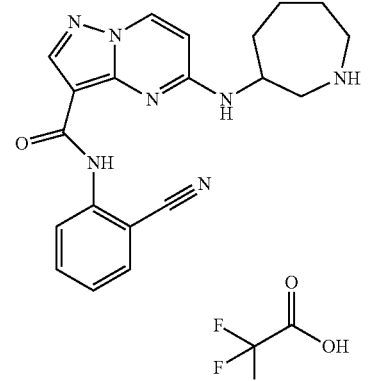 | 5-(azepan-3-ylamino)-N-(2-cyanophenyl)pyrazolo[1,5-a]pyrimidine-3-carboxamide trifluoroacetate | Calc'd 376.2, found 376.4 |
| 273 | 1363 | 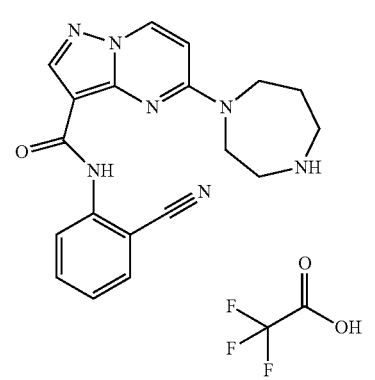 [SMILES: N#Cc1ccccc1NC(=O)c1cnn2ccc(N3CCCNCC3)nc12 ; O=C(O)C(F)(F)F] | N-(2-cyanophenyl)-5-(1,4-diazepan-1-yl)pyrazolo[1,5-a]pyrimidine-3-carboxamide trifluoroacetate | Calc'd 362.2, found 362.4 |

| Example # | IRAK4 IC$_{50}$ (nM) | Structure | IUPAC Name | Exact Mass [M + H]+ |
|---|---|---|---|---|
| 274 | 660 | 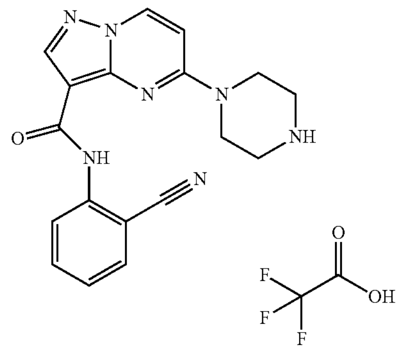 [SMILES: N#Cc1ccccc1NC(=O)c1cnn2ccc(N3CCNCC3)nc12 ; O=C(O)C(F)(F)F] | N-(2-cyanophenyl)-5-piperazin-1-ylpyrazolo[1,5-a]pyrimidine-3-carboxamide trifluoroacetate | Calc'd 348.2, found 348.4 |

Example 275

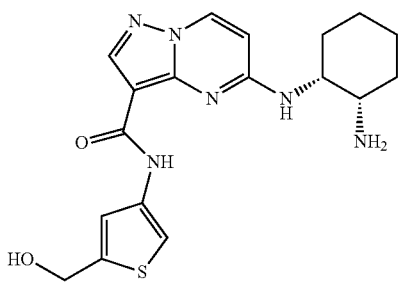 [SMILES: N[C@H]1CCCC[C@H]1Nc1ccn2ncc(C(=O)Nc3csc(CO)c3)c2n1]

5-(((1R,2S)-2-Aminocyclohexyl)amino)-N-(5-(hydroxymethyl)thiophen-3-yl)pyrazolo[1,5-a]pyrimidine-3-carboxamide (IRAK4 IC$_{50}$=17 nM)

Step 1: Into a 50 mL round bottomed flask were added 5-chloropyrazolo[1,5-a]pyrimidine-3-carbonyl chloride (480 mg, 2.2 mmol), dichloromethane (10 mL), methyl 4-aminothiophene-2-carboxylate (420 mg, 2.7 mmol) and diisopropylethylamine (0.4 mL, 2.2 mmol) and the reaction mixture was stirred at room temperature for 2 h. The reaction mixture was diluted with dichloromethane and washed with water and brine, dried over anhydrous sodium sulfate, filtered and concentrated. The residue was purified by flash chromatography eluting with methanol in dichloromethane (7-9%) to afford methyl 4-(5-chloropyrazolo[1,5-a]pyrimidine-3-carboxamido)thiophene-2-carboxylate as a solid. $^1$H NMR (DMSO-d$_6$, 400 MHz): δ 10.24 (s, 1H), 9.35 (d, J=7.2 Hz, 1H), 8.75 (s, 1H), 7.99-7.98 (m, 2H), 7.40 (d, J=7.2 Hz, 1H), 3.83 (s, 3H). MS calc'd [M+H]$^+$ 337.0, found 337.0.

Step 2: A mixture of methyl 4-(5-chloropyrazolo[1,5-a]pyrimidine-3-carboxamido)thiophene-2-carboxylate (250 mg, 0.8 mmol), tert-butyl ((1S,2R)-2-aminocyclohexyl)carbamate (175 mg, 0.8 mmol), N,N-diisopropylethylamine (1.4 mL, 0.8 mmol) and ethanol (10 mL) in a 20 mL sealed tube and heated at 90° C. for 12 h. The solvent was removed under reduced pressure and the residue was purified by flash chromatography eluting with ethyl acetate in petroleum ether (35-45%) to afford methyl 4-(5-(((1R,2S)-2-((tert-butoxycarbonyl)amino)cyclohexyl)amino)pyrazolo[1,5-a]pyrimidine-3-carboxamido)thiophene-2-carboxylate as a solid. MS calc'd [M+H]$^+$ 515.2, found 515.2.

Step 3: Into a 10 mL round bottom flask containing a solution of methyl 4-(5-(((1R,2S)-2-((tert-butoxycarbonyl)amino)cyclohexyl)amino)pyrazolo[1,5-a]pyrimidine-3-carboxamido)thiophene-2-carboxylate (50 mg, 0.1 mmol) in dichloromethane (1 mL) was added trifluoroacetic acid (1 mL) and the reaction was stirred for 1 h. The solvent was removed under reduced pressure and the crude methyl 4-(5-(((1R,2S)-2-aminocyclohexyl)amino)pyrazolo[1,5-a]pyrimidine-3-carboxamido)thiophene-2-carboxylate (35 mg) was directly taken to the next step without further purification. MS calc'd [M+H]$^+$ 415.1, found 415.2.

Step 4: Into a 25 mL round bottom flask containing a solution of methyl 4-(5-(((1R,2S)-2-aminocyclohexyl)amino)pyrazolo[1,5-a]pyrimidine-3-carboxamido)thiophene-2-carboxylate (40 mg, 0.1 mmol) in tetrahydrofuran (5 mL) was added lithium aluminum hydride solution (2M in tetrahydrofuran, 0.06 mL, 0.12 mmol) at 0° C. and the reaction was stirred for 2 h. The reaction mixture was treated with saturated sodium sulfate solution and the solid formed was filtered through celite and washed with tetrahydrofuran and the filtrate was concentrated under reduced pressure. The residue was purified by preparative HPLC to afford 5-(((1R,2S)-2-aminocyclohexyl)amino)-N-(5-(hydroxymethyl)thiophen-3-yl)pyrazolo[1,5-a]pyrimidine-3-carboxamide trifluoroacetate. $^1$H NMR (CD$_3$OD, 400 MHz): δ 8.43 (d, J=7.6 Hz, 1H), 8.27 (s, 1H), 7.48 (d, J=1.6 Hz, 1H), 7.08 (s, 1H), 6.57 (d, J=7.6 Hz, 1H), 4.72 (s, 2H), 4.54 (brs, 1H), 3.60-3.48 (m, 1H), 2.16-1.96 (m, 1H), 1.91-1.49 (m, 5H), 1.56-1.52 (m, 2H). MS calc'd [M+H]$^+$ 387.2, found 387.2.

Example 276

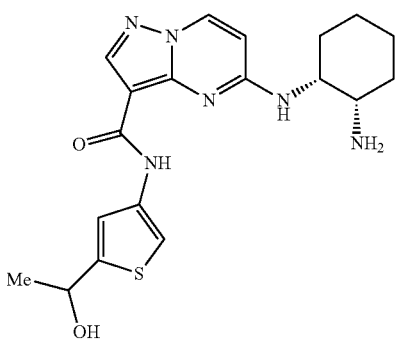 [SMILES: CC(O)c1cc(NC(=O)c2cnn3ccc(N[C@@H]4CCCC[C@@H]4N)nc23)cs1]

5-(((1R,2S)-2-Aminocyclohexyl)amino)-N-(5-(1-hydroxyethyl)thiophen-3-yl)pyrazolo[1,5-a]pyrimidine-3-carboxamide (IRAK4 $IC_{50}$=64 nM)

Step 1: Into a 25 mL round bottom flask containing a solution of methyl 4-(5-(((1R,2S)-2-((tert-butoxycarbonyl)amino)cyclohexyl)amino)pyrazolo[1,5-a]pyrimidine-3-carboxamido)thiophene-2-carboxylate (240 mg, 0.5 mmol) in tetrahydrofuran (5 mL) was added lithium aluminum hydride (20 mg, 0.5 mmol) at 0° C. and the reaction was stirred for 15 min. The reaction mixture was treated with saturated sodium sulfate solution and the solid formed was filtered through celite and washed with tetrahydrofuran and the filtrate was concentrated under reduced pressure. The residue was purified by flash chromatography eluting with ethyl acetate in petroleum ether (50-65%) to afford tert-butyl ((1S,2R)-2-((3-((5-(hydroxymethyl)thiophen-3-yl)carbamoyl)pyrazolo[1,5-a]pyrimidin-5-yl)amino)cyclohexyl)carbamate as a solid. MS calc'd [M+H]$^+$ 487.2, found 487.4.

Step 2: A mixture of tert-butyl ((1S,2R)-2-((3-((5-(hydroxymethyl)thiophen-3-yl)carbamoyl)pyrazolo[1,5-a]pyrimidin-5-yl)amino)cyclohexyl)carbamate (90 mg, 0.2 mmol) and Des-Martin periodinane (120 mg, 0.3 mmol) in dichloromethane (5 mL) was taken into a 25 mL round bottom flask and the reaction was stirred at room temperature for 1 h. The reaction mixture was diluted with dichloromethane (20 mL) and washed with sodium bicarbonate solution (10% in water, 20 mL), water and brine, dried over sodium sulfate, filtered and concentrated under reduced pressure. The residue was purified by flash chromatography eluting with ethyl acetate in petroleum ether (35-50%) to afford tert-butyl ((1S,2R)-2-((3-((5-formylthiophen-3-yl)carbamoyl)pyrazolo[1,5-a]pyrimidin-5-yl)amino)cyclohexyl)carbamate as a solid. MS calc'd [M+H]$^+$ 485.2, found 485.2.

Step 3: Into a 25 mL round bottom flask containing a solution of tert-butyl ((1S,2R)-2-((3-((5-formylthiophen-3-yl)carbamoyl)pyrazolo[1,5-a]pyrimidin-5-yl)amino)cyclohexyl)carbamate (45 mg, 0.1 mmol) in tetrahydrofuran (5 mL) was added methylmagnesium bromide (3 M in tetrahydrofuran, 0.05 mL, 0.14 mmol) at 0° C. and the reaction mixture was stirred at room temperature for 2 h. The reaction mixture was cooled to 0° C., treated with aqueous ammonium chloride solution and extracted with ethyl acetate. The organic fraction was washed with water and brine, dried over anhydrous sodium sulfate, filtered and concentrated under reduced pressure. The crude tert-butyl ((1S,2R)-2-((3-((5-(1-hydroxyethyl)thiophen-3-yl)carbamoyl)pyrazolo[1,5-a]pyrimidin-5-yl)amino)cyclohexyl)carbamate (35 mg) was taken to the next step without further purification. MS calc'd [M+H]$^+$ 501.2, found 501.4.

Step 4: A mixture of tert-butyl ((1S,2R)-2-((3-((5-(1-hydroxyethyl)thiophen-3-yl)carbamoyl)pyrazolo[1,5-a]pyrimidin-5-yl)amino)cyclohexyl)carbamate (35 mg, 0.07 mmol) and tetra-n-butylammonium fluoride (1M in tetrahydrofuran, 0.35 mL, 0.35 mmol) was taken in a 10 mL round bottom flask and heated at 70° C. for 12 h. The reaction mixture was concentrated under reduced pressure and the residue was purified by preparative HPLC to afford 5-(((1R,2S)-2-aminocyclohexyl)amino)-N-(5-(1-hydroxyethyl)thiophen-3-yl)pyrazolo[1,5-a]pyrimidine-3-carboxamide trifluoroacetate. $^1$H NMR (CD$_3$OD, 400 MHz): δ 8.47 (d, J=7.6 Hz, 1H), 8.29 (s, 1H), 7.45 (t, J=1.4 Hz, 1H), 7.07 (s, 1H), 6.59 (d, J=7.6 Hz, 1H), 4.82-4.80 (m, 1H), 4.56-4.54 (m, 1H), 3.63-3.58 (m, 1H), 1.98 (s, 3H), 1.88-1.84 (m, 2H), 1.80-1.77 (m, 2H), 1.64-1.52 (m, 6H). MS calc'd [M+H]$^+$ 401.2, found 401.4.

Example 277

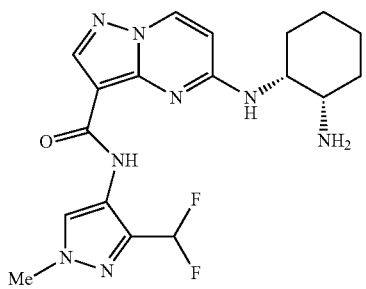 [SMILES: Cn1cc(NC(=O)c2cnn3ccc(N[C@@H]4CCCC[C@@H]4N)nc23)c(C(F)F)n1]

5-(((1R,2S)-2-Aminocyclohexyl)amino)-N-(3-(difluoromethyl)-1-methyl-1H-pyrazol-4-yl)pyrazolo[1,5-a]pyrimidine-3-carboxamide (IRAK4 $IC_{50}$=0.2 nM)

Step 1: A mixture of ethyl 5-chloropyrazolo[1,5-a]pyrimidine-3-carboxylate (500 mg, 2.2 mmol) and tert-butyl ((1S,2R)-2-aminocyclohexyl)carbamate (475 mg, 2.2 mmol) in ethanol (5 mL) was taken in a 25 mL sealed tube, and the mixture was heated at 90° C. for 8 h. The reaction mixture was cooled to room temperature and concentrated under reduced pressure. The residue was purified by flash chromatography eluting with ethyl acetate in petroleum ether (20-30%) to yield ethyl 5-(((1R,2S)-2-((tert-butoxycarbonyl)amino)cyclohexyl)amino)pyrazolo[1,5-a]pyrimidine-3-carboxylate as a solid. $^1$H NMR (DMSO-d$_6$, 400 MHz): δ 8.48 (d, J=7.5 Hz, 1H), 8.12 (s, 1H), 7.48 (d, J=7.3 Hz, 1H), 6.61 (d, J=8.3 Hz, 1H), 6.45 (d, J=7.5 Hz, 1H), 4.31-4.22 (m, 1H), 4.17 (q, J=6.7 Hz, 2H), 4.03-4.01 (m, 1H), 1.85-1.48 (m, 8H), 1.36 (s, 9H), 1.31 (t, J=6.7 Hz, 3H). MS calc'd [M+H]$^+$ 404.2, found 404.4.

Step 2: Into a 25 mL round bottom flask containing a solution of ethyl 5-(((1R,2S)-2-((tert-butoxycarbonyl)amino)cyclohexyl)amino)pyrazolo[1,5-a]pyrimidine-3-carboxylate (500 mg, 1.2 mmol) in tetrahydrofuran (2 mL) and water (5 mL) was added lithium hydroxide (150 mg, 3.7 mmol) and the mixture was stirred for 12 h. The mixture was diluted with water, acidified to pH 2 using hydrochloric acid (1.5 N HCl in water) and extracted with ethyl acetate (2×10 mL). The combined organic fractions were concentrated and the crude was purified by flash chromatography eluting with methanol in dichloromethane (0-2%) to afford 5-(((1R,2S)-2-((tert-butoxycarbonyl)amino)cyclohexyl)amino)pyrazolo[1,5-a]pyrimidine-3-carboxylic acid as a liquid. $^1$H NMR (DMSO-$d_6$, 300 MHz): δ 11.45 (s, 1H), 8.49 (d, J=7.1 Hz, 1H), 8.09 (s, 1H), 7.48 (brs, 1H), 6.60 (brs, 1H), 6.47 (d, J=7.2 Hz, 1H), 4.29-4.26 (m, 1H), 3.83-3.80 (m, 1H), 1.79-1.54 (m, 5H), 1.35-1.21 (12H). MS calc'd [M+H]$^+$ 376.2, found 376.4.

Step 3: Into a 25 mL round bottom flask containing a solution of 3-(difluoromethyl)-1-methyl-1H-pyrazol-4-amine (20 mg, 1.3 mmol) in acetonitrile (5 mL) were added 5-(((1R,2S)-2-((tert-butoxycarbonyl)amino)cyclohexyl)amino)pyrazolo[1,5-a]pyrimidine-3-carboxylic acid (50 mg, 0.1 mmol), HATU (76 mg, 0.2 mmol) and diisopropylethylamine (0.05 mL, 0.3 mmol) and the reaction mixture was heated at 60° C. for 6 h. The reaction mixture was cooled to room temperature, diluted with ethyl acetate (15 mL), washed with water and brine, dried over sodium sulfate, filtered and concentrated under reduced pressure. The residue was purified by flash column chromatography eluting with methanol in dichloromethane (0-5%) to furnish tert-butyl ((1S,2R)-2-((3-((3-(difluoromethyl)-1-methyl-1H-pyrazol-4-yl)carbamoyl)pyrazolo[1,5-a]pyrimidin-5-yl)amino)cyclohexyl)carbamate. $^1$H NMR (CD$_3$OD, 300 MHz): δ 8.36 (d, J=7.7 Hz, 1H), 8.25 (s, 1H), 8.24 (s, 1H), 7.01 (t, J=54.0 Hz, 1H), 6.50 (d, J=7.7 Hz, 1H), 4.81-4.79 (m, 1H), 3.94 (s, 3H), 3.91-2.89 (m, 1H), 1.75-1.63 (m, 8H), 1.36 (s, 9H). MS calc'd [M+H]$^+$ 505.2, found 505.4.

Step 4: Into a 10 mL round bottom flask containing a solution of tert-butyl ((1S,2R)-2-((3-((3-(difluoromethyl)-1-methyl-1H-pyrazol-4-yl)carbamoyl)pyrazolo[1,5-a]pyrimidin-5-yl)amino)cyclohexyl)carbamate (40 mg, 0.07 mmol) in dichloromethane (2 mL) was added trifluoroacetic acid (0.5 mL) and the reaction was stirred at room temperature for 2 h. The solvent was removed under reduced pressure and the residue was purified by trituration with dichloromethane and hexanes to afford 5-(((1R,2S)-2-aminocyclohexyl)amino)-N-(3-(difluoromethyl)-1-methyl-1H-pyrazol-4-yl)pyrazolo[1,5-a]pyrimidine-3-carboxamide trifluoroacetate as a solid. $^1$H NMR (CD$_3$OD, 400 MHz): δ 8.50 (d, J=7.6 Hz, 1H), 8.29 (s, 2H), 6.95 (t, J=54.1 Hz, 1H), 6.64 (d, J=7.6 Hz, 1H), 5.08 (brs, 1H), 3.93 (s, 3H), 3.58-3.53 (m, 1H), 1.96-1.64 (m, 8H). MS calc'd [M+H]$^+$ 405.2, found 405.2.

The following examples were prepared in an analogous manner of that described in Example 277.

| Example # | IRAK4 IC$_{50}$ (nM) | Structure | IUPAC Name | Exact Mass [M + H]$^+$ |
|---|---|---|---|---|
| 278 | 9 | 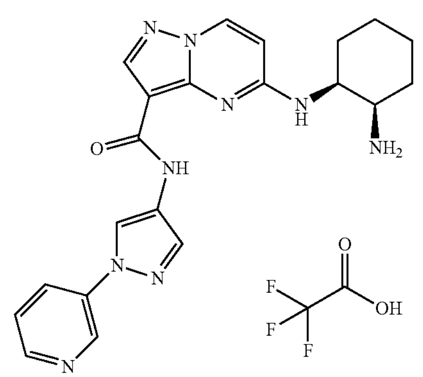 [SMILES: N[C@@H]1CCCC[C@@H]1Nc1ccn2ncc(C(=O)Nc3cnn(-c4cccnc4)c3)c2n1 ; O=C(O)C(F)(F)F] | 5-{[(1S,2R)-2-aminocyclohexyl]amino}-N-(1-pyridin-3-yl-1H-pyrazol-4-yl)pyrazolo[1,5-a]pyrimidine-3-carboxamide trifluoroacetate | Calc'd 418.1, found 418.4 |
| 279 | 14 | 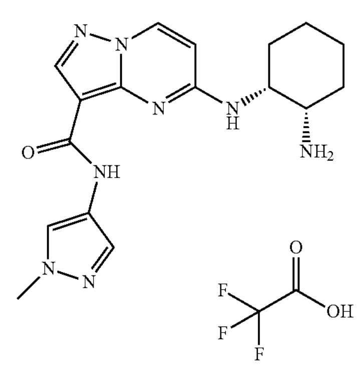 [SMILES: Cn1cc(NC(=O)c2cnn3ccc(N[C@@H]4CCCC[C@@H]4N)nc23)cn1 ; O=C(O)C(F)(F)F] | 5-{[(1R,2S)-2-aminocyclohexyl]amino}-N-(1-methyl-1H-pyrazol-4-yl)pyrazolo[1,5-a]pyrimidine-3-carboxamide trifluoroacetate | Calc'd 355.2, found 355.4 |

-continued

| Example # | IRAK4 IC$_{50}$ (nM) | Structure | IUPAC Name | Exact Mass [M + H]$^+$ |
|---|---|---|---|---|
| 280 | 6 | 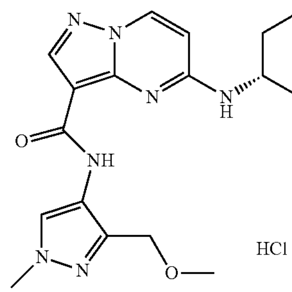 | 5-{[(1R,2S)-2-aminocyclohexyl]amino}-N-[3-(methoxymethyl)-1-methyl-1H-pyrazol-4-yl]pyrazolo[1,5-a]pyrimidine-3-carboxamide hydrochloride | Calc'd 399.2, found 399.4 |
| 281 | 6 | 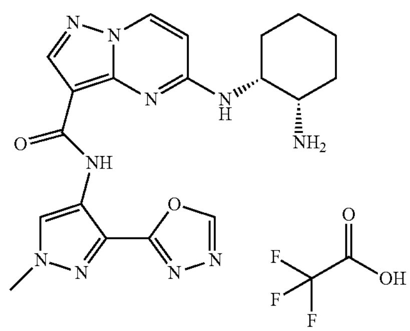 [SMILES: Cn1cc(NC(=O)c2cnn3ccc(N[C@@H]4CCCC[C@@H]4N)nc23)c(-c2nnco2)n1 ; O=C(O)C(F)(F)F] | 5-{[(1R,2S)-2-aminocyclohexyl]amino}-N-[1-methyl-3-(1,3,4-oxadiazol-2-yl)-1H-pyrazol-4-yl]pyrazolo[1,5-a]pyrimidine-3-carboxamide trifluoroacetate | Calc'd 423.2, found 423.4 |
| 282 | 0.8 | 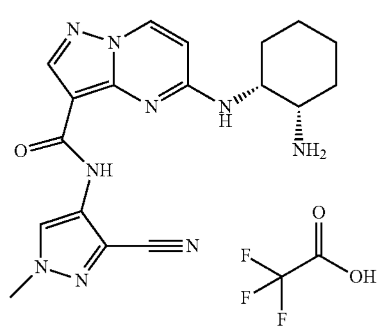 | 5-{[(1R,2S)-2-aminocyclohexyl]amino}-N-(3-cyano-1-methyl-1H-pyrazol-4-yl)pyrazolo[1,5-a]pyrimidine-3-carboxamide trifluoroacetate | Calc'd 380.2, found 380.4 |
| 283 | 76 | 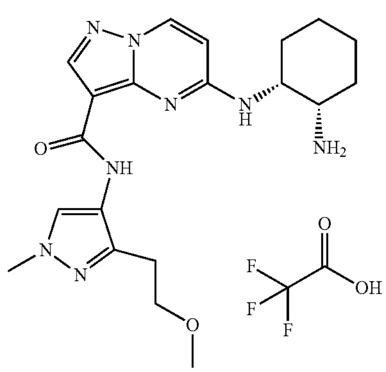 [SMILES: COCCc1nn(C)cc1NC(=O)c1cnn2ccc(N[C@@H]3CCCC[C@@H]3N)nc12 ; O=C(O)C(F)(F)F] | 5-{[(1R,2S)-2-aminocyclohexyl]amino}-N-[3-(2-methoxyethyl)-1-methyl-1H-pyrazol-4-yl]pyrazolo[1,5-a]pyrimidine-3-carboxamide trifluoroacetate | Calc'd 413.2, found 413.4 |

| Example # | IRAK4 IC$_{50}$ (nM) | Structure | IUPAC Name | Exact Mass [M + H]$^+$ |
|---|---|---|---|---|
| 284 | 62 | 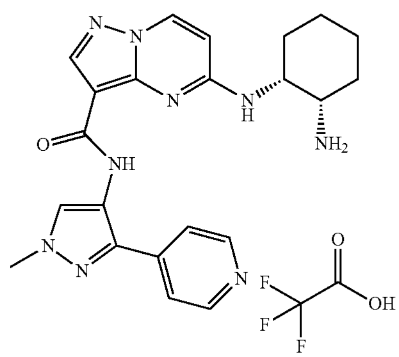 | 5-{[(1R,2S)-2-aminocyclohexyl]amino}-N-(1-methyl-3-pyridin-4-yl-1H-pyrazol-4-yl)pyrazolo[1,5-a]pyrimidine-3-carboxamide trifluoroacetate | Calc'd 432.2, found 432.2 |
| 285 | 24 | 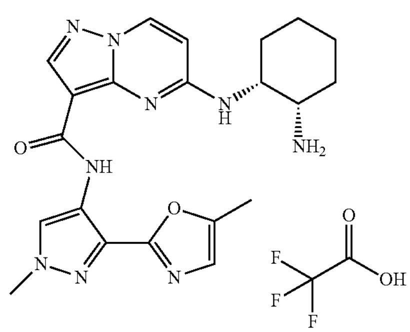 [SMILES: Cc1cnc(-c2nn(C)cc2NC(=O)c2cnn3ccc(N[C@@H]4CCCC[C@@H]4N)nc23)o1 ; O=C(O)C(F)(F)F] | 5-{[(1R,2S)-2-aminocyclohexyl]amino}-N-[1-methyl-3-(5-methyl-1,3-oxazol-2-yl)-1H-pyrazol-4-yl]pyrazolo[1,5-a]pyrimidine-3-carboxamide trifluoroacetate | Calc'd 436.2, found 436.4 |
| 286 | 7 | 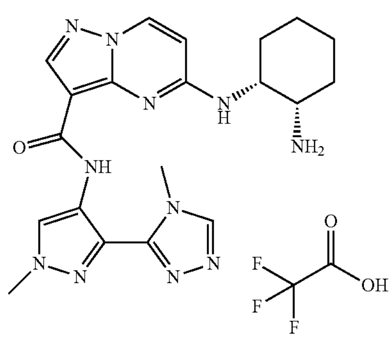 | 5-{[(1R,2S)-2-aminocyclohexyl]amino}-N-[1-methyl-3-(4-methyl-4H-1,2,4-triazol-3-yl)-1H-pyrazol-4-yl]pyrazolo[1,5-a]pyrimidine-3-carboxamide trifluoroacetate | Calc'd 436.2, found 436.2 |
| 287 | 163 | 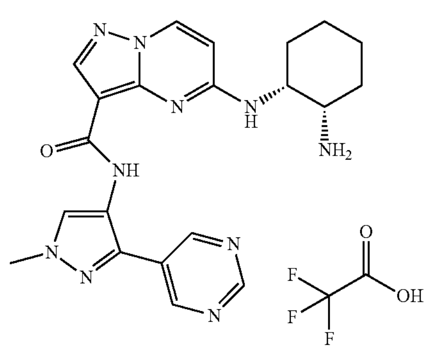 | 5-{[(1R,2S)-2-aminocyclohexyl]amino}-N-(1-methyl-3-pyrimidin-5-yl-1H-pyrazol-4-yl)pyrazolo[1,5-a]pyrimidine-3-carboxamide trifluoroacetate | Calc'd 433.2, found 433.4 |

-continued

| Example # | IRAK4 IC$_{50}$ (nM) | Structure | IUPAC Name | Exact Mass [M + H]$^+$ |
|---|---|---|---|---|
| 288 | 10 | 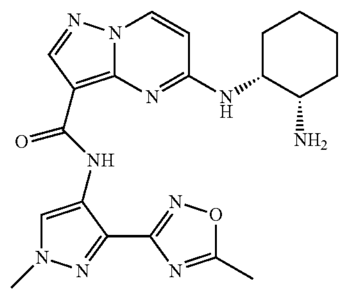 [SMILES: Cc1nc(-c2nn(C)cc2NC(=O)c2cnn3ccc(N[C@@H]4CCCC[C@@H]4N)nc23)no1] | 5-{[(1R,2S)-2-aminocyclohexyl]amino}-N-[1-methyl-3-(5-methyl-1,2,4-oxadiazol-3-yl)-1H-pyrazol-4-yl]pyrazolo[1,5-a]pyrimidine-3-carboxamide | Calc'd 437.2, found 437.2 |
| 289 | 3 | 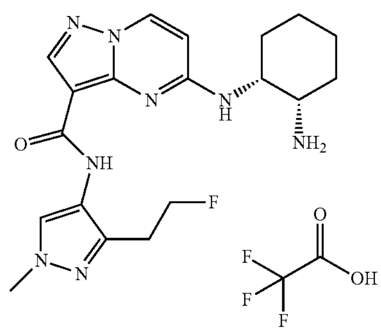 [SMILES: Cn1cc(NC(=O)c2cnn3ccc(N[C@@H]4CCCC[C@@H]4N)nc23)c(CCF)n1 ; O=C(O)C(F)(F)F] | 5-{[(1R,2S)-2-aminocyclohexyl]amino}-N-[3-(2-fluoroethyl)-1-methyl-1H-pyrazol-4-yl]pyrazolo[1,5-a]pyrimidine-3-carboxamide trifluoroacetate | Calc'd 401.2, found 401.2 |
| 290 | 977 | 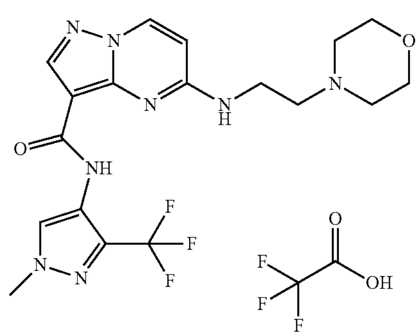 [SMILES: Cn1cc(NC(=O)c2cnn3ccc(NCCN4CCOCC4)nc23)c(C(F)(F)F)n1 ; O=C(O)C(F)(F)F] | N-[1-methyl-3-(trifluoromethyl)-1H-pyrazol-4-yl]-5-[(2-morpholin-4-ylethyl)amino]pyrazolo[1,5-a]pyrimidine-3-carboxamide trifluoroacetate | Calc'd 439.2, found 439.2 |
| 291 | 0.8 | 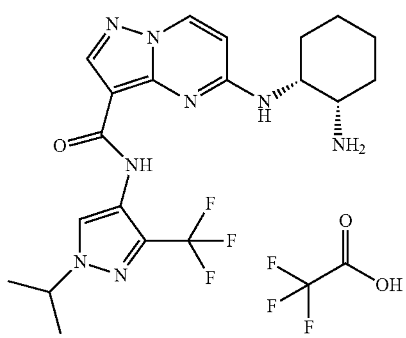 | 5-{[(1R,2S)-2-aminocyclohexyl]amino}-N-[1-(1-methylethyl)-3-(trifluoromethyl)-1H-pyrazol-4-yl]pyrazolo[1,5-a]pyrimidine-3-carboxamide trifluoroacetate | Calc'd 451.2, found 451.2 |

-continued

| Example # | IRAK4 IC$_{50}$ (nM) | Structure | IUPAC Name | Exact Mass [M + H]$^+$ |
|---|---|---|---|---|
| 292 | 0.8 | 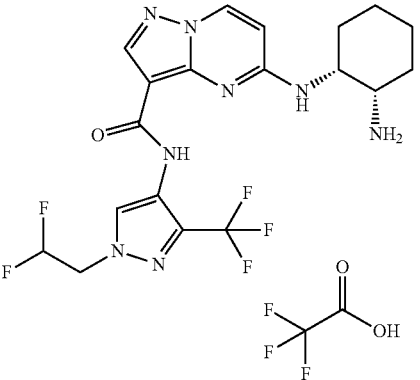 | 5-{[(1R,2S)-2-aminocyclohexyl]amino}-N-[1-(2,2-difluoroethyl)-3-(trifluoromethyl)-1H-pyrazol-4-yl]pyrazolo[1,5-a]pyrimidine-3-carboxamide trifluoroacetate | Calc'd 473.2, found 473.2 |
| 293 | 0.4 | 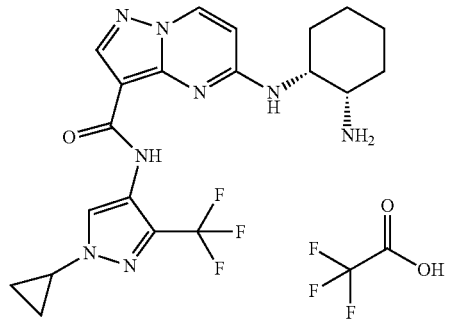 [SMILES: N[C@H]1CCCC[C@H]1Nc1ccn2ncc(C(=O)Nc3cn(C4CC4)nc3C(F)(F)F)c2n1 ; O=C(O)C(F)(F)F] | 5-{[(1R,2S)-2-aminocyclohexyl]amino}-N-[1-cyclopropyl-3-(trifluoromethyl)-1H-pyrazol-4-yl]pyrazolo[1,5-a]pyrimidine-3-carboxamide trifluoroacetate | Calc'd 449.2, found 449.2 |
| 294 | 1 | 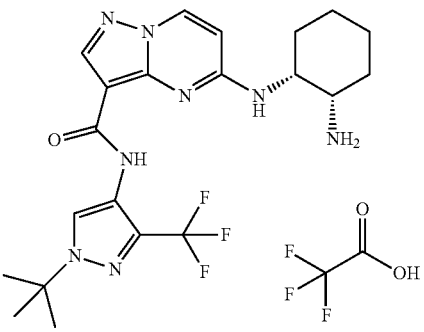 [SMILES: CC(C)(C)n1cc(NC(=O)c2cnn3ccc(N[C@@H]4CCCC[C@@H]4N)nc23)c(C(F)(F)F)n1 ; O=C(O)C(F)(F)F] | 5-{[(1R,2S)-2-aminocyclohexyl]amino}-N-[1-tert-butyl-3-(trifluoromethyl)-1H-pyrazol-4-yl]pyrazolo[1,5-a]pyrimidine-3-carboxamide trifluoroacetate | Calc'd 465.2, found 465.2 |
| 295 | 1 | 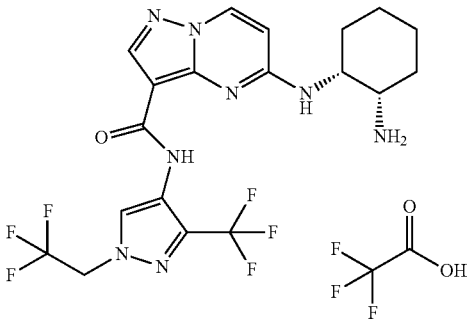 [SMILES: N[C@H]1CCCC[C@H]1Nc1ccn2ncc(C(=O)Nc3cn(CC(F)(F)F)nc3C(F)(F)F)c2n1 ; O=C(O)C(F)(F)F] | 5-{[(1R,2S)-2-aminocyclohexyl]amino}-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 491.2, found 491.2 |

-continued

| Example # | IRAK4 IC$_{50}$ (nM) | Structure | IUPAC Name | Exact Mass [M + H]$^+$ |
|---|---|---|---|---|
| 296 | 2 | 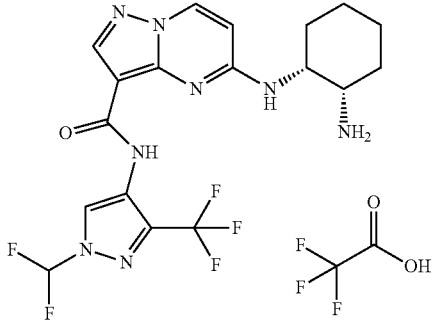 [SMILES: N[C@H]1CCCC[C@H]1Nc1ccn2ncc(C(=O)Nc3cn(C(F)F)nc3C(F)(F)F)c2n1 ; O=C(O)C(F)(F)F] | 5-{[(1R,2S)-2-aminocyclohexyl]amino}-N-[1-(difluoromethyl)-3-(trifluoromethyl)-1H-pyrazol-4-yl]pyrazolo[1,5-a]pyrimidine-3-carboxamide trifluoroacetate | Calc'd 459.2, found 459.2 |
| 297 | 2 | 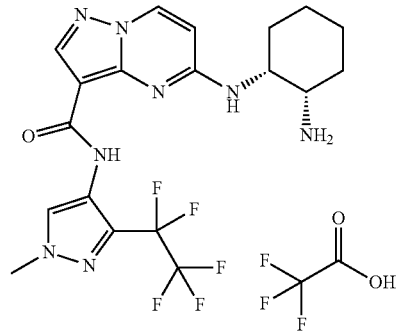 | 5-{[(1R,2S)-2-aminocyclohexyl]amino}-N-[1-methyl-3-(pentafluoroethyl)-1H-pyrazol-4-yl]pyrazolo[1,5-a]pyrimidine-3-carboxamide trifluoroacetate | Calc'd 473.2, found 473.2 |
| 298 | 17 | 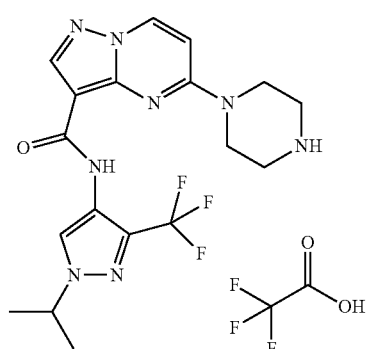 | N-[1-(1-methylethyl)-3-(trifluoromethyl)-1H-pyrazol-4-yl]-5-piperazin-1-ylpyrazolo[1,5-a]pyrimidine-3-carboxamide trifluoroacetate | Calc'd 423.2, found 423.4 |
| 299 | 81 | 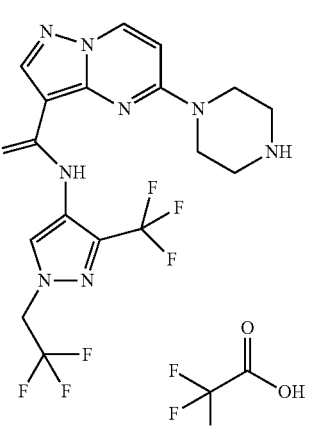 | 5-piperazin-1-yl-N-[1-(2,2,2-trifluoroethyl)-3-(trifluoromethyl)-1H-pyrazol-4-yl]pyrazolo[1,5-a]pyrimidine-3-carboxamide trifluoroacetate | Calc'd 463.1, found 463.4 |

| Example # | IRAK4 IC$_{50}$ (nM) | Structure | IUPAC Name | Exact Mass [M + H]$^+$ |
|---|---|---|---|---|
| 300 | 55 | 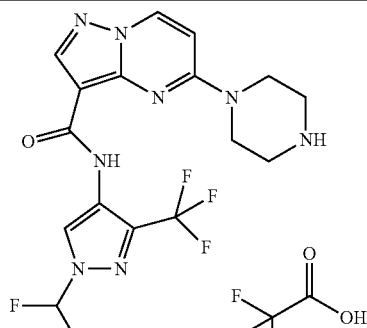 | N-[1-(difluoromethyl)-3-(trifluoromethyl)-1H-pyrazol-4-yl]-5-piperazin-1-ylpyrazolo[1,5-a]pyrimidine-3-carboxamide trifluoroacetate | Calc'd 431.1, found 431.4 |
| 301 | 0.8 | 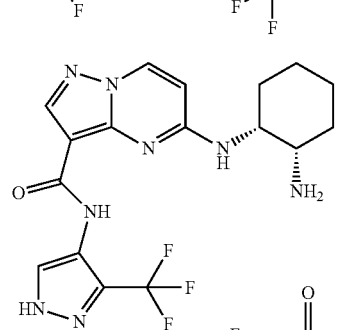 | 5-{[(1R,2S)-2-aminocyclohexyl]amino}-N-[3-(trifluoromethyl)-1H-pyrazol-4-yl]pyrazolo[1,5-a]pyrimidine-3-carboxamide trifluoroacetate | Calc'd 409.2, found 409.4 |

Biological Data

Compounds of the instant invention were tested by the assay described below and were found to have IRAK4 inhibitory activity. Data is shown for all compounds in the representative table(s) and Examples. Other assays are known in the literature and could be readily performed by those of skill in the art.

IRAK4 Kinase Assay

The kinase activity of IRAK4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 µL reaction mixture contains 10 mM TriHCl, pH 7.2, 0.5 nM GST tagged IRAK4 (SignalChem), 100 nM fluorescent peptide substrate (RP7030, Molecular Devices), 100 µM ATP, 1 mM DDT, 1 mM MgCl$_2$, and 0.01% Tween 20. The reaction is initiated by the addition of ATP. After incubation for 30 minutes at 25° C., 60 µL of Progressive IMAP Reagent (Molecular Devices) is added to stop the reaction. Change in RP7030's FP is determined by a FP reader (Analyst HT, LJL BioSystems).

What is claimed is:
1. A compound of Formula I:

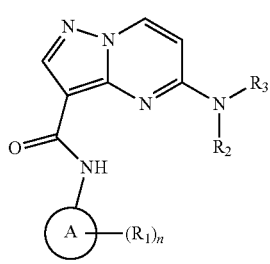

I wherein:
Ring A is pyrazolyl, pyridinyl, thiophenyl, furanyl or phenyl;
n is 0, 1 or 2;
$R_1$ is independently selected from: $(C_1-C_4)$alkyl, cyclopropyl, oxadiazolyl, pyridinyl, oxazolyl, triazolyl, pyriminidyl, $CF_3$, $CHF_2$, CN and halo, said alkyl, cyclopropyl, oxadiazolyl, pyridinyl, oxazolyl, triazolyl and pyriminidyl are optionally substituted with halo, OH, $CH_3$, and $OCH_3$;
$R_2$ is H and $R_3$ is independently selected from: cyclohexyl, cycloheptyl, piperidinyl and azepanyl each optionally substituted with one or more F, OH, $N(R_b)_2$, or morpholinyl, or $R_2$ and $R_3$ can be taken together with the nitrogen to which they are attached to form a heterocyclyl selected from piperazinyl, diazepanyl, diazabicyclooctyl, diazabicycloheptyl, diazaspirononyl, hexahydropyrrolopyrazinyl, piperidinyl, diazabicyclononyl, oxadiazabicyclodecyl and diazatricyclodecyl, said heterocyclyl optionally substituted with one or more substituents selected from $R_a$;

$R_a$ is independently selected from $(C_1-C_4)$alkyl, cyclopropyl, $CF_3$, $CHF_2$, OH, F and $NH_2$, said alkyl optionally substituted with cyclopropyl or $CF_3$; and $R_b$ is independently selected from H and methyl;

or a pharmaceutically acceptable salt thereof.

2. A compound according to claim 1 which is selected from:

N-[1-methyl-3-(trifluoromethyl)-1H-pyrazol-4-yl]-5-piperazin-1-ylpyrazolo[1,5-a]pyrimidine-3-carboxamide;

5-{[(1R,2S)-2-aminocyclohexyl]amino}-N-[1-methyl-3-(trifluoromethyl)-1H-pyrazol-4-yl]pyrazolo[1,5-a]pyrimidine-3-carboxamide;

5-(cyclohexylamino)-N-(1-methyl-1H-pyrazol-4-yl)pyrazolo[1,5-a]pyrimidine-3-carboxamide;

5-{[(1R,2R)-2-amino-3,3-difluorocyclohexyl]amino}-N-[1-methyl-3-(trifluoromethyl)-1H-pyrazol-4-yl]pyrazolo[1,5-a]pyrimidine-3-carboxamide;

5-(cyclohexylamino)-N-[1-methyl-3-(trifluoromethyl)-1H-pyrazol-4-yl]pyrazolo[1,5-a]pyrimidine-3-carboxamide;

5-[4-(cyclopropylmethyl)piperazin-1-yl]-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-(piperidin-4-ylamino)pyrazolo[1,5-a]pyrimidine-3-carboxamide;

5-(1,4-diazepan-1-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-[(3R)-piperidin-3-ylamino]pyrazolo[1,5-a]pyrimidine-3-carboxamide;

5-(4-ethyl-1,4-diazepan-1-yl)-N-[1-methyl-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-methyl-3-(trifluoromethyl)-1H-pyrazol-4-yl]pyrazolo[1,5-a]pyrimidine-3-carboxamide;

5-(azepan-3-ylamino)-N-[1-methyl-3-(trifluoromethyl)-1H-pyrazol-4-yl]pyrazolo[1,5-a]pyrimidine-3-carboxamide;

5-(2,5-diazabicyclo[2.2.1]hept-2-yl)-N-[1-methyl-3-(trifluoromethyl)-1H-pyrazol-4-yl]pyrazolo[1,5-a]pyrimidine-3-carboxamide;

5-(5,8-diazaspiro[2.6]non-5-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-[3-(trifluoromethyl)piperazin-1-yl]pyrazolo[1,5-a]pyrimidine-3-carboxamide;

5-[3-(difluoromethyl)piperazin-1-yl]-N-[1-methyl-3-(trifluoromethyl)-1H-pyrazol-4-yl]pyrazolo[1,5-a]pyrimidine-3-carboxamide;

5-(azepan-4-ylamino)-N-[1-methyl-3-(trifluoromethyl)-1H-pyrazol-4-yl]pyrazolo[1,5-a]pyrimidine-3-carboxamide;

5-(hexahydropyrrolo[1,2-a]pyrazin-2(1H)-yl)-N-[1-methyl-3-(trifluoromethyl)-1H-pyrazol-4-yl]pyrazolo[1,5-a]pyrimidine-3-carboxamide;

5-(3,6-diazabicyclo[3.1.1]hept-3-yl)-N-[1-methyl-3-(trifluoromethyl)-1H-pyrazol-4-yl]pyrazolo[1,5-a]pyrimidine-3-carboxamide;

5-{([(1S,2R)-2-hydroxycyclohexyl]amino}-N-[1-methyl-3-(trifluoromethyl)-1H-pyrazol-4-yl]pyrazolo[1,5-a]pyrimidine-3-carboxamide;

5-[(3S,5S)-3,5-dihydroxypiperidin-1-yl]-N-[1-methyl-3-(trifluoromethyl)-1H-pyrazol-4-yl]pyrazolo[1,5-a]pyrimidine-3-carboxamide;

5-[(3S)-3-hydroxypiperidin-1-yl]-N-[1-methyl-3-(trifluoromethyl)-1H-pyrazol-4-yl]pyrazolo[1,5-a]pyrimidine-3-carboxamide;

5-[(3R)-3-hydroxypiperidin-1-yl]-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-[(3R,5R)-3,5-dihydroxypiperidin-1-yl]pyrazolo[1,5-a]pyrimidine-3-carboxamide;

N-[3-(difluoromethyl)-1-methyl-1H-pyrazol-4-yl]-5-[(3R)-3-hydroxypiperidin-1-yl]pyrazolo[1,5-a]pyrimidine-3-carboxamide;

N-[3-(difluoromethyl)-1-methyl-1H-pyrazol-4-yl]-5-[(3S)-3-hydroxypiperidin-1-yl]pyrazolo[1,5-a]pyrimidine-3-carboxamide;

5-(6-fluoro-1,4-diazepan-1-yl)-N-[1-methyl-3-(trifluoromethyl)-1H-pyrazol-4-yl]pyrazolo[1,5-a]pyrimidine-3-carboxamide;

5-(3-cyclopropylpiperazin-1-yl)-N-[1-methyl-3-(trifluoromethyl)-1H-pyrazol-4-yl]pyrazolo[1,5-a]pyrimidine-3-carboxamide;

5-(2-cyclopropylpiperazin-1-yl)-N-[1-methyl-3-(trifluoromethyl)-1H-pyrazol-4-yl]pyrazolo[1,5-a]pyrimidine-3-carboxamide;

5-(3,3-dimethylpiperazin-1-yl)-N-[1-methyl-3-(trifluoromethyl)-1H-pyrazol-4-yl]pyrazolo[1,5-a]pyrimidine-3-carboxamide;

5-{([(1R,2S)-2-aminocyclohexyl]amino}-N-[3-(trifluoromethyl)pyridin-4-yl]pyrazolo[1,5-a]pyrimidine-3-carboxamide;

5-[(3R)-3-aminopiperidin-1-yl]-N-[1-methyl-3-(trifluoromethyl)-1H-pyrazol-4-yl]pyrazolo[1,5-a]pyrimidine-3-carboxamide;

5-{([(1S,2R)-2-aminocycloheptyl]amino}-N-[1-methyl-3-(trifluoromethyl)-1H-pyrazol-4-yl]pyrazolo[1,5-a]pyrimidine-3-carboxamide;

5-(4-methylpiperazin-1-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-(2,2,4-trimethylpiperazin-1-yl)pyrazolo[1,5-a]pyrimidine-3-carboxamide;

5-(6,6-difluoro-1,4-diazepan-1-yl)-N-[1-methyl-3-(trifluoromethyl)-1H-pyrazol-4-yl]pyrazolo[1,5-a]pyrimidine-3-carboxamide;

5-{([(1R,2S)-2-hydroxycyclohexyl]amino}-N-[1-methyl-3-(trifluoromethyl)-1H-pyrazol-4-yl]pyrazolo[1,5-a]pyrimidine-3-carboxamide;

5-{([(1R,2S)-2-aminocyclohexyl]amino}-N-[2-(trifluoromethyl)phenyl]pyrazolo[1,5-a]pyrimidine-3-carboxamide;

5-{([(1R,2S)-2-aminocyclohexyl]amino}-N-(4-cyanothiophen-3-yl)pyrazolo[1,5-a]pyrimidine-3-carboxamide;

5-(1,4-diazabicyclo[3.2.2]non-4-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-[2-(2,2,2-trifluoroethyl)piperazin-1-yl]pyrazolo[1,5-a]pyrimidine-3-carboxamide;

5-{[(1R,2S)-2-aminocyclohexyl]amino}-N-(2-cyanothiophen-3-yl)pyrazolo[1,5-a]pyrimidine-3-carboxamide;

5-(1,4-diazabicyclo[3.2.1]oct-4-yl)-N-[1-methyl-3-(trifluoromethyl)-1H-pyrazol-4-yl]pyrazolo[1,5-a]pyrimidine-3-carboxamide;

5-[(3S)-3-aminopiperidin-1-yl]-N-[1-methyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[2-(trifluoromethyl)furan-3-yl]pyrazolo[1,5-a]pyrimidine-3-carboxamide;

N-[1-tert-butyl-3-(trifluoromethyl)-1H-pyrazol-4-yl]-5-piperazin-1-ylpyrazolo[1,5-a]pyrimidine-3-carboxamide;

N-[1-tert-butyl-3-(trifluoromethyl)-1H-pyrazol-4-yl]-5-(5,8-diazaspiro[2.6]non-5-yl)pyrazolo[1,5-a]pyrimidine-3-carboxamide;

N-[1-tert-butyl-3-(trifluoromethyl)-1H-pyrazol-4-yl]-5-{[(1R,2S)-2-hydroxycyclohexyl]amino}pyrazolo[1,5-a]pyrimidine-3-carboxamide;

5-{[(1R,2R)-2-amino-3,3-difluorocyclohexyl]amino}-N-[1-tert-butyl-3-(trifluoromethyl)-1H-pyrazol-4-yl]pyrazolo[1,5-a]pyrimidine-3-carboxamide;

N-[1-tert-butyl-3-(trifluoromethyl)-1H-pyrazol-4-yl]-5-(2,5-diazabicyclo[2.2.2]oct-2-yl)pyrazolo[1,5-a]pyrimidine-3-carboxamide;

5-(5,8-diazaspiro[2.6]non-5-yl)-N-[1-(1-methylethyl)-3-(tifluoromethyl)-1H-pyrazol-4-yl]pyrazolo[1,5-a]pyrimidine-3-carboxamide;

5-{[(1R,2S)-2-hydroxycyclohexyl]amino}-N-[1-(1-methylethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(1-methylethyl)-3-(trifluoromethyl)-1H-pyrazol-4-yl]pyrazolo[1,5-a]pyrimidine-3-carboxamide;

5-{[(1R,2S)-2-aminocycloheptyl]amino}-N-[1-methyl-3-(trifluoromethyl)-1H-pyrazol-4-yl]pyrazolo[1,5-a]pyrimidine-3-carboxamide;

5-{[(1R,2S)-2-aminocycloheptyl]amino}-N-[1-methyl-3-(trifluoromethyl)-1H-pyrazol-4-yl]pyrazolo[1,5-a]pyrimidine-3-carboxamide;

5-{[(1R,2R)-2-amino-3,3-difluorocyclohexyl]amino}-N-[1-(1-methylethyl)-3-(trifluoromethyl)-1H-pyrazol-4-yl]pyrazolo[1,5-a]pyrimidine-3-carboxamide;

5-{[(1R,2S)-2-hydroxycyclohexyl]amino}-N-[1-(2,2,2-trifluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(2,2,2-trifluoroethyl)-3-(trifluoromethyl)-1H-pyrazol-4-yl]pyrazolo[1,5-a]pyrimidine-3-carboxamide;

5-(5-amino-3,3-difluoropiperidin-1-yl)-N-[1-methyl-3-(trifluoromethyl)-1H-pyrazol-4-yl]pyrazolo[1,5-a]pyrimidine-3-carboxamide;

5-[(5R)-5-amino-3,3-difluoropiperidin-1-yl]-N-[1-methyl-3-(trifluoromethyl)-1H-pyrazol-4-yl]pyrazolo[1,5-a]pyrimidine-3-carboxamide;

5-[(5S)-5-amino-3,3-difluoropiperidin-1-yl]-N-[1-methyl-3-(trifluoromethyl)-1H-pyrazol-4-yl]pyrazolo[1,5-a]pyrimidine-3-carboxamide;

N-[1-(2,2-difluoroethyl)-3-(trifluoromethyl)-1H-pyrazol-4-yl]-5-piperazin-1-ylpyrazolo[1,5-a]pyrimidine-3-carboxamide;

N-[1-(2,2-difluoroethyl)-3-(trifluoromethyl)-1H-pyrazol-4-yl]-5-{([(1R,2S)-2-hydroxycyclohexyl]amino}pyrazolo[1,5-a]pyrimidine-3-carboxamide;

5-(5,8-diazaspiro[2.6]non-5-yl)-N-[1-(2,2-difluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(2,2-difluoroethyl)-3-(trifluoromethyl)-1H-pyrazol-4-yl]pyrazolo[1,5-a]pyrimidine-3-carboxamide;

5-{([(1R,2R)-2-amino-3,3-difluorocyclohexyl]amino}-N-[1-(2,2-difluoroethyl)-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[1-(difluoromethyl)-3-(trifluoromethyl)-1H-pyrazol-4-yl]pyrazolo[1,5-a]pyrimidine-3-carboxamide;

5-(5,8-diazaspiro[2.6]non-5-yl)-N-[1-(difluoromethyl)-3-(trifluoromethyl)-1H-pyrazol-4-yl]pyrazolo[1,5-a]pyrimidine-3-carboxamide;

5-{([(1R,2R)-2-amino-3,3-difluorocyclohexyl]amino}-N-[1-(2,2,2-trifluoroethyl)-3-(trifluoromethyl)-1H-pyrazol-4-yl]pyrazolo[1,5-a]pyrimidine-3-carboxamide;

5-(5,8-diazaspiro[2.6]non-5-yl)-N-[1-(2,2,2-trifluoroethyl)-3-(trifluoromethyl)-1H-pyrazol-4-yl]pyrazolo[1,5-a]pyrimidine-3-carboxamide;

5-{([(1R,2R)-2-amino-3,3-difluorocyclohexyl]amino}-N-[1-(difluoromethyl)-3-(trifluoromethyl)-1H-pyrazol-4-yl]pyrazolo[1,5-a]pyrimidine-3-carboxamide;

N-[1-(difluoromethyl)-3-(trifluoromethyl)-1H-pyrazol-4-yl]-5-{[(1R,2S)-2-hydroxycyclohexyl]amino}pyrazolo[1,5-a]pyrimidine-3-carboxamide;

5-(2,6-diazabicyclo[3.2.2]non-6-yl)-N-[1-methyl-3-(trifluoromethyl)-1H-pyrazol-4-yl]pyrazolo[1,5-a]pyrimidine-3-carboxamide;

5-(2,6-diazabicyclo[3.2.1]oct-6-yl)-N-[1-methyl-3-(trifluoromethyl)-1H-pyrazol-4-yl]pyrazolo[1,5-a]pyrimidine-3-carboxamide;

5-[(2R,5R)-2,5-dimethylpiperazin-1-yl]-N-[1-methyl-3-(trifluoromethyl)-1H-pyrazol-4-yl]pyrazolo[1,5-a]pyrimidine-3-carboxamide;

5-{([(1R,2S)-2-aminocyclohexyl]amino}-N-(4-bromothiophen-3-yl)pyrazolo[1,5-a]pyrimidine-3-carboxamide;

5-[(1R,4R)-2,5-diazabicyclo[2.2.2]oct-2-yl]-N-[1-methyl-3-(trifluoromethyl)-1H-pyrazol-4-yl]pyrazolo[1,5-a]pyrimidine-3-carboxamide;

5-[(1S,4S)-2,5-diazabicyclo[2.2.2]oct-2-yl]-N-[1-methyl-3-(trifluoromethyl)-1H-pyrazol-4-yl]pyrazolo[1,5-a]pyrimidine-3-carboxamide;

5-(2,5-dimethylpiperazin-1-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-(3-oxa-7,9-diazabicyclo[3.3.2]dec-7-yl)pyrazolo[1,5-a]pyrimidine-3-carboxamide;

5-(3,8-diazabicyclo[3.2.1]oct-3-yl)-N-[1-methyl-3-(trifluoromethyl)-1H-pyrazol-4-yl]pyrazolo[1,5-a]pyrimidine-3-carboxamide;

5-(3,6-diazabicyclo[3.2.1]oct-6-yl)-N-[1-methyl-3-(trifluoromethyl)-1H-pyrazol-4-yl]pyrazolo[1,5-a]pyrimidine-3-carboxamide;

5-[(1S,5R)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide;

5-[(1R,5S)-3,6-diazabicyclo[3.2.1]oct-6-yl]-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-{([(1R,2S)-2-hydroxycyclohexyl]amino}pyrazolo[1,5-a]pyrimidine-3-carboxamide;

5-(5,8-diazaspiro[2.6]non-5-yl)-N-[3-(difluoromethyl)-1-methyl-1H-pyrazol-4-yl]pyrazolo[1,5-a]pyrimidine-3-carboxamide;

5-(1,4-diazepan-1-yl)-N-[3-(difluoromethyl)-1-methyl-1H-pyrazol-4-yl]pyrazolo[1,5-a]pyrimidine-3-carboxamide;

N-[3-(difluoromethyl)-1-methyl-1H-pyrazol-4-yl]-5-piperazin-1-ylpyrazolo[1,5-a]pyrimidine-3-carboxamide;

5-(3,9-diazabicyclo[4.2.1]non-3-yl)-N-[1-methyl-3-(trifluoromethyl)-1H-pyrazol-4-yl]pyrazolo[1,5-a]pyrimidine-3-carboxamide;

5-[(3R)-3-aminopiperidin-1-yl]-N-[3-(difluoromethyl)-1-methyl-1H-pyrazol-4-yl]pyrazolo[1,5-a]pyrimidine-3-carboxamide;

N-[3-(difluoromethyl)-1-methyl-1H-pyrazol-4-yl]-5-[(3R)-piperidin-3-ylamino]pyrazolo[1,5-a]pyrimidine-3-carboxamide;

5-[(1R,2R,5 S,6S)-9,10-diazatricyclo[4.2.1.1~2,5~]dec-9-yl]-N-[1-methyl-3-(trifluoromethyl)-1H-pyrazol-4-yl]pyrazolo[1,5-a]pyrimidine-3-carboxamide;

5-[(2R,5S)-2,5-dimethylpiperazin-1-yl]-N-[1-methyl-3-(trifluoromethyl)-1H-pyrazol-4-yl]pyrazolo[1,5-a]pyrimidine-3-carboxamide;

5-(3,9-diazabicyclo[4.2.1]non-3-yl)-N-[1-methyl-3-(trifluoromethyl)-1H-pyrazol-4-yl]pyrazolo[1,5-a]pyrimidine-3-carboxamide;

5-(4,7-diazaspiro[2.6]non-4-yl)-N-[1-methyl-3-(trifluoromethyl)-1H-pyrazol-4-yl]pyrazolo[1,5-a]pyrimidine-3-carboxamide;

5-(2,5-diazabicyclo[2.2.2]oct-2-yl)-N-[3-(difluoromethyl)-1-methyl-1H-pyrazol-4-yl]pyrazolo[1,5-a]pyrimidine-3-carboxamide;

5-{([(1R,2R)-2-amino-3,3-difluorocyclohexyl]amino}-N-[3-(difluoromethyl)-1-methyl-1H-pyrazol-4-yl]pyrazolo[1,5-a]pyrimidine-3-carboxamide;

5-(4,8-diazaspiro[2.6]non-4-yl)-N-[1-methyl-3-(trifluoromethyl)-1H-pyrazol-4-yl]pyrazolo[1,5-a]pyrimidine-3-carboxamide;

5-(azepan-3-ylamino)-N-[3-(difluoromethyl)-1-methyl-1H-pyrazol-4-yl]pyrazolo[1,5-a]pyrimidine-3-carboxamide;

5-(5,8-diazaspiro[2.6]non-5-yl)-N-(2-iodophenyl)pyrazolo[1,5-a]pyrimidine-3-carboxamide;

5-{([(1R,2S)-2-hydroxycyclohexyl]amino}-N-(2-iodophenyl)pyrazolo[1,5-a]pyrimidine-3-carboxamide;

5-(2,7-diazatricyclo[4.4.0.0~3,8~]dec-2-yl)-N-[1-methyl-3-(trifluoromethyl)-1H-pyrazol-4-yl]pyrazolo[1,5-a]pyrimidine-3-carboxamide;

5-(2,5-diazabicyclo[2.2.2]oct-2-yl)-N-(2-iodophenyl)pyrazolo[1,5-a]pyrimidine-3-carboxamide;

5-{([(1R,2S)-2-aminocyclohexyl]amino}-N-(2-chlorophenyl)pyrazolo[1,5-a]pyrimidine-3-carboxamide;

N-(2-chlorophenyl)-5-(1,4-diazepan-1-yl)pyrazolo[1,5-a]pyrimidine-3-carboxamide;

5-{([(1R,2R)-2-amino-3,3-difluorocyclohexyl]amino}-N-(2-chlorophenyl)pyrazolo[1,5-a]pyrimidine-3-carboxamide;

N-(2-chlorophenyl)-5-(2,5-diazabicyclo[2.2.2]oct-2-yl)pyrazolo[1,5-a]pyrimidine-3-carboxamide;

5-{([(1R,2R)-2-amino-3,3-difluorocyclohexyl]amino}-N-(2-bromophenyl)pyrazolo[1,5-a]pyrimidine-3-carboxamide;

N-(2-bromophenyl)-5-(1,4-diazepan-1-yl)pyrazolo[1,5-a]pyrimidine-3-carboxamide;

N-(2-cyanothiophen-3-yl)-5-(2,5-diazabicyclo[2.2.2]oct-2-yl)pyrazolo[1,5-a]pyrimidine-3-carboxamide;

N-(2-cyanothiophen-3-yl)-5-(1,4-diazepan-1-yl)pyrazolo[1,5-a]pyrimidine-3-carboxamide;

N-(2-bromophenyl)-5-(2,5-diazabicyclo[2.2.2]oct-2-yl)pyrazolo[1,5-a]pyrimidine-3-carboxamide;

5-{([(1R,2S)-2-aminocyclohexyl]amino}-N-(2-bromophenyl)pyrazolo[1,5-a]pyrimidine-3-carboxamide;

5-{([(1R,2R)-2-amino-3,3-difluorocyclohexyl]amino}-N-[2-(trifluoromethyl)phenyl]pyrazolo[1,5-a]pyrimidine-3-carboxamide;

5-(2,5-diazabicyclo[2.2.2]oct-2-yl)-N-[2-(trifluoromethyl)phenyl]pyrazolo[1,5-a]pyrimidine-3-carboxamide;

5-{([(1R,2S)-2-aminocyclohexyl]amino}-N-(2-chlorothiophen-3-yl)pyrazolo[1,5-a]pyrimidine-3-carboxamide;

N-(2-chlorothiophen-3-yl)-5-(1,4-diazepan-1-yl)pyrazolo[1,5-a]pyrimidine-3-carboxamide;

5-{([(1R,2R)-2-amino-3,3-difluorocyclohexyl]amino}-N-(2-chlorothiophen-3-yl)pyrazolo[1,5-a]pyrimidine-3-carboxamide;

5-{([(1R,2S)-2-aminocyclohexyl]amino}-N-[4-(difluoromethyl)thiophen-3-yl]pyrazolo[1,5-a]pyrimidine-3-carboxamide;

5-(1,4-diazepan-1-yl)-N-[4-(difluoromethyl)thiophen-3-yl]pyrazolo[1,5-a]pyrimidine-3-carboxamide;

5-{([(1R,2R)-2-amino-3,3-difluorocyclohexyl]amino}-N-[4-(difluoromethyl)thiophen-3-yl]pyrazolo[1,5-a]pyrimidine-3-carboxamide;

5-{([(1R,2R)-2-amino-3,3-difluorocyclohexyl]amino}-N-(4-bromothiophen-3-yl)pyrazolo[1,5-a]pyrimidine-3-carboxamide;

N-(4-bromothiophen-3-yl)-5-(1,4-diazepan-1-yl)pyrazolo[1,5-a]pyrimidine-3-carboxamide;

N-(4-bromothiophen-3-yl)-5-(2,5-diazabicyclo[2.2.2]oct-2-yl)pyrazolo[1,5-a]pyrimidine-3-carboxamide;

N-(3-cyano-1-methyl-1H-pyrazol-4-yl)-5-(1,4-diazepan-1-yl)pyrazolo[1,5-a]pyrimidine-3-carboxamide;

5-{([(1R,2R)-2-amino-3,3-difluorocyclohexyl]amino}-N-(3-cyano-1-methyl-1H-pyrazol-4-yl)pyrazolo[1,5-a]pyrimidine-3-carboxamide;

N-(2-bromothiophen-3-yl)-5-(1,4-diazepan-1-yl)pyrazolo[1,5-a]pyrimidine-3-carboxamide;

5-{[(1R,2R)-2-amino-3,3-difluorocyclohexyl]amino}-N-(2-bromothiophen-3-yl)pyrazolo[1,5-a]pyrimidine-3-carboxamide;

5-{([(1R,2S)-2-aminocyclohexyl]amino}-N-(2-bromothiophen-3-yl)pyrazolo[1,5-a]pyrimidine-3-carboxamide;

5-(1,4-diazepan-1-yl)-N-[2-(difluoromethyl)phenyl]pyrazolo[1,5-a]pyrimidine-3-carboxamide;

5-{([(1R,2S)-2-aminocyclohexyl]amino}-N-[2-(difluoromethyl)phenyl]pyrazolo[1,5-a]pyrimidine-3-carboxamide;

5-{([(1R,2R)-2-amino-3,3-difluorocyclohexyl]amino}-N-[2-(difluoromethyl)phenyl]pyrazolo[1,5-a]pyrimidine-3-carboxamide;

5-{([(1R,2R)-2-amino-3,3-difluorocyclohexyl]amino}-N-(2-cyanothiophen-3-yl)pyrazolo[1,5-a]pyrimidine-3-carboxamide;

N-(2-chlorothiophen-3-yl)-5-(2,5-diazabicyclo[2.2.2]oct-2-yl)pyrazolo[1,5-a]pyrimidine-3-carboxamide;

5-(2,5-diazabicyclo[2.2.2]oct-2-yl)-N-[4-(difluoromethyl)thiophen-3-yl]pyrazolo[1,5-a]pyrimidine-3-carboxamide;

N-(3-cyano-1-methyl-1H-pyrazol-4-yl)-5-(2,5-diazabicyclo[2.2.2]oct-2-yl)pyrazolo[1,5-a]pyrimidine-3-carboxamide;

N-(3-bromo-1-methyl-1H-pyrazol-4-yl)-5-(1,4-diazepan-1-yl)pyrazolo[1,5-a]pyrimidine-3-carboxamide;
5-{[[(1R,2S)-2-aminocyclohexyl]amino}-N-(3-bromo-1-methyl-1H-pyrazol-4-yl)pyrazolo[1,5-a]pyrimidine-3-carboxamide;
5-{([[(1R,2R)-2-amino-3,3-difluorocyclohexyl]amino}-N-(3-bromo-1-methyl-1H-pyrazol-4-yl)pyrazolo[1,5-a]pyrimidine-3-carboxamide;
N-(3-bromo-1-methyl-1H-pyrazol-4-yl)-5-(2,5-diazabicyclo[2.2.2]oct-2-yl)pyrazolo[1,5-a]pyrimidine-3-carboxamide;
N-(4-cyanothiophen-3-yl)-5-(1,4-diazepan-1-yl)pyrazolo[1,5-a]pyrimidine-3-carboxamide;
N-(2-bromothiophen-3-yl)-5-(2,5-diazabicyclo[2.2.2]oct-2-yl)pyrazolo[1,5-a]pyrimidine-3-carboxamide;
5-{[(1R,2R)-2-amino-3,3-difluorocyclohexyl]amino}-N-(4-cyanothiophen-3-yl)pyrazolo[1,5-a]pyrimidine-3-carboxamide;
5-{([[(1R,2S)-2-aminocyclohexyl]amino}-N-[2-(trifluoromethyl)thiophen-3-yl]pyrazolo[1,5-a]pyrimidine-3-carboxamide;
N-(4-cyanothiophen-3-yl)-5-(2,5-diazabicyclo[2.2.2]oct-2-yl)pyrazolo[1,5-a]pyrimidine-3-carboxamide;
5-(2,5-diazabicyclo[2.2.2]oct-2-yl)-N-[2-(difluoromethyl)phenyl]pyrazolo[1,5-a]pyrimidine-3-carboxamide;
5-(2,5-diazabicyclo[2.2.2]oct-2-yl)-N-[2-(trifluoromethyl)thiophen-3-yl]pyrazolo[1,5-a]pyrimidine-3-carboxamide;
N-(3-chloro-1-methyl-1H-pyrazol-4-yl)-5-(1,4-diazepan-1-yl)pyrazolo[1,5-a]pyrimidine-3-carboxamide;
5-{([[(1R,2S)-2-aminocyclohexyl]amino}-N-(3-chloro-1-methyl-1H-pyrazol-4-yl)pyrazolo[1,5-a]pyrimidine-3-carboxamide;
5-{([[(1R,2R)-2-amino-3,3-difluorocyclohexyl]amino}-N-(3-chloro-1-methyl-1H-pyrazol-4-yl)pyrazolo[1,5-a]pyrimidine-3-carboxamide;
N-(3-chloro-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-chloro-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-(1,4-diazepan-1-yl)-N-[2-(trifluoromethyl)thiophen-3-yl]pyrazolo[1,5-a]pyrimidine-3-carboxamide;
5-[(1S,4S)-2,5-diazabicyclo[2.2.2]oct-2-yl]-N-[4-(difluoromethyl)thiophen-3-yl]pyrazolo[1,5-a]pyrimidine-3-carboxamide;
5-[(1R,4R)-2,5-diazabicyclo[2.2.2]oct-2-yl]-N-[4-(difluoromethyl)thiophen-3-yl]pyrazolo[1,5-a]pyrimidine-3-carboxamide;
N-(3-cyano-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-cyano-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-[(1S,4S)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide;
5-[(3S)-azepan-3-ylamino]-N-[1-methyl-3-(trifluoromethyl)-1H-pyrazol-4-yl]pyrazolo[1,5-a]pyrimidine-3-carboxamide;
5-[(3R)-azepan-3-ylamino]-N-[1-methyl-3-(trifluoromethyl)-1H-pyrazol-4-yl]pyrazolo[1,5-a]pyrimidine-3-carboxamide;
5-[(1R,4R)-2,5-diazabicyclo[2.2.2]oct-2-yl]-N-[3-(difluoromethyl)-1-methyl-1H-pyrazol-4-yl]pyrazolo[1,5-a]pyrimidine-3-carboxamide;
5-[(3R)-azepan-3-ylamino]-N-[3-(difluoromethyl)-1-methyl-1H-pyrazol-4-yl]pyrazolo[1,5-a]pyrimidine-3-carboxamide;
5-[(3S)-azepan-3-ylamino]-N-[3-(difluoromethyl)-1-methyl-1H-pyrazol-4-yl]pyrazolo[1,5-a]pyrimidine-3-carboxamide;
N-(3-bromo-1-methyl-1H-pyrazol-4-yl)-5-[(1S,4S)-2,5-diazabicyclo[2.2.2]oct-2-yl]pyrazolo[1,5-a]pyrimidine-3-carboxamide;
N-(3-bromo-1-methyl-1H-pyrazol-4-yl)-5-[(1R,4R)-2,5-diazabicyclo[2.2.2]oct-2-yl]pyrazolo[1,5-a]pyrimidine-3-carboxamide;
5-{([[(1R,2S)-2-aminocyclohexyl]amino}-N-[1-methyl-5-(trifluoromethyl)-1H-pyrazol-4-yl]pyrazolo[1,5-a]pyrimidine-3-carboxamide;
N-(4-chlorothiophen-3-yl)-5-(1,4-diazepan-1-yl)pyrazolo[1,5-a]pyrimidine-3-carboxamide;
5-{([[(1R,2S)-2-aminocyclohexyl]amino}-N-(4-chlorothiophen-3-yl)pyrazolo[1,5-a]pyrimidine-3-carboxamide;
N-(4-chlorothiophen-3-yl)-5-[(1S,4S)-2,5-diazabicyclo[2.2.2]oct-2-yl]pyrazolo[1,5-a]pyrimidine-3-carboxamide;
5-{([[(1R,2R)-2-amino-3,3-difluorocyclohexyl]amino}-N-[2-(difluoromethyl)thiophen-3-yl]pyrazolo[1,5-a]pyrimidine-3-carboxamide;
N-(4-chlorothiophen-3-yl)-5-[(1R,4R)-2,5-diazabicyclo[2.2.2]oct-2-yl]pyrazolo[1,5-a]pyrimidine-3-carboxamide;
5-(3,8-diazabicyclo[3.2.1]oct-3-yl)-N-[3-(difluoromethyl)-1-methyl-1H-pyrazol-4-yl]pyrazolo[1,5-a]pyrimidine-3-carboxamide;
5-(5-amino-3,3-difluoropiperidin-1-yl)-N-[3-(difluoromethyl)-1-methyl-1H-pyrazol-4-yl]pyrazolo[1,5-a]pyrimidine-3-carboxamide;
5-[(3R,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3R,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4R)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4S)-3-amino-4-fluoropiperidin-1-yl]-N-[1-methyl-3-(trifluoromethyl)-1H-pyrazol-4-yl]pyrazolo[1,5-a]pyrimidine-3-carboxamide;
5-[(3S,4R)-3-amino-4-fluoropiperidin-1-yl]-N-[3-(difluoromethyl)-1-methyl-1H-pyrazol-4-yl]pyrazolo[1,5-a]pyrimidine-3-carboxamide;
5-[(3S,4R)-3-amino-4-fluoropiperidin-1-yl]-N-[3-(difluoromethyl)-1-methyl-1H-pyrazol-4-yl]pyrazolo[1,5-a]pyrimidine-3-carboxamide;
5-(5-amino-3,3-difluoropiperidin-1-yl)-N-[3-(difluoromethyl)-1-methyl-1H-pyrazol-4-yl]pyrazolo[1,5-a]pyrimidine-3-carboxamide;
5-{[(1R,2S)-2-aminocyclohexyl]amino}-N-thiophen-3-ylpyrazolo[1,5-a]pyrimidine-3-carboxamide;
5-[(1S,5S)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;
5-[(1S,5S)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;

5-[(1R,5R)-3,6-diazabicyclo[3.2.1]oct-3-yl]-N-[3-(difluoromethyl)-1-methyl-1H-pyrazol-4-yl]pyrazolo[1,5-a]pyrimidine-3-carboxamide;

N-(2-chlorothiophen-3-yl)-5-{([(1R,2S)-2-hydroxycyclohexyl]amino}pyrazolo[1,5-a]pyrimidine-3-carboxamide;

N-(3-chloro-1-methyl-1H-pyrazol-4-yl)-5-{[(1R,2S)-2-hydroxycyclohexyl]amino}pyrazolo[1,5-a]pyrimidine-3-carboxamide;

N-(2-cyanothiophen-3-yl)-5-{[(1R,2S)-2-hydroxycyclohexyl]amino}pyrazolo[1,5-a]pyrimidine-3-carboxamide;

5-(3-amino-4,4-difluoropiperidin-1-yl)-N-[1-methyl-3-(trifluoromethyl)-1H-pyrazol-4-yl]pyrazolo[1,5-a]pyrimidine-3-carboxamide;

5-(3-amino-4,4-difluoropiperidin-1-yl)-N-[3-(difluoromethyl)-1-methyl-1H-pyrazol-4-yl]pyrazolo[1,5-a]pyrimidine-3-carboxamide;

5-{[(1R,2R)-2-amino-3,3-difluorocyclohexyl]amino}-N-(2-chlorothiophen-3-yl)pyrazolo[1,5-a]pyrimidine-3-carboxamide;

5-{([(1R,2R)-2-amino-3,3-difluorocyclohexyl]amino}-N-(2-cyanothiophen-3-yl)pyrazolo[1,5-a]pyrimidine-3-carboxamide;

5-(3-amino-4,4-difluoropiperidin-1-yl)-N-[1-methyl-3-(trifluoromethyl)-1H-pyrazol-4-yl]pyrazolo[1,5-a]pyrimidine-3-carboxamide;

5-(3-amino-4,4-difluoropiperidin-1-yl)-N-[3-(difluoromethyl)-1-methyl-1H-pyrazol-4-yl]pyrazolo[1,5-a]pyrimidine-3-carboxamide;

N-(2-chlorophenyl)-5-{[(1R,2S)-2-hydroxycyclohexyl]amino}pyrazolo[1,5-a]pyrimidine-3-carboxamide;

N-(2-bromophenyl)-5-{([(1R,2S)-2-hydroxycyclohexyl]amino})pyrazolo[1,5-a]pyrimidine-3-carboxamide;

N-(2-bromothiophen-3-yl)-5-{([(1R,2S)-2-hydroxycyclohexyl]amino})pyrazolo[1,5-a]pyrimidine-3-carboxamide;

N-[1-tert-butyl-3-(difluoromethyl)-1H-pyrazol-4-yl]-5-{([(1R,2S)-2-hydroxycyclohexyl]amino}pyrazolo[1,5-a]pyrimidine-3-carboxamide;

5-{([(1R,2R)-2-amino-3,3-difluorocyclohexyl]amino}-N-[1-tert-butyl-3-(difluoromethyl)-1H-pyrazol-4-yl]pyrazolo[1,5-a]pyrimidine-3-carboxamide;

N-[3-(difluoromethyl)-1-(1-methylethyl)-1H-pyrazol-4-yl]-5-{[[(1R,2S)-2-hydroxycyclohexyl]amino}pyrazolo[1,5-a]pyrimidine-3-carboxamide;

5-{([(1R,2R)-2-amino-3,3-difluorocyclohexyl]amino}-N-[3-(difluoromethyl)-1-(1-methylethyl)-1H-pyrazol-4-yl]pyrazolo[1,5-a]pyrimidine-3-carboxamide;

5-{([(1R,2R)-2-amino-3-hydroxycyclohexyl]amino}-N-[1-methyl-3-(trifluoromethyl)-1H-pyrazol-4-yl]pyrazolo[1,5-a]pyrimidine-3-carboxamide;

5-{([(1R,2R)-2-amino-6-hydroxycyclohexyl]amino}-N-[1-methyl-3-(trifluoromethyl)-1H-pyrazol-4-yl]pyrazolo[1,5-a]pyrimidine-3-carboxamide;

5-{([(1R,2R)-2-amino-3-fluorocyclohexyl]amino}-N-[1-methyl-3-(trifluoromethyl)-1H-pyrazol-4-yl]pyrazolo[1,5-a]pyrimidine-3-carboxamide;

5-{([(1S,2R)-2-amino-5,5-difluorocyclohexyl]amino}-N-[1-methyl-3-(trifluoromethyl)-1H-pyrazol-4-yl]pyrazolo[1,5-a]pyrimidine-3-carboxamide;

5-{([(1S,2R)-2-amino-4,4-difluorocyclohexyl]amino}-N-[1-methyl-3-(trifluoromethyl)-1H-pyrazol-4-yl]pyrazolo[1,5-a]pyrimidine-3-carboxamide;

5-{([(1S,2R)-2-amino-5,5-difluorocyclohexyl]amino}-N-[1-methyl-3-(trifluoromethyl)-1H-pyrazol-4-yl]pyrazolo[1,5-a]pyrimidine-3-carboxamide;

5-{([(1S,2R)-2-amino-4,4-difluorocyclohexyl]amino}-N-[1-methyl-3-(trifluoromethyl)-1H-pyrazol-4-yl]pyrazolo[1,5-a]pyrimidine-3-carboxamide;

5-{([(1S,2R)-2-amino-5,5-difluorocyclohexyl]amino}-N-[3-(difluoromethyl)-1-methyl-1H-pyrazol-4-yl]pyrazolo[1,5-a]pyrimidine-3-carboxamide;

5-{([(1S,2R)-2-amino-4,4-difluorocyclohexyl]amino}-N-[3-(difluoromethyl)-1-methyl-1H-pyrazol-4-yl]pyrazolo[1,5-a]pyrimidine-3-carboxamide;

5-{([(1S,2R)-2-amino-5,5-difluorocyclohexyl]amino}-N-[3-(difluoromethyl)-1-methyl-1H-pyrazol-4-yl]pyrazolo[1,5-a]pyrimidine-3-carboxamide;

5-{([(1S,2R)-2-amino-4,4-difluorocyclohexyl]amino}-N-[3-(difluoromethyl)-1-methyl-1H-pyrazol-4-yl]pyrazolo[1,5-a]pyrimidine-3-carboxamide;

N-[1-methyl-3-(trifluoromethyl)-1H-pyrazol-4-yl]-5-(3-oxa-7,9-diazabicyclo[3.3.2]dec-9-yl)pyrazolo[1,5-a]pyrimidine-3-carboxamide;

5-[(1S,5R)-2,6-diazabicyclo[3.2.1]oct-2-yl]-N-[1-methyl-3-(trifluoromethyl)-1H-pyrazol-4-yl]pyrazolo[1,5-a]pyrimidine-3-carboxamide;

5-(3,6-diazabicyclo[3.1.1]hept-6-yl)-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-[2-(trifluoromethyl)piperazin-1-yl]pyrazolo[1,5-a]pyrimidine-3-carboxamide;

5-(2,2-dimethylpiperazin-1-yl)-N-[1-methyl-3-(trifluoromethyl)-1H-pyrazol-4-yl]pyrazolo[1,5-a]pyrimidine-3-carboxamide;

5-[(5,5-difluoropiperidin-3-yl)amino]-N-[1-methyl-3-(trifluoromethyl)-1H-pyrazol-4-yl]pyrazolo[1,5-a]pyrimidine-3-carboxamide;

5-{([(3S)-5,5-difluoropiperidin-3-yl]amino}-N-[1-methyl-3-(trifluoromethyl)-1H-pyrazol-4-yl]pyrazolo[1,5-a]pyrimidine-3-carboxamide;

5-{[(3R)-5,5-difluoropiperidin-3-yl]amino}-N-[1-methyl-3-(trifluoromethyl)-1H-pyrazol-4-yl]pyrazolo[1,5-a]pyrimidine-3-carboxamide;

5-(4,7-diazaspiro[2.6]non-7-yl)-N-[1-methyl-3-(trifluoromethyl)-1H-pyrazol-4-yl]pyrazolo[1,5-a]pyrimidine-3-carboxamide;

5-(3,9-diazabicyclo[4.2.1]non-9-yl)-N-[1-methyl-3-(trifluoromethyl)-1H-pyrazol-4-yl]pyrazolo[1,5-a]pyrimidine-3-carboxamide;

5-(3,9-diazabicyclo[4.2.1]non-9-yl)-N-[1-methyl-3-(trifluoromethyl)-1H-pyrazol-4-yl]pyrazolo[1,5-a]pyrimidine-3-carboxamide;

5-(3,6-diazabicyclo[3.2.1]oct-3-yl)-N-[1-methyl-3-(trifluoromethyl)-1H-pyrazol-4-yl]pyrazolo[1,5-a]pyrimidine-3-carboxamide;

5-[(1S,5S)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide;

5-[(1R,5R)-3,6-diazabicyclo[3.2.1]oct-3-yl]-N-[1-methyl-3-(trifluoromethyl)-1H-pyrazol-4-yl]pyrazolo[1,5-a]pyrimidine-3-carboxamide;

5-(3,8-diazabicyclo[3.2.1]oct-8-yl)-N-[1-methyl-3-(trifluoromethyl)-1H-pyrazol-4-yl]pyrazolo[1,5-a]pyrimidine-3-carboxamide;

5-(4,8-diazaspiro[2.6]non-8-yl)-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-[(5,5-difluoropiperidin-3-yl)amino]pyrazolo[1,5-a]pyrimidine-3-carboxamide;

5-(3,8-diazabicyclo[3.2.1]oct-8-yl)-N-[3-(difluoromethyl)-1-methyl-1H-pyrazol-4-yl]pyrazolo[1,5-a]pyrimidine-3-carboxamide;

5-{[(3R,4S)-4-fluoropiperidin-3-yl]amino}-N-[1-methyl-3-(trifluoromethyl)-1H-pyrazol-4-yl]pyrazolo[1,5-a]pyrimidine-3-carboxamide;

5-{[(3S,4R)-4-fluoropiperidin-3-yl]amino}-N-[1-methyl-3-(trifluoromethyl)-1H-pyrazol-4-yl]pyrazolo[1,5-a]pyrimidine-3-carboxamide;

5-{[(3R,4R)-4-fluoropiperidin-3-yl]amino}-N-[1-methyl-3-(trifluoromethyl)-1H-pyrazol-4-yl]pyrazolo[1,5-a]pyrimidine-3-carboxamide;

5-{[(3S,4S)-4-fluoropiperidin-3-yl]amino}-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-[(4-fluoropiperidin-3-yl)amino]pyrazolo[1,5-a]pyrimidine-3-carboxamide;

N-[3-(difluoromethyl)-1-methyl-1H-pyrazol-4-yl]-5-[(5,5-difluoropiperidin-3-yl)amino]pyrazolo[1,5-a]pyrimidine-3-carboxamide;

N-[3-(difluoromethyl)-1-methyl-1H-pyrazol-4-yl]-5-[(4-fluoropiperidin-3-yl)amino]pyrazolo[1,5-a]pyrimidine-3-carboxamide;

N-[3-(difluoromethyl)-1-methyl-1H-pyrazol-4-yl]-5-[(4-fluoropiperidin-3-yl)amino]pyrazolo[1,5-a]pyrimidine-3-carboxamide;

5-[(1S,5R)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;

5-[(1S,5R)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;

5-[(1R,5S)-3,6-diazabicyclo[3.2.1]oct-6-yl]-N-[3-(difluoromethyl)-1-methyl-1H-pyrazol-4-yl]pyrazolo[1,5-a]pyrimidine-3-carboxamide;

N-[3-(difluoromethyl)-1-methyl-1H-pyrazol-4-yl]-5-[(4-fluoropiperidin-3-yl)amino]pyrazolo[1,5-a]pyrimidine-3-carboxamide;

N-[3-(difluoromethyl)-1-methyl-1H-pyrazol-4-yl]-5-[(4,4-difluoropiperidin-3-yl)amino]pyrazolo[1,5-a]pyrimidine-3-carboxamide;

5-[(4,4-difluoropiperidin-3-yl)amino]-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-[(4,4-difluoropiperidin-3-yl)amino]pyrazolo[1,5-a]pyrimidine-3-carboxamide;

5-[(4,4-difluoropiperidin-3-yl)amino]-N-[1-methyl-3-(trifluoromethyl)-1H-pyrazol-4-yl]pyrazolo[1,5-a]pyrimidine-3-carboxamide;

5-[(3S,5R)-3-amino-5-fluoropiperidin-1-yl]-N-[1-methyl-3-(trifluoromethyl)-1H-pyrazol-4-yl]pyrazolo[1,5-a]pyrimidine-3-carboxamide;

5-[(3S,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide;

5-[(3S,5S)-3-amino-5-fluoropiperidin-1-yl]-N-[3-(difluoromethyl)-1-methyl-1H-pyrazol-4-yl]pyrazolo[1,5-a]pyrimidine-3-carboxamide;

5-[(3S,5R)-3-amino-5-fluoropiperidin-1-yl]-N-[3-(difluoromethyl)-1-methyl-1H-pyrazol-4-yl]pyrazolo[1,5-a]pyrimidine-3-carboxamide;

5-[(3R,5S)-3-amino-5-fluoropiperidin-1-yl]-N-[1-methyl-3-(trifluoromethyl)-1H-pyrazol-4-yl]pyrazolo[1,5-a]pyrimidine-3-carboxamide;

5-[(3R,5S)-3-amino-5-fluoropiperidin-1-yl]-N-[3-(difluoromethyl)-1-methyl-1H-pyrazol-4-yl]pyrazolo[1,5-a]pyrimidine-3-carboxamide;

5-[(3R,5R)-3-amino-5-fluoropiperidin-1-yl]-N-[1-methyl-3-(trifluoromethyl)-1H-pyrazol-4-yl]pyrazolo[1,5-a]pyrimidine-3-carboxamide;

5-[(3R,5R)-3-amino-5-fluoropiperidin-1-yl]-N-[3-(difluoromethyl)-1-methyl-1H-pyrazol-4-yl]pyrazolo[1,5-a]pyrimidine-3-carboxamide;

5-{[(3S,5R)-5-fluoropiperidin-3-yl]amino}-N-[1-methyl-3-(trifluoromethyl)-1H-pyrazol-4-yl]pyrazolo[1,5-a]pyrimidine-3-carboxamide;

5-{[(3S,5S)-5-fluoropiperidin-3-yl]amino}-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-{([(3S,5S)-5-fluoropiperidin-3-yl]amino})pyrazolo[1,5-a]pyrimidine-3-carboxamide;

5-{[(3R,5S)-5-fluoropiperidin-3-yl]amino}-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-{([(3R,5S)-5-fluoropiperidin-3-yl]amino})pyrazolo[1,5-a]pyrimidine-3-carboxamide;

N-[3-(difluoromethyl)-1-methyl-1H-pyrazol-4-yl]-5-{([(3S,5R)-5-fluoropiperidin-3-yl]amino})pyrazolo[1,5-a]pyrimidine-3-carboxamide;

5-{[(3R,5R)-5-fluoropiperidin-3-yl]amino}-N-[1-methyl-3-(trifluoromethyl)-1H-pyrazol-4-yl]pyrazolo[1,5-a]pyrimidine-3-carboxamide;

N-[3-(difluoromethyl)-1-methyl-1H-pyrazol-4-yl]-5-{([(3R,5R)-5-fluoropiperidin-3-yl]amino})pyrazolo[1,5-a]pyrimidine-3-carboxamide;

5-{([(1R,2S)-2-(methylamino)cyclohexyl]amino}-N-[1-methyl-3-(trifluoromethyl)-1H-pyrazol-4-yl]pyrazolo[1,5-a]pyrimidine-3-carboxamide;

5-{([(1R,2S)-2-(dimethylamino)cyclohexyl]amino}-N-[1-methyl-3-(trifluoromethyl)-1H-pyrazol-4-yl]pyrazolo[1,5-a]pyrimidine-3-carboxamide;

N-[1-methyl-3-(trifluoromethyl)-1H-pyrazol-4-yl]-5-{([(1R,2S)-2-morpholin-4-ylcyclohexyl]amino}pyrazolo[1,5-a]pyrimidine-3-carboxamide;

5-{([(1R,2S)-2-aminocyclohexyl]amino}-N-(2-cyanophenyl)pyrazolo[1,5-a]pyrimidine-3-carboxamide;

N-(2-cyanophenyl)-5-{([(1R,2S)-2-hydroxycyclohexyl]amino}pyrazolo[1,5-a]pyrimidine-3-carboxamide;

N-(2-cyanophenyl)-5-(5,8-diazaspiro[2.6]non-5-yl)pyrazolo[1,5-a]pyrimidine-3-carboxamide;

5-{([(1R,2R)-2-amino-3,3-difluorocyclohexyl]amino}-N-(2-cyanophenyl)pyrazolo[1,5-a]pyrimidine-3-carboxamide;

5-[(3R)-3-aminopiperidin-1-yl]-N-(2-cyanophenyl)pyrazolo[1,5-a]pyrimidine-3-carboxamide;

N-(2-cyanophenyl)-5-[(3R)-piperidin-3-ylamino]pyrazolo[1,5-a]pyrimidine-3-carboxamide;

N-(2-cyanophenyl)-5-(2,5-diazabicyclo[2.2.2]oct-2-yl)pyrazolo[1,5-a]pyrimidine-3-carboxamide;

5-(azepan-3-ylamino)-N-(2-cyanophenyl)pyrazolo[1,5-a]pyrimidine-3-carboxamide;

N-(2-cyanophenyl)-5-(1,4-diazepan-1-yl)pyrazolo[1,5-a]pyrimidine-3-carboxamide;

N-(2-cyanophenyl)-5-piperazin-1-ylpyrazolo[1,5-a]pyrimidine-3-carboxamide;

5-{([(1R,2S)-2-aminocyclohexyl]amino}-N-[5-(hydroxymethyl)thiophen-3-yl]pyrazolo[1,5-a]pyrimidine-3-carboxamide;

5-{([(1R,2S)-2-aminocyclohexyl]amino}-N-[5-(1-hydroxyethyl)thiophen-3-yl]pyrazolo[1,5-a]pyrimidine-3-carboxamide;

5-{([(1R,2S)-2-aminocyclohexyl]amino}-N-[3-(difluoromethyl)-1-methyl-1H-pyrazol-4-yl]pyrazolo[1,5-a]pyrimidine-3-carboxamide;

5-{([(1S,2R)-2-aminocyclohexyl]amino}-N-(1-pyridin-3-yl-1H-pyrazol-4-yl)pyrazolo[1,5-a]pyrimidine-3-carboxamide;

5-{([(1R,2S)-2-aminocyclohexyl]amino}-N-(1-methyl-1H-pyrazol-4-yl)pyrazolo[1,5-a]pyrimidine-3-carboxamide;

5-{([(1R,2S)-2-aminocyclohexyl]amino}-N-[3-(methoxymethyl)-1-methyl-1H-pyrazol-4-yl]pyrazolo[1,5-a]pyrimidine-3-carboxamide;

5-{([(1R,2S)-2-aminocyclohexyl]amino}-N-[1-methyl-3-(1,3,4-oxadiazol-2-yl)-1H-pyrazol-4-yl]pyrazolo[1,5-a]pyrimidine-3-carboxamide;

5-{([(1R,2S)-2-aminocyclohexyl]amino}-N-(3-cyano-1-methyl-1H-pyrazol-4-yl)pyrazolo[1,5-a]pyrimidine-3-carboxamide;

5-{([(1R,2S)-2-aminocyclohexyl]amino}-N-[3-(2-methoxyethyl)-1-methyl-1H-pyrazol-4-yl]pyrazolo[1,5-a]pyrimidine-3-carboxamide;

5-{([(1R,2S)-2-aminocyclohexyl]amino}-N-(1-methyl-3-pyridin-4-yl-1H-pyrazol-4-yl)pyrazolo[1,5-a]pyrimidine-3-carboxamide;

5-{([(1R,2S)-2-aminocyclohexyl]amino}-N-[1-methyl-3-(5-methyl-1,3-oxazol-2-yl)-1H-pyrazol-4-yl]pyrazolo[1,5-a]pyrimidine-3-carboxamide;

5-{([(1R,2S)-2-aminocyclohexyl]amino}-N-[1-methyl-3-(4-methyl-4H-1,2,4-triazol-3-yl)-1H-pyrazol-4-yl]pyrazolo[1,5-a]pyrimidine-3-carboxamide;

5-{([(1R,2S)-2-aminocyclohexyl]amino}-N-(1-methyl-pyrimidin-5-yl-1H-pyrazol-4-yl)pyrazolo[1,5-a]pyrimidine-3-carboxamide;

5-{([(1R,2S)-2-aminocyclohexyl]amino}-N-[1-methyl-3-(5-methyl-1,2,4-oxadiazol-3-yl)-1H-pyrazol-4-yl]pyrazolo[1,5-a]pyrimidine-3-carboxamide;

5-{[(1R,2S)-2-aminocyclohexyl]amino}-N-[3-(2-fluoroethyl)-1-methyl-1H-pyrazol-4-yl]pyrazolo[1,5-a]pyrimidine-3-carboxamide;

N-[1-methyl-3-(trifluoromethyl)-1H-pyrazol-4-yl]-5-[(2-morpholin-4-ylethyl)amino]pyrazolo[1,5-a]pyrimidine-3-carboxamide;

5-{[(R,2S)-2-aminocyclohexyl]amino}-N-[1-(1-methylethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(2,2-difluoroethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-cyclopropyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-tert-butyl-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(2,2,2-trifluoroethyl)-3-(trifluoromethyl)-1H-pyrazol-4-yl]pyrazolo[1,5-a]pyrimidine-3-carboxamide;

5-{[(1R,2S)-2-aminocyclohexyl]amino}-N-[1-(difluoromethyl)-3-(trifluoromethyl)-H-pyrazol-4-yl]pyrazolo[1,5-a]pyrimidine-3-carboxamide;

5-{[(1R,2S)-2-aminocyclohexyl]amino}-N-[1-methyl-3-(pentafluoroethyl)-1H-pyrazol-4-yl]pyrazolo[1,5-a]pyrimidine-3-carboxamide;

N-[1-(1-methylethyl)-3-(trifluoromethyl)-1H-pyrazol-4-yl]-5-piperazin-1-ylpyrazolo[1,5-a]pyrimidine-3-carboxamide;

5-piperazin-1-yl-N-[1-(2,2,2-trifluoroethyl)-3-(trifluoromethyl)-1H-pyrazol-4-yl]pyrazolo[1,5-a]pyrimidine-3-carboxamide;

N-[1-(difluoromethyl)-3-(trifluoromethyl)-1H-pyrazol-4-yl]-5-piperazin-1-ylpyrazolo[15-a]pyrimidine-3-carboxamide; and 5-{[(1R,2S)-2-aminocyclohexyl]amino}-N-[3-(trifluoromethyl)-H-pyrazol-4-yl]pyrazolo[1,5-a]pyrimidine-3-carboxamide;

or a pharmaceutically acceptable salt thereof.

3. A pharmaceutical composition comprising a pharmaceutical carrier and a therapeutically effective amount of a compound of claim 1.

4. A compound which is selected from:

5-{[(1R,2S)-2-aminocyclohexyl]amino}-N-[1-methyl-3-(trifluoromethyl)-1H-pyrazol-4-yl]pyrazolo[1,5-a]pyrimidine-3-carboxamide;

5-[(5S)-5-amino-3,3-difluoropiperidin-1-yl]-N-[1-methyl-3-(trifluoromethyl)-1H-pyrazol-4-yl]pyrazolo[1,5-a]pyrimidine-3-carboxamide;

5-[(4R)- or (4.5)-(5-amino-3,3-difluoropiperidin-1-yl)-N-[3-(difluoromethyl)-1-methyl-1H-pyrazolo-4-yl]pyrazolo[1,5-a]pyrimidine-3-carboxamide;

5-[(3R,5R)-3-amino-5-:fluoropiperidin-1-yl]-N-[3-(difluoromethyl)-1-methyl-1H-pyrazol-4-yl]pyrazolo[1,5-a]pyrimidine-3-carboxamide; and 5-(((1R,2S)-2-Aminocyclohexyl)amino)-N-(3-(difluoromethyl)-1-methyl-1H-pyrazol-4-yl)pyrazolo[1,5-a]pyrimidine-3-carboxamide;

or a pharmaceutically acceptable salt thereof.

5. A pharmaceutical composition comprising a pharmaceutical carrier and a therapeutically effective amount of a compound of claim 4.

* * * * *